(12) United States Patent
Stanton et al.

(10) Patent No.: US 6,709,855 B1
(45) Date of Patent: Mar. 23, 2004

(54) METHODS FOR DETECTION AND USE OF DIFFERENTIALLY EXPRESSED GENES IN DISEASE STATES

(75) Inventors: Lawrence W. Stanton, Redwood City, CA (US); R. Tyler White, Fremont, CA (US); Deborah L. Damm, Redwood City, CA (US); John A. Lewicki, Los Gatos, CA (US); Alison Joly, San Mateo, CA (US); George F. Schreiner, Los Altos Hills, CA (US)

(73) Assignee: Scios, Inc., Fremont, CA (US)

( * ) Notice: Subject to any disclaimer, the term of this patent is extended or adjusted under 35 U.S.C. 154(b) by 0 days.

(21) Appl. No.: 09/461,912

(22) Filed: Dec. 15, 1999

Related U.S. Application Data

(60) Provisional application No. 60/113,008, filed on Dec. 18, 1998.

(51) Int. Cl.[7] .................. C12M 1/34; C12M 01/00; C12Q 1/68; C07H 21/02; C07H 21/04
(52) U.S. Cl. ................. 435/283.1; 435/287.2; 435/6; 536/24.3; 536/24.33; 536/24.31; 536/23.1
(58) Field of Search .................. 536/23.1, 24.5, 536/24.31, 24.33; 435/6, 91.1, 91.2, 287.2, 283.1

(56) References Cited

U.S. PATENT DOCUMENTS

| | | | |
|---|---|---|---|
| 4,843,155 A | | 6/1989 | Chomczynski |
| 5,262,311 A | | 11/1993 | Pardee et al. |
| 5,700,637 A | * | 12/1997 | Southern |
| 6,025,194 A | * | 2/2000 | Funk |

FOREIGN PATENT DOCUMENTS

| WO | WO 9429448 | 12/1994 |
|---|---|---|
| WO | WO 9602257 | 2/1996 |
| WO | WO 9938973 | 8/1999 |

OTHER PUBLICATIONS

Zhu et al. "Cellular Gene Expression Altered by Human cytomegalovirus: Global monitoring with oligonucleotide arrays", PNAS, Vol 95, pp. 14470–14475, Nov. 1998.*

Lewin et al., "Molecular analysis of a human interferon-inducible gene family," *Eur J. Biochem.* 199:417–423 (1991).

Masuda et al., "Bone mass loss due to estrogen deficiency is compensated in transgenic mice overexpressing human osteoblast stimulating factor–1," *Biochemical and Biophysical Research Communications*, 238:528–533 (1997).

Imai et al., "Osteoblast recruitment and bone formation enchanced by cell matrix-associated heparin-binding growth-associated molecule (HB-GAM)," *Journal of Cell Biology* 143, No. 4:1113–1128 (1998).

(List continued on next page.)

Primary Examiner—Karen A. Lacourciere
(74) Attorney, Agent, or Firm—Morrison & Foerster LLP

(57) ABSTRACT

The present invention relates to methods and compositions for the detection, diagnosis, prevention and treatment of a disease, specifically cardiac, kidney or inflammatory disease, and related disorders. The present invention also relates to compositions and methods useful in the diagnosis, prevention and therapeutic treatment of a disease, specifically cardiac, kidney or inflammatory disease. Specifically, methods and compositions are provided for the diagnostic evaluation and prognosis of conditions involving a disease, specifically cardiac, kidney or inflammatory disease, for the identification of subjects exhibiting a predisposition to such conditions, for the effect of these differentially expressed genes, for monitoring patients undergoing clinical evaluation for the prevention and treatment of a disease, specifically cardiac, kidney or inflammatory disease, and its disorders, and for monitoring the efficacy of compounds used in clinical trials.

12 Claims, 74 Drawing Sheets

OTHER PUBLICATIONS

Colley et al., "Antisense oligonucleotides of pleiotrophin," XP002136678 abstracts & WO 96 02257 (Georgetown University).

Mizushima et al., "DNA encoding a protein promoting PG12 production," XP002136679 abstract & WO 94 29448 (Nawata H).

Maeda et al., "Analysis of an expression profile to genes in the human adipose tissue," Gene 190:227–235 (1997).

Heller et al., "Discovery and analysis of inflammatory disease–related genes using cDNA microarrays," Proc.Natl. Acad. Sci. USA 94:2150–2155 (1997).

Schena et al., "Parallel human genome analysis: Microarray–based expression monitoring of 1000 genes," Proc. Natl. Acad. Sci. USA 93:10614–10619 (1996).

Komuro et al., "Control of cardiac gene expression by mechanical stress," Ann. Rev. Physiol. 55:55–75 (1993).

Schunkert et al., "Increased rat cardiac angiotensin converting enzyme activity and mRNA expression in pressure overload left ventricular hypertrophy," J. Clin. Invest. 86(6):1913–20 (1990).

Izumo et al., "Protoonocogene induction and reprogramming of cardiac gene expression by pressure overload," Proc. Natl. Acad. Sci. USA 85(2):339–43 (1988).

Schunkert et al., "Alteration of growth responses in established cardiac pressure overload hypertrophy in rats with aortic banding," J. Clin. Invest. 96(6):2768–74 (1995).

DeRisi et al., "Use of a cDNA microarray to analyse gene expression patterns in human cancer," Nat. Genet. 14(4):457–60 (1996).

Heller et al., "Discovery and analysis of inflammatory disease–related genes using cDNA microarrays," Proc. Natl. Acad. Sci. USA 94(6):2150–55 (1997).

Wetmur et al., "Kinetics of Renaturation of DNA," J. Mol. Biol. 31:349–70 (1966).

Wetmur, "DBA Probes: Applications of the Principles of Nucleic Acid Hybridization," Critical Reviews in Biochemistry and Molecular Biology 26(34):227–59 (1991).

Smith et al., "Comparison of biosequences," Adv. Appl. Math. 2:482 (1981).

Needleman et al., "A general method applicable to the search for similarities in the amino acid sequence of two proteins," J. Mol. Biol. 48:443 (1970).

Pearson et al., "Improved tools for biological sequence comparison," Proc. Natl. Acad. Sci. USA 85:2444 (1988).

Altschul et al., "Gapped BLAST and PSI–BLAST: a new generation of protein database search programs," Nucleic Acids Res. 25:3389–3402 (1997).

Aziz, "Animal models of polycystic kidney disease," bioeassays, 17:8 703–12 (1995).

Tedder et al., "Isolation and structure of a cDNA encoding the B1 (CD20) cell–surface antigen of human B lymphocytes," Proc. Natl. Acad. Sci. USA 85:208–12 (1988).

Hedrick et al., "Isolation of cDNA clones encoding T cell–specific membrane–associated proteins," Nature 308: (1984).

Lee et al., "Positive selection of candidate tumor–supressor genes by subtractive hybridization," Proc. Natl. Acad. Sci. USA 88:2825 (1984).

Schena et al., "Parallel human genome analysis: microarray–based expression monitoring of 1000 genes," Proc. Natl. Acad. Sci. USA 93(20:10614–9 (1996).

Arola et al., "Experimental Myocarditis induced by two different coxsackievirus B3 variants: aspects of pathogenesis and comparison of diagnostic methods," J. Med. Virol. 47:252–259 (1995).

Chow et al., "Differential effects of myocarditic variants of coxsackievirus B3 in inbred mice, A pathologic characterization of heart tissue damage," Lab. Invest. 64:55–64 (1991).

McManus et al., "Direct myocardial injury by enterovirus: a central role in the evolution of murine myocarditis," Clin. Immunol. Immunopathol. 68:159–169 (1993).

Anderson et al., "Direct interactins of coxsackievirus B3 with immune cells in the splenic compartment of mice susceptible or resistant to myocarditis," J. Virol 70:4632–4645 (1996).

Kaspari–Rittinghausen et al., "A new rat model for polycystic kidney disease of humans," Transplant Proc. 6:2582–3 (1990).

Cowley et al., "Autosomal–dominant polycystic kidney disease in the rat," Kidney Int. 43:522–34 (1993).

Bishop et al., "Three abundance classes in HeLa cell messenger RNA," Nature 250(463):199–204 (1974).

Soares et al., "Construction and characterization of a normalized cDNA library," Proc Natl. Acad. Sci. USA 91(20):9228–32 (1994).

Bonaldo et al., Genome Res. 6(9):791–806 (1996).

Chinault et al., "Overlap hybridization screeing: isolation and characterization of overlapping DNA fragments surrounding the leu2 gene on yeast chromosome III," Gene 5:111–26 (1979).

Pfeffer et al., "Influence of Chronic Captopril Therapy on the Infacted Left Ventricle of the Rat," Circ. Res. 57:84–95 (1985).

Krah et al., "A two–subunit type I DNA topoisomerase (reverse Gyrase) from an extreme hyperthemophile," Proc. Natl. Acad. Sci. USA, 93:106–110 (1996).

* cited by examiner

FIGURE 3
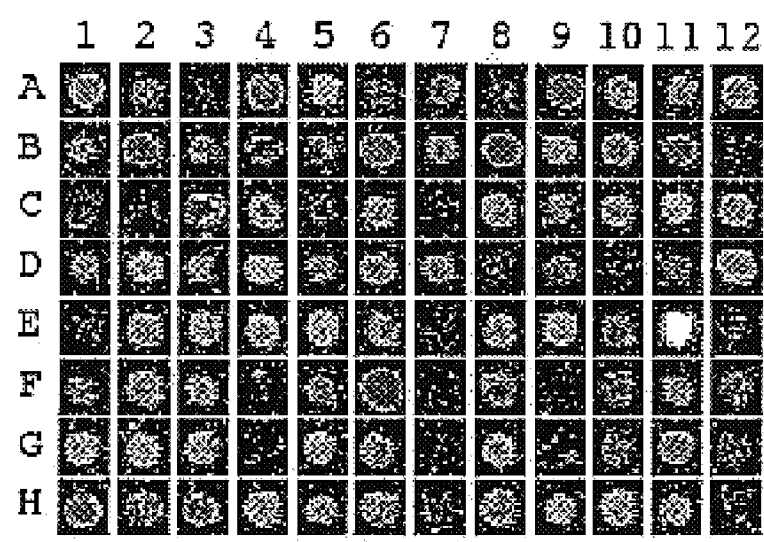
Cy 5: Rat Heart (Scios)

FIGURE 4

Expression Report

| CloneID | Name | MI Left Ventricle | | | | | MI Septum | | | | | Viral myocarditis | | | LVH | PKD |
|---|---|---|---|---|---|---|---|---|---|---|---|---|---|---|---|---|
| | | 2w | 4w | 8w | 12w | 16w | 2w | 4w | 8w | 12w | 16w | 3d | 9d | 30d | 10w | |
| P0182_F08 | BTG2 | -1.9 | -1.4 | -1.6 | 1.2 | 1.0 | -2.2 | -2.4 | -1.6 | -1.0 | 1.2 | 5.4 | 2.0 | -1.5 | 1.5 | -1.1 |
| P0204_E06 | 1-8U | 2.0 | 2.3 | 2.4 | 2.1 | 2.1 | 1.3 | 1.7 | 1.7 | 1.4 | 1.4 | 4.1 | 4.3 | 1.5 | -1.4 | 1.9 |
| P0207_C03 | gas-1 | 1.3 | 1.5 | 1.1 | -1.1 | 1.0 | 1.1 | 1.4 | 1.2 | 1.1 | -1.3 | -1.3 | -1.3 | -1.3 | | -1.1 |
| P0214_A11 | YMP | 1.7 | 2.4 | 1.5 | 1.9 | 1.6 | 1.3 | 1.3 | 1.3 | 1.2 | 1.0 | -1.2 | 2.0 | 1.4 | -1.4 | 2.4 |
| P0219_H09 | SDF1a | -1.0 | 1.2 | -1.1 | 1.1 | -1.0 | -1.1 | 1.3 | -1.1 | -1.1 | 1.1 | -1.3 | -1.3 | -1.0 | 2.0 | -1.9 |
| P0228_H09 | tissue specific mRNA | 1.5 | 2.2 | 1.9 | 1.9 | 1.5 | 1.4 | 1.2 | 1.3 | 1.6 | 1.3 | 2.0 | 3.0 | 1.6 | -1.2 | 1.6 |
| P0242_B03 | peripheral benzodiazepine receptor | 1.1 | 1.0 | 1.6 | 1.2 | 1.2 | 1.4 | 1.0 | 1.4 | 1.4 | 1.3 | 2.3 | 6.0 | 1.7 | -2.1 | 2.0 |
| P0246_H10 | IGFBP-6 | 2.1 | 2.4 | 2.4 | 2.7 | 2.7 | 1.1 | 1.4 | 1.5 | 1.3 | 1.5 | | 1.2 | -1.1 | 1.5 | 1.1 |
| P0248_D11 | osf-2 | 6.2 | 8.4 | 4.3 | 4.3 | 4.7 | 2.2 | 4.1 | 2.2 | 1.5 | 2.1 | -1.3 | 2.2 | 1.1 | 1.5 | |
| P0267_B09 | OSF-1 | 1.5 | 2.1 | 1.2 | 1.3 | 1.6 | 1.3 | 1.4 | 1.3 | -1.4 | 1.0 | | 1.1 | 1.3 | | -2.6 |
| P0267_E02 | prostacyclin-stimulating factor | 2.7 | 3.3 | 2.7 | 2.4 | 2.4 | 1.3 | 1.7 | 1.5 | 1.3 | 1.3 | -1.1 | 1.7 | 1.2 | 1.5 | -1.3 |
| P0268_G09 | cellular ligand of annexin II (p11) | 3.2 | 3.2 | 2.7 | 3.1 | 2.6 | 2.3 | 1.8 | 2.1 | 1.6 | 1.4 | 1.0 | 4.2 | 1.3 | -1.8 | 3.4 |

FIGURE 5A

X61381: R. rattus interferon induced mRNA (SEQ ID NO:1)
X57352: Human 1-8U gene from interferon-inducible gene family (SEQ ID NO:2)

Percent Similarity: 75.691   Percent Identity: 75.691

X61381.seq x X57352.seq

```
 25 ACCATGAACCACACTTCTCAAGCCTTCGTGAACGCTGCCACTGGGGGACA  74
    |||||||  ||||||   ||| ||||||  |       ||| ||   | || ||
235 ACCATGAGTCACACTGTCCAAACCTTCTTCTCTCCTGTCAACAGTGGCCA 284

75 ACCCCCAAACTACGAAAGAATCAAGGAAGAATATGAGGTGTCTGAACTGG 124
    |||||  |||||  ||  |   |||||||| ||  | ||||||  ||||  ||||
285 GCCCCCCAACTATGAGATGCTCAAGGAGGAGCACGAGGTGGCTGTGCTGG 334

125 GGGCTCCCCACGGATCGGCTTCTGTCAGAACTACCGTGATCAACATGCCC 174
    |||   ||||||      |  ||||  |      |   |  |||||||||| |||| |  |
335 GGGGGCCCCACAACCCTGCTCCCCCGACGTCCACCGTGATCCACATCCGC 384

175 AGAGAGGTCTCTGTGCCTGACCATGTGGTCTGGTCCCTGTTCAATACGCT 224
    ||  |||   |||  ||||| ||||||||  ||||||||||||||||||||||||||||  || ||
385 AGCGAGACCTCCGTGCCCGACCATGTCGTCTGGTCCCTGTTCAACACCCT 434

225 CTTCATGAACTTCTGCTGCCTGGGCTTCATTGCCTATGCCTACTCTGTGA 274
    |||||||||||   ||||||||||||||||||||||||| ||  |  ||||||||| ||||
435 CTTCATGAACCCCTGCTGCCTGGGCTTCATAGCATTCGCCTACTCCGTGA 484

275 AGTCTAGGGATCGGAAGATGGTGGGTGATATGACTGGAGCCCAGGCCTAC 324
    |||||||||||  |||||||||||| ||  ||   ||||  ||  ||||||||||||
485 AGTCTAGGGACAGGAAGATGGTTGGCGACGTGACCGGGGCCCAGGCCTAT 534

325 GCATCCACTGCCAAATGCCTGAACATCAGCTCCCTGGTCCTCAGCATCCT 374
    ||  ||||||  |||||  |||||||||||||||| |   |||||  |  ||   |||||||
535 GCCTCCACCGCCAAGTGCCTGAACATCTGGGCCCTGATTCTGGGCATCCT 584

375 CATGGTCATTAT 386
    ||||    ||||  |
585 CATGACCATTCT 596
```

FIGURE 5B

P0267_E02 (SEQ ID NO.3)
S75725:  prostacyclin-stimulating factor (SEQ ID NO.4)

Percent Similarity: 79.087   Percent Identity: 78.707

P0267_E02.seq x S75725.seq

```
  1 TACGAGTGCCACGCGTCCAATT.CCAAGGACAGGCTTCAGCGTCGGCCAA  49
    || ||||||||  || |||||||  ||||||||||||||||||| || || ||
758 TATGAGTGCCATGCATCCAATTCCCAAGGACAGGCTTCAGCATCAGCAAA  807

50 AATTACAGTGGTTGATGCCATACACGAAATACCAGTGAAAAAGGTGAAG   99
    |||||||||||||||||| ||||  |||| ||||||||||||||||||||||||||
808 AATTACAGTGGTTGATGCCTTACATGAAATACCAGTGAAAAAGGTGAAG  857

100 GTGCTCAGCTATAAACCTGC.GAATA.CATTAGCCTCTGTAGCTGACGCG  147
    ||||  ||||||||||| | |||||  ||||| ||     | | |
858 GTGCCGAGCTATAAACCTCCAGAATATTATTAGTCTGCATGGTT......  901

148 CTCTCAGACAGCTGACAGCTGTAAC.......CCCACTCCTGCCTGACAT  190
      | ||  | ||     |·||||      ||  || |||||  | |
902 ......AAAAGTAGTCATGGATAACTACATTACCTGTTCTTGCCTAATAA  945

191 ATTCCTTTGAACCTAACACACTAACACTTTATTACAGCCAGCTGATTTTA  240
    || ||||  || | ||  ||||||||||||| |          ||| |||||
946 GTTTCTTTTAATCCAATCCACTAACACTTTAGTTATATTCACTGGTTTTA  995

241 CACAG........AAATCNAAGATAACACAT.AAGACTATCTAC       275
    || ||   ·     |||  :|||||| ||||||| |||||||||||||
996 CACAGAGAAATACAAAATAAAGATCACACATCAAGACTATCTAC        1039
```

FIGURE 5C

P0248_D11.seq (SEQ ID NO:5)
D13665:    Human mRNA for osteoblast specific factor 2 (OSF-2p1)
           (SEQ ID NO:6)

Percent Similarity: 85.039   Percent Identity: 85.039

P0248_D11.seq x D13665.seq

```
   1 AAGCAAAATCTATGTGAAAGGAGTCAATGAAGACGCTTTTGGTGAATGAG  50
     |||||||||||  ||||||  ||| ||||  ||  ||| ||||||||||
1797 AAGCAAAATCTTTCTGAAAGAAGTAAATG.ATACACTTCTGGTGAATGAA 1845

51 TTGAAGTCCAAAGAATCTGACATCATGACAACAAACGGCGTCATTCACGT 100
     ||||| || |||||||||||||||||||||||||| || || ||||| ||
1846 TTGAAATCAAAAGAATCTGACATCATGACAACAAATGGTGTAATTCATGT 1895

101 TGTGGACAAACTCCTCTATCCAGCAGACATTCCGGTTGGAAATGATCAGC 150
     ||| || |||||||||||||||||||||| || ||||||||||||||| |
1896 TGTAGATAAACTCCTCTATCCAGCAGACACACCTGTTGGAAATGATCAAC 1945

151 TCTTGGAATTACTGAACAAACTGATAAAATACATCCAAATTAAGTTCGTT 200
     |  ||||| |||| || ||| | || ||||||||||||||||||| |||
1946 TGCTGGAAATACTTAATAAATTAATCAAATACATCCAAATTAAGTTTGTT 1995

201 CGTGGCAGCACCTTCAAAGAAAATCCCCATGACTGTCTATACAACTAAAA 250
     |||||  ||||||||||| ||||||| ||||||||||||||  |  |  |
1996 CGTGGTAGCACCTTCAAAG.AAATCCCCGTGACTGTCTATAAGCCAATTA 2044

251 TTATAA 256
     ||| ||
2045 TTAAAA 2050
```

FIGURE 5D

P0228_H09.seq (SEQ ID NO:7)
X67698: H.sapiens tissue specific mRNA (SEQ ID NO:8)

Percent Similarity: 79.715  Percent Identity: 79.359

P0228_H09.seq x X67698.seq

```
  1 GATGAGCTTCCTGAC.CCCACGATCCTGCTGCTGGCGCTGGTCGCCGCCA  49
    ||||  ||||||  |   |  ||  |||||||  ||||||||   |  ||||
 10 GATGCGTTTCCTGGCAGCTACATTCCTGCTCCTGGCGCTCAGCACCGCTG  59

50 CCCAGGCCGAGCCCCTGCACTTCAAGGACTGCGGTTCTAAGGTGGGAGTT  99
    |||||||||  ||   ||||  |||||||||||||||||||  ||  ||||||
 60 CCCAGGCCGAACCGGTGCAGTTCAAGGACTGCGGTTCTGTGGATGGAGTT 109

100 ATAAAGGAAGTGAATGTGAGCCCATGCCCTACCCAGCCCTGTCAGCTACA 149
    ||||||||||||||||||||||||||||  |||||  |||||  ||||||
110 ATAAAGGAAGTGAATGTGAGCCCATGCCCCACCCAACCCTGCCAGCTGAG 159

150 CAAAGGCCAGTCCTACAGTGTCAACGTCACCTTTACTAGCGGCACTCAGT 199
    ||||||  |||||  |||||  ||||||||||  ||  |||   |   |||||
160 CAAAGGACAGTCTTACAGCGTCAATGTCACCTTCACCAGCAATATTCAGT 209

200 CCCAGAACAGCACGGCCTTGGTCCACGGCATCTTGGCAGGGGTCCCAGTC 249
    |   |   ||||||  ||||  ||||  ||  |||||||  ||   ||  |||||||||
210 CTAAAAGCAGCAAGGCCGTGGTGCATGGCATCCTGATGGGCGTCCCAGTT 259

250 TACTTCCCTATTCCTGAGCCTGACNGTTGTAA 281
    |||  ||  |||||||||||||||||| :|||||||
260 CCCTTTCCCATTCCTGAGCCTGATGGTTGTAA 291
```

FIGURE 5E-1

M69055: Rat insulin-like growth factor binding protein (rIGFBP-6)
(SEQ ID NO:9)

M62402: Human insulin-like growth factor binding protein 6 (IGFBP6)
(SEQ ID NO:10)

Percent Similarity: 76.053   Percent Identity: 76.053

M69055.seq x M62402.seq

```
  4 CCATGACCTGGGACGGACTGCCCACACAGCCGCTGTTGATGCTGTTAATG  53
    ||||||||    || | ||||  ||    ||||||| || ||||| ||
 52 CCATGACCCCCACAGGCTGCTGCCA...CCGCTGCTGCTGCTGCTAGCT  98

54 CTGTTGTTCGCTGCGGGCTCCGAGTCCGCCTTAGCGGGGTGCCCGGGCTG 103
    ||| || ||||||||  || | |   ||||||  || ||||||| |||||
 99 CTGCTGCTCGCTGCCAGCCCAGGAGGCGCCTTGGCGCGGTGCCCAGGCTG 148

104 CGGGCCGGGGGTGC..................AGGAGGAAG 126
    |||||  |||||||                  |||||||  |
149 CGGGCAAGGGGTGCAGGCGGGTTGTCCAGGGGGCTGCGTGGAGGAGGAGG 198

127 ACGCGGGGTCGCCTGCAGACGGCTGTGCAGAGACCGGAGGCTGTTTCAGG 176
     | | |||||||||  || || |||||| || || | | |||||| ||||
199 ATGGGGGGTCGCCAGCCGAGGGCTGCGCGGAAGCTGAGGGCTGTCTCAGG 248

177 AGAGAGGGGCAACCGTGCGGGGTCTACATCCCTAAGTGCGCCCCAGGACT 226
    || ||||||||    |||||||||||||  ||||||| ||||||||||||
249 AGGGAGGGGCAGGAGTGCGGGGTCTACACCCCTAACTGCGCCCCAGGACT 298

227 GCAGTGCCAACCCCGAGAGAACGAAGAGACACCTTTGCGGGCGCTGCTGA 276
    ||||||||| || ||   || |||| ||| | ||||||||||||||||||
299 GCAGTGCCATCCGCCCAAGGACGACGAGGCGCCTTTGCGGGCGCTGCTGC 348

277 TCGGCCAGGGCCGCTGTCAACGCGCCAGAGGGCC......GTCGGAAGAG 320
    ||||||  |||||||||  |  | ||| | |||       | || |||
349 TCGGCCGAGGCCGCTGCCTTCCGGCCCGCGCGCCTGCTGTTGCAGAGGAG 398

321 ACTACCAAGGAGAGCAAACCCCATGGAGGCGCCTCCCGCCCACGTGA... 367
    | | | |||||||||| ||||||| |||| | |||||||||| ||  | ||
399 AATCCTAAGGAGAGTAAACCCCAAGCAGGCACTGCCCGCCCACAGGATGT 448

368 ......CAGAGACCGGCAAAAGAATCCACGGACCTCGGCTGCCCCTATAA 411
          ||||||||  || | |||||||| | |||||  |  | |||
449 GAACCGCAGAGACCAACAGAGGAATCCAGGCACCTCTACCACGCCCTCCC 498

412 GGCCCAGTCC......TGTTCAAGATGGTGAAATGGGCCCCTGCCGCAGA 455
    ||||| | |       ||| ||||||  ||| |||||||||| ||| |||
499 AGCCCAATTCTGCGGGTGTCCAAGACACTGAGATGGGCCCATGCCGTAGA 548
```

FIGURE 5E-2

```
456 CACTTGGATTCAGTACTGCAGCAGCTCCAGACTGAGGTCTTCAGAGGCGG 505
    ||  ||||  |||||  ||||||||  ||||||||||||||||  |  ||||  ||
549 CATCTGGACTCAGTGCTGCAGCAACTCCAGACTGAGGTCTACCGAGG.GG 597

506 AGCAAATGGGCTCTATGTGCCAAACTGTGACCTCAGAGGTTTCTACCGCA 555
    ||||      |||||  |||||  ||  |||||||      ||||  ||||||||  |
598 CTCAAA..CACTCTACGTGCCCAATTGTGACCATCGAGGCTTCTACCGGA 645

556 AGCAGCAGTGTCGTTCCTCGCAGGGGAATCGCCGTGGTCCCTGCTGGTGT 605
    |||  ||||||  ||  |||||  ||||||  |  |||||  ||||||||||||||||
646 AGCGGCAGTGCCGCTCCTCCCAGGGGCAGCGCCGAGGTCCCTGCTGGTGT 695

606 GTGGATCCGATGGGCCAGCCTTTGCCAGTGTCTCCAGATGGCCAGGGAAG 655
    |||||||  ||||||||  ||  |  ||||||  |||||||||||||||  |||||
696 GTGGATCGGATGGGCAAGTCCCTGCCAGGGTCTCCAGATGGCAATGGAAG 745

656 CTCTCAGTGCTCTGCCAGGAGCAGCGGGTGAAACCTGGTG.....GGAGC 700
    |||   ||| |  |  ||||  |||||  |  ||  |  ||  |       ||  ||
746 CTCCTCCTGCCCCACTGGGAGTAGCGGCTAAAGCTGGGGATAGAGGGGC 795

701 CTCCAGGACCCTGGCAGGAGCATGGGGCTGTCATTTGAGCTCTATGTGAA 750
    |  ||  |  ||||  ||||  |||||  ||||||||                    |
796 TGCAGGGCCACTGGAAGGAACATGGAGCTGTCAT..............CA 831

751 GTGATGATAACTCTGTGCCCCGAGATGAGACCCACCTTCAAGCCCTACCC 800
    |  |  |  ||  |  |  |||   ||       ||||||||||  ||||  |||
832 CTCAACAAAAAACCGAGGCCCTCAAT.....CCACCTTCAGGCCCCGCCC 876

801 CATTGTCCCTGTCACCCCTGGGCCTTTACACAGCAAGTTAGAAAGA...T 847
    |||  |  |||  |||||  |||              |||  ||||||   |
877 CATGGGCCC.CTCACCGCTG...............GTTGGAAAGAGTGT 909

848 TGTTGTTGGCTTGTGTACTAATAAAGCTG 876
    ||  |||||||||  |  ||    ||||||||||
910 TGGTGTTGGCTGGGGTGTCAATAAAGCTG 938
```

FIGURE 5F-1

M55601: R.norvegicus heparin-binding growth associated molecule (SEQ ID NO:11)
D90226: Human mRNA for OSF-1 (SEQ ID NO:12)

Percent Similarity: 88.177   Percent Identity: 88.177

M55601.seq x D90226.seq

```
142 GGGGAGAGC.GCAGCCGCCCAGGCAGGAGCAGCAGCCAGC...GATACCTG 188
    ||||||||| |||||  |||||  ||||||||| |||||  |||  | |||||||
  1 GGGGAGAGCAGCAGCGGCCCAAGCAGGAGCTGCAGCGAGCCGGGTACCTG 50

189 GAGTCCGTTGCAGAAACCTCGCCCTGCACTTTGCAACAAAGGCAGCCTG. 237
    || || |  | || ||||||||||  | |||||||||||||||| |||
 51 GACTCAGCGGTAGCAACCTCGCC.....CCTTGCAACAAAGGCAGACTGA 95

238 CTGTCAGCGAGGACATCTGCCAAGCCAAAAAATGTCGTCCCAGCAATACC 287
    |  ||| |||||||  |  |   ||| |||||||| |  || ||.||||
 96 GCGCCAGAGAGGACGTTT...CCAACTCAAAAATGCAGGCTCAACAGTACC 143

288 AGCAGCAACGTCGAAAATTTGCAGCTGCCTTCCTGGCTTTGATTTTCATC 337
    ||||||| |||||||||||||||||||||||| |||| || ||||||||
144 AGCAGCAGCGTCGAAAATTTGCAGCTGCCTTCTTGGCATTCATTTTCATA 193

338 CTGGCAGCCGTGGACACTGCTGAGGCCGGGAAAAAAGAGAAACCAGAAAA 387
    |||||||| |||||  |||||||| | ||||| |||||||||||||||||
194 CTGGCAGCTGTGGATACTGCTGAAGCAGGGAAGAAAGAGAAACCAGAAAA 243

388 AAAGGTGAAAAAATCTGACTGTGGAGAATGGCAATGGAGTGTGTGCGTGC 437
    ||| |||||  || |||||||||||||||||||| ||||||||||| |||
244 AAAAGTGAAGAAGTCTGACTGTGGAGAATGGCAGTGGAGTGTGTGTGTGC 293

438 CCACCAGCGGGGACTGTGGTCTAGGCACCCGGGAGGGCACTCGCACTGGT 487
    ||||||| || ||||||||| || |||||  |||||||||||||| |||||
294 CCACCAGTGGAGACTGTGGGCTGGGCACACGGGAGGGCACTCGGACTGGA 343

488 GCCGAGTGCAAACAAACCATGAAGACTCAGAGATGTAAGATCCCTTGCAA 537
    || ||||||||| ||||||||||| | |||||||||||||||||| |||||
344 GCTGAGTGCAAGCAAACCATGAAGACCCAGAGATGTAAGATCCCCTGCAA 393

538 CTGGAAGAAGCAGTTTGGAGCTGAGTGCAAATACCAGTTCCAGGCTTGGG 587
    ||||||||||||| |||| || ||||||||||||||||||||||||||||
394 CTGGAAGAAGCAATTTGGCGCGGAGTGCAAATACCAGTTCCAGGCCTGGG 443

588 GAGAATGTGACCTCAATACCGCCTTGAAGACCAGAACTGGCAGTCTGAAG 637
    |||||||||||||| || || ||| |||||||||||||||| ||||||||
444 GAGAATGTGACCTGAACACAGCCCTGAAGACCAGAACTGGAAGTCTGAAG 493
```

FIGURE - 5F-2

```
638 AGAGCTCTGCACAATGCCGACTGTCAGAAAACTGTCACCATCTCCAAGCC 687
    ||||  ||||||||||||||| |  |  ||||||  ||||||||||||||||||||
494 CGAGCCCTGCACAATGCCGAATGCCAGAAGACTGTCACCATCTCCAAGCC 543

688 CTGTGGCAAACTCACCAAGCCCAAGCCTCAAGCGGAATCAAAGAAGAAGA 737
    |||||||||||| ||||||||||||| |||||| ||||| |||||||||
544 CTGTGGCAAACTGACCAAGCCCAAACCTCAAGCAGAATCTAAGAAGAAGA 593

738 AAAAGGAAGGCAAGAAACAGGAGAAGATGCTGGATTAAAAGAGGCCACCT 787
    ||||||||||||||||||||||||||||||||||||||||||| ||||
594 AAAAGGAAGGCAAGAAACAGGAGAAGATGCTGGATTAAAAGATGTCACC. 642

788 TTTGTGGACAAGGAAAAGGACATCAGCAAGCAGGATCAGTTAACTATTAC 837
    ||||||  |  |||||||||||||||||||| ||||||||||||||||| |
643 ..TGTGGAACATAAAAAGGACATCAGCAAACAGGATCAGTTAACTATTGC 690

838 ATTTATACCTACTGTAGGCTTTTTATTCAACAGTTATCTGTAGCTTAAGT 887
    ||||||| ||| |||||||||| ||||||| | |||||| ||||  |||||
691 ATTTATATGTACCGTAGGCTTTGTATTCAAAAATTATCTATAGC.TAAGT 739

888 ACATGATAGGCAAAAACAAAGAGAAAAGAAATGTTTTGTAGTAGCATTT 937
    |||  |||  ||||||||||  ||||||||||   |||||||||||| |||
740 ACACAATAAGCAAAAACAAAAAGAAAAGAAA.ATTTTGTAGTAGCGTTT 788

938 TTTAATGTATACCATAGTACCAGTAGG 965
    ||| ||||||||| |||||||||||||
789 TTTAAATGTATACTATAGTACCAGTAGG 816
```

FIGURE 5G

P0207_C03.seq (SEQ ID NO:13)
L13698: Human gas-1 gene, complete cds (SEQ ID NO:14)

Percent Similarity: 68.519   Percent Identity: 64.815

P0207_C03.seq x L13698.seq

```
222 AGCCGGGAACGGANGAGCCNCCGGCCACACGACCTTCTGCAGGCGCCTTG 271
    ||||||  |  ||  : ||||: | ||   |||       ||||||||||   |
  4 AGCCGGCACGGGGACAGCCGGCCGCACAACG..GATCTGCAGGCGCGGAG 51

272 CACCAT 277
    ||  ||
 52 CAAAAT 57
```

FIGURE 5H

P0214_A11.seq (SEQ ID NO:15)
U52101:     Human YMP mRNA, complete cds (SEQ ID NO:16)

Percent Similarity: 90.299   Percent Identity: 90.299

P0214_A11.seq x U52101.seq

```
179 GCAGCCATGTCACTCCTCCTGTTGGTGGTCTCTGCCCTTCACATCCTCAT 228
    ||||||||||||||||||| || ||||||||| |||||||||||||||||
 44 GCAGCCATGTCACTCCTCTTGCTGGTGGTCTCAGCCCTTCACATCCTCAT  93

229 TCTTGTCTTGCTTTTCGTGGCCACTCTGGACAAGTCCTGGTGGACTCTCC 278
    |||| |  ||||||||||||||||| ||||||||||||||||||||||||
 94 TCTTATACTGCTTTTCGTGGCCACTTTGGACAAGTCCTGGTGGACTCTCC 143

279 CAGAGAAGGAGTCCCTGAACCTGTGGTATGACTG 312
    | |  ||| |||||||||| ||  ||||| |||||
144 CTGGGAAAGAGTCCCTGAATCTCTGGTACGACTG 177
```

FIGURE 5I-1

M60921: Rat PC3 NGF-inducible anti-proliferative putative secreted protein (SEQ ID NO:17)
U72649: Human BTG2 (BTG2) mRNA, complete cds (SEQ ID NO:18)

Percent Similarity: 82.724   Percent Identity: 82.724

M60921.seq x U72649.seq

```
 61 CGGTATGAGCCACGGGAAGAGAACCGACATGCTCCCGGAGATCGCCGCCG 110
    ||  ||||||||||||||| ||||||||||||||||||||||||||||||
 68 CGACATGAGCCACGGGAAGGGAACCGACATGCTCCCGGAGATCGCCGCCG 117

111 CCGTAGGTTTCCTCACCAGTCTCCTGAGGACTCGGGGCTGCGTGAGCGAG 160
    ||||  || ||||||  |||| |||||||||| |||||||||||||||||
118 CCGTGGGCTTCCTCTCCAGCCTCCTGAGGACCCGGGGCTGCGTGAGCGAG 167

161 CAGAGACTCAAGGTTTTCAGTAGGGCGCTCCAGGACGCACTGACCGATCA 210
    |||| || |||||  ||||| |||||||||||||| ||||| || || ||
168 CAGAGGCTTAAGGTCTTCAGCGGGGCGCTCCAGGAGGCACTCACAGAGCA 217

211 TTACAAACACCACTGGTTTCCAGAAAAGCCATCCAAGGGCTCCGGCTATC 260
    | |||||||||||||||||||  |||||| |||||||||||||||||| |
218 CTACAAACACCACTGGTTTCCCGAAAAGCCGTCCAAGGGCTCCGGCTACC 267

261 GCTGTATCCGCATCAACCACAAGATGGACCCCATCATCAGCAAGGTGGCC 310
    ||||  ||||||||||||||||||||||||||||||||||| ||||||||
268 GCTGCATTCGCATCAACCACAAGATGGACCCCATCATCAGCAGGGTGGCC 317

311 AGCCAGATCGGACTCAGCCAGCCCCAGCTGCACCAGCTCCTGCCCAGCGA 360
    |||||||||||||||||||||||||||||||||| ||||| |||||||||
318 AGCCAGATCGGACTCAGCCAGCCCCAGCTGCACCAGCTGCTGCCCAGCGA 367

361 GCTGACCCTGTGGGTCGATCCCTACGAAGTGTCCTACCGCATCGGGGAAG 410
    |||||||||||||||  |||||| || ||||||||||||||||  |||| 
368 GCTGACCCTGTGGGTGGACCCCTATGAGGTGTCCTACCGCATTGGGGAGG 417

411 ATGGATCCATCTGCGTGCTGTATGAGGAGGCGCCGGTGGCCACCTCCTAC 460
    | || |||||||||||| ||||||||||||||   ||||| ||||||   
418 ACGGCTCCATCTGCGTCTTGTACGAGGAGGCCCACTGGCCGCCTCCTGT  467

461 GGGCTCCTCACCTGCAAGAACCAGATGATGCTGGGCAGGAGCAGTCCATC 510
    |||||||||||||||||| ||||  ||||||| |||| |||||| || ||
468 GGGCTCCTCACCTGCAAGAACCAAGTGCTGCTGGGCCGGAGCAGCCCCTC 517

511 GAAGAACTACGTGATGACTGTCTCCAGCTAGAGAGGAGCCGCCCCGCCCT 560
    |||||||||||||  | ||||||||||||| |   | ||||||||||| |
518 CAAGAACTACGTGATGGCAGTCTCCAGCTAGGCCCTTCCGCCCCCGCCCT 567
```

FIGURE 5I-2

```
561  GGCACTCTACTGTTCTCATGCTGCCCTGACAACAGGCCACCGTATACCTC 610
     ||  | |  | || ||||||||||| ||||||||||||||  |||||||
568  GG.GCGCCGCCGTGCTCATGCTGCCGTGACAACAGGCCACCACATACCTC 616

611  AACCTGGGGAACTGTATTTTTAAAGTGAAGAGCTATTTATACATGTTATT 660
     |||||||||||||||||||||||||  ||||||||||||||||||| |||
617  AACCTGGGGAACTGTATTTTTAAA.TGAAGAGCTATTTATATATATTA.. 663

661  TTTTTTTTTAAGAAAAGAGGAGGAAAAAAACCAAAAGTTTTTTTTAAAA 710
     |||||||||||||||  |||||  ||| |||||||||||||||||| | ||
664  TTTTTTTTAAGAAAGGAGGA...AAAGAAACCAAAAGTTTTTTTTAAGAA 711

711  AAACAAAAAAGAAAAAACAATTCGTTAACGGGAGCTGCTTGGAAGTGGTC 760
     |||                 || || || | ||||||||||||||||||| |
712  AAA...............AAATCCTTCAAGGGAGCTGCTTGGAAGTGGCC 746

761  TCCCCAGGTGCCTTTGGAGAGAACTGTT.CTTGATTGAGTCTATGAGCCA 809
     ||||||||||||||||||||||||||||| | || ||||||||| |||||||
747  TCCCCAGGTGCCTTTGGAGAGAACTGTTGCGTGCTTGAGTCTGTGAGCCA 796

810  GTGTTTGCCTA......GGGGAGTGGGTTGGGGATTGGCCTAGCCAAGGT 853
     ||||  ||||||       ||||||  | |  |||| |  | |||||||||||
797  GTGTCTGCCTATAGGAGGGGGAGCTGTTAGGGGGTAGACCTAGCCAAGGA 846

854  AAAAGGGGATTC..TTGGCTGATCCCCCAGGAGGTGGTGGAAGGG....A 897
     ||   ||||   |    ||||||        ||||||||| |   |||| ||||    |
847  GAAGTGGGAGACGTTTGGCTAGCACCCCAGGAAGATGTGAGAGGGAGCAA 896

898  GCAAGGTTAGCAACTGTGAACGAGAGGGGTCAGGGTCTGCTCTGGG.... 943
     |||||||||||||||||||||||| |||| |||| ||  | ||| |||||
897  GCAAGGTTAGCAACTGTGAAC.AGAGAGGTCGGGATTTGCCCTGGGGGAG 945

944  ..........TTACCGTTCCCGCTG............GGATGCCTGT 968
             | | |  |   | |||                 || ||||
946  GAAGAGAGGCCAAGTTCAGAGCTCTCTGTCTCCCCCAGCCAGACACCTGC 995

969  ATTCCTGGTCCCTCTCTTACTCAGGGGCATTCAAGCCTGGTCTCAAATAA 1018
     ||  |||||  |||||  ||||||||||||||||  ||||||||| || ||| ||
996  ATCCCTGGCTCCTCTATTACTCAGGGGCATTCATGCCTGGACTTAAACAA 1045

1019 TACTACATTGCCTAATCTTCTCTTTTGTTTTCTGCTGAGATCCTGGGCA 1068
     |||||  ||     ||||| ||||||  ||||||  ||||  |||||||||
1046 TACTATGTT.....ATCTTTCTTTTATTTTCTAATGAGGTCCTGGGCA 1090

1069 CA...CGGAAAGGCCTCTCCTG.TCCCTTCCGT.CTGAGCAGAGTTTCTT 1113
     |       |   ||||||||||||||| | ||| |  || || ||| |    ||||||
1091 GAGAGTGAAAAGGCCTCTCCTGATTCCTACTGTCCTAAGCTGCTTTTCTT 1140

1114 GAAACTGTGTCTCGTTTCTGATCCTACCCTCGGGGTCCTGAAGAGGTGGT 1163
     ||||   || ||  ||||||| ||  |||||||||| |||| |||| || |
1141 GAAATCATGACTTGTTTCTAATTCTACCCTCAGGGGCCTGTAGATGTTGC 1190
```

FIGURE 5I-3

```
1164 TTCCCGGCCTAGAATCT..ATCTAAACGTTTTTGGAGGG............ 1200
      || || |||  ||||||  | ||   |||||  |||||
1191 TTTCCAGCCAGGAATCTAAAGCTTTGGGTTTTCTGAGGGGGGGAGGAGGG 1240

1201 ...TGGGCTATAAGGCAGATATAATGGAGGGGAA...CCGCACAAACCCTT 1245
        |||   || | | ||  ||||| |||||  | ||||||| ||||
1241 AACTGGAGGTTATTGGGGTTAGGATGGAAGGGAACTCTGCACAAACCTT 1290

1246 TGCTTTGCTCTGTGCTGCTTTGTATGGATGGTTAATAACTTAGGGA 1295
     ||||||||| ||||||||||||| || ||| ||| ||||| || |||
1291 TGCTTTGCT.AGTGCTGCTTTGTGTGTATGTGTGGCAAATAATTTGGGGG 1339

1296 TGATTTGCAATGGAATTTTGGGACCCAAAGAGTATCCAATGGGGTGGGT 1345
     |||||||||||| |||||||||||||||||||||||||||| ||||| ||
1340 TGATTTGCAATGAAATTTGGGACCCAAAGAGTATCCACTGGGGATG... 1386

1346 GTTTTGGACCTAAGCCCTCCTTTTGGGAACCACGTGACAGTCTGAATGCT 1395
     ||||  | || || | || | |||  ||||||||| ||| |||||  |||||
1387 TTTTTTGGCCAAAACTCTTCCTTTTGGAACCACATGAAAGTCTTGATGCT 1436

1396 GCTACCATTATTCCTTTGAGAGGTGGCTC.AAAGCTCCAGGGAACTCCAG 1444
     |||  ||||  || |||||||||||||||||||| |||||| ||||||||||||
1437 GCTGCCATGATCCCTTTGAGAGGTGGCTCAAAAGCTACAGGGAACTCCAG 1486

1445 GTCCTTTCTTACTGCCTTCTCTTCAAGAGCA.ACCTCCCCAT....TTC 1489
     |||||||  ||||||||||||| |||||  |||| |  |||  ||  |   ||
1487 GTCCTTTATTACTGCCTTCTTTTCAAAAGCACAACTCTCCTCTAACCCTC 1536

1490 TTTTCCCTCTTTCCTGC.GGTTGGGTCCTGGAG.GGCCCCATTTCCTAGG 1537
     ||||  |||  |||  |  |||  |||||  | |||    ||  ||||  |||||
1537 CCCTCCCCCTTCCCTTCTGGTCGGGTCATAGAGCTACCGTATTTTCTAGG 1586

1538 ACAAGAGTTCTCAATCACTGTGCAATA..........GTCCCAGGAAGCT 1577
     ||||||||||||| |||||||||||||||          |||||||||| | |
1587 ACAAGAGTTCTCAGTCACTGTGCAATATGCCCCCTGGGTCCCAGGAGGGT 1636

1578 CTGG.....AACTGGGCCTCCCAGCCCCTCCTGATTCCTGGTGGGTTTTA 1622
     ||||     ||||||  ||. |||  ||||||||| || |  ||  |||
1637 CTGGAGGAAAACTGG...CTATCAGAACCTCCTGATGCCCTGGTGGGCTTA 1684

1623 GGACCCCGCCTTCCCCGTTCTTC........TGACTGGCTGGTGGGCCT 1663
     ||  || || || | ||| |        || ||||||  || ||||
1685 GGGAACCATCTCTCCTGCTCTCCTTGGCATGATGGCTGGCTAGTCAGCCT 1734

1664 TGAGGAGATCTCCCTCGGCCGCA...GGGAGGGCACCTGTGCACTGCAGG 1710
       |  | |  | | |||  |||  | |   | ||| || ||  || ||||| |
1735 T...GCATGTATTCCTTGGCTGAATGGGAGAGTGC.CCCATGTTCTGCAAG 1781

1711 ACTACCTGGTACTCCTGTGGGGCTGCCAC....GGAGAGCCAAACCTTAG 1756
     |||||  |||||  || ||| |||| | |||     |  |||||||||| |
1782 ACTACTTGGTATTCTTGTAGGGCCGACACTAAATAAAAGCCAAACCTTGG 1831
```

FIGURE 5I-4

```
1757 GCATAGCTTTGTCTCCTCGGTGCTCAGAGCACCTGCAGGGGGAGGTTGC. 1805
     ||| | ||| |||||  ||||||||||||||||| ||| |||||||
1832 GCACTGTTTTTCTCCCTGGTGCTCAGAGCACCTG.TGGGAAAGGTTGCT 1880

1806 ..CCCCCTCAGTAAAAATCCAAATTTATTTGTAGATGTGTGCAATATTTA 1853
       |  ||||||  |  ||||||||||||  |  |||||  ||||||||||  ||
1881 GTCTGTCTCAGT.ACAATCCAAATTT.GTCGTAGACTTGTGCAATATATA 1928

1854 CTGTTCTGGGTTGGAGAAAATCGGGAA...ACACTGGGAAGAAGTGGCCT 1900
     ||||| |||||||||||||| || || |||||||||||| |||
1929 CTGTTGTGGGTTGGAGAAAAGTGGAAAGCTACACTGGGAAGAAACTCCCT 1978

1901 TCCTTCAGGT..TCAGTGACACTGATGAGGGCTTCTCAGAAGGCCTCGAG 1948
     ||||||| | ||||||||| |||||||| | |||| ||| |||||||
1979 TCCTTCAATTTCTCAGTGACATTGATGAGGGGTCCTCAAAAGACCTCGAG 2028

1949 TCTCTCAAACC............AAAGGACAGAGCTAGAG.......... 1976
     | || ||||||             |||||||| ||||| |
2029 TTTCCCAAACCGAATCACCTTAAGAAGGACAGGGCTAGGGCATTTGGCCA 2078

1977 ............CCAGCCAGTCACCCTTAGTGAGGA............. 2000
                 || ||   |  |||||||||||||
2079 GGATGGCCACCCTCCTGCTGTTGCCCCTTAGTGAGGAATCTTCACCCCAC 2128

2001 .TCCCCTTCCCCATGTCTCTCCACTGCCGTGGCA.TCCCATGTCCTGGAT 2048
      ||| || ||||  |  ||||| |  |  | || |||| | |||||||
2129 TTCCTCTACCCCCAGGTTCTCCTCCCCACAGCCAGTCCCCTTTCCTGGAT 2178

2049 TTCTCAATTCCTCAGTTTCTACTCAAAGGTGCTACTTACCAAACACTCTG 2098
     |||| || | |||| |||   ||||||||||||| |||||||||||||||
2179 TTCTAAACTGCTCAATTTTGACTCAAAGGTGCTATTTACCAAACACTCTC 2228

2099 C........CCGTCCCGCTCTCCC.......CAGCTTCGCACA...... 2126
     |         |.| || ||||| ||      || ||  ||||
2229 CCTACCCATTCCTGCCAGCTCTGCCTCCTTTCAACTCTCCACATTTTGT 2278

2127 ...GCCGTCCCAG.GTGGCTTC...GTCTCTCCTGCTTTAAAGTTAACTTT 2170
        ||| |||||    |||||    |||| | ||||||||||||| |||||
2279 ATTGCCTTCCCAGACCTGCTTCCAGTCTTTATTGCTTTAAAGTTCACTTT 2328

2171 GGGCCCACAGACCCGAGAGC.............TGTGGGTTGAAGCAAAG 2207
     ||||||||||||| |||||              |||||||||| |||||
2329 GGGCCCACAGACCCAAGAGCTAATTTCTGGTTTGTGGGTTGAAACAAAG 2378

2208 CTGTGAATCGCTCCAGATGGTCCCTGTGTTC........TGTCCACACAC 2249
     |||||||||| || |||    ||||||||        ||||  || ||
2379 CTGTGAATCACTGCAG......GCTGTGTTCTTGCATCTTGTCTGCAAAC 2422

2250 AGGTCCCCGCCTTTTTAGAAGCAGCCTCCTGGTCTCATGCTTAAATCTGT 2299
     ||||||| ||||||||||||||||||| ||||||||||||||| |||||
2423 AGGTCCCTGCCTTTTTAGAAGCAGCCTCATGGTCTCATGCTTAATCTTGT 2472
```

FIGURE 5I-5

```
2300 TCCTCACTGCCC.........GTGTTCACTTTAGAAATGGCAGAACCACA 2340
     ||| || | |           ||||||||||| |||   || ||||| |
2473 ..CTCTCTTCTCTTCTTTATGATGTTCACTTTAAAAACAACAAAACCCCT 2520

2341 GAGCTGGACTGTTGAGCAGGCCTGTCTCTCTCATTAAATAGAAATA.... 2386
     ||||||||||||||||||||||||||||||||| ||||| || |||||
2521 GAGCTGGACTGTTGAGCAGGCCTGTCTCTCCTATTAAGTAAAAATAAATA 2570

2387 .....AGTAAGTTTGTAAGCTATTCCGACAGAAGAGACAAAGGTTACTGA 2431
          ||||  ||||||||||||||| ||||||| ||||||||||||| |
2571 GTAGTAGTATGTTTGTAAGCTATTCTGACAGAAAAGACAAAGGTTACTAA 2620

2432 TTGTACAATAGCGCTTTTATATGGAAGACTGTACAGCTTTATGGACAAAT 2481
     |||||  ||||  | |||||||||||||  |||||||| |||||||||||
2621 TTGTATGATAGTGTTTTATATGGAAGAATGTACAGC.TTATGGACAAAT 2669

2482 GTAAAACTTTTT.TGTTTTAATAAAAATGTAGCAG 2516
     ||| | |||||| |   |||||||||||||||| ||
2670 GTACACCTTTTTGTTACTTTAATAAAAATGTAGTAG 2705
```

FIGURE 5J

P0219_H09.seq (SEQ ID NO:19)
L36034:    Human pre-B cell stimulating factor homologue (SDF1a)
           (SEQ ID NO:20)

Percent Similarity: 88.559   Percent Identity: 88.136

P0219_H09.seq x L36034.seq

```
 27 CCTCCGGCGCGCCCTCCCGCCCACGCCATGGACGCCAAGGTCGTCGCCGT  76
    ||  ||  || ||||| ||||||| |||||||  |||||||||||| | |||
 53 CCGCCCGCCCGCCCGCCCGCCCGCGCCATGAACGCCAAGGTCGTGGTCGT 102

77 GCTGGCCCTGGTGCTGGCCGCGCTCTGCATCAGTGACGGTAAGCCAGTCA 126
    |||||  |||  |||||| |||||||||||| |||| ||||| ||||| ||||
103 GCTGGTCCTCGTGCTGACCGCGCTCTGCCTCAGCGACGGGAAGCCCGTCA 152

127 GCCTGAGCTACAGATGCCCCTGCCGATTCTTCGAGAGCCATGTCGCCAGA 176
    |||||||||||||||||||| |||||||||||||||||| ||||||| ||||||
153 GCCTGAGCTACAGATGCCCATGCCGATTCTTCGAAAGCCATGTTGCCAGA 202

177 NCCAACGTCAAACATCTGAAAATCCTCAACACTCCAAACTGTGCCCTTCA 226
    :||||||||| |||| ||||| ||||||||||||||||||||||||||||||
203 GCCAACGTCAAGCATCTCAAAATTCTCAACACTCCAAACTGTGCCCTTCA 252

227 GATTGTTGCAAAGCTGAAAAGCAACAACAGACAAGT 262
    ||||||  ||    ||||||  | |||||||||||||||||
253 GATTGTAGCCCGGCTGAAGAACAACAACAGACAAGT 288
```

FIGURE 5K-1

J05122: Rat peripheral-type benzodiazepine receptor (PKBS) mRNA (SEQ ID NO:21)

M36035: Human peripheral benzodiazepine receptor (hpbs) (SEQ ID NO:22)

Percent Similarity: 74.613    Percent Identity: 74.485

J05122.seq x M36035.seq

```
  5 GATCTTTCCAGAACAGCAGTTGCAATCACTATGTCTCAATCCTGGGTACC  54
    || ||  ||  ||||||||| ||||     | |||  |    |||||||  ||
 32 GAGCTCCCCTGAACAGCAGCTGCAGCAGCCATGGCCCCGCCCTGGGTGCC  81

55 CGCCGTGGGCCTCACTCTGGTGCCCAGCCTGGGGGGCTTCATGGGAGCCT  104
    ||||  |||||  ||||  ||||  ||||||||||||||| |||||  ||
 82 CGCCATGGGCTTCACGCTGGCGCCCAGCCTGGGGTGCTTCGTGGGCTCCC  131

105 ACTTTGTGCGTGGTGAGGGCCTCCGCTGGTATGCTAGCTTGCAGAAACCC  154
    ||||||   |  ||||||  ||||||||||| |  ||  |||||||| |||
132 GCTTTGTCCACGGCGAGGGTCTCCGCTGGTACGCCGGCCTGCAGAAGCCC  181

155 TCCTGGCATCCGCCTCGCTGGACACTCGCTCCCATCTGGGGCACACTGTA  204
    ||  |||||  |||||   |||||     || |   ||  ||||||||  ||  ||
182 TCGTGGCACCCGCCCCACTGGGTGCTGGGCCCTGTCTGGGGCACGCTCTA  231

205 TTCGGCCATGGGGTATGGCTCCTACATAATCTGGAAAGAGCTGGGAGGTT  254
    ||  |||||||||||  |||||||||| |  ||||||||||||||||||||||  |
232 CTCAGCCATGGGGTACGGCTCCTACCTGGTCTGGAAAGAGCTGGGAGGCT  281

255 TCACAGAGGAGGCTATGGTTCCCTTGGGTCTCTACACTGGTCAGCTGGCT  304
    ||||||||  |||||| |||||| ||||||| ||||||||||| ||||||||  ||||||||
282 TCACAGAGAAGGCTGTGGTTCCCCTGGGCCTCTACACTGGGCAGCTGGCC  331

305 CTGAACTGGGCATGGCCCCCCATCTTCTTTGGTGCCCGGCAGATGGGCTG  354
    |||||||||||||||||||||||||||||||||||||||||||  || ||||||||||
332 CTGAACTGGGCATGGCCCCCCATCTTCTTTGGTGCCCGACAAATGGGCTG  381

355 GGCTTTGGTGGACCTCATGCTTGTCAGTGGGGTGGCAACCGCCACTACCC  404
    ||| |||||||||  ||||  |||||| |||||||||  |||||||||||||  ||||||||||
382 GGCCTTGGTGGATCTCCTGCTGGTCAGTGGGGCGGCGGCNGCCACTACCG  431

405 TGGCTTGGCACCGAGTGAGCCCACCGGCTGCCCGCTTGCTGTATCCTTAC  454
    |||| ||| |||   |||||||| | ||| ||||||  ||||  ||  ||  |||
432 TGGCCTGGTACCAGGTGAGCCCGCTGGCCGCCCGCCTGCTCTACCCCTAC  481

455 CTGGCCTGGCTGGCCTTTGCCACCATGCTCAACTACTATGTATGGCGTGA  504
    ||||||||||||||||||| ||  ||||  |||||||||||| |||||||| ||
482 CTGGCCTGGCTGGCCTTCGCGACCACACTCAACTACTGCGTATGGCGGGA  531
```

FIGURE 5K-2

```
505 TAACTCTGGTCGGCGAGGGGGCTCCCGGCTCACAGAGTGAGGACACCTAG 554
    |||  |||  |||  |||||      |||||  ||||||||| || |
532 CAACCATGGCTGGCATGGGGGACGGCGGCTGCCAGAGTGAGTGCCCGGCC 581

555 CCATCAGGAATGCAGCCCTGCCAGC.........CAGGCATCATGGGTTG 595
    |       |||  |||||||    |||||        || ||  |  || |
582 CACCAGGGACTGCAGCTGCACCAGCAGGTGCCATCACGCTTGTGATGTGG 631

596 AGGTCATCCTGCTTTCATGACCATTGGGCCTGCTGGTCTACCTGGTCTTA 645
    .|| |·||  |||||||||||||||  ||||||||||  |  || | |
632 TGGCCGTCACGCTTTCATGACCACTGGGCCTGCTAGTCTGTCAGGGCCTT 681

646 GTCCAGGAAGCCACCAGGTAGGTCAAGGTGGTCAGTGCTAAGTCCCATGC 695
    |  ||  |   |  ||  |||       ||||  |  .|| || |||    |
682 GGCCCAGGGGTCAGCAGAGCTTCAGAGGTTGCCCCACCTGAGCCCCCACC 731

696 GGGGACAGTTGTACCTGCTTTTCTGCACTGCTGCAGGCGTGCCCTAGGAG 745
    ||||    ||| |   ||||||||  ||||      ·|| || || |||
732 CGGGAGCAGTGTCCTGTGCTTTCTGCA.TGCTTAGAGCATGTTCTTGGAA 780

746 CATGGGGCCTTTAAAGCTAAATAAAGTCTTTAACTT 781
    |||||      ||  |||||·| |||||||||  |||  ||·||
781 CATGGAATTTTATAAGCTGAATAAAGTTTTTGACTT 816
```

FIGURE 5L-1

J03627: Rat S-100 related protein mRNA (SEQ ID NO:23)
M38591: Homo sapiens cellular ligand of annexin II (p11) (SEQ ID NO:24)

Percent Similarity: 84.381   Percent Identity: 84.381

J03627.seq x M38591.seq

```
  3 GACTGCAGCGCCTCAGGGCCCAGGTTTCAACAGA.TTCTTCAAAATGCCA  51
    | | || |||||||   ||| ||| |||||| ||   | |||||||||
 71 GTCCGCCGCGCCTC...GCCAAGGCTTCAACGGACCACACCAAAATGCCA 117

52 TCCCAAATGGAGCATGCCATGGAAACCATGATGCTTACATTTCACAGGTT 101
    || |||||||| || ||||||||||||||||| |||||||||||| ||
118 TCTCAAATGGAACACGCCATGGAAACCATGATGTTTACATTTCACAAATT 167

102 TGCAGGGGAAAAAAACTACTTGACAAAGGAGGACCTGAGAGTGCTCATGG 151
    || ||||| |||   |||||| |||||||||||||||||||| |||||||
168 CGCTGGGGATAAAGGCTACTTAACAAAGGAGGACCTGAGAGTACTCATGG 217

152 AAAGGGAGTTCCCTGGGTTTTGGAAAATCAAAAGGACCCTCTGGCTGTG 201
    ||| |||||||||||| |||||||||||||||| ||||||||||||||||
218 AAAAGGAGTTCCCTGGATTTTGGAAAATCAAAAGACCCTCTGGCTGTG 267

202 GACAAAATAATGAAAGACCTGGACCAGTGCCGAGATGGAAAAGTGGGCTT 251
    |||||||||||||| ||||||||||||||   |||||||  |||||||||
268 GACAAAATAATGAAGGACCTGGACCAGTGTAGAGATGGCAAAGTGGGCTT 317

252 CCAGAGCTTTCTATCACTAGTGGCGGGGCTCATCATTGCATGCAATGACT 301
    ||||||||  |  || ||| |·||||| |||| |||||||||||||||||
318 CCAGAGCTTCTTTTCCCTAATTGCGGGCCTCACCATTGCATGCAATGACT 367

302 ATTTTGTAGTACACATGAAGCAG......AAGAAGTAGGCCAACTGGAGC 345
    |||||||||||||||||||||||      |||||||||| ||    |||
368 ATTTTGTAGTACACATGAAGCAGAAGGGAAAGAAGTAGGCAGAAATGAG. 416

346 CCTGGTACCCACACCTTGATGCGTCCTCTCCCATGGGGTCAACTGAGGAA 395
    | |  |  | ||  |||| |   | |   |||||  |  |   | |||||
417 .CAGTTCGCTCCTCCCTGATAAGAGTTGT.CCAAAGGGTCGCTTAAGGAA 464

396 TCTGCCCCACTGCTTCC...............TGTGAGCAGATCAGGACC 430
    ||||||||| |||||||               ||||||||||||||||||
465 TCTGCCCCACAGCTTCCCCCATAGAAGGATTTCATGAGCAGATCAGGACA 514

431 CTTAGGAAATGTGCAAATAACATCCAACTCCAATTCGACAAGCAGAGAAA 480
    ||||| ||||||  |||||| ||| |||| ||| ||||||||||||||||
515 CTTAGCAAATGTAAAAATAAAATCTAACTCTCATTTGACAAGCAGAGAAA 564

481 GAAAAGTTAATCCAATGACAGAGGAGCTTTCGAGTTTTATATTGTTTGCA 530
    ||||||||    ||| ||||  |||||| || |||| |||||||||||||
565 GAAAAGTTA....AATACCAGATAAGCTTTTGATTTTGTATTGTTTGCA 610
```

FIGURE 5L-2

```
531 TCCGGTTGCCCTCAATAAAGAAAGTCTTTTTTTTTAAGTTCC 572
    |||  ||||||||||.||||||  ||||   || ||||| ||||||
611 TCCCCTTGCCCTCAATAAATAAAG...TTCTTTTTTAGTTCC 649
```

FIGURE 6A-1

X57352:   1-8U, CDS 238...639

```
151 TTGAGAAACCGAAACTACTGGGGAAAGGGAGGGCTCACTGAGTAACCATC 200
                           | |    | |  ||||
  1 .................................GAATTCGGCACGAGGCATC  19

201 CCAGTAACCCGACCGCCGCTGGTCTTCGCTGGACACCATGAGTCACACTG 250
    ||||||||||||| ||||||||||||||||||||||||| |||||||||
 20 CCAGTAACCCGACCACCGCTGGTCTTCGCTGGACACCATGAATCACACTG  69

251 TCCAAACCTTCTTCTCCTGTCAACAGTGGCCAGCCCCCAACTATGAG 300
    |||||||||||||||||||||||||||||||||||||||||||||||||
 70 TCCAAACCTTCTTCTCCTGTCAACAGTGGCCAGCCCCCAACTATGAG 119

301 ATGCTCAAGGAGGAGCACGAGGTGGCTGTGCTGGGGGGGCCCCACAACCC 350
    |||||||||||||||||||||||||||||||||||||||| |||||||||
120 ATGCTCAAGGAGGAGCACGAGGTGGCTGTGCTGGGGGCGCCCCACAACCC 169

351 TGCTCCCCCGACGTCCACCGTGATCCACATCCGCAGCGAGACCTCCGTGC 400
    ||||||||||||||||||||||||||||||||||||||||||||||||||
170 TGCTCCCCCGACGTCCACCGTGATCCACATCCGCAGCGAGACCTCCGTGC 219

401 CCGACCATGTCGTCTGGTCCCTGTTCAACACCCTCTTCATGAACCCCTGC 450
    ||||||||||||||||||||||||||||||||||||||||||||||||||
220 CCGACCATGTCGTCTGGTCCCTGTTCAACACCCTCTTCATGAACCCCTGC 269

451 TGCCTGGGCTTCATAGCATTCGCCTACTCCGTGAAGTCTAGGGACAGGAA 500
    ||||||||||||||||||||||||||||||||||||||||||||||||||
270 TGCCTGGGCTTCATAGCATTCGCCTACTCCGTGAAGTCTAGGGACAGGAA 319

501 GATGGTTGGCGACGTGACCGGGGCCCAGGCCTATGCCTCCACCGCCAAGT 550
    ||||||||||||||||||||||||||||||||||||||||||||||||||
320 GATGGTTGGCGACGTGACCGGGGCCCAGGCCTATGCCTCCACCGCCAAGT 369

551 GCCTGAACATCTGGGCCCTGATTCTGGGCATCCTCATGACCATTCTGCTC 600
    ||||||||||||||||||||||||||||||||||||||||||||||||||
370 GCCTGAACATCTGGGCCCTGATTCTGGGCATCCTCATGACCATTCTGCTC 419

601 ATCGTCATCCCAGTGCTGATCTTCCAGGCCTATGGATAGATCAGGAGGCA 650
    ||||||||||||||||||||||||||||||||||||||||||||||||||
420 ATCGTCATCCCAGTGCTGATCTTCCAGGCCTATGGATAGATCAGGAGGCA 469

651 TCACTGAGGCCAGGAGCTCTGCCCATGACCTGTATCCCACGTACTCCAAC 700
    ||||||||||||||||||||||||||||||||||||||||||||||||||
470 TCACTGAGGCCAGGAGCTCTGCCCATGACCTGTATCCCACGTACTCCAAC 519

701 TTCCATTCCTCGCCCTGCCCCCGGAGCCGAGTCCTGTATCAGCCCTTTAT 750
    ||||||||||||||||||||||||||||||||||||||||||||||||||
520 TTCCATTCCTCGCCCTGCCCCCGGAGCCGAGTCCTGTATCAGCCCTTTAT 569
```

FIGURE 6A-2

```
751 CCTCACACGCTTTTCTACAATGGCATTCAATAAAGTGCACGTGTTTCTGG 800
    ||||||||||||||||||||||||||||||||||||||||||||||||||
570 CCTCACACGCTTTTCTACAATGGCATTCAATAAAGTGCACGTGTTTCTGG 619

801 TGCTGCTG......................... 808
    |
620 TAAAAAAAAAAAAAAAAAAAAAAAAAGATGCGGCCGC 655

201 CCAGTAACCCGACCGCCGCTGGTCTTCGCTGGACACCATGAGTCACACTG 250
                ||         |||||||||||||| ||||||||
  1 ..........GAATTCGGCACGAGGCGCTGGACACCATGAATCACACTG  39

251 TCCAAACCTTCTTCTCTCCTGTCAACAGTGGCCAGCCCCCCAACTATGAG 300
    ||||||||||||||||||||||||||||||||||||||||||||||||||
 40 TCCAAACCTTCTTCTCTCCTGTCAACAGTGGCCAGCCCCCCAACTATGAG  89

301 ATGCTCAAGGAGGAGCACGAGGTGGCTGTGCTGGGGGGGCCCCACAACCC 350
    |||||||||||||||||||||||||||||||||||||| |||||||||||
 90 ATGCTCAAGGAGGAGCACGAGGTGGCTGTGCTGGGGGCGCCCCACAACCC 139

351 TGCTCCCCCGACGTCCACCGTGATCCACATCCGCAGCGAGACCTCCGTGC 400
    ||||||||||||||||||||||||||||||||||||||||||||||||||
140 TGCTCCCCCGACGTCCACCGTGATCCACATCCGCAGCGAGACCTCCGTGC 189

401 CCGACCATGTCGTCTGGTCCCTGTTCAACACCCTCTTCATGAACCCCTGC 450
    ||||||||||||||||||||||||||||||||||||||||||||||||||
190 CCGACCATGTCGTCTGGTCCCTGTTCAACACCCTCTTCATGAACCCCTGC 239

451 TGCCTGGGCTTCATAGCATTCGCCTACTCCGTGAAGTCTAGGGACAGGAA 500
    ||||||||||||||||||||||||||||||||||||||||||||||||||
240 TGCCTGGGCTTCATAGCATTCGCCTACTCCGTGAAGTCTAGGGACAGGAA 289

501 GATGGTTGGCGACGTGACCGGGGCCCAGGCCTATGCCTCCACCGCCAAGT 550
    ||||||||||||||||||||||||||||||||||||||||||||||||||
290 GATGGTTGGCGACGTGACCGGGGCCCAGGCCTATGCCTCCACCGCCAAGT 339

551 GCCTGAACATCTGGGCCCTGATTCTGGGCATCCTCATGACCATTCTGCTC 600
    ||||||||||||||||||||||||||||||||||||||||||||||||||
340 GCCTGAACATCTGGGCCCTGATTCTGGGCATCCTCATGACCATTCTGCTC 389

601 ATCGTCATCCCAGTGCTGATCTTCCAGGCCTATGGATAGATCAGGAGGCA 650
    ||||||||||||||||||||||||||||||||||||||||||||||||||
390 ATCGTCATCCCAGTGCTGATCTTCCAGGCCTATGGATAGATCAGGAGGCA 439

651 TCACTGAGGCCAGGAGCTCTGCCCATGACCTGTATCCCACGTACTCCAAC 700
    ||||||||||||||||||||||||||||||||||||||||||||||||||
440 TCACTGAGGCCAGGAGCTCTGCCCATGACCTGTATCCCACGTACTCCAAC 489

701 TTCCATTCCTCGCCCTGCCCCCGGAGCCGAGTCCTGTATCAGCCCTTTAT 750
    ||||||||||||||||||||||||||||||||||||||||||||||||||
490 TTCCATTCCTCGCCCTGCCCCCGGAGCCGAGTCCTGTATCAGCCCTTTAT 539
```

FIGURE 6A-3

```
751 CCTCACACGCTTTTCTACAATGGCATTCAATAAAGTGCACGTGTTTCTGG 800
    ||||||||||||||||||||||||||||||||||||||||||||||||||
540 CCTCACACGCTTTTCTACAATGGCATTCAATAAAGTGCACGTGTTTCTGG 589

801 TGCTGCTG..................... 808
    |
590 TAAAAAAAAAAAAAAAAAAAGATGCGGCCGC 619
```

FIGURE 6B-1

X67698: Tissue specific mRNA, CDS 11...466

```
  1 ...................CGGATTCCGGATGCGTTTCCTGGCAGC  27
                              || |  ||||||||||||||||||
  1 GAATTCGGCACGAGTGGAACTTCGTTATCCGCGATGCGTTTCCTGGCAGC  50

28 TACATTCCTGCTCCTGGCGCTCAGCACCGCTGCCCAGGCCGAACCGGTGC  77
    ||||||||||||||||||||||||||||||||||||||||||||||||||
 51 TACATTCCTGCTCCTGGCGCTCAGCACCGCTGCCCAGGCCGAACCGGTGC 100

78 AGTTCAAGGACTGCGGTTCTGTGGATGGAGTTATAAAGGAAGTGAATGTG 127
    ||||||||||||||||||||||||||||||||||||||||||||||||||
101 AGTTCAAGGACTGCGGTTCTGTGGATGGAGTTATAAAGGAAGTGAATGTG 150

128 AGCCCATGCCCCACCCAACCCTGCCAGCTGAGCAAAGGACAGTCTTACAG 177
    ||||||||||||||||||||||||||||||||||||||||||||||||||
151 AGCCCATGCCCCACCCAACCCTGCCAGCTGAGCAAAGGACAGTCTTACAG 200

178 CGTCAATGTCACCTTCACCAGCAATATTCAGTCTAAAAGCAGCAAGGCCG 227
    |||||  |||||||||||||||||||||||||||||||||||||||||||
201 CGTCAGCGTCACCTTCACCAGCAATATTCAGTCTAAAAGCAGCAAGGCCG 250

228 TGGTGCATGGCATCCTGATGGGCGTCCCAGTTCCCTTTCCCATTCCTGAG 277
    ||||||||||||||||||||||||||||||||||||||||||||||||||
251 TGGTGCATGGCATCCTGATGGGCGTCCCAGTTCCCTTTCCCATTCCTGAG 300

278 CCTGATGGTTGTAAGAGTGGAATTAACTGCCCTATCCAAAAAGACAAGAC 327
    ||||||||||||||||||||||||||||||||||||||||||||||||||
301 CCTGATGGTTGTAAGAGTGGAATTAACTGCCCTATCCAAAAAGACAAGAC 350

328 CTATAGCTACCTGAATAAACTACCAGTGAAAAGCGAATATCCCTCTATAA 377
    ||||||||||||||||||||||||||||||||||||||||||||||||||
351 CTATAGCTACCTGAATAAACTACCAGTGAAAAGCGAATATCCCTCTATAA 400

378 AACTGGTGGTGGAGTGGCAACTTCAGGATGACAAAAACCAAAGTCTCTTC 427
    ||||||||||||||||||||||||||||||||||||||||||||||||||
401 AACTGGTGGTGGAGTGGCAACTTCAGGATGACAAAAACCAAAGTCTCTTC 450

428 TGCTGGGAAATCCCAGTACAGATCGTTTCTCATCTCTAAGTGCCTCATTG 477
    ||||||||||||||||||||||||||||||||||||||||||||||||||
451 TGCTGGGAAATCCCAGTACAGATCGTTTCTCATCTCTAAGTGCCTCATTG 500

478 AGTTCGGTGCATCTGGCCAATGAGTCTGCTGAGACTCTTGACAGCACCTC 527
    ||||||||||||||||||||||||||||||||||||||||||||||||||
501 AGTTCGGTGCATCTGGCCAATGAGTCTGCTGAGACTCTTGACAGCACCTC 550

528 CAGCTCTGCTGCTTCAACAACAGTGACTTGCTCTCCAATGGTATCCAGTG 577
    ||||||||||||||||||||||||||||||||||||||||||||||||||
551 CAGCTCTGCTGCTTCAACAACAGTGACTTGCTCTCCAATGGTATCCAGTG 600

578 ATTCGTTGAAGAGGAGGTGCTCTGTAGCAGAAACTGAGCTCCGGGTGGCT 627
    ||||||||||||||||||||||||||||||||||||||||||||||||||
601 ATTCGTTGAAGAGGAGGTGCTCTGTAGCAGAAACTGAGCTCCGGGTGGCT 650
```

FIGURE 6B-2

```
628 GGTTCTCAGTGGTTGTCTCATGTCTCTTTTTCTGTCTTAGGTGGTTTCAT 677
    ||||||||||||||||||||||||||||||||||||||||||||||||||
651 GGTTCTCAGTGGTTGTCTCATGTCTCTTTTTCTGTCTTAGGTGGTTTCAT 700

678 TAAATGCAGCACTTGGTTAGCAGATGTTTAATTTTTTTTTTAACAACAT  727
    ||||||||||||||||||||  | |   ||           |  |  ·|
701 TAAATGCAGCACTTGGTTAAAAAAAAAAAAAAAAAAAAAAAGATCTTTAA 750

728 TAACTTGTGGCCTCTTTCTACACCTGGAAATTTACTCTTGAATAAATAAA 777
    | |
751 TTAA.............................................. 754

1 ................CGGATTCCGGATGCGTTTCCTGGCAGCTACATT  33
                       || |  ||||||||||||||||||||||||||
  1 GAATTCGGCACGAGTTCGTTATCCGCGATGCGTTTCCTGGCAGCTACATT  50

34 CCTGCTCCTGGCGCTCAGCACCGCTGCCCAGGCCGAACCGGTGCAGTTCA  83
    ||||||||||||||||||||||||||||||||||||||||||||||||||
 51 CCTGCTCCTGGCGCTCAGCACCGCTGCCCAGGCCGAACCGGTGCAGTTCA 100

84 AGGACTGCGGTTCTGTGGATGGAGTTATAAAGGAAGTGAATGTGAGCCCA 133
    ||||||||||||||||||||||||||||||||||||||||||||||||||
101 AGGACTGCGGTTCTGTGGATGGAGTTATAAAGGAAGTGAATGTGAGCCCA 150

134 TGCCCCACCCAACCCTGCCAGCTGAGCAAAGGACAGTCTTACAGCGTCAA 183
    ||||||||||||||||||||||||||||||||||||||||||||||||||
151 TGCCCCACCCAACCCTGCCAGCTGAGCAAAGGACAGTCTTACAGCGTCAA 200

184 TGTCACCTTCACCAGCAATATTCAGTCTAAAAGCAGCAAGGCCGTGGTGC 233
    ||||||||||||||||||||||||||||||||||||||||||||||||||
201 TGTCACCTTCACCAGCAATATTCAGTCTAAAAGCAGCAAGGCCGTGGTGC 250

234 ATGGCATCCTGATGGGCGTCCCAGTTCCCTTTCCCATTCCTGAGCCTGAT 283
    ||||||||||||||||||||||||||||||||||||||||||||||||||
251 ATGGCATCCTGATGGGCGTCCCAGTTCCCTTTCCCATTCCTGAGCCTGAT 300

284 GGTTGTAAGAGTGGAATTAACTGCCCTATCCAAAAAGACAAGACCTATAG 333
    ||||||||||||||||||||||||||||||||||||||||||||||||||
301 GGTTGTAAGAGTGGAATTAACTGCCCTATCCAAAAAGACAAGACCTATAG 350

334 CTACCTGAATAAACTACCAGTGAAAAGCGAATATCCCTCTATAAAACTGG 383
    ||||||||||||||||||||||||||||||||||||||||||||||||||
351 CTACCTGAATAAACTACCAGTGAAAAGCGAATATCCCTCTATAAAACTGG 400

384 TGGTGGAGTGGCAACTTCAGGATGACAAAAACCAAAGTCTCTTCTGCTGG 433
    ||||||||||||||||||||||||||||||||||||||||||||||||||
401 TGGTGGAGTGGCAACTTCAGGATGACAAAAACCAAAGTCTCTTCTGCTGG 450

434 GAAATCCCAGTACAGATCGTTTCTCATCTCTAAGTGCCTCATTGAGTTCG 483
    ||||||||||||||||||||||||||||||||||||||||||||||||||
451 GAAATCCCAGTACAGATCGTTTCTCATCTCTAAGTGCCTCATTGAGTTCG 500
```

FIGURE 6B-3

```
484 GTGCATCTGGCCAATGAGTCTGCTGAGACTCTTGACAGCACCTCCAGCTC 533
    ||||||||||||||||||||||||||||||||||||||||||||||||||
501 GTGCATCTGGCCAATGAGTCTGCTGAGACTCTTGACAGCACCTCCAGCTC 550

534 TGCTGCTTCAACAACAGTGACTTGCTCTCCAATGGTATCCAGTGATTCGT 583
    ||||||||||||||||||||||||||||||||||||||||||||||||||
551 TGCTGCTTCAACAACAGTGACTTGCTCTCCAATGGTATCCAGTGATTCGT 600

584 TGAAGAGGAGGTGCTCTGTAGCAGAAACTGAGCTCCGGGTGGCTGGTTCT 633
    ||||||||||||||||||||||||||||||||||||||||||||||||||
601 TGAAGAGGAGGTGCTCTGTAGCAGAAACTGAGCTCCGGGTGGCTGGTTCT 650

634 CAGTGGTTGTCTCATGTCTCTTTTCTGTCTTAGGTGGTTTCATTAAATG 683
    ||||||||||||||||||||||||||||||||||||||||||||||||||
651 CAGTGGTTGTCTCATGTCTCTTTTCTGTCTTAGGTGGTTTCATTAAATG 700

684 CAGCACTTGGTTAGCAGATGTTTAATTTTTTTTTAACAACATTAACTT 733
    |||||||||||||||||||||||||| |||||||||||||||||||||
701 CAGCACTTGGTTAGCAGATGTTTAA.TTTTTTTTTAACAACATTAACTT 749

734 GTGGCCTCTTTCTACACCTGGAAATTTACTCTTGAATAAATAAAAACTCG 783
    ||||||||||||||||||||||||||||||||||||||||||||||||||
750 GTGGCCTCTTTCTACACCTGGAAATTTACTCTTGAATAAATAAAAACTCG 799

784 TTTGTCTTGTAAAAAAAAAAAAAAA..................... 808
    |||||||||        ||||||||
800 TTTGTCTTGTCTTCTGCAAAAAAAAAAAAAAAAAAAAGATCTTTAATTAA 848
```

FIGURE 6C-1

U52101:   YMP, CDS 50...541

```
  1 .............................CCGACTCCA   9
                                  |||||||||
  1 GAATTCGGCACGAGGCGGAGGCCCGAGCGAGGGACAAGACTCCGACTCCA  50

10 GCTCTGACTTTTTTCGCGGCTCTCGGCTTCCACTGCAGCCATGTCACTCC  59
    |||||||||||||||||||||||||||||||||||||||||||||||||
 51 GCTCTGACTTTTTTCGCGGCTCTCGGCTTCCACTGCAGCCATGTCACTCC 100

60 TCTTGCTGGTGGTCTCAGCCCTTCACATCCTCATTCTTATACTGCTTTTC 109
    |||||||||||||||||||||||||||||||||||||||||||||||||
101 TCTTGCTGGTGGTCTCAGCCCTTCACATCCTCATTCTTATACTGCTTTTC 150

110 GTGGCCACTTTGGACAAGTCCTGGTGGACTCTCCCTGGGAAAGAGTCCCT 159
    |||||||||||||||||||||||||||||||||||||||||||||||||
151 GTGGCCACTTTGGACAAGTCCTGGTGGACTCTCCCTGGGAAAGAGTCCCT 200

160 GAATCTCTGGTACGACTGCACGTGGAACAACGACACCAAAACATGGGCCT 209
    |||||||||||||||||||||||||||||||||||||||||||||||||
201 GAATCTCTGGTACGACTGCACGTGGAACAACGACACCAAAACATGGGCCT 250

210 GCAGTAATGTCAGCGAGAATGGCTGGCTGAAGGCGGTGCAGGTCCTCATG 259
    |||||||||||||||||||||||||||||||||||||||||||||||||
251 GCAGTAATGTCAGCGAGAATGGCTGGCTGAAGGCGGTGCAGGTCCTCATG 300

260 GTGCTCTCCCTCATTCTCTGCTGTCTCCTTCATCCTGTTCATGTTCCA 309
    |||||||||||||||||||||||||||||||||||||||||||||||||
301 GTGCTCTCCCTCATTCTCTGCTGTCTCCTTCATCCTGTTCATGTTCCA 350

310 GCTCTACACCATGCGACGAGGAGGTCTCTTCTATGCCACCGGCCTCTGCC 359
    |||||||||||||||||||||||||||||||||||||||||||||||||
351 GCTCTACACCATGCGACGAGGAGGTCTCTTCTATGCCACCGGCCTCTGCC 400

360 AGCTTTGCACCAGCGTGGCGGTGTTTACTGGCGCCTTGATCTATGCCATT 409
    |||||||||||||||||||||||||||||||||||||||||||||||||
401 AGCTTTGCACCAGCGTGGCGGTGTTTACTGGCGCCTTGATCTATGCCATT 450

410 CACGCCGAGGAGATCCTGGAGAAGCACCCGCGAGGGGGCAGCTTCGGATA 459
    |||||||||||||||||||||||||||||||||||||||||||||||||
451 CACGCCGAGGAGATCCTGGAGAAGCACCCGCGAGGGGGCAGCTTCGGATA 500

460 CTGCTTCGCCCTGGCCTGGGTGGCCTTCCCCCTCGCCCTGGTCAGCGGCA 509
    |||||||||||||||||||||||||||||||||||||||||||||||||
501 CTGCTTCGCCCTGGCCTGGGTGGCCTTCCCCCTCGCCCTGGTCAGCGGCA 550

510 TCATCTACATCCACCTACGGAAGCGGGAGTGAGCGCCGCGCCTCGCTCGG 559
    |||||||||||||||||||||||||||||| |||||||||||
551 TCATCTACATCCACCTACGGAAGCGGGAGTGAGCGCCCCGCCTCGCTCGG 600

560 CTGCCCCCGCCCCTTCCGGGCCCCCCT.GCCGCGCGTCCTCC........ 600
    ||||||||||||||||||| ||||||||| |||||||||||
601 CTGCCCCCGCCCCTTCCGGCCCCCCTCGCCGCGCGTCCTCCAAAAAATA 650
```

FIGURE 6C-2

```
  1 ..................CCGACTCCAGCTCTGACTTTTTCG  25
                      |||||||||||||||||||||||||
  1 GAATTCGGCACGAGGGGACAAGACTCCGACTCCAGCTCTGACTTTTTCG  50

26 CGGCTCTCGGCTTCCACTGCAGCCATGTCACTCCTCTTGCTGGTGGTCTC  75
    ||||||||||||||||||||||||||||||||||||||||||||||||||
 51 CGGCTCTCGGCTTCCACTGCAGCCATGTCACTCCTCTTGCTGGTGGTCTC 100

76 AGCCCTTCACATCCTCATTCTTATACTGCTTTTCGTGGCCACTTTGGACA 125
    ||||||||||||||||||||||||||||||||||||||||||||||||||
101 AGCCCTTCACATCCTCATTCTTATACTGCTTTTCGTGGCCACTTTGGACA 150

126 AGTCCTGGTGGACTCTCCCTGGGAAGAGTCCCTGAATCTCTGGTACGAC 175
    |||||||||||||||||||||||||||||||||||||||||||||||||
151 AGTCCTGGTGGACTCTCCCTGGGAAGAGTCCCTGAATCTCTGGTACGAC 200

176 TGCACGTGGAACAACGACACCAAAACATGGGCCTGCAGTAATGTCAGCGA 225
    ||||||||||||||||||||||||||||||||||||||||||||||||||
201 TGCACGTGGAACAACGACACCAAAACATGGGCCTGCAGTAATGTCAGCGA 250

226 GAATGGCTGGCTGAAGGCGGTGCAGGTCCTCATGGTGCTCTCCCTCATTC 275
    ||||||||||||||||||||||||||||||||||||||||||||||||||
251 GAATGGCTGGCTGAAGGCGGTGCAGGTCCTCATGGTGCTCTCCCTCATTC 300

276 TCTGCTGTCTCTCCTTCATCCTGTTCATGTTCCAGCTCTACACCATGCGA 325
    ||||||||||||||||||||||||||||||||||||||||||||||||||
301 TCTGCTGTCTCTCCTTCATCCTGTTCATGTTCCAGCTCTACACCATGCGA 350

326 CGAGGAGGTCTCTTCTATGCCACCGGCCTCTGCCAGCTTTGCACCAGCGT 375
    ||||||||||||||||||||||||||||||||||||||||||||||||||
351 CGAGGAGGTCTCTTCTATGCCACCGGCCTCTGCCAGCTTTGCACCAGCGT 400

376 GGCGGTGTTTACTGGCGCCTTGATCTATGCCATTCACGCCGAGGAGATCC 425
    ||||||||||||||||||||||||||||||||||||||||||||||||||
401 GGCGGTGTTTACTGGCGCCTTGATCTATGCCATTCACGCCGAGGAGATCC 450

426 TGGAG.AGCACCCGCGAGGGGGCAGCTTCGGATACTGCTTCGCCCTGGCC 474
    ||||| ||||||||||||||||||||||||||||||||||||||||||||
451 TGGAGAAGCACCCGCGAGGGGGCAGCTTCGGATACTGCTTCGCCCTGGCC 500

475 TGGGTGGCCTTCCCCCTCGCCCTGGTCAGCGGCATCATCTACATCCACCT 524
    ||||||||||||||||||||||||||||||||||||||||||||||||||
501 TGGGTGGCCTTCCCCCTCGCCCTGGTCAGCGGCATCATCTACATCCACCT 550

525 ACGGAAGCGGGAGTGAGCGCCGCGCCTCGCTCGGCTGCCCCGCCCCTTC 574
    ||||||||||||||||||| ||||||||||||||||||||||||||||||
551 ACGGAAGCGGGAGTGAGCGCCCCGCCTCGCTCGGCTGCCCCGCCCCTTC 600

575 CGGGCCCCCCT.GCCGCGCGTCCTCC.................. 599
    | ||||||||| |||||||||||||
601 CCGGCCCCCCTCGCCGCGCGTCCTCCAAAAAATAAAACCTTAACCGCGGG 650
```

FIGURE 6C-3

L36034: SDF1a, CDS 80...349

```
  1 ..........TCTCCGTCAGCCGCATTGCCCGCTCGGCGTCCGGCCCCG  40
             ||||||||||||||||||||||||||||||||||||||||
  1 AAGCTTGGCACGAGGGTCAGCCGCATTGCCCGCTCGGCGTCCGGCCCCG  50

41 ACCCGTGCTCGTCCGCCCGCCCGCCCGCCCGCGCCATGAACGCCAA  90
    |||||  |||||||||||||||||||||||||||||||||||||||
 51 ACCCGCGCTCGTCCGCCCGCCCGCCCGCCCGCGCCATGAACGCCAA 100

91 GGTCGTGGTCGTGCTGGTCCTCGTGCTGACCGCGCTCTGCCTCAGCGACG 140
    ||||||||||||||||||||||||||||||||||||||||||||||||||
101 GGTCGTGGTCGTGCTGGTCCTCGTGCTGACCGCGCTCTGCCTCAGCGACG 150

141 GGAAGCCCGTCAGCCTGAGCTACAGATGCCCATGCCGATTCTTCGAAAGC 190
    ||||||||||||||||||||||||||||||||||||||||||||||||||
151 GGAAGCCCGTCAGCCTGAGCTACAGATGCCCATGCCGATTCTTCGAAAGC 200

191 CATGTTGCCAGAGCCAACGTCAAGCATCTCAAAATTCTCAACACTCCAAA 240
    ||||||||||||||||||||||||||||||||||||||||||||||||||
201 CATGTTGCCAGAGCCAACGTCAAGCATCTCAAAATTCTCAACACTCCAAA 250

241 CTGTGCCCTTCAGATTGTAGCCCGGCTGAAGAACAACAACAGACAAGTGT 290
    ||||||||||||||||||||||||||||||||||||||||||||||||||
251 CTGTGCCCTTCAGATTGTAGCCCGGCTGAAGAACAACAACAGACAAGTGT 300

291 GCATTGACCCGAAGCTAAAGTGGATTCAGGAGTACCTGGAGAAAGCTTTA 340
    ||||||||||||||||||||||||||||||||||||||||||||||||||
301 GCATTGACCCGAAGCTAAAGTGGATTCAGGAGTACCTGGAGAAAGCTTTA 350

341 AACAAGTAAGCACAACAGCCAAAAAGGACTTTCCGCTAGACCCACTCGAG 390
    ||||||||||||||||||||||||||||||||||||||||||||||||||
351 AACAAGTAAGCACAACAGCCAAAAAGGACTTTCCGCTAGACCCACTCGAG 400

391 GAAAACTAAAACCTTGTGAGAGATGAAAGGGCAAAGACGTGGGGGAGGGG 440
    ||||||||||||||||||||||||||||||||||||||||||||||||||
401 GAAAACTAAAACCTTGTGAGAGATGAAAGGGCAAAGACGTGGGGGAGGGG 450

441 GCCTTAACCATGAGGACCAGGTGTGTGTGTGGGGTGGGCACATTGATCTG 490
    ||||||||||||||||||||||||||||||||||||||||||||||||||
451 GCCTTAACCATGAGGACCAGGTGTGTGTGTGGGGTGGGCACATTGATCTG 500

491 GGATCGGGCCTGAGGTTTGCAGCATTTAGACCCTGCATTTATAGCATACG 540
    ||||||||||||||||||
501 GGATCGGGCCTGAGGTTT..................518
```

FIGURE 6D-1

M36035: Peripheral benzodiazepine receptor, CDS 62..571

```
  1 ..............AGTGCCCTTCCCGGAGCGTGCCCTCGCCGCTGAGCT  36
                 || |  |||||||||||||||||||||||||||||
  1 TCGAGGCCAAGAATTCGGCACGAGCCGGAGCGTGCCCTCGCCGCTGAGCT  50

37 CCCCTGAACAGCAGCTGCAGCAGCCATGGCCCCGCCCTGGGTGCCCGCCA  86
    ||||||||||||||||||||||||||||||||||||||||||||||||||
 51 CCCCTGAACAGCAGCTGCAGCAGCCATGGCCCCGCCCTGGGTGCCCGCCA 100

87 TGGGCTTCACGCTGGCGCCCAGCCTGGGGTGCTTCGTGGGCTCCCGCTTT 136
    ||||||||||||||||||||||||||||||||||||||||||||||||||
101 TGGGCTTCACGCTGGCGCCCAGCCTGGGGTGCTTCGTGGGCTCCCGCTTT 150

137 GTCCACGGCGAGGGTCTCCGCTGGTACGCCGGCCTGCAGAAGCCCTCGTG 186
    ||||||||||||||||||||||||||||||||||||||||||||||||||
151 GTCCACGGCGAGGGTCTCCGCTGGTACGCCGGCCTGCAGAAGCCCTCGTG 200

187 GCACCCGCCCCACTGGGTGCTGGGCCCTGTCTGGGGCACGCTCTACTCAG 236
    ||||||||||||||||||||||||||||||||||||||||||||||||||
201 GCACCCGCCCCACTGGGTGCTGGGCCCTGTCTGGGGCACGCTCTACTCAG 250

237 CCATGGGGTACGGCTCCTACCTGGTCTGGAAAGAGCTGGGAGGCTTCACA 286
    ||||||||||||||||||||||||||||||||||||||||||||||||||
251 CCATGGGGTACGGCTCCTACCTGGTCTGGAAAGAGCTGGGAGGCTTCACA 300

287 GAGAAGGCTGTGGTTCCCCTGGGCCTCTACACTGGGCAGCTGGCCCTGAA 336
    ||||||||||||||||||||||||||||||||||||||||||||||||||
301 GAGAAGGCTGTGGTTCCCCTGGGCCTCTACACTGGGCAGCTGGCCCTGAA 350

337 CTGGGCATGGCCCCCCATCTTCTTTGGTGCCCGACAAATGGGCTGGGCCT 386
    ||||||||||||||||||||||||||||||||||||||||||||||||||
351 CTGGGCATGGCCCCCCATCTTCTTTGGTGCCCGACAAATGGGCTGGGCCT 400

387 TGGTGGATCTCCTGCTGGTCAGTGGGGCGGCGGCNGCCACTACCGTGGCC 436
    ||||||||||||||||||||||||||||||||||| ||||||||||||||
401 TGGTGGATCTCCTGCTGGTCAGTGGGGCGGCGGCAGCCACTACCGTGGCC 450

437 TGGTACCAGGTGAGCCCGCTGGCCGCCCGCCTGCTCTACCCCTACCTGGC 486
    ||||||||||||||||||||||||||||||||||||||||||||||||||
451 TGGTACCAGGTGAGCCCGCTGGCCGCCCGCCTGCTCTACCCCTACCTGGC 500

487 CTGGCTGGCCTTCGCGACCACACTCAACTACTGCGTATGGCGGGACAACC 536
    ||||||||||||||||||||||||||||||||||||||||||||||||||
501 CTGGCTGGCCTTCGCGACCACACTCAACTACTGCGTATGGCGGGACAACC 550

537 ATGGCTGGCATGGGGACGGCGGCTGCCAGAGTGAGTGCCCGGCCCACCA  586
    ||||||||| ||||||||||||||||||||||||||   |||||||||||
551 ATGGCTGGCGTGGGGACGGCGGCTGCCAGAGTGAGGGCCCGGCCCACCA  600

587 GGGACTGCAGCTGCACCAGCAGGTGCCATCACGCTTGTGATGTGGTGGCC 636
    ||||||||||||||||||||||||||||||||||||||||||||||||||
601 GGGACTGCAGCTGCACCAGCAGGTGCCATCACGCTTGTGATGTGGTGGCC 650
```

FIGURE 6D-2

```
637 GTCACGCTTTCATGACCACTGGGCCTGCTAGTCTGTCAGGGCCTTGGCCC 686
    ||||||||||||||||||||||||||||||||||||||||||||||||||
651 GTCACGCTTTCATGACCACTGGGCCTGCTAGTCTGTCAGGGCCTTGGCCC 700

687 AGGGGTCAGCAGAGCTTCAGAGGTTGCCCCACCTGAGCCCCACCCGGGA 736
    |||||||||||||||||||||||||| ||||||||||||||||||||||
701 AGGGGTCAGCAGAGCTTCAGAGGTGGCCCCACCTGAGCCCCACCCGGGA 750

737 GCAGTGTCCTGTGCTTTCTGCATGCTTAGAGCATGTTCTTGGAACATGGA 786
    ||||||||||||||||||||||||||||||||||||||||||||||||||
751 GCAGTGTCCTGTGCTTTCTGCATGCTTAGAGCATGTTCTTGGAACATGGA 800

787 ATTTTATAAGCTGAATAAAGTTTTTGACTTCCTTT............ 821
    |||||||||||||||||||||||||||||||||||
801 ATTTTATAAGCTGAATAAAGTTTTTGACTTCCTTTAAAAAAAAAAAAAAA 850

1 ...............AGTGCCCTTCCCGGAGCGTGCCCTCGCCGCTGAGC 35
                   || |   |||||||||||||||||||||||||||
  1 CTCGAGGCCAAGAATTCGGCACGAGCCGGAGCGTGCCCTCGCCGCTGAGC 50

36 TCCCCTGAACAGCAGCTGCAGCAGCCATGGCCCCGCCCTGGGTGCCCGCC 85
    ||||||||||||||||||||||||||||||||||||||||||||||||||
 51 TCCCCTGAACAGCAGCTGCAGCAGCCATGGCCCCGCCCTGGGTGCCCGCC 100

86 ATGGGCTTCACGCTGGCGCCCAGCCTGGGGTGCTTCGTGGGCTCCCGCTT 135
    ||||||||||||||||||||||||||||||||||||||||||||||||||
101 ATGGGCTTCACGCTGGCGCCCAGCCTGGGGTGCTTCGTGGGCTCCCGCTT 150

136 TGTCCACGGCGAGGGTCTCCGCTGGTACGCCGGCCTGCAGAAGCCCTCGT 185
    ||||||||||||||||||||||||||||||||||||||||||||||||||
151 TGTCCACGGCGAGGGTCTCCGCTGGTACGCCGGCCTGCAGAAGCCCTCGT 200

186 GGCACCCGCCCCACTGGGTGCTGGGCCCTGTCTGGGGCACGCTCTACTCA 235
    ||||||||||||||||||||||||||||||||||||||||||||||||||
201 GGCACCCGCCCCACTGGGTGCTGGGCCCTGTCTGGGGCACGCTCTACTCA 250

236 GCCATGGGGTACGGCTCCTACCTGGTCTGGAAAGAGCTGGGAGGCTTCAC 285
    ||||||||||||||||||||||||||||||||||||||||||||||||||
251 GCCATGGGGTACGGCTCCTACCTGGTCTGGAAAGAGCTGGGAGGCTTCAC 300

286 AGAGAAGGCTGTGGTTCCCCTGGGCCTCTACACTGGGCAGCTGGCCCTGA 335
    ||||||||||||||||||||||||||||||||||||||||||||||||||
301 AGAGAAGGCTGTGGTTCCCCTGGGCCTCTACACTGGGCAGCTGGCCCTGA 350

336 ACTGGGCATGGCCCCCATCTTCTTTGGTGCCCGACAAATGGGCTGGGCC 385
    ||||||||||||||||||||||||||||||||||||||||||||||||||
351 ACTGGGCATGGCCCCCATCTTCTTTGGTGCCCGACAAATGGGCTGGGCC 400

386 TTGGTGGATCTCCTGCTGGTCAGTGGGGCGGCGGCNGCCACTACCGTGGC 435
    |||||||||||||||||||||||||||||||||||:||||||||||||||
401 TTGGTGGATCTCCTGCTGGTCAGTGGGGCGGCGGCAGCCACTACCGTGGC 450
```

FIGURE 6D-3

```
436 CTGGTACCAGGTGAGCCCGCTGGCCGCCCGCCTGCTCTACCCCTACCTGG 485
    ||||||||||||||||||||||||||||||||||||||||||||||||||
451 CTGGTACCAGGTGAGCCCGCTGGCCGCCCGCCTGCTCTACCCCTACCTGG 500

486 CCTGGCTGGCCTTCGCGACCACACTCAACTACTGCGTATGGCGGGACAAC 535
    ||||||||||||||||||||||||||||||||||||||||||||||||||
501 CCTGGCTGGCCTTCGCGACCACACTCAACTACTGCGTATGGCGGGACAAC 550

536 CATGGCTGGCATGGGGGACGGCGGCTGCCAGAGTGAGTGCCCGGCCCACC 585
    ||||||||||||||||||||||||||||||||||||||||||||||||||
551 CATGGCTGGCATGGGGGACGGCGGCTGCCAGAGTGAGTGCCCGGCCCACC 600

586 AGGGACTGCAGCTGCACCAGCAGGTGCCATCACGCTTGTGATGTGGTGGC 635
    ||||||||||||||||||||||||||||||||||||||||||||||||||
601 AGGGACTGCAGCTGCACCAGCAGGTGCCATCACGCTTGTGATGTGGTGGC 650

636 CGTCACGCTTTCATGACCACTGGGCCTGCTAGTCTGTCAGGGCCTTGGCC 685
    ||||||||||||||||||||||||||||||||||||||||||||||||||
651 CGTCACGCTTTCATGACCACTGGGCCTGCTAGTCTGTCAGGGCCTTGGCC 700

686 CAGGGGTCAGCAGAGCTTCAGAGGTTGCCCCACCTGAGCCCCCACCCGGG 735
    ||||||||||||||||||||||||||||||||||||||||||||||||||
701 CAGGGGTCAGCAGAGCTTCAGAGGTTGCCCCACCTGAGCCCCCACCCGGG 750

736 AGCAGTGTCCTGTGCTTTCTGCATGCTTAGAGCATGTTCTTGGAACATGG 785
    ||||||||||||||||||||||||||||||||||||||||||||||||||
751 AGCAGTGTCCTGTGCTTTCTGCATGCTTAGAGCATGTTCTTGGAACATGG 800

786 AATTTTATAAGCTGAATAAAGTTTTGACTTCCTTT............... 821
    ||||||||||||||||||||||||||||||||||
801 AATTTTATAAGCTGAATAAAGTTTTGACTTCCTTTAAAAAAAAAAAAAA 850
```

FIGURE 6E-1

M38591: cellular ligand of annexin II (p11), CDS 112...405

```
  1 ......AGAATACACTCACAAGCCACTCCGCTGCTCGCCTCTCCG....C  40
         | |  || | |   || ·| | |   ||||    |    |    |
  1 AATTTAATACGACTCACTATAGGGAATTTGGCCCTCGAGGCCAAGAATTC  50

41 CCCGCGTCCAGCTCGCCCAGCTCGCCCAGCGTCCGCCGCGCCTC.GCCAA  89
    | ||    |||||||||||||||||||||||||||||||||||| |||||
 51 GGCACGAGGAGCTCGCCCAGCTCGCCCAGCGTCCGCCGCGCCTCGGCCAA 100

90 GGCTTCAACGGACCACACCAAAATGCCATCTCAAATGGAACACGCCATGG 139
    |||||||||||||||||||||||||||||||||||||||||||||||||
101 GGCTTCAACGGACCACACCAAAATGCCATCTCAAATGGAACACGCCATGG 150

140 AAACCATGATGTTTACATTTCACAAATTCGCTGGGGATAAAGGCTACTTA 189
    |||||||||||||||||||||||||||||||||||||||||||||||||
151 AAACCATGATGTTTACATTTCACAAATTCGCTGGGGATAAAGGCTACTTA 200

190 ACAAAGGAGGACCTGAGAGTACTCATGGAAAAGGAGTTCCCTGGATTTTT 239
    |||||||||||||||||||||||||||||||||||||||||||||||||
201 ACAAAGGAGGACCTGAGAGTACTCATGGAAAAGGAGTTCCCTGGATTTTT 250

240 GGAAAATCAAAAAGACCCTCTGGCTGTGGACAAAATAATGAAGGACCTGG 289
    |||||||||||||||||||||||||||||||||||||||||||||||||
251 GGAAAATCAAAAAGACCCTCTGGCTGTGGACAAAATAATGAAGGACCTGG 300

290 ACCAGTGTAGAGATGGCAAAGTGGGCTTCCAGAGCTTCTTTTCCCTAATT 339
    |||||||||||||||||||||||||||||||||||||||||||||||||
301 ACCAGTGTAGAGATGGCAAAGTGGGCTTCCAGAGCTTCTTTTCCCTAATT 350

340 GCGGGCCTCACCATTGCATGCAATGACTATTTGTAGTACACATGAAGCA 389
    |||||||||||||||||||||||||||||||||||||||||||||||||
351 GCGGGCCTCACCATTGCATGCAATGACTATTTGTAGTACACATGAAGCA 400

390 GAAGGGAAAGAAGTAGGCAGAAATGAGCAGTTCGCTCCTCCCTGATAAGA 439
    |||||||||||||||||||||||||||||||||||||||||||||||||
401 GAAGGGAAAGAAGTAGGCAGAAATGAGCAGTTCGCTCCTCCCTGATAAGA 450

440 GTTGT.CCAAAGGGTCGCTTAAGGAATCTGCCCCACAGCTTCCCCCATAG 488
    ||||| |||||||||||||||||||||||||||||||||||||||||||
451 GTTGTCCCAAAGGGTCGCTTAAGGAATCTGCCCCACAGCTTCCCCCATAG 500

489 AAGGATTTCATGAGCAGATCAGGACACTTAGCAAATGTAAAAATAAAATC 538
    |||||||||||||||||||||||||||||||||||||||||||||||||
501 AAGGATTTCATGAGCAGATCAGGACACTTAGCAAATGTAAAAATAAAATC 550

539 TAACTCTCATTTGACAAGCAGAGAAAGAAAAGTTAAATACCAGATAAGCT 588
    |||||||||||||||||||||||||||||||||||||||||||||||||
551 TAACTCTCATTTGACAAGCAGAGAAAGAAAAGTTAAATACCAGATAAGCT 600

589 TTTGATTTTGTATTGTTTGCATCCCCTTGCCCTCAATAAATAAAGTTCT 638
    |||||||||||||||||||||||||||||||||||||||||||||||||
601 TTTGATTTTGTATTGTTTGCATCCCCTTGCCCTCAATAAATAAAGTTCT 650
```

FIGURE 6E-2

```
639 TTTTTAGTTCC......................................  649
    |||||||||||
651 TTTTTAGTTCCAAAAAAAAAAAAAAAAAAAAAAAGATGCGGCCGCAAGCT  700

1 ..........AGAATACACTCACAAGCCACTCCGCTGCTCGCCTCTCCG   39
             |  |||      |||     |            ||   |
  1 TAATACGACTCACTATAGGGAATTTGGCCCTCGAGGCCAAGAATTCGGCA   50

40 CCCCGCGTCCAGCTCGCCCAGCTCGCCCAGCGTCCGCCGCGCCTC.GCCA   88
    |   ||||||||||||||||||||||||||||||||||||||||| ||||
 51 CGAGGCGTCCAGCTCGCCCAGCTCGCCCAGCGTCCGCCGCGCCTCGGCCA  100

89 AGGCTTCAACGGACCACACCAAAATGCCATCTCAAATGGAACACGCCATG  138
    |||||||||||||||||||||||||||||||||||||||||||||||||
101 AGGCTTCAACGGACCACACCAAAATGCCATCTCAAATGGAACACGCCATG  150

139 GAAACCATGATGTTTACATTTCACAAATTCGCTGGGGATAAAGGCTACTT  188
    |||||||||||||||||||||||||||||||||||||||||||||||||
151 GAAACCATGATGTTTACATTTCACAAATTCGCTGGGGATAAAGGCTACTT  200

189 AACAAAGGAGGACCTGAGAGTACTCATGGAAAAGGAGTTCCCTGGATTTT  238
    |||||||||||||||||||||||||||||||||||||||||||||||||
201 AACAAAGGAGGACCTGAGAGTACTCATGGAAAAGGAGTTCCCTGGATTTT  250

239 TGGAAAATCAAAAAGACCCTCTGGCTGTGGACAAAATAATGAAGGACCTG  288
    |||||||||||||||||||||||||||||||||||||||||||||||||
251 TGGAAAATCAAAAAGACCCTCTGGCTGTGGACAAAATAATGAAGGACCTG  300

289 GACCAGTGTAGAGATGGCAAAGTGGGCTTCCAGAGCTTCTTTTCCCTAAT  338
    |||||||||||||||||||||||||||||||||||||||||||||||||
301 GACCAGTGTAGAGATGGCAAAGTGGGCTTCCAGAGCTTCTTTTCCCTAAT  350

339 TGCGGGCCTCACCATTGCATGCAATGACTATTTTGTAGTACACATGAAGC  388
    |||||||||||||||||||||||||||||||||||||||||||||||||
351 TGCGGGCCTCACCATTGCATGCAATGACTATTTTGTAGTACACATGAAGC  400

389 AGAAGGGAAAGAAGTAGGCAGAAATGAGCAGTTCGCTCCTCCCTGATAAG  438
    |||||||||||||||||||||||||||||||||||||||||||||||||
401 AGAAGGGAAAGAAGTAGGCAGAAATGAGCAGTTCGCTCCTCCCTGATAAG  450

439 AGTTGT.CCAAAGGGTCGCTTAAGGAATCTGCCCCACAGCTTCCCCCATA  487
    ||||||  ||||||||||||||||||||||||||||||||||||||||||
451 AGTTGTCCCAAAGGGTCGCTTAAGGAATCTGCCCCACAGCTTCCCCCATA  500

488 GAAGGATTTCATGAGCAGATCAGGACACTTAGCAAATGTAAAAATAAAAT  537
    |||||||||||||||||||||||||||||||||||||||||||||||||
501 GAAGGATTTCATGAGCAGATCAGGACACTTAGCAAATGTAAAAATAAAAT  550

538 CTAACTCTCATTTGACAAGCAGAGAAAGAAAAGTTAAATACCAGATAAGC  587
    |||||||||||||||||||||||||||||||||||||||||||||||||
551 CTAACTCTCATTTGACAAGCAGAGAAAGAAAAGTTAAATACCAGATAAGC  600
```

FIGURE 6E-3

```
588 TTTTGATTTTTGTATTGTTTGCATCCCCTTGCCCTCAATAAATAAAGTTC 637
    ||||||||||||||||||||||||||||||||||||||||||||||||||
601 TTTTGATTTTTGTATTGTTTGCATCCCCTTGCCCTCAATAAATAAAGTTC 650

638 TTTTTAGTTCC....................................... 649
    |||||||||||
651 TTTTTAGTTCCAAAAAAAAAAAAAAAAAAAGATGCGGCCGCAAGCTTATT 700
```

FIGURE 7A

SEQ ID NO:25
X57352    Human 1-8U gene from interferon inducible gene family
          CDS 238...639

```
tgctcccttg ggctctagag aggaggcccc tcttagccct cagcccctcc ttcctctcta  60
tcttaaagta atttgatcct caggaatttg ttccgccctc atctggcccg gccaaatccc 120
gatttgacaa atgccaggaa aaggaaactg ttgagaaacc gaaactactg gggaaaggga 180
gggctcactg agtaaccatc ccagtaaccc gaccgccgct ggtcttcgct ggacaccatg 240
agtcacactg tccaaacctt cttctctcct gtcaacagtg gccagccccc caactatgag 300
atgctcaagg aggagcacga ggtggctgtg ctggggggc cccacaaccc tgctcccccg 360
acgtccaccg tgatccacat ccgcagcgag acctccgtgc ccgaccatgt cgtctggtcc 420
ctgttcaaca ccctcttcat gaaccctgc tgcctgggct tcatagcatt cgcctactcc 480
gtgaagtcta gggacaggaa gatggttggc gacgtgaccg ggcccaggc ctatgcctcc 540
accgccaagt gcctgaacat ctgggccctg attctgggca tcctcatgac cattctgctc 600
atcgtcatcc cagtgctgat cttccaggcc tatggataga tcaggaggca tcactgaggc 660
caggagctct gcccatgacc tgtatcccac gtactccaac ttccattcct cgccctgccc 720
ccggagccga gtcctgtatc agccctttat cctcacacgc ttttctacaa tggcattcaa 780
taaagtgcac gtgtttctgg tgctgctg 808
```

FIGURE 7B

SEQ ID NO:26
S75725    Human prostacyclin-stimulating factor
          CDS 23...871

```
gccgctgcca ccgcaccccg ccatggagcg gccgtcgctg cgcgccctgc tcctcggcgc    60
cgctgggctg ctgctcctgc tcctgcccct ctcctcttcc tcctcttcgg acacctgcgg   120
cccctgcgag ccggcctcct gcccgcccct gccccgctg ggctgcctgc tgggcgagac   180
ccgcgacgcg tgcggctgct gccctatgtg cgcccgcggc gagggcgagc cgtgcggggg   240
tggcggcgcc ggcaggggt actgcgcgcc gggcatggag tgcgtgaaga gccgcaagag   300
gcggaagggt aaagccgggg cagcagccgg cggtccgggt gtaagcggcg tgtgcgtgtg   360
caagagccgc tacccggtgt gcggcagcga cggcaccacc tacccgagcg gctgccagct   420
gcgcgccgcc agccagaggg ccgagagccg cggggagaag gccatcaccc aggtcagcaa   480
gggcacctgc gagcaaggtc cttccatagt gacgcccccc aaggacatct ggaatgtcac   540
tggtgcccag gtgtacttga gctgtgaggt catcggaatc ccgacacctg tcctcatctg   600
gaacaaggta aaaggggtc actatggagt tcaaaggaca gaactcctgc ctggtgaccg   660
ggacaacctg ccattcaga cccggggtgg cccagaaaag catgaagtaa ctggctgggt   720
gctggtatct cctctaagta aggaagatgc tggagaatat gagtgccatg catccaattc   780
ccaaggacag gcttcagcat cagcaaaaat tacagtggtt gatgccttac atgaaatacc   840
agtgaaaaaa ggtgaaggtg ccgagctata aacctccaga atattattag tctgcatggt   900
taaaagtagt catggataac tacattacct gttcttgcct aataagtttc ttttaatcca   960
atccactaac actttagtta tattcactgg ttttacacag agaaatacaa aataaagatc  1020
acacatcaag actatctaca aaatttatt atatatttac agaagaaaag catgcatatc  1080
attaaacaaa taaaatactt tttatcacaa aaaaaaaaa aaaa                    1124
```

FIGURE 7C-1

SEQ ID NO:27
D13665       Human osf-2
             CDS  28...2367

```
aacagaactg caacggagag actcaagatg attcccttt tacccatgtt ttctctacta   60
ttgctgctta ttgttaaccc tataaacgcc aacaatcatt atgacaagat cttggctcat  120
agtcgtatca ggggtcggga ccaaggccca aatgtctgtg cccttcaaca gattttgggc  180
accaaaaaga aatacttcag cacttgtaag aactggtata aaagtccat ctgtggacag   240
aaaacgactg ttttatatga atgttgccct ggttatatga gaatggaagg aatgaaaggc  300
tgcccagcag ttttgcccat tgaccatgtt tatggcactc tgggcatcgt gggagccacc  360
acaacgcagc gctattctga cgcctcaaaa ctgaggagg agatcgaggg aaagggatcc  420
ttcacttact ttgcaccgag taatgaggct tgggacaact tggattctga tatccgtaga  480
ggtttggaga gcaacgtgaa tgttgaatta ctgaatgctt tacatagtca catgattaat  540
aagagaatgt tgaccaagga cttaaaaaat ggcatgatta ttccttcaat gtataacaat  600
ttggggcttt tcattaacca ttatcctaat ggggttgtca ctgttaattg tgctcgaatc  660
atccatggga accagattgc aacaaatggt gttgtccatg tcattgaccg tgtgcttaca  720
caaattggta cctcaattca agacttcatt gaagcagaag atgacctttc atcttttaga  780
gcagctgcca tcacatcgga catattggag gcccttggaa gagacggtca cttcacactc  840
tttgctccca ccaatgaggc ttttgagaaa cttccacgag gtgtcctaga aaggttcatg  900
ggagacaaag tggcttccga agctcttatg aagtaccaca tcttaaatac tctccagtgt  960
tctgagtcta ttatgggagg agcagtcttt gagacgctgg aaggaaatac aattgagata 1020
ggatgtgacg gtgacagtat aacagtaaat ggaatcaaaa tggtgaacaa aaaggatatt 1080
gtgacaaata atggtgtgat ccatttgatt gatcaggtcc taattcctga ttctgccaaa 1140
caagttattg agctggctgg aaaacagcaa accaccttca ggatcttgt ggcccaatta  1200
ggcttggcat ctgctctgag gccagatgga gaatacactt tgctggcacc tgtgaataat 1260
gcatttctg atgatactct cagcatggtt cagcgcctc ttaaattaat tctgcagaat  1320
cacatattga aagtaaaagt tggccttaat gagctttaca acgggcaaat actggaaacc 1380
atcggaggca aacagctcag agtcttcgta tatcgtacag ctgtctgcat tgaaaattca 1440
tgcatggaga aagggagtaa gcaagggaga aacggtgcga ttcacatatt ccgcgagatc 1500
atcaagccag cagagaaatc cctccatgaa aagttaaaac aagataagcg ctttagcacc 1560
ttcctcagcc tacttgaagc tgcagacttg aaagagctcc tgacacaacc tggagactgg 1620
```

FIGURE 7C-2

```
acattatttg tgccaaccaa tgatgctttt aagggaatga ctagtgaaga aaaagaaatt  1680
ctgatacggg acaaaaatgc tcttcaaaac atcattcttt atcacctgac accaggagtt  1740
ttcattggaa aaggatttga acctggtgtt actaacattt aaagaccac acaaggaagc   1800
aaaatctttc tgaagaagt aaatgataca cttctggtga atgaattgaa atcaaaagaa   1860
tctgacatca tgacaacaaa tggtgtaatt catgttgtag ataaactcct ctatccagca  1920
gacacacctg ttggaaatga tcaactgctg gaaatactta ataaattaat caaatacatc  1980
caaattaagt ttgttcgtgg tagcaccttc aaagaaatcc ccgtgactgt ctataagcca  2040
attattaaaa aatacaccaa aatcattgat ggagtgcctg tggaaataac tgaaaaagag  2100
acacgagaag aacgaatcat tacaggtcct gaaataaaat acactaggat ttctactgga  2160
ggtggagaaa cagaagaaac tctgaagaaa ttgttacaag aagaggtcac caaggtcacc  2220
aaattcattg aaggtggtga tggtcattta tttgaagatg aagaattaa aagactgctt   2280
cagggagaca cacccgtgag gaagttgcaa gccaacaaaa aagttcaagg ttctagaaga  2340
cgattaaggg aaggtcgttc tcagtgaaaa tccaaaaacc agaaaaaaat gtttatacaa  2400
ccctaagtca ataacctgac cttagaaaat tgtgagagcc aagttgactt caggaactga  2460
aacatcagca caaagaagca atcatcaaat aattctgaac acaaatttaa tatttttttt  2520
tctgaatgag aaacatgagg gaaattgtgg agttagcctc ctgtggagtt agcctcctgt  2580
ggtaaaggaa ttgaagaaaa tataacacct tacacccttt tcatcttga cattaaaagt   2640
tctggctaac tttggaatcc attagagaaa atccttgtc accagattca ttacaattca   2700
aatcgaagag ttgtgaactg ttatcccatt gaaaagaccg agccttgtat gtatgttatg  2760
gatacataaa atgcacgcaa gccattatct ctccatggga agctaagtta taaaaatagg  2820
tgcttggtgt acaaaacttt ttatatcaaa aggctttgca catttctata tgagtgggtt  2880
tactggtaaa ttatgttatt ttttacaact aattttgtac tctcagaatg tttgtcatat  2940
gcttcttgca atgcatattt tttaatctca aacgtttcaa taaaaccatt tttcagatat  3000
aaagagaatt acttcaaatt gagtaattca gaaaactca agatttaagt taaaaagtgg   3060
tttggacttg ggaacag                                                 3077
```

FIGURE 7D

SEQ ID NO:28
X67698    Human tissue specific mRNA
          CDS 11...466

```
cggattccgg atgcgtttcc tggcagctac attcctgctc ctggcgctca gcaccgctgc   60
ccaggccgaa ccggtgcagt tcaaggactg cggttctgtg gatggagtta taaaggaagt  120
gaatgtgagc ccatgcccca cccaaccctg ccagctgagc aaaggacagt cttacagcgt  180
caatgtcacc ttcaccagca atattcagtc taaaagcagc aaggccgtgg tgcatggcat  240
cctgatgggc gtcccagttc cctttcccat tcctgagcct gatggttgta agagtggaat  300
taactgccct atccaaaaag acaagaccta tagctacctg aataaactac cagtgaaaag  360
cgaatatccc tctataaaac tggtggtgga gtggcaactt caggatgaca aaaccaaag  420
tctcttctgc tgggaaatcc cagtacagat cgtttctcat ctctaagtgc ctcattgagt  480
tcggtgcatc tggccaatga gtctgctgag actcttgaca gcacctccag ctctgctgct  540
tcaacaacag tgacttgctc tccaatggta ccagtgatt cgttgaagag gaggtgctct   600
gtagcagaaa ctgagctccg ggtggctggt tctcagtggt tgtctcatgt ctcttttct   660
gtcttaggtg gtttcattaa atgcagcact tggttagcag atgtttaatt tttttttta   720
acaacattaa cttgtggcct ctttctacac ctggaatttt actcttgaat aaataaaaac  780
tcgtttgtct tgtaaaaaaa aaaaaaa   808
```

FIGURE 7E

SEQ ID NO:29
M62402    Human insulin-like growth factor binding protein 6
          CDS  54...776

```
gcagctgcgc tgcgactgct ctggaaggag aggacggggc acaaaccctg accatgaccc   60
cccacaggct gctgccaccg ctgctgctgc tgctagctct gctgctcgct gccagcccag  120
gaggcgcctt ggcgcggtgc ccaggctgcg ggcaaggggt gcaggcgggt tgtccagggg  180
gctgcgtgga ggaggaggat gggggtcgc cagccgaggg ctgcgcggaa gctgagggct  240
gtctcaggag ggaggggcag gagtgcgggg tctacacccc taactgcgcc caggactgc   300
agtgccatcc gcccaaggac gacgaggcgc ctttgcgggc gctgctgctc ggccgaggcc  360
gctgccttcc ggcccgcgcg cctgctgttg cagaggagaa tcctaaggag agtaaacccc  420
aagcaggcac tggccgccca caggatgtga accgcagaga ccaacagagg aatccaggca  480
cctctaccac gccctcccag cccaattctg cgggtgtcca agacactgag atgggcccat  540
gccgtagaca tctggactca gtgctgcagc aactccagac tgaggtctac cgagggctc   600
aaacactcta cgtgcccaat tgtgaccatc gaggcttcta ccggaagcgg cagtgccgct  660
cctcccaggg gcagcgccga ggtccctgct ggtgtgtgga tcggatgggc aagtccctgc  720
cagggtctcc agatggcaat ggaagctcct cctgccccac tgggagtagc ggctaaagct  780
gggggataga ggggctgcag gccactggaa ggaacatgg agctgtcatc actcaacaaa  840
aaaccgaggc cctcaatcca ccttcaggcc ccgccccatg ggccctcac cgctggttgg  900
aaagagtgtt ggtgttggct ggggtgtcaa taaagctgtg cttggggtca aa          952
```

FIGURE 7F

SEQ ID NO:30
D90226   Human OSF-1
         CDS 125...631

```
ggggagagca gcagcggccc aagcaggagc tgcagcgagc cgggtacctg gactcagcgg    60
tagcaacctc gccccttgca acaaaggcag actgagcgcc agagaggacg tttccaactc   120
aaaaatgcag gctcaacagt accagcagca gcgtcgaaaa tttgcagctg ccttcttggc   180
attcattttc atactggcag ctgtggatac tgctgaagca gggaagaaag agaaaccaga   240
aaaaaagtg aagaagtctg actgtggaga atggcagtgg agtgtgtgtg tgcccaccag   300
tggagactgt gggctgggca cacgggaggg cactcggact ggagctgagt gcaagcaaac   360
catgaagacc cagagatgta agatcccctg caactggaag aagcaatttg gcgcggagtg   420
caaataccag ttccaggcct ggggagaatg tgacctgaac acagccctga agaccagaac   480
tggaagtctg aagcgagccc tgcacaatgc cgaatgccag aagactgtca ccatctccaa   540
gccctgtggc aaactgacca agcccaaacc tcaagcagaa tctaagaaga gaaaaaagga   600
aggcaagaaa caggagaaga tgctggatta aaagatgtca cctgtggaac ataaaaagga   660
catcagcaaa caggatcagt taactattgc atttatatgt accgtaggct ttgtattcaa   720
aaattatcta tagctaagta cacaataagc aaaaacaaaa agaaaagaaa atttttgtag   780
tagcgttttt taaatgtata ctatagtacc agtagg            816
```

FIGURE 7G-1

SEQ ID NO:31
L13698 - Human gas-1
CDS 411...1448

```
agcagccggc acggggacag ccggccgcac aacggatctg caggcgcgga gcaaaatgca    60
cccgccgcgc cgcgcggtcc tgcagcccg ccacggcccc gcggcccgca ccccccggg    120
gcgacagtga gcctctcccg ccaccaccgg gggccgagcg gagggctctc gggtgggaga   180
gcgggaccag atctcgacag ctgttcattt ccaggaagcc accgcagcca gagcgaaagg   240
ggaccttctg ccaccagcgg ggcatcagcc agcggcgcgc atggatttat gaagacactc   300
atgcaagaag tgggcaggac ttggacaaac ttttccaccg gctccgcgtc cgccgctccc   360
cgcgcctcgt ctcctttccc ctcctctccc ggcggccgcc gctgcccgcg atggtggccg   420
cgctgctggg cggcggcggc gaggcccgcg ggggacagt gccgggcgcc tggctgtgcc   480
tgatggcgct gctgcagctg ctgggctcgg cgccgcgggg atcggggctg gcgcacggcc   540
gccgcctcat ctgctggcag gcgctgctgc agtgccaggg ggagccggag tgcagctacg   600
cctacaacca gtacgccgag gcgtgcgcgc cggtgctggc gcagcacggc gggggcgacg   660
cgcccggggc cgccgccgcc gctttcccgg cctcggccgc ctctttctcg tcgcgctggc   720
gctgcccgag tcactgcatc tcggccctca ttcagctcaa ccacacgcgc cgcgggcccg   780
ccctggagga ctgtgactgc gcgcaggacg agaactgcaa gtccaccaag cgcgccattg   840
agccgtgcct gccccggacg agcggcggcg cgcgggcgg ccccggcgcg gcggggtca    900
tgggctgcac cgaggcccgg cggcgctgcg accgcgacag ccgctgcaac ctggcgctga   960
gccgctacct gacctactgc ggcaaagtct tcaacgggct gcgctgcacg gacgaatgcc  1020
gcaccgtcat tgaggacatg ctggctatgc ccaaggtggc gctgctcaac gactgcgtgt  1080
gcgacggcct cgagcggccc atctgcgagt cggtcaagga gaacatggcc cgcctgtgct  1140
tcggcgccga gctgggcaac ggccccggca gcagcggctc ggacgggggc ctggacgact  1200
actacgatga ggactacgat gacgagcagc gcaccggggg cgcgggtggt gagcagccgc  1260
tggacgacga cgacggcgtc ccgcacccac cgcgcccggg cagcggcgct gctgcatcgg  1320
gcggccgcgg ggacctgccc tatgggcctg ggcgcaggag cagcggcggc ggcggccgct  1380
tggcgccccg gggcgcctgg accccactcg cctccatctt gctgctgctg cttgggccgc  1440
tcttttagcc ctcgcgcccc cgccgttgg ctgcgggaga gcccgcgtcc cactcccgtg   1500
ctcgcctcga ccccgcgccg ggcacctgtg gcttgggaca gatagaaggg atggttgggg  1560
```

FIGURE 7G-2

```
atacttccca aaacttttc caagtcaact tggtgtagcc ggttccccgg ccacgactct   1620
gggcacttcc cctgaagctc ctctccggag cttgacttct tggacctcct ccccgcccc   1680
aattccaagc tccagaaact cccaactcgt ctgccgtcca gaaagctagc tgcagtgttc   1740
aggacgtccg ggaggaagca agcatgtggg ggacagaaca gtagtcctgg actcgaaagg   1800
gaaggtgctg accagtgggg ccttagcaat ttgaagggtt gggaaggagg aattatattt   1860
gcaaaggggc tgtctattag catatttcct ttgaggggggc aaaaaaagt gccagtatcg   1920
acttttacag attgtggcca gtgaggatat tataatccta tgtaaacaga aagtcccac    1980
ttaccgattc attctttcac tgtttgtatc tgcgcccaga attctcagtg acgtgggggt   2040
gagggtgggt ggcgattgcc ttagagggaa cccctaaatt ggttttggat aagtttgagc   2100
ccttgacctt aatttcattg ctaccactct gatctcttag cacatttctt aggattaagg   2160
gtccaaaaat gctgatctaa ggggttgcca tggtgttgaa caatgcaact ttttatttaa   2220
aaaagctctg cactgccatg tatgaaagtc tctttatgat gtttgttttt ttgtcatttt   2280
tgttctttac atcaagaaat tttatgttta aatatgcgga gaatgtatat tgcctctgct   2340
cctatcaggg ttgctaaacc ctggtacatc gtatataaaa tgtattaaaa ctggggtttg   2400
ttaccagttg ctgtactttg tatatagaat ttttataaat tgtatgcttc agaaataatt   2460
tatttttaaa aagaaattaa aagttttaaa ctcacatcca tattacacct ttcccccctg   2520
aaatgtatag aatccatttg tcatcaggaa tcaaaaccca cagtccattg tgaagtgtgc   2580
tatatttaga acagtcttaa aatgtacagt gtatttata gaattgaagt taacattctt    2640
attttcaaga gaatttatgg acgttgtaga aatgtacaaa tgcatttcca aactgcctta   2700
aacgttgtat ttttatagac atgttttttt aaaaatccta agttttaaa taactatgga    2760
tttgtgtatt ttttttggtt atttgtttta ttaaaacatg tacatcagta aagagtttta   2820
aacaatga    2828
```

FIGURE 7H

SEQ ID NO:32
U52101    Human YMP
          CDS 50...541

```
ccgactccag ctctgacttt tttcgcggct ctcggcttcc actgcagcca tgtcactcct  60
cttgctggtg gtctcagccc ttcacatcct cattcttata ctgcttttcg tggccacttt  120
ggacaagtcc tggtggactc tccctgggaa agagtccctg aatctctggt acgactgcac  180
gtggaacaac gacaccaaaa catgggcctg cagtaatgtc agcgagaatg gctggctgaa  240
ggcggtgcag gtcctcatgg tgctctccct cattctctgc tgtctctcct tcatcctgtt  300
catgttccag ctctacacca tgcgacgagg aggtctcttc tatgccaccg gcctctgcca  360
gctttgcacc agcgtggcgg tgtttactgg cgccttgatc tatgccattc acgccgagga  420
gatcctggag aagcacccgc gaggggcag cttcggatac tgcttcgccc tggcctgggt  480
ggccttcccc ctcgccctgg tcagcggcat catctacatc cacctacgga agcgggagtg  540
agcgccgcgc ctcgctcggc tgcccccgcc ccttccgggc cccctgccg cgcgtcctcc  600
```

FIGURE 7I-1

SEQ ID NO:33
U72649      Human BTG2
            CDS 72...548

| | | | | | |
|---|---|---|---|---|---|
| cagggtaacg | ctgtcttgtg | gacccgcact | tcccacccga | gacctctcac | tgagcccgag | 60 |
| ccgcgcgcga | catgagccac | gggaagggaa | ccgacatgct | cccggagatc | gccgccgccg | 120 |
| tgggcttcct | ctccagcctc | ctgaggaccc | ggggctgcgt | gagcgagcag | aggcttaagg | 180 |
| tcttcagcgg | ggcgctccag | gaggcactca | cagagcacta | caaacaccac | tggtttcccg | 240 |
| aaaagccgtc | caagggctcc | ggctaccgct | gcattcgcat | caaccacaag | atggacccca | 300 |
| tcatcagcag | ggtggccagc | cagatcggac | tcagccagcc | ccagctgcac | cagctgctgc | 360 |
| ccagcgagct | gaccctgtgg | gtggacccct | atgaggtgtc | ctaccgcatt | ggggaggacg | 420 |
| gctccatctg | cgtcttgtac | gaggaggccc | cactggccgc | ctcctgtggg | ctcctcacct | 480 |
| gcaagaacca | agtgctgctg | ggccggagca | gcccctccaa | gaactacgtg | atggcagtct | 540 |
| ccagctaggc | ccttccgccc | ccgccctggg | cgccgccgtg | ctcatgctgc | cgtgacaaca | 600 |
| ggccaccaca | tacctcaacc | tggggaactg | tatttttaaa | tgaagagcta | tttatatata | 660 |
| ttattttttt | ttaagaaagg | aggaaaagaa | accaaaagtt | ttttttaaga | aaaaaatcc | 720 |
| ttcaagggag | ctgcttggaa | gtggcctccc | caggtgcctt | tggagagaac | tgttgcgtgc | 780 |
| ttgagtctgt | gagccagtgt | ctgcctatag | gagggggagc | tgttaggggg | tagacctagc | 840 |
| caaggagaag | tgggagacgt | ttggctagca | ccccaggaag | atgtgagagg | gagcaagcaa | 900 |
| ggttagcaac | tgtgaacaga | gaggtcggga | tttgccctgg | gggaggaaga | gaggccaagt | 960 |
| tcagagctct | ctgtctcccc | cagccagaca | cctgcatccc | tggctcctct | attactcagg | 1020 |
| ggcattcatg | cctggactta | aacaatacta | tgttatcttt | tcttttattt | ttctaatgag | 1080 |
| gtcctgggca | gagagtgaaa | aggcctctcc | tgattcctac | tgtcctaagc | tgcttttctt | 1140 |
| gaaatcatga | cttgtttcta | attctaccct | cagggcctg | tagatgttgc | tttccagcca | 1200 |
| ggaatctaaa | gctttgggtt | ttctgagggg | gggaggaggg | aactggaggt | tattggggtt | 1260 |
| aggatggaag | ggaactctgc | acaaaacctt | tgctttgcta | gtgctgcttt | gtgtgtatgt | 1320 |
| gtggcaaata | atttgggggt | gatttgcaat | gaaattttgg | gacccaaaga | gtatccactg | 1380 |
| gggatgtttt | ttggccaaaa | ctcttccttt | tggaaccaca | tgaaagtctt | gatgctgctg | 1440 |
| ccatgatccc | tttgagaggt | ggctcaaaag | ctacagggaa | ctccaggtcc | tttattactg | 1500 |
| ccttcttttc | aaaagcacaa | ctctcctcta | accctcccct | ccccttccc | ttctggtcgg | 1560 |

FIGURE 7I-2

```
gtcatagagc taccgtattt tctaggacaa gagttctcag tcactgtgca atatgccccc 1620
tgggtcccag gagggtctgg aggaaaactg gctatcagaa cctcctgatg ccctggtggg 1680
cttagggaac catctctcct gctctccttg ggatgatggc tggctagtca gccttgcatg 1740
tattccttgg ctgaatggga gagtgcccca tgttctgcaa gactacttgg tattcttgta 1800
gggccgacac taaataaaag ccaaaccttg ggcactgttt tttctccctg gtgctcagag 1860
cacctgtggg aaaggttgct gtctgtctca gtacaatcca aatttgtcgt agacttgtgc 1920
aatatatact gttgtgggtt ggagaaaagt ggaaagctac actgggaaga aactcccttc 1980
cttcaatttc tcagtgacat tgatgagggg tcctcaaaag acctcgagtt tcccaaaccg 2040
aatcaccttga agaaggacag ggctagggca tttggccagg atggccaccc tcctgctgtt 2100
gccccttagt gaggaatctt cacccccactt cctctacccc caggttctcc tccccacagc 2160
cagtccccttt cctggatttt ctaaactgct caattttgac tcaaaggtgc tatttaccaa 2220
acactctccc tacccattcc tgccagctct gcctcctttt caactctcca catttttgtat 2280
tgccttccca gacctgcttc cagtctttat tgctttaaag ttcactttgg gcccacagac 2340
ccaagagcta attttctggt ttgtgggttg aaacaaagct gtgaatcact gcaggctgtg 2400
ttcttgcatc ttgtctgcaa acaggtccct gccttttag aagcagcctc atggtctcat 2460
gcttaatctt gtctctcttc tcttctttat gatgttcact ttaaaaacaa caaaacccct 2520
gagctggact gttgagcagg cctgtctctc ctattaagta aaataaata gtagtagtat 2580
gtttgtaagc tattctgaca gaaagacaa aggttactaa ttgtatgata gtgtttttat 2640
atggaagaat gtacagctta tggacaaatg tacaccttttt gttacttta ataaaaatgt 2700
agtaggataa aaaaaaa 2717
```

FIGURE 7J-1

SEQ ID NO:34
L36034 - Human pre-B cell stimulating factor homolog (SDF1a)
CDS 80...349

```
tctccgtcag ccgcattgcc cgctcggcgt ccggcccccg acccgtgctc gtccgcccgc    60
ccgcccgccc gcccgcgcca tgaacgccaa ggtcgtggtc gtgctggtcc tcgtgctgac   120
cgcgctctgc ctcagcgacg ggaagcccgt cagcctgagc tacagatgcc catgccgatt   180
cttcgaaagc catgttgcca gagccaacgt caagcatctc aaaattctca cactccaaa    240
ctgtgccctt cagattgtag cccggctgaa gaacaacaac agacaagtgt gcattgaccc   300
gaagctaaag tggattcagg agtacctgga gaaagcttta aacaagtaag cacaacagcc   360
aaaaaggact ttccgctaga cccactcgag gaaaactaaa accttgtgag agatgaaagg   420
gcaaagacgt gggggagggg gccttaacca tgaggaccag gtgtgtgtgt ggggtgggca   480
cattgatctg ggatcgggcc tgaggtttgc agcatttaga ccctgcattt atagcatacg   540
gtatgatatt gcagcttata ttcatccatg ccctgtacct gtgcacgttg gaactcttat   600
tactggggtt tttctaagaa agaaattgta ttatcaacag cattttcaag cagttagttc   660
cttcatgatc atcacaatca tcatcattct cattctcatt ttttaaatca acgagtactt   720
caagatctga atttggcttg tttggagcat ctcctctgct cccctgggga gtctgggcac   780
agtcaggtgg tggcttaaca gggagctgga aaagtgtcc tttcttcaga cactgaggct   840
cccgcagcag cgcccctccc aagaggaagg cctctgtggc actcagatac cgactggggc   900
tggggcgccg ccactgcctt cacctcctct ttcaaacctc agtgattggc tctgtgggct   960
ccatgtagaa gccactatta ctgggactgt ctcagagacc cctctcccag ctattcctac  1020
tctctccccg actccgagag catgcttaat cttgcttctg cttctcattt ctgtagcctg  1080
atcagcgccg caccagccgg gaagagggtg attgctgggg ctcgtgccct gcatccctct  1140
cctcccaggg cctgccccac agctcgggcc ctctgtgaga tccgtctttg gcctcctcca  1200
gaatggagct ggccctctcc tggggatgtg taatggtccc cctgcttacc cgcaaaagac  1260
aagtctttac agaatcaaat gcaattttaa atctgagagc tcgcttgagt gactgggttt  1320
gtgattgcct ctgaagccta tgtatgccat ggaggcacta acaaactctg aggtttccga  1380
aatcagaagc gaaaaaatca gtgaataaac catcatcttg ccactacccc ctcctgaagc  1440
cacagcaggg gttcaggttc caatcagaac tgttggcaag gtgacatttc catgcataga  1500
tgcgatccac agaaggtcct ggtggtattt gtaactttt gcaaggcatt ttttatata   1560
```

FIGURE 7J-2

```
tatttttgtg cacatttttt tttacgattc tttagaaaac aaatgtattt caaaatatat  1620
ttatagtcga acaagtcata tatatgaatg agagccatat gaatgtcagt agtttatact  1680
tctctattat ctcaaactac tggcaatttg taaagaaata tatatgatat ataaatgtga  1740
ttgcagcttt tcaatgttag ccacagtgta tttttttcact tgtactaaaa ttgtatcaaa  1800
tgtgacatta tatgcactag caataaaatg ctaattgttt catggta     1847
```

FIGURE 7K

SEQ ID NO:35
M36035    Human peripheral benzodiazepine receptor
          CDS 62...571

```
agtgcccttc ccggagcgtg ccctcgccgc tgagctcccc tgaacagcag ctgcagcagc    60
catggccccg ccctgggtgc ccgccatggg cttcacgctg gcgcccagcc tggggtgctt   120
cgtgggctcc cgctttgtcc acggcgaggg tctccgctgg tacgccggcc tgcagaagcc   180
ctcgtggcac ccgccccact gggtgctggg ccctgtctgg ggcacgctct actcagccat   240
ggggtacggc tcctacctgg tctggaaaga gctgggaggc ttcacagaga aggctgtggt   300
tcccctgggc ctctacactg ggcagctggc cctgaactgg gcatggcccc ccatcttctt   360
tggtgcccga caaatgggct gggccttggt ggatcctctg ctggtcagtg gggcggcggc   420
ngccactacc gtggcctggt accaggtgag cccgctggcc gcccgcctgc tctacccta   480
cctggcctgg ctggccttcg cgaccacact caactactgc gtatggcggg acaaccatgg   540
ctggcatggg ggacggcggc tgccagagtg agtgcccggc ccaccaggga ctgcagctgc   600
accagcaggt gccatcacgc ttgtgatgtg gtggccgtca cgctttcatg accactgggc   660
ctgctagtct gtcagggcct tggcccaggg gtcagcagag cttcagaggt tgccccacct   720
gagcccccac ccgggagcag tgtcctgtgc tttctgcatg cttagagcat gttcttggaa   780
catggaattt tataagctga ataaagtttt tgacttcctt t                       821
```

FIGURE 7L

SEQ ID NO:36
M38591    Homo sapiens cellular ligand of annexin II (p11)
          CDS 113...405

```
agaatacact cacaagccac tccgctgctc gcctctccgc cccgcgtcca gctcgcccag  60
ctcgcccagc gtccgccgcg cctcgccaag gcttcaacgg accacaccaa aatgccatct  120
caaatggaac acgccatgga aaccatgatg tttacatttc acaaattcgc tggggataaa  180
ggctacttaa caaggagga cctgagagta ctcatggaaa aggagttccc tggattttg   240 gaaaatcaaa aagaccctct ggctgtggac aaaataatga aggacctgga ccagtgtaga  300
gatggcaaag tgggcttcca gagcttcttt tccctaattg cgggcctcac cattgcatgc  360
aatgactatt ttgtagtaca catgaagcag aagggaaaga agtaggcaga atgagcagt   420 tcgctcctcc ctgataagag ttgtccaaag ggtcgcttaa ggaatctgcc ccacagcttc  480
ccccatagaa ggatttcatg agcagatcag gacacttagc aaatgtaaaa ataaaatcta  540
actctcattt gacaagcaga gaaagaaaag ttaaatacca gataagcttt tgattttgt   600 attgtttgca tccccttgcc ctcaataaat aaagttcttt tttagttcc              649
```

FIGURE 8A

SEQ ID NO:37
X57352   Human 1-8U gene from interferon inducible gene family
         CDS   238...639

```
                                    10                                              20
Met Ser His Thr Val Gln Thr Phe Phe Ser Pro Val Asn Ser Gly Gln Pro Pro Asn Tyr
                                    30                                              40
Glu Met Leu Lys Glu Glu His Glu Val Ala Val Leu Gly Gly Pro His Asn Pro Ala Pro
                                    50                                              60
Pro Thr Ser Thr Val Ile His Ile Arg Ser Glu Thr Ser Val Pro Asp His Val Val Trp
                                    70                                              80
Ser Leu Phe Asn Thr Leu Phe Met Asn Pro Cys Cys Leu Gly Phe Ile Ala Phe Ala Tyr
                                    .90                                            100
Ser Val Lys Ser Arg Asp Arg Lys Met Val Gly Asp Val Thr Gly Ala Gln Ala Tyr Ala
                                    110                                            120
Ser Thr Ala Lys Cys Leu Asn Ile Trp Ala Leu Ile Leu Gly Ile Leu Met Thr Ile Leu
                                    130         133
Leu Ile Val Ile Pro Val Leu Ile Phe Gln Ala Tyr Gly
```

FIGURE 8B

SEQ ID NO:38
S75725    Human prostacyclin-stimulating factor
          CDS 23...871

```
                                      10                                          20
Met Glu Arg Pro Ser Leu Arg Ala Leu Leu Leu Gly Ala Ala Gly Leu Leu Leu Leu Leu
                                      30                                          40
Leu Pro Leu Ser Ser Ser Ser Ser Ser Asp Thr Cys Gly Pro Cys Glu Pro Ala Ser Cys
                                      50                                          60
Pro Pro Leu Pro Pro Leu Gly Cys Leu Leu Gly Glu Thr Arg Asp Ala Cys Gly Cys Cys
                                      70                                          80
Pro Met Cys Ala Arg Gly Glu Gly Glu Pro Cys Gly Gly Gly Gly Ala Gly Arg Gly Tyr
                                      90                                         100
Cys Ala Pro Gly Met Glu Cys Val Lys Ser Arg Lys Arg Arg Lys Gly Lys Ala Gly Ala
                                     110                                         120
Ala Ala Gly Gly Pro Gly Val Ser Gly Val Cys Val Cys Lys Ser Arg Tyr Pro Val Cys
                                     130                                         140
Gly Ser Asp Gly Thr Thr Tyr Pro Ser Gly Cys Gln Leu Arg Ala Ala Ser Gln Arg Ala
                                     150                                         160
Glu Ser Arg Gly Glu Lys Ala Ile Thr Gln Val Ser Lys Gly Thr Cys Glu Gln Gly Pro
                                     170                                         180
Ser Ile Val Thr Pro Pro Lys Asp Ile Trp Asn Val Thr Gly Ala Gln Val Tyr Leu Ser
                                     190                                         200
Cys Glu Val Ile Gly Ile Pro Thr Pro Val Leu Ile Trp Asn Lys Val Lys Arg Gly His
                                     210                                         220
Tyr Gly Val Gln Arg Thr Glu Leu Leu Pro Gly Asp Arg Asp Asn Leu Ala Ile Gln Thr
                                     230                                         240
Arg Gly Gly Pro Glu Lys His Glu Val Thr Gly Trp Val Leu Val Ser Pro Leu Ser Lys
                                     250                                         260
Glu Asp Ala Gly Glu Tyr Glu Cys His Ala Ser Asn Ser Gln Gly Gln Ala Ser Ala Ser
                                     270                                         280
Ala Lys Ile Thr Val Val Asp Ala Leu His Glu Ile Pro Val Lys Lys Gly Glu Gly Ala
    282
Glu Leu
```

FIGURE 8C-1

SEQ ID NO:39
D13665    Human osf-2
         CDS  28...2367

```
             10                                              20
Met Ile Pro Phe Leu Pro Met Phe Ser Leu Leu Leu Leu Ile Val Asn Pro Ile Asn
             30                                              40
Ala Asn Asn His Tyr Asp Lys Ile Leu Ala His Ser Arg Ile Arg Gly Arg Asp Gln Gly
             50                                              60
Pro Asn Val Cys Ala Leu Gln Gln Ile Leu Gly Thr Lys Lys Lys Tyr Phe Ser Thr Cys
             70                                              80
Lys Asn Trp Tyr Lys Lys Ser Ile Cys Gly Gln Lys Thr Thr Val Leu Tyr Glu Cys Cys
             90                                             100
Pro Gly Tyr Met Arg Met Glu Gly Met Lys Gly Cys Pro Ala Val Leu Pro Ile Asp His
            110                                             120
Val Tyr Gly Thr Leu Gly Ile Val Gly Ala Thr Thr Thr Gln Arg Tyr Ser Asp Ala Ser
            130                                             140
Lys Leu Arg Glu Glu Ile Glu Gly Lys Gly Ser Phe Thr Tyr Phe Ala Pro Ser Asn Glu
            150                                             160
Ala Trp Asp Asn Leu Asp Ser Asp Ile Arg Arg Gly Leu Glu Ser Asn Val Asn Val Glu
            170                                             180
Leu Leu Asn Ala Leu His Ser His Met Ile Asn Lys Arg Met Leu Thr Lys Asp Leu Lys
            190                                             200
Asn Gly Met Ile Ile Pro Ser Met Tyr Asn Asn Leu Gly Leu Phe Ile Asn His Tyr Pro
            210                                             220
Asn Gly Val Val Thr Val Asn Cys Ala Arg Ile Ile His Gly Asn Gln Ile Ala Thr Asn
            230                                             240
Gly Val Val His Val Ile Asp Arg Val Leu Thr Gln Ile Gly Thr Ser Ile Gln Asp Phe
            250                                             260
Ile Glu Ala Glu Asp Asp Leu Ser Ser Phe Arg Ala Ala Ala Ile Thr Ser Asp Ile Leu
            270                                             280
Glu Ala Leu Gly Arg Asp Gly His Phe Thr Leu Phe Ala Pro Thr Asn Glu Ala Phe Glu
            290                                             300
Lys Leu Pro Arg Gly Val Leu Glu Arg Phe Met Gly Asp Lys Val Ala Ser Glu Ala Leu
            310                                             320
Met Lys Tyr His Ile Leu Asn Thr Leu Gln Cys Ser Glu Ser Ile Met Gly Gly Ala Val
            330                                             340
Phe Glu Thr Leu Glu Gly Asn Thr Ile Glu Ile Gly Cys Asp Gly Asp Ser Ile Thr Val
            350                                             360
Asn Gly Ile Lys Met Val Asn Lys Lys Asp Ile Val Thr Asn Asn Gly Val Ile His Leu
            370                                             380
Ile Asp Gln Val Leu Ile Pro Asp Ser Ala Lys Gln Val Ile Glu Leu Ala Gly Lys Gln
            390                                             400
Gln Thr Thr Phe Thr Asp Leu Val Ala Gln Leu Gly Leu Ala Ser Ala Leu Arg Pro Asp
            410                                             420
Gly Glu Tyr Thr Leu Leu Ala Pro Val Asn Asn Ala Phe Ser Asp Asp Thr Leu Ser Met
```

FIGURE 8C-2

```
                              430                                          440
Val Gln Arg Leu Leu Lys Leu Ile Leu Gln Asn His Ile Leu Lys Val Lys Val Gly Leu
                              450                                          460
Asn Glu Leu Tyr Asn Gly Gln Ile Leu Glu Thr Ile Gly Gly Lys Gln Leu Arg Val Phe
                              470                                          480
Val Tyr Arg Thr Ala Val Cys Ile Glu Asn Ser Cys Met Glu Lys Gly Ser Lys Gln Gly
                              490                                          500
Arg Asn Gly Ala Ile His Ile Phe Arg Glu Ile Ile Lys Pro Ala Glu Lys Ser Leu His
                              510                                          520
Glu Lys Leu Lys Gln Asp Lys Arg Phe Ser Thr Phe Leu Ser Leu Leu Glu Ala Ala Asp
                              530                                          540
Leu Lys Glu Leu Leu Thr Gln Pro Gly Asp Trp Thr Leu Phe Val Pro Thr Asn Asp Ala
                              550                                          560
Phe Lys Gly Met Thr Ser Glu Glu Lys Glu Ile Leu Ile Arg Asp Lys Asn Ala Leu Gln
                              570                                          580
Asn Ile Ile Leu Tyr His Leu Thr Pro Gly Val Phe Ile Gly Lys Gly Phe Glu Pro Gly
                              590                                          600
Val Thr Asn Ile Leu Lys Thr Thr Gln Gly Ser Lys Ile Phe Leu Lys Glu Val Asn Asp
                              610                                          620
Thr Leu Leu Val Asn Glu Leu Lys Ser Lys Glu Ser Asp Ile Met Thr Thr Asn Gly Val
                              630                                          640
Ile His Val Val Asp Lys Leu Leu Tyr Pro Ala Asp Thr Pro Val Gly Asn Asp Gln Leu
                              650                                          660
Leu Glu Ile Leu Asn Lys Leu Ile Lys Tyr Ile Gln Ile Lys Phe Val Arg Gly Ser Thr
                              670                                          680
Phe Lys Glu Ile Pro Val Thr Val Tyr Lys Pro Ile Ile Lys Lys Tyr Thr Lys Ile Ile
                              690                                          700
Asp Gly Val Pro Val Glu Ile Thr Glu Lys Glu Thr Arg Glu Glu Arg Ile Ile Thr Gly
                              710                                          720
Pro Glu Ile Lys Tyr Thr Arg Ile Ser Thr Gly Gly Gly Glu Thr Glu Glu Thr Leu Lys
                              730                                          740
Lys Leu Leu Gln Glu Glu Val Thr Lys Val Thr Lys Phe Ile Glu Gly Gly Asp Gly His
                              750                                          760
Leu Phe Glu Asp Glu Glu Ile Lys Arg Leu Leu Gln Gly Asp Thr Pro Val Arg Lys Leu
                              770                                          779
Gln Ala Asn Lys Lys Val Gln Gly Ser Arg Arg Arg Leu Arg Glu Gly Arg Ser Gln
```

FIGURE 8D

SEQ ID NO:40
X67698      Human tissue specific mRNA
            CDS 11...466

```
                              10                                        20
Met Arg Phe Leu Ala Ala Thr Phe Leu Leu Ala Leu Ser Thr Ala Ala Gln Ala Glu
                              30                                        40
Pro Val Gln Phe Lys Asp Cys Gly Ser Val Asp Gly Val Ile Lys Glu Val Asn Val Ser
                              50                                        60
Pro Cys Pro Thr Gln Pro Cys Gln Leu Ser Lys Gly Gln Ser Tyr Ser Val Asn Val Thr
                              70                                        80
Phe Thr Ser Asn Ile Gln Ser Lys Ser Lys Ala Val Val His Gly Ile Leu Met Gly
                              90                                       100
Val Pro Val Pro Phe Pro Ile Pro Glu Pro Asp Gly Cys Lys Ser Gly Ile Asn Cys Pro
                             110                                       120
Ile Gln Lys Asp Lys Thr Tyr Ser Tyr Leu Asn Lys Leu Pro Val Lys Ser Glu Tyr Pro
                             130                                       140
Ser Ile Lys Leu Val Val Glu Trp Gln Leu Gln Asp Asp Lys Asn Gln Ser Leu Phe Cys
                             151
Trp Glu Ile Pro Val Gln Ile Val Ser His Leu
```

FIGURE 8E

SEQ ID NO:41
M62402    Human insulin-like growth factor binding protein 6
          CDS 54...776

```
                                        10                                          20
Met Thr Pro His Arg Leu Leu Pro Pro Leu Leu Leu Leu Leu Ala Leu Leu Leu Ala Ala 30                                          40
Ser Pro Gly Gly Ala Leu Ala Arg Cys Pro Gly Cys Gly Gln Gly Val Gln Ala Gly Cys 50                                          60
Pro Gly Gly Cys Val Glu Glu Glu Asp Gly Gly Ser Pro Ala Glu Gly Cys Ala Glu Ala 70                                          80
Glu Gly Cys Leu Arg Arg Glu Gly Gln Glu Cys Gly Val Tyr Thr Pro Asn Cys Ala Pro 90                                         100
Gly Leu Gln Cys His Pro Pro Lys Asp Asp Glu Ala Pro Leu Arg Ala Leu Leu Leu Gly 110                                         120
Arg Gly Arg Cys Leu Pro Ala Arg Ala Pro Ala Val Ala Glu Glu Asn Pro Lys Glu Ser 130                                         140
Lys Pro Gln Ala Gly Thr Ala Arg Pro Gln Asp Val Asn Arg Arg Asp Gln Gln Arg Asn 150                                         160
Pro Gly Thr Ser Thr Thr Pro Ser Gln Pro Asn Ser Ala Gly Val Gln Asp Thr Glu Met 170                                         180
Gly Pro Cys Arg Arg His Leu Asp Ser Val Leu Gln Gln Leu Gln Thr Glu Val Tyr Arg 190                                         200
Gly Ala Gln Thr Leu Tyr Val Pro Asn Cys Asp His Arg Gly Phe Tyr Arg Lys Arg Gln 210                                         220
Cys Arg Ser Ser Gln Gly Gln Arg Arg Gly Pro Cys Trp Cys Val Asp Arg Met Gly Lys 230                                         240
Ser Leu Pro Gly Ser Pro Asp Gly Asn Gly Ser Ser Ser Cys Pro Thr Gly Ser Ser Gly
```

FIGURE 8F

SEQ ID NO:42
D90226   Human OSF-1
         CDS 125...631

```
                             10                                          20
Met Gln Ala Gln Gln Tyr Gln Gln Gln Arg Arg Lys Phe Ala Ala Ala Phe Leu Ala Phe
                             30                                          40
Ile Phe Ile Leu Ala Ala Val Asp Thr Ala Glu Ala Gly Lys Lys Glu Lys Pro Glu Lys
                             50                                          60
Lys Val Lys Lys Ser Asp Cys Gly Glu Trp Gln Trp Ser Val Cys Val Pro Thr Ser Gly
                             70                                          80
Asp Cys Gly Leu Gly Thr Arg Glu Gly Thr Arg Thr Gly Ala Glu Cys Lys Gln Thr Met
                             90                                         100
Lys Thr Gln Arg Cys Lys Ile Pro Cys Asn Trp Lys Lys Gln Phe Gly Ala Glu Cys Lys
                            110                                         120
Tyr Gln Phe Gln Ala Trp Gly Glu Cys Asp Leu Asn Thr Ala Leu Lys Thr Arg Thr Gly
                            130                                         140
Ser Leu Lys Arg Ala Leu His Asn Ala Glu Cys Gln Lys Thr Val Thr Ile Ser Lys Pro
                            150                                         160
Cys Gly Lys Leu Thr Lys Pro Lys Pro Gln Ala Glu Ser Lys Lys Lys Lys Glu Gly
                            168
Lys Lys Gln Glu Lys Met Leu Asp
```

FIGURE 8G

SEQ ID NO:43
L13698    Human gas-1
          CDS 411...1448

```
                              10                                              20
Met Val Ala Ala Leu Leu Gly Gly Gly Gly Glu Ala Arg Gly Gly Thr Val Pro Gly Ala
                              30                                              40
Trp Leu Cys Leu Met Ala Leu Leu Gln Leu Leu Gly Ser Ala Pro Arg Gly Ser Gly Leu
                              50                                              60
Ala His Gly Arg Arg Leu Ile Cys Trp Gln Ala Leu Leu Gln Cys Gln Gly Glu Pro Glu
                              70                                              80
Cys Ser Tyr Ala Tyr Asn Gln Tyr Ala Glu Ala Cys Ala Pro Val Leu Ala Gln His Gly
                              90                                             100
Gly Gly Asp Ala Pro Gly Ala Ala Ala Ala Phe Pro Ala Ser Ala Ala Ser Phe Ser
                             110                                             120
Ser Arg Trp Arg Cys Pro Ser His Cys Ile Ser Ala Leu Ile Gln Leu Asn His Thr Arg
                             130                                             140
Arg Gly Pro Ala Leu Glu Asp Cys Asp Cys Ala Gln Asp Glu Asn Cys Lys Ser Thr Lys
                             150                                             160
Arg Ala Ile Glu Pro Cys Leu Pro Arg Thr Ser Gly Gly Gly Ala Gly Gly Pro Gly Ala
                             170                                             180
Gly Gly Val Met Gly Cys Thr Glu Ala Arg Arg Arg Cys Asp Arg Asp Ser Arg Cys Asn
                             190                                             200
Leu Ala Leu Ser Arg Tyr Leu Thr Tyr Cys Gly Lys Val Phe Asn Gly Leu Arg Cys Thr
                             210                                             220
Asp Glu Cys Arg Thr Val Ile Glu Asp Met Leu Ala Met Pro Lys Val Ala Leu Leu Asn
                             230                                             240
Asp Cys Val Cys Asp Gly Leu Glu Arg Pro Ile Cys Glu Ser Val Lys Glu Asn Met Ala
                             250                                             260
Arg Leu Cys Phe Gly Ala Glu Leu Gly Asn Gly Pro Gly Ser Ser Gly Ser Asp Gly Gly
                             270                                             280
Leu Asp Asp Tyr Tyr Asp Glu Asp Tyr Asp Asp Glu Gln Arg Thr Gly Gly Ala Gly Gly
                             290                                             300
Glu Gln Pro Leu Asp Asp Asp Asp Gly Val Pro His Pro Pro Arg Pro Gly Ser Gly Ala
                             310                                             320
Ala Ala Ser Gly Gly Arg Gly Asp Leu Pro Tyr Gly Pro Gly Arg Arg Ser Ser Gly Gly
                             330                                             340
Gly Gly Arg Leu Ala Pro Arg Gly Ala Trp Thr Pro Leu Ala Ser Ile Leu Leu Leu Leu
           345
Leu Gly Pro Leu Phe
```

FIGURE 8H

SEQ ID NO:44
U52101     Human YMP
            CDS 50...541

```
                                  10                                      20
Met Ser Leu Leu Leu Leu Val Val Ser Ala Leu His Ile Leu Ile Leu Ile Leu Leu Phe
                                  30                                      40
Val Ala Thr Leu Asp Lys Ser Trp Trp Thr Leu Pro Gly Lys Glu Ser Leu Asn Leu Trp
                                  50                                      60
Tyr Asp Cys Thr Trp Asn Asn Asp Thr Lys Thr Trp Ala Cys Ser Asn Val Ser Glu Asn
                                  70                                      80
Gly Trp Leu Lys Ala Val Gln Val Leu Met Val Leu Ser Leu Ile Leu Cys Cys Leu Ser
                                  90                                     100
Phe Ile Leu Phe Met Phe Gln Leu Tyr Thr Met Arg Arg Gly Gly Leu Phe Tyr Ala Thr
                                 110                                     120
Gly Leu Cys Gln Leu Cys Thr Ser Val Ala Val Phe Thr Gly Ala Leu Ile Tyr Ala Ile
                                 130                                     140
His Ala Glu Glu Ile Leu Glu Lys His Pro Arg Gly Gly Ser Phe Gly Tyr Cys Phe Ala
                                 150                                     160
Leu Ala Trp Val Ala Phe Pro Leu Ala Leu Val Ser Gly Ile Ile Tyr Ile His Leu Arg
            163
Lys Arg Glu
```

FIGURE 81

SEQ ID NO:45
U72649    Human BTG2
          CDS  72...548

```
                                   10                                          20
Met Ser His Gly Lys Gly Thr Asp Met Leu Pro Glu Ile Ala Ala Ala Val Gly Phe Leu
                                   30                                          40
Ser Ser Leu Leu Arg Thr Arg Gly Cys Val Ser Glu Gln Arg Leu Lys Val Phe Ser Gly
                                   50                                          60
Ala Leu Gln Glu Ala Leu Thr Glu His Tyr Lys His His Trp Phe Pro Glu Lys Pro Ser
                                   70                                          80
Lys Gly Ser Gly Tyr Arg Cys Ile Arg Ile Asn His Lys Met Asp Pro Ile Ile Ser Arg
                                   90                                         100
Val Ala Ser Gln Ile Gly Leu Ser Gln Pro Gln Leu His Gln Leu Leu Pro Ser Glu Leu
                                  110                                         120
Thr Leu Trp Val Asp Pro Tyr Glu Val Ser Tyr Arg Ile Gly Glu Asp Gly Ser Ile Cys
                                  130                                         140
Val Leu Tyr Glu Glu Ala Pro Leu Ala Ala Ser Cys Gly Leu Leu Thr Cys Lys Asn Gln
                                  150                                      158
Val Leu Leu Gly Arg Ser Ser Pro Ser Lys Asn Tyr Val Met Ala Val Ser Ser
```

FIGURE 8J

SEQ ID NO:46
L36034      Human pre-B cell stimulating factor homolog (SDF1a)
            CDS 80...349

```
                                10                                      20
Met Asn Ala Lys Val Val Val Val Leu Val Leu Val Leu Thr Ala Leu Cys Leu Ser Asp
                                30                                      40
Gly Lys Pro Val Ser Leu Ser Tyr Arg Cys Pro Cys Arg Phe Phe Glu Ser His Val Ala
                                50                                      60
Arg Ala Asn Val Lys His Leu Lys Ile Leu Asn Thr Pro Asn Cys Ala Leu Gln Ile Val
                                70                                      80
Ala Arg Leu Lys Asn Asn Asn Arg Gln Val Cys Ile Asp Pro Lys Leu Lys Trp Ile Gln
                        89
Glu Tyr Leu Glu Lys Ala Leu Asn Lys
```

FIGURE 8K

SEQ ID NO:47
M36035    Human peripheral benzodiazepine receptor
         CDS 62...571

```
                                    10                                          20
Met Ala Pro Pro Trp Val Pro Ala Met Gly Phe Thr Leu Ala Pro Ser Leu Gly Cys Phe
                                    30                                          40
Val Gly Ser Arg Phe Val His Gly Glu Gly Leu Arg Trp Tyr Ala Gly Leu Gln Lys Pro
                                    50                                          60
Ser Trp His Pro Pro His Trp Val Leu Gly Pro Val Trp Gly Thr Leu Tyr Ser Ala Met
                                    70                                          80
Gly Tyr Gly Ser Tyr Leu Val Trp Lys Glu Leu Gly Gly Phe Thr Glu Lys Ala Val Val
                                    90                                         100
Pro Leu Gly Leu Tyr Thr Gly Gln Leu Ala Leu Asn Trp Ala Trp Pro Pro Ile Phe Phe
                                   110                                         120
Gly Ala Arg Gln Met Gly Trp Ala Leu Val Asp Leu Leu Leu Val Ser Gly Ala Ala Ala
                                   130                                         140
Ala Thr Thr Val Ala Trp Tyr Gln Val Ser Pro Leu Ala Ala Arg Leu Leu Tyr Pro Tyr
                                   150                                         160
Leu Ala Trp Leu Ala Phe Ala Thr Thr Leu Asn Tyr Cys Val Trp Arg Asp Asn His Gly
                       169
Trp His Gly Gly Arg Arg Leu Pro Glu
```

FIGURE 8L

SEQ ID NO:48
M38591    Homo sapiens cellular ligand of annexin II (p11)
          CDS  113...405

```
                              10                                      20
Met Pro Ser Gln Met Glu His Ala Met Glu Thr Met Met Phe Thr Phe His Lys Phe Ala
                              30                                      40
Gly Asp Lys Gly Tyr Leu Thr Lys Glu Asp Leu Arg Val Leu Met Glu Lys Glu Phe Pro
                              50                                      60
Gly Phe Leu Glu Asn Gln Lys Asp Pro Leu Ala Val Asp Lys Ile Met Lys Asp Leu Asp
                              70                                      80
Gln Cys Arg Asp Gly Lys Val Gly Phe Gln Ser Phe Phe Ser Leu Ile Ala Gly Leu Thr
                              90                          97
Ile Ala Cys Asn Asp Tyr Phe Val Val His Met Lys Gln Lys Gly Lys Lys
```

FIGURE 9

| | Human Match | cDNA Size (nt) | CDS | Protein Size (aa) | Signal | TM |
|---|---|---|---|---|---|---|
| X57352 | Human 1-8U gene from interferon inducible gene family | 808 | 238...639 | 133 | unlikely | Yes |
| S75725 | Human prostacyclin-stimulating factor | 1124 | 23...871 | 282 | Yes | possible |
| D13665 | Human osf-2 | 3077 | 28...2367 | 779 | Yes | unlikely |
| X67698 | Human tissue specific mRNA | 808 | 11...466 | 151 | Yes | No |
| M62402 | Human insulin-like growth factor binding protein 6 | 952 | 54...776 | 240 | Yes | No |
| D90226 | Human OSF-1 | 816 | 125...631 | 168 | Yes | No |
| L13698 | Human gas-1 | 2828 | 411...1448 | 345 | Yes | possible |
| U52101 | Human YMP | 600 | 50...541 | 163 | Yes | Yes 3 TM |
| U72649 | Human BTG2 | 2717 | 72...548 | 158 | Yes | unlikely |
| L36034 | Human pre-B cell stimulating factor homolog (SDF1a) | 1847 | 80...349 | 89 | Yes | No |
| M36035 | Human peripheral benzodiazepine receptor | 821 | 62...571 | 169 | Yes | possible |
| M38591 | Homo sapiens cellular ligand of annexin II (p11) | 649 | 112...405 | 97 | No | possible |

METHODS FOR DETECTION AND USE OF DIFFERENTIALLY EXPRESSED GENES IN DISEASE STATES

This application claims the priority under 35 U.S.C. § 119(e) of U.S. provisional application 60/113,008 filed on Dec. 18, 1998.

I. INTRODUCTION

The present invention relates to methods and compositions for the detection, diagnosis, prevention and treatment of disease states and related disorders. The disease states of the present invention include cardiac, kidney and inflammatory disease. Specifically, genes that are differentially expressed in the cells, tissues, or peripheral blood of a subject suffering from, or predisposed to, such disease states may be identified through the methods of the present invention.

The present invention also relates to compositions and methods useful in the diagnosis, prevention and therapeutic treatment of disease states through the use of the differentially expressed genes of the present invention. Methods and compositions are provided for the diagnostic evaluation and prognosis of conditions involving such disease states, for the identification of subjects exhibiting a predisposition to such conditions, for therapeutic uses, e.g., modulating the effect of such differentially expressed genes, for monitoring subjects undergoing clinical evaluation for the prevention and treatment of a disease and its disorders, and for monitoring the efficacy of compounds used in clinical trials.

II. BACKGROUND OF THE INVENTION

The present invention relates generally to methods and compositions for the detection, diagnosis, prevention and treatment of a disease, specifically cardiac, kidney or inflammatory disease, and related disorders. Particularly, the present invention relates to methods useful in diagnosing, identifying, monitoring, preventing, and treating the onset and progression of such disease states through the use of genes and gene products differentially expressed in a disease, specifically cardiac, kidney or inflammatory disease, along with modulators thereof.

By way of example, congestive heart failure (CHF) is a major cardiac disease associated with extensive morbidity and mortality. Traditionally, CHF has been treated by a series of agents including diuretics, vasodilators, angiotensin converting enzyme inhibitors, β-adrenergic antagonists, and positive inotropes like digoxin. These drugs, however, principally provide symptomatic relief and typically only extend the life of one suffering from the disease for periods ranging from 6–12 months.

In response to hormonal, physiological, hemodynamic and pathological stimuli, adult ventricular muscle cells can adapt to increased workloads through the activation of a hypertrophic process. This process is characterized by an increase in the contractile protein content of cardiac muscle cells without a proliferative response because the adult cardiomyocyte is terminally differentiated and has lost its ability to divide. Cardiac growth during the hypertrophic process therefore results primarily from an increase in protein content per individual cardiomyocyte, with little or no change in cell number. The acquisition of the cardiac hypertrophic phenotype is in part dependent upon the activation of cardiac muscle gene program.

In addition to the induction of specific contractile protein components ventricular hypertrophy is also characterized by alterations in the expression of certain non-contractile proteins, such as atrial natriuretic peptide (ANP, also known as ANF). During embryonic development, the ANP gene is expressed in both the atrium and the ventricle. However, shortly after birth ANP expression is down regulated in the ventricle and expression is mainly confined to the atrium. Following induction of hypertrophy, ANP is reexpressed in the ventriculum. Thus, ANP expression can be considered to be a non-contractile protein marker of cardiac ventricular hypertrophy.

Ventricular hypertrophy is initially a compensatory mechanism by which the heart is attempting to counteract the effects of conditions like pressure overload, loss of contractile tissue, obstruction of blood flow, or increased peripheral demand for blood flow, all of which can be generated by a variety of physiological or pathological stimuli. In some circumstances, such as, injury or functional compromise of the heart, a typically short term, compensated hypertrophic response is desirable. Similarly, cardiac, e.g. left ventricular, hypertrophy (physiological hypertrophy) is often observed in some highly trained athletes, without any apparent cardiovascular complications. However, under some circumstances the hypertrophic response may eventually contribute to cardiac dysfunction. These circumstances include, but are not limited to, excessive hypertrophy, prolonged hypertrophy, or hypertrophy occurring in the context of toxic factors or toxic concentrations of factors that, when combined with the hypertrophic response of cardiac myocytes, result in mechanical dysfunction, electrical conduction dysfunction, loss of cardiac wall elasticity, or stimulation of fibrosis. In these cases hypertrophy is termed decompensated hypertrophy, and antagonism of cardiac hypertrophy is considered desirable. Once the transition from compensated to decompensated hypertrophy is achieved, the progression to a terminal heart failure phenotype often rapidly follows.

Heart failure affects approximately five million Americans. New cases of heart failure number about 400,000 each year. The pathophysiology of CHF is rather complex. Generally, the central hallmark of the disease is the inability of the heart to pump sufficient oxygenated blood to meet the demands of peripheral tissues. Numerous etiologies contribute to the development of CHF, including primary diseases of, or insults to, the myocardium itself, cardiac defects, hypertension, inflammation, kidney disease and vascular disease. These conditions lead to the hypertrophy and remodeling of the cardiac ventricles which, if unchecked, ultimately reduce the mechanical performance of the heart. Forces associated with the inability of the heart to pump blood ultimately lead to the release of neurohormones like catecholamines, renin-angiotensin, aldosterone, endothelin and related factors into the circulation. It has been demonstrated that elevations in plasma levels of many of these circulating neurohormones have a deleterious impact on the outcome of patients with CHF. Local production of these neurohormonal factors in the heart is believed to contribute centrally to the disease. Thus, an important therapeutic strategy has been to block this neurohormonal axis contributing to the pathogenesis of this disease.

Factors known to contribute centrally to the pathophysiology of heart disease are biosynthesized in the heart itself. These factors are produced in cardiac myocytes, fibroblasts, smooth muscle and endothelial cells, and inflammatory cells associated with the myocardium. For example, the heart has been shown to contain its own renin-angiotensin system. Blockade of the cardiac renin-angiotensin system is believed to contribute significantly to the therapeutic efficacy of the therapeutic class of agents known as angiotensin converting enzyme (ACE) inhibitors.

The heart also produces other factors including, but not limited to, endothelins, bradykinin, adrenomedullin, tumor necrosis factor, transforming growth factors, and natriuretic peptides. Unfortunately, therapeutic strategies are limited to the modulation of such substances, which are already known to contribute to the disease. Indeed, it is estimated that the functional contributions of only a minor fraction of all known secreted factors encoded by the human genome have been defined. Thus, it would be beneficial to discover differentially expressed genes related to disease states, in addition to methods and compositions for the diagnostic evaluation and prognosis of conditions involving such diseases, for the identification of subjects exhibiting a predisposition to such conditions, for modulating the effect of these differentially expressed genes and their expression products, for monitoring patients undergoing clinical evaluation for the prevention and treatment of a disease, specifically cardiac, kidney or inflammatory disease, and its disorders, and for monitoring the efficacy of compounds used in clinical trials. There is a particularly great interest in trying to understand the mechanisms which induce and control ventricular hypertrophy and indeed to dissect the transition from compensated to decompensated hypertrophy.

Recent observations, for example, show that the expression of genes encoding the natriuretic peptides, Atrial Natriuretic Peptide ("ANP") and Brain Natriuretic Peptide ("BNP"), which are believed to play important cardioprotective roles in CHF, is markedly up regulated (i.e., differentially expressed) in association with the progression of CHF in animal models and humans. Levels of messenger RNAs encoding endothelin, angiotensin converting enzyme, transforming growth factor and its receptors, and adrenomedullin are all changed during the progression of cardiac disease. Indeed, the differential expression of a gene in association with a disease implicates the gene as playing a key role in the progression of the disease itself. Accordingly, a strategy aimed at the identification of genes which are differentially expressed in association with a disease, specifically cardiac, kidney or inflammatory disease, will likely elucidate expression products or other factors that can contribute to or ameliorate the symptoms of the disease state and are potential candidate targets for therapeutic modulation or which are potentially therapeutic themselves. Such genes can also contribute to methodologies for diagnosing, evaluating, preventing and treating such diseases.

The primary goal of therapy for cardiac diseases has been the relief of symptoms associated with reduced cardiac output. Although current drugs provide some improvement in cardiac output, they fail to address the underlying mechanisms that lead to heart failure. A lack of understanding of the mechanisms responsible for progressive heart failure has made it difficult to devise long term strategies for treatment. Recently, investigators have begun to examine the underlying biology of the failing heart by examining the changes in gene expression that coincide with disease progression, however, the ability to comprehensively examine gene regulation in congestive heart failure has been technologically restricted. Understanding the fundamentals of heart disease should aid in the development of new drugs which not only improve cardiac function acutely, but also lead to improvements in long term survival. This holds true for other diseases as well.

Patients with symptomatic heart failure present with shortness of breath, edema, and extreme fatigue, often leading to death. The transition to end-stage failure can occur shortly or long after initial damage. To compensate for increased load due to damage, the left ventricle undergoes a hypertrophic response, characterized by increases in size of the cardiomyocyte without cell proliferation. In addition to changes in mass, the heart tissue also remodels the cellular architecture of the cardiomyocyte, evident as alterations in sarcomeric structure and contractile fiber formation. Following initial compensatory changes, the myocardium can ultimately fail due to irreversible enlargement and dilation. To afford the cellular changes in the tissues of the remodeling heart, there are many documented molecular changes, which are controlled by changes in cardiac gene expression (Komuro el al., *Ann. Rev. Physiol.* 55:55–75 (1993)). Such changes are not, however, confined to the cardiac myocyte. As important are the alterations and remodeling of the interstitial compartment. For example, proliferation and activation of cardiac myocytes in the failing heart lead to extracellular matrix deposition, which negatively affects the contractility of the ventricle wall.

Many studies, which examine molecular and cellular changes in various diseases, have been conducted using animal models of disease states. In one model, surgical placement of a steel band around the ascending aorta causes pressure overload on the heart (Schunkert et al., *J. Clin. Invest.* 86(6):1913–20 (1990)). To compensate for the increase in pressure due to the aortic constriction, the left ventricle increases in mass via cellular hypertrophy of the cardiacmyocyte. Left ventricular hypertrophy (LVH) displayed in the banded rat is strikingly similar to human heart disease associated with hypertension or valvular disease, which expose the myocardium to prolonged pressure overload. Continued pressure overload in the rat model of LVH ultimately leads to heart failure. This represents a recapitulation of the chronic hypertensive condition observed in humans. As in humans, a compensated hypertrophic heart can maintain diastolic and systolic function, but eventually the LVH response is exhausted, and continued cell loss and fibrosis leads to a demise of the heart. The rat LVH model is well suited to examine cellular and molecular changes associated with early responses to pressure overload, long term compensation, and late stage failure.

Several groups have exploited the rat LYH model to study gene expression related to heart disease. Within an hour of pressure induction, a change in mRNA levels for certain growth response genes such as c-fos, c-myc, and hsp70 has been observed (Izumo et al., *Proc. Natl. Acad. Sci. USA* 85(2):339–43 (1988)). Induction of hypertrophy in rats responding to chronic pressure overload for 8–12 weeks is accompanied by a shift in expression of several genes from adult to fetal isoforms. This period of time is characterized by remodeling of the myofibrillary composition of the cardiomyocyte in the left ventricle. During this cellular transition, expression of adult myosin heavy chain, cardiac actin, and tropomyosin is replaced by that of isoforms typically expressed in the developing fetus (Izumo et al., supra). Others have shown that the natriuretic hormones ANP (Mercadier et al., *Am. J. Physiol.* 257(3 Pt. 2):H979–87 (1989)) and BNP (Hama et al., *Circulation* 92(6):1558–64 (1995)), and their corresponding mRNAs, are elevated in hypertrophic rat myocardium as seen in human heart disease. In addition, it has been shown that mRNA levels of calcium ATPase and phospholamban decrease (Komuro et al., supra), and angiotensin converting ACE enzyme (Schunkert et al., *J. Clin. Invest.* 96(6):2768–74 (1995)) mRNA levels increase in LVH.

Although the numerous findings on the changes in gene expression in disease are enlightening, the story is certainly incomplete. Most published works in this field have concentrated on expression analysis of a limited number of genes. For example, fewer than 100 genes have been evaluated for transcriptional control in cardiac hypertrophy, representing a small fraction of all genes expressed in the heart. It is anticipated that expression of hundreds of genes are altered in the failing heart, and their discovery could reveal additional information about fundamental aspects of cardiac biology and how the heart responds to chronic pressure overload.

Techniques have been developed to efficiently analyze the level of expression of specific genes in cells and tissues. These techniques include, but are not limited to, quantitative PCR, RNA diagnosticing, SAGE (sequential analysis of gene expression), differential display, and microarrays. The application of these techniques affords a most powerful analysis of gene expression, substantially more efficient than older methods used for this purpose. A particularly attractive method for assessing gene expression is the DNA microarray technique. In this method, nucleotide sequences of interest are plated, or arrayed, on a microchip substrate. The arrayed sequences are then hybridized with specific DNA probes from cells or tissues of interest.

A particularly important application of the microarray method allows for the assessment of differential gene expression in pairs of mRNA samples from two different tissues, or in the same tissue comparing normal versus disease states or time progression of the disease. Microarray analysis allows one to analyze the expression of known genes of interest, or for the discovery of novel genes expressed differentially in tissue pairs of interest. Thus, an attractive application of this technology is as a fundamental discovery tool to identify new genes, and their corresponding expression products, which contribute to the pathogenesis of disease and related conditions.

Microarray technology has been successfully applied to large-scale analysis of human gene expression to identify cancer-specific genes and inflammatory-specific genes (DeRisi et al., Nat. Genet. 14(4):457–60 (1996); Heller et al., Proc. Natl. Acad. Sci. USA 94(6):2150–55 (1997)). DeRisi et al. examined a pre-selected set of 870 different genes for their expression in a melanoma cell line and a non-tumorigenic version of the same cell line. The microarray analysis revealed a decrease in expression for 15/870 (1.7%) and an increase in expression for 63/870 (7.3%) of the genes in non-tumorigenic relative to tumorigenic cells (only signals <0.52 or >2.4 were deemed significant). Heller et al. employed microarrays to evaluate the expression of 1000 genes in cells taken from normal and inflamed human tissues. The results indicated that altered expression was evident in genes encoding inflammatory mediators such as IL-3, and a tissue metalloprotease. These results demonstrate the utility of applying microarray technology to complex human diseases, as described in detail supra.

In one embodiment of the present invention, genes, which are differentially expressed in association with a disease, specifically cardiac, kidney or inflammatory disease, are identified using the methods of the present invention. In a preferred embodiment, DNA microarrays are utilized to identify the genes of the present invention. The present invention emphasizes the importance of gene regulation in association with a disease, specifically cardiac, kidney or inflammatory disease. One skilled in the art, in view of the present disclosure, recognizes that the expression products of these genes have application as therapeutic agents, or targets for therapeutic modulation in a disease and its related conditions. The present invention also relates to the use of these genes, their expression products, and their modulators, in the detection, diagnosis, prevention, and treatment of disease.

Specifically, the present invention addresses deficiencies in the prior art by providing methods for identifying specific genes that are differentially expressed in subjects in response to a disease, specifically a cardiac, kidney or inflammatory disease, state, at a different level than such genes are expressed in a biological sample (e.g., cells, tissue or peripheral blood) obtained from a normal subject (i.e., a subject who is not suffering from or predisposed to the disease, e.g., a control subject). In a preferred embodiment, a disease state associated with the differentially expressed genes of the present invention may be detected, or diagnosed, by examining a blood sample rather than relying on a more invasive or less sensitive test to derive a prognosis. In addition, a subject may be monitored for disease progression, status, and response to therapies through monitoring of the expression of differentially expressed genes. Within the context of the present invention a "patient," "individual," or "subject" are interchangeable terms and may be an animal, including a laboratory animal or other animal species, or a human.

As demonstrated herein, certain differentially expressed genes and methods of identifying such genes have been applied for the detection and treatment of a disease, specifically cardiac, kidney or inflammatory disease, and related conditions. Such cardiac diseases include CHF, dilated congestive cardiomyopathy, hypertrophic cardiomyopathy, restrictive cardiomyopathy, mitral valve disease, aortic valve disease, tricuspid valve disease, angina pectoris, myocardial infarction, cardiac arrhythmia, pulmonary hypertension, arterial hypertension, renovascular hypertension, arteriosclerosis, atherosclerosis, and cardiac tumors. Such kidney diseases include acute renal failure, glomerulonephritis, chronic renal failure, azotemia, uremia, immune renal disease; acute nephritic syndrome, rapidly progressive nephritic syndrome, nephrotic syndrome, Berger's Disease, chronic nephritic/proteinuric syndrome, tubulointerstital disease, nephrotoxic disorders, renal infarction, atheroembolic renal disease, renal cortical necrosis, malignant nephroangiosclerosis, renal vein thrombosis, renal tubular acidosis, renal glucosuria, nephrogenic diabetes insipidus, Bartter's Syndrome, Liddle's Syndrome, polycystic renal disease, interstitial nephritis, acute hemolytic uremic syndrome, medullary cystic disease, medullary sponge kidney, hereditary nephritis, and nail-patella syndrome. Such inflammatory diseases include myocarditis, asthma, chronic inflammation, autoimmune diabetes, tumor angiogenesis, rheumatoid arthritis, rheumatoid spondylitis, osteoarthritis, gouty arthritis and other arthritic conditions, sepsis, septic shock, endotoxic shock, Gram-negative sepsis, toxic shock syndrome, asthma, adult respiratory distress syndrome, stroke, reperfusion injury, CNS injuries such as neural trauma and ischemia, psoriasis restenosis, cerebral malaria, chronic pulmonary inflammatory disease, silicosis, pulmonary sarcosis, bone resorption diseases such as osteoporosis, graft versus host reaction, Crohn's Disease, ulcerative colitis including inflammatory bowel disease (IBD), and pyresis.

III. SUMMARY OF THE INVENTION

As a result of functional genomic studies, we have identified a number of genes that are differentially expressed in several animal models of cardiac, kidney and/or inflammatory diseases.

Accordingly, the present invention relates to methods and compositions for the detection, diagnosis, prevention, and treatment of a disease, specifically cardiac, kidney or inflammatory disease. Specifically, genes are identified and described which are differentially expressed in cells, tissue or peripheral blood relative to normal cells, tissue or peripheral blood and/or to cells, tissue or peripheral blood at a different stage of a disease, specifically cardiac, kidney or inflammatory disease. For example, genes are identified which are differentially expressed in subjects suffering from a disease, specifically cardiac, kidney or inflammatory disease, relative to normal subjects. The modulation of the expression of the identified genes and/or the activity of the identified gene products can be utilized therapeutically to prevent or treat a disease, specifically cardiac, kidney or inflammatory disease, and related disorders. As such, methods and compositions are described for the identification of novel therapeutic compounds for the inhibition of such diseases.

Further, the identified genes and/or gene products and/or modulators can be used to identify cells exhibiting or predisposed to a disorder involving a disease phenotype, thereby diagnosing individuals having, or at risk for developing, such disorders. Additionally, the identified genes and/or gene products can be used to determine severity or duration of such diseases. Furthermore, the detection of the differential expression of identified genes can be used to devise treatments for a disease, specifically cardiac, kidney or inflammatory disease. Still further, the detection of differential expression of identified genes can be used to design a preventive intervention for subjects at risk of such diseases.

One such method for the treatment of a disease, specifically cardiac, kidney or inflammatory disease, and most specifically cardiac disease, comprises the administration to a subject of an effective amount of a modulator of one or more genes encoding human proteins of the group consisting of native sequence 1–8U, native sequence prostacyclin-stimulating factor, native sequence osf-2, native sequence tissue specific mRNA protein, native sequence IGFBP-6, native sequence OSF-1, native sequence gas-1, native sequence YMP, native sequence BTG2, native sequence SDF1a, native sequence peripheral benzodiazepine receptor, and native sequence cellular ligand of annexin II. Another such method comprises the administration to a subject of an effective amount of a modulator of one or more human proteins of the group consisting of native sequence 1–8U, native sequence prostacyclin-stimulating factor, native sequence osf-2, native sequence tissue specific mRNA protein, native sequence IGFBP-6, native sequence OSF-1, native sequence gas-1, native sequence YMP, native sequence BTG2, native sequence SDF1a, native sequence peripheral benzodiazepine receptor, and native sequence cellular ligand of annexin II. The subject may preferably be a human patient.

This modulator may be positive or negative; consist of one or more human proteins of the group consisting of 1–8U, prostacyclin-stimulating factor, osf-2, tissue specific mRNA protein, IGFBP-6, OSF-1, gas-1, YMP, BTG2, SDF1a, peripheral benzodiazepine receptor, and cellular ligand of annexin II; and be selected from the group consisting of peptides, phosphopeptides, small organic or inorganic molecules, antibodies, and epitope-binding fragments. In addition, a modulator may be selected from the group consisting of antisense, ribozyme, and triple helix molecules.

Yet another such method for the treatment of a disease, specifically cardiac, kidney or inflammatory disease, and most specifically cardiac disease, comprises the administration to a human patient of an effective amount of one or more isolated human proteins of the group consisting of native sequence 1–8U, native sequence prostacyclin-stimulating factor, native sequence osf-2, native sequence tissue specific mRNA protein, native sequence IGFBP-6, native sequence OSF-1, native sequence gas-1, native sequence YMP, native sequence BTG2, native sequence SDF1a, native sequence peripheral benzodiazepine receptor, and native sequence cellular ligand of annexin II. Further methods of the present invention comprise the administration to a human patient of an effective dose of an antibody to a cellular receptor of, an organic molecule inhibitor capable of binding to a cellular receptor of, an expression product of an isolated nucleotide sequence encoding, or a syngeneic host cell transformed with an isolated nucleotide sequence encoding one or more human proteins.

This isolated nucleotide sequence may comprise an antisense oligonucleotide capable of hybridizing with, and inhibiting the translation of, the mRNA encoded by a gene encoding one or more of the human proteins of the group consisting of 1–8U, prostacyclin-stimulating factor, osf-2, tissue specific mRNA protein, IGFBP-6, OSF-1, gas-1, YMP, BTG2, SDF1a, peripheral benzodiazepine receptor, and cellular ligand of annexin II. Further embodiments of the present invention may use this DNA molecule as a vector or operably linked to a regulatory sequence that controls expression of the coding sequence in a host cell, said host cell preferably comprising a human cell such as a cardiac cell, more preferably a left ventricle cell.

Another embodiment of the present invention provides for the screening of a subject suspected of having a disease, specifically cardiac, kidney, or inflammatory disease, and more specifically cardiac disease. The expression of one or more proteins selected from the group consisting of 1–8U, prostacyclin-stimulating factor, osf-2, tissue specific mRNA protein, IGFBP-6, OSF-1, gas-1, YMP, BTG2, SDF1a, peripheral benzodiazepine receptor, and cellular ligand of annexin II is determined in a subject suspected of having, or being predisposed to, a cardiac disease, and compared to the expression levels of the one or more proteins in a normal subject. Further, this difference in expression is preferably at least about two-fold or more in the subject, and the subject is preferably a human patient.

In another embodiment, an array comprising one or more oligonucleotides complementary to reference DNA or RNA sequences encoding one or more human proteins selected from the group consisting of 1–8U, prostacyclin-stimulating factor, osf-2, tissue specific mRNA protein, IGFBP-6, OSF-1, gas-1, YMP, BTG2, SDF1a, peripheral benzodiazepine receptor, and cellular ligand of annexin II is used for detecting disease, specifically cardiac, kidney, or inflammatory disease. The reference DNA or RNA preferably is obtained from a biological sample from a normal subject and from a subject exhibiting a disease, specifically cardiac, disease. Such subjects are preferably humans. The biological sample preferably comprises peripheral blood or tissue, preferably a cell such as a cardiac cell, and more preferably a left ventricle cell.

Yet another embodiment of the present invention provides for diagnosing a disease, specifically cardiac, kidney, or inflammatory disease, and more specifically cardiac disease, in a human patient. The expression level of one or more proteins selected from the group consisting of 1–8U, prostacyclin-stimulating factor, osf-2, tissue specific mRNA protein, IGFBP-6, OSF-1, gas-1, YMP, BTG2, SDF1a, peripheral benzodiazepine receptor, and cellular ligand of annexin II is determined in the subject and compared to the expression levels of the one or more proteins in a normal subject. Such subjects are preferably humans. Further, this difference in expression is preferably at least about two-fold or more. A tissue sample from the human patient may be obtained from cardiac tissue, specifically left ventricle tissue, or from the subject's blood. cDNA probes are hybridized on the array to create fluorometric, colorimetric or such identifying emissions, which are then compared with the existing encoded proteins.

Further, a diagnostic kit comprising said array is contemplated and used for detecting and diagnosing a disease, specifically cardiac, kidney or inflammatory disease. This kit may comprise control oligonucleotide probes, PCR reagents and detectable labels. In addition, this kit may comprise biological samples taken from human subjects, said samples comprising blood or tissue, preferably cardiac tissue, more preferably left ventricle cells. Such diagnostic kits may also comprise antibodies to the differentially expressed disease state genes of the present invention, which may be monoclonal.

In still another embodiment of the present invention, a method is provided for identifying a modulator of a differentially expressed disease state gene comprising contacting a biological sample from a subject having a disease, specifically cardiac, kidney or inflammatory disease, with a compound and determining the expression level of said differentially expressed gene. Comparison may be made between the expression level of the differentially expressed gene in a normal subject or said subject prior to contact with a compound and the expression level of the differentially expressed gene after contact with a compound, said compound selected from the group consisting of small molecules, active polypeptides and antibodies.

IV. DESCRIPTION OF THE FIGURES

FIG. 1 shows RNA blot analysis of ANP and BNP in LVH rats. Aortic banded and sham operated control rats were sacrificed at 10 weeks and 20 weeks post surgery. RNA was extracted from the left ventricle of each animal and probed on Northern blots for ANP and BNP transcripts using specific oligonucleotide probes.

FIG. 2 shows PCR amplified DNA from 96 random clones of rat left ventricle. PCR product (10% of total) from 96 clones was loaded onto a 1.0% agarose gel and visualized by ethidium bromide staining.

FIG. 3 shows a microarray analysis of 96 clones expressed in rat heart. Randomly chosen clones from a rat left ventricle cDNA library were printed onto a microarray and hybridized with Cy5-labeled rat left ventricle cDNA. The intensity of each probe is expressed in pseudo-color according to the scale shown. Blank spots resulted from lack of PCR amplifiable insert DNA from the corresponding clone.

FIG. 4 shows the differential expression data of representative genes obtained through the disease models of the present invention and determined via microarray analysis. Those representative disease model differentially expressed genes (clone ID nos. P0204_E06, P0237_E02, P0248_D11, P0228_H09, P0246_H10, P0237_B09, P0207_C03, P0214_A11, P0182_F08, P0219_H09, P0242_B03, P0268_G09) were found to correspond to human genes encoding 1–8U, prostacyclin-stimulating factor, osf-2, tissue specific mRNA, insulin-like growth factor binding protein-6, OSF-1, gas-1, YMP, BTG2, pre-B cell stimulating factor homolog (SDF1a), peripheral benzodiazepine receptor, and cellular ligand of annexin II (p11), respectively.

FIGS. 5A–5L show alignment data comparing the cDNA encoding the differentially expressed animal disease-model genes with human cDNA corresponding to 1–8U (SEQ ID NO:1; SEQ ID NO:2), prostacyclin-stimulating factor (SEQ ID NO:3; SEQ ID NO:4), osf-2 (SEQ ID NO:5; SEQ ID NO:6), tissue specific mRNA (SEQ ID NO:7; SEQ ID NO:8), insulin-like growth factor binding protein 6 (SEQ ID NO:9; SEQ ID NO:10), OSF-1 (SEQ ID NO:11; SEQ ID NO:12), gas-1 (SEQ ID NO:13; SEQ ID NO:14), YMP (SEQ ID NO:15; SEQ ID NO:16), BTG2 (SEQ ID NO:17; SEQ ID NO:18), pre-B cell stimulating factor homolog (SDF1a) (SEQ ID NO:19; SEQ ID NO:20), peripheral benzodiazepine receptor (SEQ ID NO:21; SEQ ID NO:22), and cellular ligand of annexin II (p11) (SEQ ID NO:23; SEQ ID NO:24), respectively.

FIGS. 6A–6E show alignment data comparing human cDNA sequences from the GenBank database with multiple cDNA clones encoding the differentially expressed animal disease model genes of the present invention, corresponding to 1–8U, tissue specific mRNA, YMP, pre-B cell stimulating factor homolog (SDF1a), peripheral benzodiazepine receptor, and cellular ligand of annexin II (p11).

FIGS. 7A–L show the nucleotide sequences encoding the polypeptides corresponding to 1–8U (SEQ ID NO:25), prostacyclin-stimulating factor (SEQ ID NO:26), osf-2 (SEQ ID NO:27), tissue specific mRNA (SEQ ID NO:28), insulin-like growth factor binding protein 6 (SEQ ID NO:29), OSF-1 (SEQ ID NO:30), gas-1 (SEQ ID NO:31), YMP (SEQ ID NO:32), BTG2 (SEQ ID NO:33), pre-B cell stimulating factor homolog (SDF1a) (SEQ ID NO:34), peripheral benzodiazepine receptor (SEQ ID NO:35), and cellular ligand of annexin II (p11) (SEQ ID NO:36).

FIGS. 8A–L show the amino acid sequences encoding the polypeptides corresponding to 1–8U (SEQ ID NO:37), prostacyclin-stimulating factor (SEQ ID NO:38), osf-2 (SEQ ID NO:39), tissue specific mRNA (SEQ ID NO:40), insulin-like growth factor binding protein 6 (SEQ ID NO:41), OSF-1 (SEQ ID NO:42), gas-1 (SEQ ID NO:43), YMP (SEQ ID NO:44), BTG2 (SEQ ID NO:45), pre-B cell stimulating factor homolog (SDF1a) (SEQ ID NO:46), peripheral benzodiazepine receptor (SEQ ID NO:47), and cellular ligand of annexin II (p11) (SEQ ID NO:48).

FIG. 9 shows characteristics of the human cDNA corresponding to 1–8U, prostacyclin-stimulating factor, osf-2, tissue specific mRNA, insulin-like growth factor binding protein 6, OSF-1, gas-1, YMP, BTG2, pre-B cell stimulating factor homolog (SDF1a), peripheral benzodiazepine receptor, and cellular ligand of annexin II (p11), as well as characteristics of the proteins themselves.

Figure 13A:
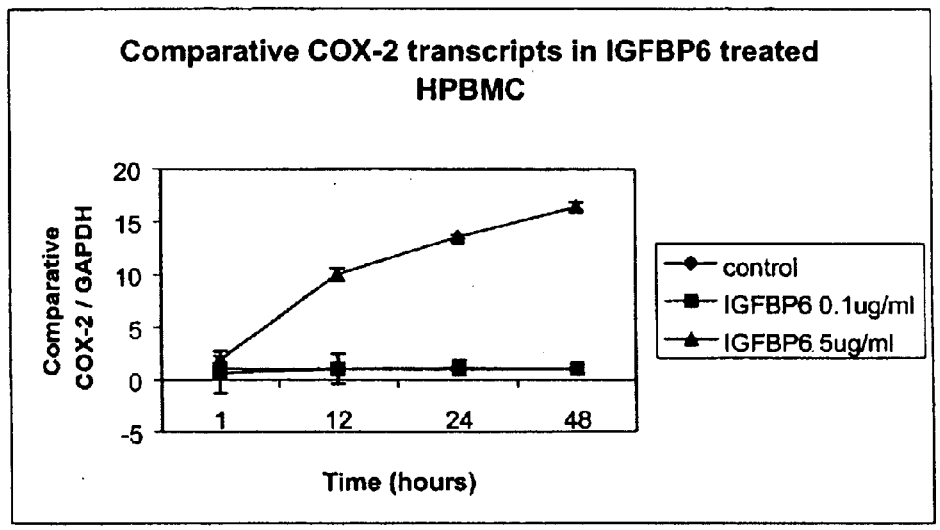
Figure 13B:
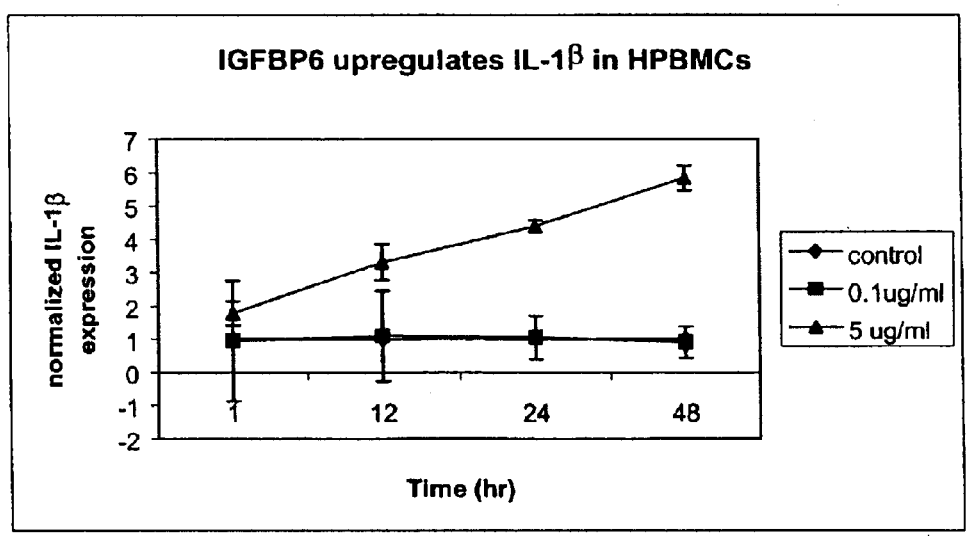

FIGS. 13 A and B illustrate the up-regulation of COX-2 and IL-1β in human peripheral blood mononuclear cells treated with 0, 0.1 or 5 μg/ml IGFBP-6.

Figure 14:
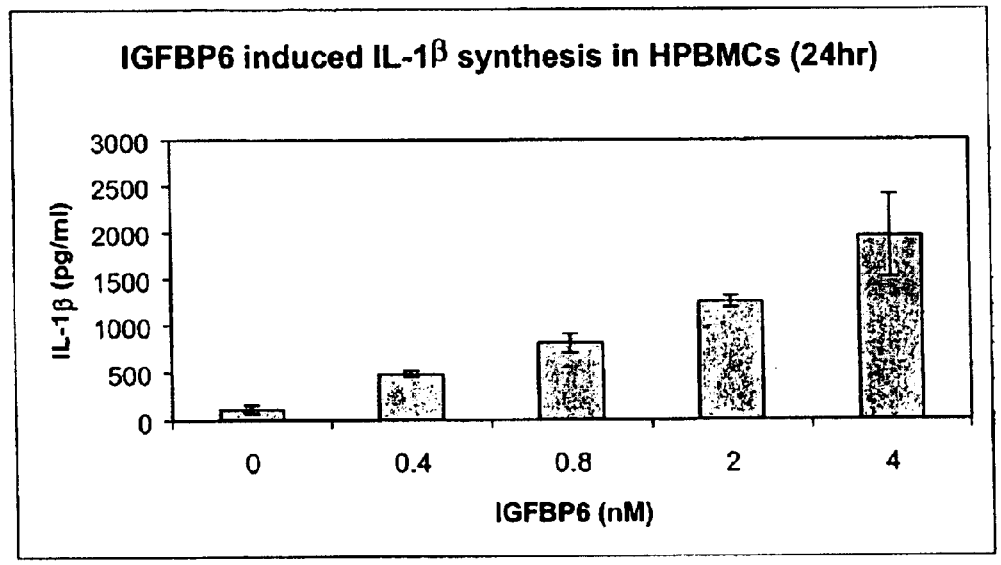

FIG. 14 illustrates the induction of IL-1β synthesis in human peripheral blood mononuclear cells (HPBMC) treated with 0, 0.4, 0.8, 2 and 4 nM concentrations of IGFBP-6.

V. DETAILED DESCRIPTION OF THE INVENTION

A. DEFINITIONS

Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, N.Y. 1994), and March, *Advanced Organic Chemistry Reactions, Mechanisms and Structure* 4th ed., John Wiley & Sons (New York, N.Y. 1992), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Kidney disease" includes acute renal failure, glomerulonephritis, chronic renal failure, azotemia, uremia, immune renal disease, acute nephritic syndrome, rapidly progressive nephritic syndrome, nephrotic syndrome, Berger's Disease, chronic nephritic/proteinuric syndrome, tubulointerstital disease, nephrotoxic disorders, renal infarction, atheroembolic renal disease, renal cortical necrosis, malignant nephroangiosclerosis, renal vein thrombosis, renal tubular acidosis, renal glucosuria, nephrogenic diabetes insipidus, Bartter's Syndrome, Liddle's Syndrome, polycystic renal disease, medullary cystic disease, medullary sponge kidney, hereditary nephritis, and nail-patella syndrome, along with any disease or disorder that relates to the renal system and related disorders, as well as symptoms indicative of, or related to, renal or kidney disease and related disorders.

"Inflammatory disease" includes myocarditis, asthma, chronic inflammation, autoimmune diabetes, tumor angiogenesis, rheumatoid arthritis, rheumatoid spondylitis, osteoarthritis, gouty arthritis and other arthritic conditions, sepsis, septic shock, endotoxic shock, Gram-negative sepsis, toxic shock syndrome, asthma, adult respiratory distress syndrome, stroke, reperfusion injury, CNS injuries such as neural trauma and ischemia, psoriasis restenosis, cerebral malaria, chronic pulmonary inflammatory disease, silicosis, pulmonary sarcosis, bone resorption diseases such as osteoporosis, graft versus host reaction, Crohn's Disease, ulcerative colitis including inflammatory bowel disease (IBD), and pyresis, along with any disease or disorder that relates to inflammation and related disorders, as well as symptoms indicative of, or related to, inflammation and related disorders.

"Cardiac disease" includes congestive heart failure, myocarditis, dilated congestive cardiomyopathy, hypertrophic cardiomyopathy, restrictive cardiomyopathy, mitral valve disease, aortic valve disease, tricuspid valve disease, angina pectoris, myocardial infarction, cardiac arrhythmia, pulmonary hypertension, arterial hypertension, renovascular hypertension, arteriosclerosis, atherosclerosis, and cardiac tumors, along with any disease or disorder that relates to the cardiovascular system and related disorders, as well as symptoms indicative of, or related to, cardiac disease and related disorders.

"Gene" includes differentially expressed genes and their expression products whose expression pattern can be utilized as part of a prognostic or diagnostic marker for the evaluation of a disorder involving a disease, specifically cardiac, kidney or inflammatory disease, or which can be used in methods for identifying compounds useful for the detection, diagnosis, prevention and treatment of such diseases and related disorders. For example, the effect of the compound on the gene expression normally displayed in connection with disorders involving a disease, specifically cardiac, kidney or inflammatory disease, can be used to evaluate the efficacy of the compound as a treatment for such a disorder, or can, additionally, be used to monitor patients undergoing clinical evaluation for the treatment of the disorder. "Gene" also includes differentially expressed genes and their expression products involved in a disease, specifically cardiac, kidney or inflammatory disease, such that modulation of the level of gene expression or of gene product activity can act to prevent or treat such a disease and related conditions. Compounds that modulate the expression of the gene or the activity of the gene product can be used in the treatment of such diseases in a subject, as well as the differentially expressed gene itself or functional variations thereof. Further, compounds that modulate the expression of the gene or activity of the gene product can be used in treatments for a disease, specifically cardiac, kidney or inflammatory disease, and related conditions. Still further, compounds that modulate the expression of the gene or activity of the gene product can be used to design a preventive intervention in individuals at risk of a disease. "Genes" may also be defined via the ability of their products to interact with other gene products involved in a disease, specifically cardiac, kidney or inflammatory disease, and include the target, interactive, and diagnostic genes of the present invention.

Genes termed "target genes" or "diagnostic genes" include genes differentially expressed in subjects with a disease, specifically cardiac, kidney or inflammatory disease, relative to their expression in normal subjects or relative to their expression at a different stage of a disease. Genes termed "interactive genes" include genes whose products exhibit an ability to interact with gene products involved in a disease, specifically cardiac, kidney or inflammatory disease. Interactive genes can additionally have diagnostic or target gene characteristics.

"Expression pattern" includes the pattern generated when the expression pattern of a series (which can range from two up to all the genes which exist for a given state) of genes is determined. An expression pattern can be used in the same diagnostic, prognostic and compound identification methods as the expression of a single gene.

An "oligonucleotide" includes a nucleic acid polymer composed of two or more nucleotides or nucleotide analogs. An oligonucleotide can be derived from natural sources but is often synthesized chemically. It is of any size.

An "oligonucleotide array or microarray" includes a spatially defined pattern of oligonucleotide probes on a solid support. A "preselected array of oligonucleotides" is an array of spatially defined oligonucleotides on a solid support.

A "nucleic acid reagent" used in standard automated oligonucleotide synthesis typically carries a protected phosphate on the 3' hydroxyl of the ribose. Thus, nucleic acid reagents are referred to as nucleotides, nucleotide reagents, nucleoside reagents, nucleoside phosphates, nucleoside-3'-phosphates, nucleoside phosphoramidites, phosphoramidites, nucleoside phosphonates, phosphonates and the like. It is generally understood that nucleotide reagents carry a protected phosphate group in order to form a phosphodiester linkage.

A "solid support" includes a fixed organizational support matrix, such as silica, polymeric materials, or glass. In some embodiments, at least one surface of the substrate is partially planar. In other embodiments, it is desirable to physically separate regions of the substrate to delineate synthetic regions, for example, with trenches, grooves, wells or the like. Examples of solid substrates include slides, beads and chips.

The term "recombinant" when used with reference to a cell, animal, or virus indicates that the cell, animal, or virus encodes a foreign DNA or RNA. For example, recombinant cells optionally express nucleic acids (e.g., RNA) not found within the native (non-recombinant) form of the cell.

"Stringent" hybridization conditions are sequence dependent and will be different with different environmental parameters (e.g., salt concentrations, and presence of organics). Generally, stringent conditions are selected to be about 5° C. to 20° C. lower than the thermal melting point ($T_m$) for the specific nucleic acid sequence at a defined ionic strength and pH. Preferably, stringent conditions are about 5° C. to 10° C. lower than the thermal melting point for a specific nucleic acid bound to a complementary nucleic acid. The $T_m$ is the temperature (under defined ionic strength and pH) at which 50% of a nucleic acid (e.g., tag nucleic acid) hybridizes to a perfectly matched probe.

"Stringent" wash conditions are ordinarily determined empirically for hybridization of each set of tags to a corresponding probe array. The arrays are first hybridized (typically under stringent hybridization conditions) and then washed with buffers containing successively lower concentrations of salts, or higher concentrations of detergents, or at increasing temperatures until the signal to noise ratio for specific to non-specific hybridization is high enough to facilitate detection of specific hybridization. Stringent temperature conditions will usually include temperatures in excess of about 30° C, more usually in excess of about 37° C., and occasionally in excess of about 45° C. Stringent salt conditions will ordinarily be less than about 1000 mM, usually less than about 500 mM, more usually less than about 400 mM, typically less than about 300 mM, preferably less than about 200 mM, and more preferably less than about 150 mM. However, the combination of parameters is more important than the measure of any single parameter. See, e.g., Wetmur et al., *J. Mol. Biol.* 31:349–70 (1966), and Wetmur, *Critical Reviews in Biochemistry and Molecular Biology* 26(34):227–59 (1991).

In a preferred embodiment, "stringent conditions" or "high stringency conditions," as defined herein, may be hybridization in 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

The term "identical" in the context of two nucleic acid sequences refers to the residues that are identical, after aligning the sequences, and introducing or deleting gaps, if necessary to achieve the maximum percent identity, and not considering any conservative substitutions as part of the sequence identity. The local homology algorithm of Smith and Waterman (Smith et al., *Adv. Appl. Math.* 2:482 (1981)) can conduct optimal alignment of sequences for comparison, e.g., by the homology alignment algorithm of Needleman and Wunsch (Needleman et al., *J. Mol. Biol.* 48:443 (1970)), by the search for similarity method of Pearson and Lipman (Pearson et al., *Proc. Natl. Acad. Sci. USA* 85:2444 (1988)), by computerized implementations of these algorithms (GAP, BESTFIT, FASTA, and TFASTA in the Wisconsin Genetics Software Package, Genetics Computer Group, 575, Science Dr., Madison, Wis.), or by inspection.

In a preferred embodiment, the homology alignment algorithms employed in the BLAST program (Altschul et al., *Nucleic Acids Res.* 25:3389–3402 (1997)) may be used. The BLAST family of programs allows all combinations of DNA or protein query sequences with searches against DNA or protein databases. Within the context of the present invention, the specific BLAST programs that may be utilized include: blastp, which compares an amino acid query sequence against a protein sequence database; blastn, which compares a nucleotide query sequence against a nucleotide sequence database; blastx, which compares the six-frame conceptual translation products of a nucleotide query sequences (both strands) against a protein sequence database; tblastn, which compares a protein query sequence against a nucleotide sequence database dynamically translated in all six reading frames (both strands); and tblastx,- which compares the six-frame translations of a nucleotide query sequence against the six-frame translations of a nucleotide sequence database. For the blastn program, the following parameters and their default values are utilized: –G: cost to open a gap, default=5; –E: cost to extend a gap, default=2; –q: penalty for a mismatch in the blast portion of run, default=–3; –r: rewared for a match in the blast portion of run, default=1; –e: expectation value (E), default=10.0; –W: word size, default is 11 for blastn, 3 for other programs; –v number of one-line descriptions (V), default=100; and –b: number of alignments to show (B), default=100.

A nucleic acid "tag" is a selected nucleic acid with a specified nucleic acid sequence. A nucleic acid "probe" hybridizes to a nucleic acid "tag." In one typical configuration, nucleic acid tags are incorporated as labels into biological libraries, and the tag nucleic acids are detected using an array of probes. A "list of tag nucleic acids" is a pool of tag nucleic acids, or a representation (i.e., an electronic or paper copy) of the sequences in the pool of tag nucleic acids. The pool of tags can be, for instance, all possible tags of a specified length (i.e., all 20-mers), or a subset thereof.

A set of nucleic acid tags binds to a probe with "minimal cross hybridization" when a single species (or "type") of tag in the tag set accounts for the majority of all tags which bind to an array comprising a probe species under stringent conditions. Typically, about 80% or more of the tags bound to the probe species are of a single species under stringent conditions. Usually about 90% or more of the tags bound to the probe species are of a single species under stringent conditions. Preferably 95% or more of the tags bound to the probe species are of a single species under stringent conditions.

In certain embodiments of the invention the terms "differentially expressed gene," "expression," "gene expressions" and "expression products" include production of a gene RNA message or the RNA message produced or both. In certain other embodiments of the invention the terms "differentially expressed gene," "expression," "gene expression" and "expression products" include either translation of a mRNA into proteins, polypeptides or peptides, or to the produced proteins, polypeptides, or peptides themselves. In certain aspects of the invention a differentially expressed gene may be a gene whose expression is activated to a higher or lower level in a subject suffering a disease, specifically a cardiac, kidney or inflammatory disease state, relative to its expression in a normal or control subject. It is also understood that a differentially expressed gene may be either activated or inhibited at the nucleic acid level or protein level, for example, by a modulator, or may it be subject to alternative splicing to result in a different polypeptide product. Such differences may be evidenced by a change in mRNA levels, surface expression, secretion or other partitioning of a polypeptide, for example. Differential gene expression may include a comparison of expression between two or more genes, or a comparison of the ratios of the expression between two or more genes, or even a comparison of two differently processed products of the same gene, which differ between normal subjects and subjects suffering from a disease, specifically a cardiac, kidney or inflammatory disease state. Differential expression includes both quantitative, as well as qualitative, differences in the temporal or cellular expression pattern in a gene or its expression products among, for example, normal and diseased cells, or among cells which have undergone different disease events or disease stages.

"Modulation" relates to a change in the production of a differentially expressed gene RNA message or the RNA message produced or both. In particular embodiments of the invention, modulation of "differentially expressed genes," "gene expression," and "expression products" may refer to either a change in the translation of a gene RNA message into proteins, polypeptides or peptides, or to the produced proteins, polypeptides, or peptides themselves. A differentially expressed gene may have its expression modulated to a higher or lower level in a subject suffering or predisposed to a disease state, thus producing the desired therapeutic or prophylactic preventative effect. It is also understood that a differentially expressed gene may be either activated or inhibited at the nucleic acid level or protein level, for example, by a modulator. Modulators, within the context of the present invention also include an antibody to, an antibody to a cellular receptor of, an organic molecule inhibitor capable of binding to a cellular receptor of one or more of these differentially expressed genes, antisense, triple helix, or ribozyme methodologies, or the gene itself and variants thereof.

The term "label" refers to a composition detectable by spectroscopic, photochemical, biochemical, immunochemical, or chemical means. For example, useful nucleic acid labels include $^{32}$P, $^{35}$S, fluorescent dyes, electron-dense reagents, enzymes (e.g., as commonly used in an ELISA), biotin, dioxigenin, or haptens and proteins for which antisera or monoclonal antibodies are available.

As used herein, "differentially expressed gene" (i.e., target and diagnostic genes) or "interactive gene" also includes (a) a gene comprising at least one of the DNA sequences disclosed herein; (b) any DNA sequence that encodes the amino acid sequence encoded by the DNA sequences disclosed herein or contained within the coding region of the gene to which the DNA sequences disclosed here belong; (c) any DNA sequence that hybridizes to the complement of the coding sequences disclosed herein or contained within the coding region of the gene to which the DNA sequences disclosed herein belong under highly stringent conditions, e.g., hybridization to filter-bound DNA in 0.5M NaHPO$_4$, 7% sodium dodecyl sulfate (SDS), 1 mM EDTA at 65° C., and washing in 0.1×SSC/0.1% SDS at 68° C. (Ausubel et al., eds., *Current Protocols in Molecular Biology, J.* Wiley and Sons (New York, N.Y. 1993)) and encodes a gene product functionally equivalent to a gene product encoded by a gene of (a) above; (d) any DNA sequence that hybridizes to the complement of: the coding sequences disclosed herein, or contained within the coding region of the gene to which DNA sequences disclosed herein, belong under less stringent conditions, such as moderately stringent conditions, e.g., washing in 0.2×SSC/0.1% SDS at 42° C. (Ausubel et al., supra), yet which still encodes a gene product functionally equivalent to a gene product encoded by a gene of (a) above; or (e) the human or animal counterpart of such a gene determined by comparison of the sequence of such a gene, or portions thereof, to known sequence information, e.g., the human GenBank database.

"Negative modulation," as used herein, refers to a reduction in the level or activity of target gene product relative to the level or activity of the target gene product in the absence of the modulatory treatment.

"Positive modulation," as used herein, refers to an increase in the level or activity of target gene product relative to the level or activity of target gene product in the absence of modulatory treatment.

The terms "treating" or "treatment," as used herein, refer to reduction or alleviation of at least one adverse effect or symptom of a disease, specifically cardiac, kidney or inflammatory disease, e.g., a disorder or disease characterized by or associated with differential polypeptide activity or nucleic acid expression.

A "cell associated activity" refers to a normal or abnormal activity or function of a cell. Examples of cell associated activities include proliferation, migration, differentiation, production or secretion of molecules such as proteins, and cell survival. In a preferred embodiment, the cell may be a cardiac cell, e.g., a cardiac myocyte or fibroblast.

The term "altered" relates to a change, e.g., an increase or decrease, of a cell associated activity. In one embodiment, the agent stimulates polypeptide activity or nucleic acid expression. Examples of such stimulatory agents include an active gene protein, a nucleic acid molecule encoding differentially expressed gene that has been introduced into the cell, and a modulatory agent which stimulates polypeptide activity or differentially expressed gene expression and which is identified using the drug screening assays described herein.

The terms "1–8U", "prostacyclin-stimulating factor", "osf-2", "tissue specific mRNA protein", "insulin-like growth factor binding protein 6 (IGFBP-6)", "OSF-1", "gas-1", "YMP", "BTG2", "pre-B cell stimulating factor homolog (SDF1a)", "peripheral benzodiazepine receptor", and "cellular ligand of annexin II (p11)" are used herein to encompass the respective native sequence polypeptides as well as their variants (which are further defined herein). The "1–8U", "prostacyclin-stimulating factor", "osf-2", "tissue specific mRNA protein", "insulin-like growth factor binding protein 6 (IGFBP-6)", "OSF-1", "gas-1", "YMP", "BTG2", "pre-B cell stimulating factor homolog (SDF1a)", "peripheral benzodiazepine receptor", and "cellular ligand of annexin II (p11)" polypeptides can be isolated from a variety of sources, such as from a variety of human tissue types, or prepared by recombinant and/or synthetic methods; all such polypeptides are specifically within the scope of the definition, regardless of their mode of preparation, and include variants thereof.

The terms "native sequence 1–8U", "native sequence prostacyclin-stimulating factor", "native sequence osf-2", "native sequence tissue specific mRNA protein", "native sequence insulin-like growth factor binding protein 6 (IGFBP-6)", "native sequence OSF-1", "native sequence gas-1", "native sequence YMP", "native sequence BTG2", "native sequence pre-B cell stimulating factor homolog (SDF1a)", "native sequence peripheral benzodiazepine receptor", and "native sequence cellular ligand of annexin II (p11)" refer to polypeptides having the same amino acid sequence as a respective polypeptide derived from nature. Such native sequence polypeptides can be isolated from nature or can be produced by recombinant and/or synthetic means. The term "native sequence" in conjunction with the designation of a particular polypeptide specifically encompasses naturally-occurring truncated or secreted forms (e.g., an extracellular domain sequence), as well as naturally occurring variant forms (e.g., alternatively spliced forms), and naturally occurring allelic variants of the named polypeptides. In one embodiment of the invention, the native sequence 1–8U polypeptide has the amino acid sequence of SEQ ID NO:37, the native sequence prostacyclin stimulating factor has the amino acid sequence of SEQ ID NO:38, the native sequence osf-2 has the amino acid sequence of SEQ ID NO:39, the native sequence tissue specific mRNA protein has the amino acid sequence of SEQ ID NO:40, the native sequence insulin-like growth factor binding protein 6 (IGFBP-2) has the amino acid sequence of SEQ ID NO:41, the native sequence OSF-1 has the amino acid sequence of SEQ ID NO:42, the native sequence gas-1 has the amino acid sequence of SEQ ID NO:43, the native sequence YMP has the amino acid sequence of SEQ ID NO:44, the native sequence BTG2 has the amino acid sequence of SEQ ID NO:45, the native sequence SDF1a has the amino acid sequence of SEQ ID NO:46, the native sequence peripheral benzodiazepin receptor has the amino acid sequence of SEQ ID NO:47, and the native sequence cellular ligand of annexin II has the amino acid sequence of SEQ ID NO:48.

The terms "variant" and "amino acid sequence variant" are used interchangeably and designate polypeptides in which one or more amino acids are added and/or substituted and/or deleted and/or inserted at the N- or C-terminus or anywhere within the corresponding native sequence, and which retain at least one activity (as defined below) of the corresponding native polypeptide. In various embodiments, a "variant" polypeptide usually has at least about 75% amino acid sequence identity, or at least about 80% amino acid sequence identity, preferably at least about 85% amino acid sequence identity, even more preferably at least about 90% amino acid sequence identity, and most preferably at least about 95% amino acid sequence identity with the amino acid sequence of the corresponding native sequence polypeptide.

"Active" or "activity" for the purposes herein refers to form(s) of the "1–8U", "prostacyclin-stimulating factor", "osf-2", "tissue specific mRNA protein", "insulin-like growth factor binding protein 6 (IGFBP-6)", "OSF-1", "gas-1", "YMP", "BTG2", "pre-B cell stimulating factor homolog (SDF1a)", "peripheral benzodiazepine receptor", or "cellular ligand of annexin II (p11)" polypeptides which retain a qualitative biological sand/or immunological property of a native sequence "1–8U", "prostacyclin-stimulating factor", "osf-2", "tissue specific mRNA protein", "insulin-like growth factor binding protein 6 (IGFBP-6)", "OSF-1", "gas-1", "YMP", "BTG2", "pre-B cell stimulating factor homolog (SDF1a)", "peripheral benzodiazepine receptor", or "cellular ligand of annexin II (p11)" polypeptide.

The phrase "immunological property" means immunological cross-reactivity with at least one epitope of a "1–8U", "prostacyclin-stimulating factor", "osf-2", "tissue specific mRNA protein", "insulin-like growth factor binding protein 6 (IGFBP-6)", "OSF-1", "gas-1", "YMP", "BTG2", "pre-B cell stimulating factor homolog (SDF1a)", "peripheral benzodiazepine receptor", or "cellular ligand of annexin II (p11)" polypeptide.

"Immunological cross-reactivity" means that the candidate polypeptide is capable of competitively inhibiting the qualitative biological activity of a "1–8U", "prostacyclin-stimulating factor", "osf-2", "tissue specific mRNA protein", "insulin-like growth factor binding protein 6 (IGFBP-6)", "OSF-1", "gas-1", "YMP", "BTG2", "pre-B cell stimulating factor homolog (SDF1a)", "peripheral benzodiazepine receptor", or "cellular ligand of annexin II (p11)" polypeptide having this activity with polyclonal antisera raised against the known active "1–8U", "prostacyclin-stimulating factor", "osf-2", "tissue specific mRNA protein", "insulin-like growth factor binding protein 6 (IGFBP-6)", "OSF-1", "gas-1", "YMP", "BTG2", "pre-B cell stimulating factor homolog (SDF1a)", "peripheral benzodiazepine receptor", or "cellular ligand of annexin II (p11)" polypeptide. The immunological cross-reactivity is preferably "specific", which means that the binding affinity of the immunologically cross-reactive molecule identified to the corresponding polypeptide herein is significantly higher (preferably at least about 2-times, more preferably at least about 4-times, most preferably at least about 6-times higher) than the binding affinity of that molecule to any other known native polypeptide.

The term "antagonist" is used in the broadest sense and includes any molecule that partially or fully blocks, inhibits or neutralizes a biological activity of a "1–8U", "prostacyclin-stimulating factor", "osf-2", "tissue specific mRNA protein", "insulin-like growth factor binding protein 6 (IGFBP-6)", "OSF-1", "gas-1", "YMP", "BTG2", "pre-B cell stimulating factor homolog (SDF1a)", "peripheral benzodiazepine receptor", or "cellular ligand of annexin II (p11)" polypeptide disclosed herein. In a similar manner, the term "agonist" is used in the broadest sense and includes any molecule that mimics the biological activity of a "1–8U", "prostacyclin-stimulating factor", "osf-2", "tissue specific mRNA protein", "insulin-like growth factor binding protein 6 (IGFBP-6)", "OSF-1", "gas-1", "YMP", "BTG2", "pre-B cell stimulating factor homolog (SDF1a)", "peripheral benzodiazepine receptor", or "cellular ligand of annexin II (p11)" polypeptide disclosed herein.

The term "antibody" is used in the broadest sense and specifically covers anti-1–8U, anti-prostacyclin-stimulating factor, anti-osf-2, anti-tissue specific mRNA protein, anti-IGFBP-6, anti-OSF-1, anti-gas-1, anti-YMP, anti-BTG2, anti-SDF1a, anti-peripheral benzodiazepine receptor, and anti-cellular ligand of annexin intact monoclonal antibodies (including agonist, antagonist, and neutralizing antibodies), polyclonal antibodies, multi-specific antibodies (e.g., bispecific antibodies), as well as antibody fragments. The monoclonal antibodies specifically includes "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851–6855 (1984)). The monoclonal antibodies further include "humanized" antibodies or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a CDR of the recipient are replaced by residues from a CDR of a non-human species (donor antibody) such as mouse, rat or rabbit having the desired specificity, affinity, and capacity. In some instances, Fv FR residues of the human immunoglobulin are replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., *Nature*, 321:522–525 (1986); and Reichmann et al., *Nature*, 332:323–329 (1988). The humanized antibody includes a PRIMATIZED™ antibody wherein the antigen-binding region of the antibody is derived from an antibody produced by immunizing macaque monkeys with the antigen of interest.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., *Protein Eng.* 8(10):1057–1062 (1995)); single-chain antibody molecules; and multispecific antibodies formed from antibody fragments.

VI. IDENTIFICATION AND CHARACTERIZATION OF GENES DIFFERENTIALLY EXPRESSED IN DISEASE

The present invention relates to methods involving in vivo and in vitro models of a disease, specifically cardiac, kidney or inflammatory disease, coupled with sensitive and high throughput assays, preferably microarray assays, to identify genes differentially expressed in such diseases. The expression of the differentially expressed genes of the present invention can be determined from peripheral blood, tissues, or cells of a subject. In a preferred embodiment, the genes of the present invention are differentially expressed in cells and peripheral blood relative to normal cells and peripheral blood or differentially expressed relative to cells and peripheral blood at different disease stages. In contrast to approaches that merely evaluate the expression of a given gene product presumed to play a role in one or another of the various stages of a disease, the methodologies used herein permit the identification of all genes, whether known or novel, which are differentially expressed in association with a disease.

This comprehensive approach and evaluation permits the discovery of novel genes and gene products, as well as the identification of an array of genes and gene products (whether novel or known) involved in interactions that play a role in disease pathology. Thus, the present invention makes possible the identification and characterization of methods and compositions useful for prognosis, diagnosis, monitoring, rational drug design, or other therapeutic intervention of a disease, specifically cardiac, kidney or inflammatory disease, and its disorders.

A. IDENTIFICATION OF DIFFERENTIALLY EXPRESSED GENES

A variety of methods can be utilized for the identification of genes involved in a disease, specifically cardiac, kidney or inflammatory disease. Described below are experimental models, which can be utilized for the generation of biological samples that can be used for the identification of such genes. Samples generated in model categories can be characterized for the presence of differentially expressed gene sequences, as discussed below.

1. Models for Identifying Differentially Expressed Genes

Representative models of disease, specifically cardiac, kidney or inflammatory disease, states are described herein. These models can be utilized within the context of the present invention, e.g., for the identification of genes which are differentially expressed in normal cells versus cells in a disease, specifically cardiac, kidney or inflammatory disease, state, in cells within different diseases, among cells within a single given disease state, in cells within different stages of a disease, or in cells within different time stages of a disease.

Once a particular differentially expressed gene has been identified through the use of one model, its expression pattern can be further characterized, for example, by studying its expression in a different model. A gene may be regulated one way, i.e., the gene can exhibit one differential gene expression pattern, in a given model, but can be regulated differently in another model. The use, therefore, of multiple models can be helpful in distinguishing the roles and relative importance of particular genes in a disease, specifically cardiac, kidney or inflammatory disease.

a. In Vivo Models

In the in vivo model, animal models of a disease, specifically cardiac, kidney or inflammatory disease, and related disorders, can be utilized to discover differentially expressed gene sequences. The in vivo nature of such disease models can prove to be especially predictive of the analogous responses in living patients, particularly human patients. Animal models for a disease, specifically cardiac, kidney or inflammatory disease, which can be utilized for in vivo models include any of the animal models described below. In a preferred embodiment, RNA from both the normal and disease state model is isolated and analyzed for differentially expressed genes using microarray analysis.

As presented in detail below, three representative in vivo cardiac disease models, a representative kidney disease model, and a representative inflammatory disease model have been successfully utilized to identify differentially expressed genes of the present invention. These genes are expressed at higher or lower levels in the disease state, relative to the normal state, and preferably are expressed at least about a two-fold higher or lower level relative to the normal state at at least one time point.

Representative in vivo animal models for use in the present invention include the following: general inflammation—carrageenan-induced paw edema, arachidonic acid-induced ear inflammation; arthritis—adjuvant-induced polyarthritis, collagen-induced arthritis, streptococcal cell wall-induced arthritis; multiple sclerosis—experimental autoimmune encephalomyelitis (EAE); Systemic Lupus Erythematosis (SLE); NZB—spontaneous SLE mouse, DNA/anti-DNA immune complex-induced SLE; insulin-dependent diabetes mellitus—NOD spontaneous diabetes mouse; inflammatory bowel disease—acetic acid or trinitrobenzene sulfonic (TNBS)-induced ulcerative colitis; respiratory disease—antigen-induced bronchoconstriction (asthma), lipopolysaccharide (LPS)-induced acute respiratory distress syndrome (ARDS); analgesia—acetic acid-induced or phenylquinone-induced writhing, latency of tail-withdrawal (hot plate); transplant organ rejection—allograft rejection (kidney, lung, heart)-acute and chronic arteriolsclerosis; kidney disease—unilateral nephrectomy (acute renal failure), cyclosporin-induced nephropathy, accelerated crescentic anti-glomerular basement membrane (GBM) glomerulonephritis, soluble immune complex-induced nephritis (see generally Aziz, *Bioessays* 17:8 703–12 (1995)); and cardiac disease—spontaneous cardiomyopathic hamsters (heart failure), pacing-induced model of failure (Riegger model), arrhythmias following myocardial infarction (Harris model), aconitine/chloroform-induced arrhythmisa, carotid artery injury (restenosis), balloon angioplasty (restenosis). One skilled in the art understands that the present invention is not limited to the in vivo models recited above and that any known models can be used within the context of the present invention.

b. In Vitro Models

Another model that can be utilized within the context of the present invention to discover differentially expressed gene sequences is the in vitro specimen model. In a preferred embodiment, the specimen model uses biological samples from subjects, e.g., peripheral blood, cells and tissues, including surgical and biopsy specimens. Such specimens can represent normal peripheral blood and tissue or peripheral blood and tissue from patients suffering from a disease, specifically cardiac, kidney or inflammatory disease, or having undergone surgical treatment for disorders involving a disease, such as, for example, coronary bypass surgery. Surgical specimens can be procured under standard conditions involving freezing and storing in liquid nitrogen (see Karmali et al., Br. *J. Cancer* 48:689–96 (1983)). RNA from specimen cells is isolated by, for example, differential centrifugation of homogenized tissue, and analyzed for differential expression relative to other specimen cells, preferably using microarray analysis.

Cell lines can also be used to identify genes that are differentially expressed in a disease, specifically cardiac, kidney or inflammatory disease. Differentially expressed genes are detected, as described herein, by comparing the pattern of gene expression between the experimental and control conditions. In such models, genetically matched disease cell lines (e.g., variants of the same cell line) may be utilized. For example, the gene expression pattern of two variant cell lines can compared wherein one variant exhibits characteristics of one disease state while the other variant exhibits characteristics of another disease state.

Alternatively, two variant cell lines, both of which exhibit characteristics of the same disease, specifically cardiac, kidney or inflammatory disease, but which exhibit differing degrees of disease disorder severity may be used. Further, genetically matched cell lines can be utilized, one of which exhibits characteristics of a disease, specifically cardiac, kidney or inflammatory disease, state, while the other exhibits a normal cellular phenotype. In accordance with this aspect of the invention, the cell line variants are cultured under appropriate conditions, harvested, and RNA is isolated and analyzed for differentially expressed genes, as with the other models. In a preferred embodiment, microarray analysis is used.

B. ANALYSIS OF MODEL SAMPLES

The differentially expressed genes of the present invention can be identified by using a variety of methods, which are well known to those of skill in the art. For example, differential screening (Tedder et al., *Proc. Natl. Acad. Sci. USA* 85:208–12 (1988)), subtractive hybridization (Hedrick et al., *Nature* 308:149–53 (1984), Lee et al., *Proc. Natl. Acad. Sci. USA* 88:2825 (1984)), and differential display (Liang et al., U.S. Pat. No. 5,262,311 (1993), which is incorporated herein by reference in its entirety), can be utilized to identify nucleic acid sequences derived from genes that are differentially expressed.

To use such techniques, RNA (either total or mRNA), can be isolated from cells utilized in models such as those described above. Any RNA isolation technique that does not select against the isolation of mRNA can be utilized for the purification of such RNA samples. See, e.g., Ausubel et al., supra. Additionally, large numbers of tissue samples can readily be processed using techniques well known to those of skill in the art, such as, for example, the single-step RNA isolation process of Chomczynski (U.S. Pat. No. 4,843,155, which is incorporated herein by reference in its entirety).

1. Microarray Analysis

In a preferred embodiment of the present invention, microarrays are utilized to assess differential expression of genes. In one aspect of the present invention, DNA microarrays preferably are utilized within the methods of the present invention to assess the expression profile of genes expressed in normal subjects and subjects suffering from a disease, specifically cardiac, kidney or inflammatory disease. Identification of the differentially expressed disease genes of the present invention can be performed by: constructing normalized and'subtracted cDNA libraries from mRNA extracted from the cells or tissue of healthy animals and an animal model of disease or of healthy patients and diseased patients, i.e., using any of the in vitro or in vivo models described herein; purifying the DNA of clones from cDNA libraries representing healthy and diseased cells or tissue, microarraying the purified DNA for expression analysis; and probing microarrays to identify the genes from the clones that are differentially expressed using labeled cDNA from healthy and diseased cells or tissues.

In a specific embodiment of the microarray technique, PCR amplified inserts of cDNA clones are applied to a substrate in a dense array. Preferably at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., *Proc. Natl. Acad. Sci. USA* 93(20):106–49 (1996)).

C. DETECTION OF DIFFERENTIALLY EXPRESSED GENES

In a specific embodiment, in vivo models of disease states were used to detect the differentially expressed genes of the present invention. By way of example, three representative cardiac disease models, a representative kidney disease model, and a representative inflammatory disease model were successfully utilized to identify specific differentially expressed genes. Summarizing the representative general protocol used for such in vivo models, separate DNA libraries were constructed from mRNA extracted from disease state tissue and normal tissue. From these libraries, at least 20,000 unidentified cDNA clones were preferably chosen for analysis and microarrayed on chips. Probes generated from normal and disease tissue, from multiple time points, were hybridized to the microarray. By this approach, genes, which are differentially expressed in normal and diseased tissue, were revealed and further identified by DNA sequencing. The analysis of the clones for differential expression reveal genes whose expression is elevated or decreased in association with a disease, specifically cardiac, kidney or inflammatory disease, in the specific in vivo model chosen.

1. In Vivo Model of Cardiac Hypertrophy

In a representative example, an in vivo model of cardiac disease, specifically, cardiac hypertrophy, was used within the context of the present invention to discover differentially expressed disease state genes. Specifically, rats with left ventricular hypertrophy (LVH) were produced essentially as described in Schunkert et al., 1990, supra. LVH was induced by pressure overload as a result of constriction of the ascending aorta. A stainless steel clip of 0.6-mm internal diameter was placed on the aorta of anesthetized weanling rats. Control animals underwent thoracotomny as a sham operation. Animals recovered from surgery and appeared healthy until 20 weeks when a few animals were in demise likely due to heart failure, which typically occurs at this point (Schunkert et al., 1990, supra). The animals were sacrificed and hearts examined 10 weeks and 20 weeks post-operation. Hypertrophy was evident at both time points as determined by changes in left ventricle weight and thickness (Table 1), similar to the findings of others. Aortic banded rats and sham operated control animals were sacrificed and measured for heart weight, left ventricle (LV) weight, left ventricle thickness, and LV weight/body weight. There were 6 animals per group. Data are expressed as average with standard deviation in parentheses.

TABLE 1

| | Heart weight Grams (stdev) | LV weight Grams (stdev) | LV thickness Mm (stdev) | LV wt/body wt Mg/g (stdev) |
|---|---|---|---|---|
| 10 Week | | | | |
| Sham (n = 6) | 1.000 (0.112) | 0.654 (0.052) | ND | 1.675 (0.125) |
| Banded (n = 6) | 1.205 (0.074) | 0.909 (0.052) | ND | 2.269 (0.104) |
| P value | 0.004 | 0.00001 | | 0.000004 |
| 26 Week | | | | |
| Sham (n = 6) | 1.053 (0.074) | 0.734 (0.049) | 1.700 (0.089) | 1.610 (0.073) |
| Banded (n-6) | 1.273 (0.293) | 0.931 (0.260) | 2.067 (0.258) | 1.962 (0.344) |
| P value | 0.1 | 0.1 | 0.008 | 0.03 |

Figure 1:
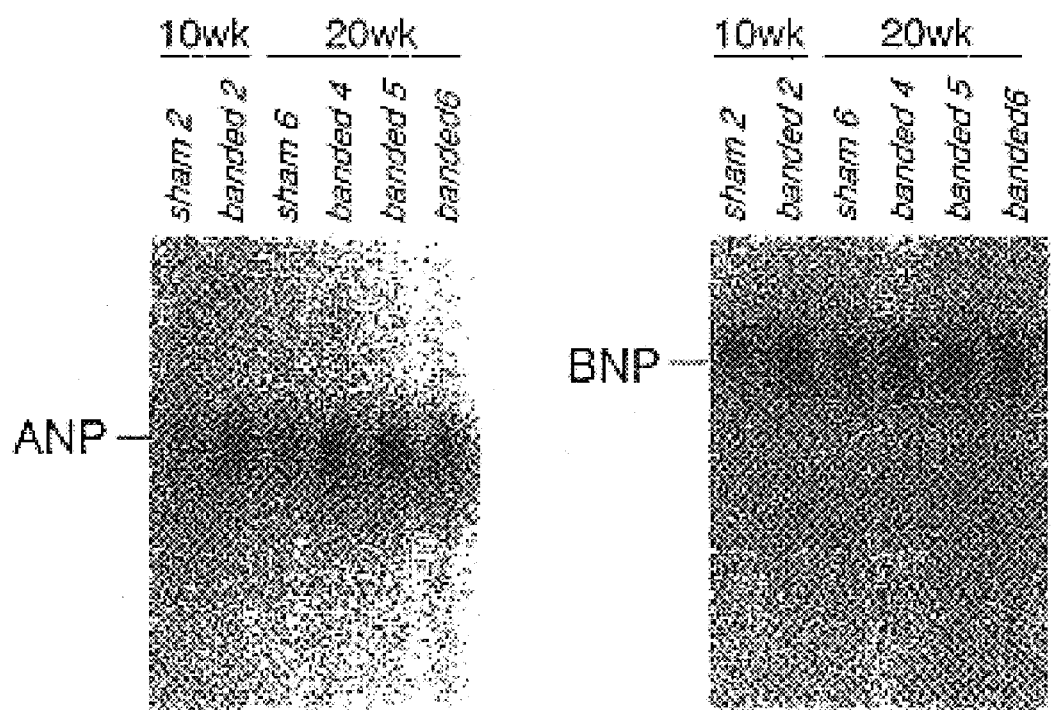

LVH rats were examined for expression of ANP mRNA which, according to published data (Schunkert et al., 1995, supra), should increase in the diseased animals. mRNA was extracted from the left ventricle of each animal and analyzed by Northern blot (FIG. 1). ANP transcripts were significantly elevated (~5-fold) at 10 weeks and 20 weeks relative to normal. The levels of mRNA were examined for BNP (FIG. 1), cardiac α-actin (not shown) and β-myosin heavy chain (not shown) by Northern blot and, as expected, these were also elevated in the diseased animals. Blots were probed for cyclophilin transcripts to attest to equal loading of mRNA. This molecular and physical data confirm that the banded rats were pressure overloaded and responded with cardiac hypertrophy. Poly A+ mRNA was prepared from each of the animals, as described herein, for assessment of differentially expressed genes in the disease state, using microarray analysis in a preferred embodiment. A summary of the findings of the microarray analysis is provided in FIG. 4, and described in detail below.

2. In Vivo Model of Viral Myocarditis

In another representative example, an in vivo model of cardiac disease, specifically, viral myocarditis, was used within the context of the present invention. CVB3 infection in mice results in myocardial disease progression, which was used as a model for examination of the pathogenesis of virus-induced human myocarditis. The virus is directly injurious to myocardial cells early following infection during the preinflammatory period as determined by light and electron microscopic cytological assessment (Arola et al., *J. Med. Virol.* 47: 251–259 (1995); Chow et al., Lab. Invest. 64: 55–64 (1991); McManus et al., *Clin. Immunol. Immunopathol.* 68:159–169 (1993); Melnick et al., *J. Expert. Med.* 93: 247–266 (1951)). Beginning by day two post-infection cytopathic lesions are evident in ventricular myocytes, characterized by cell vacuolar changes, contraction bands and coagulation necrosis (McManus et al., supra). By day 5 post-infection this myocardial injury becomes obscured by inflammatory infiltrates, cellular calcification, and tissue edema.

A/J (H-2$^a$) mice (Jackson Laboratories, Bar Harbor, Maine) were 4 weeks of age when received at St. Paul's Hospital Animal Care Facility, University of British Columbia. Mice were acclimatised for one week in a St. Paul's Hospital Animal Care Facility level 2 biohazard containment room prior to the onset of the experiment. Any mice that died naturally during the course of the disease were not included in groups of mice to be used for RNA extraction. Mice were euthanized by $CO_2$ narcosis.

Myocarditic CVB3 was kindly provided by Dr. Charles J. Gauntt (University of Texas, San Antonio, Tex.) and was stored at −80° C. Virus was propagated in HeLa cells (American Type Tissue Culture Collection, Rockville, Md.) and is routinely titred before the onset of all experiments using the plaque assay method, with modifications as previously described (Anderson et al., *J. Virol.* 70: 4632–4645 (1996)).

Adolescent A/J mice were infected with $1 \times 10^5$ pfu of myocarditic CVB3 or PBS sham and euthanized on days 3, 9, and 30 post-infection. Ten to fifteen mice per group (CVB3 infected or sham injected) per time-point (days 3, 9, and 30) were euthanized and heart muscle was removed. Following a wash in sterile phosphate buffered saline, a small portion of the apex of the heart was removed and fixed in 4% paraformaldehyde. The remainder of the heart was flash frozen in liquid nitrogen and stored at −80° C. for future RNA isolation.

Sections from the heart were fixed in fresh DPBS-buffered 4% paraformaldehyde overnight at 4° C. Fixed tissue was dehydrated in graded alcohols, cleared in xylene, embedded in paraffin, and sectioned for hematoxylin and eosin, and Masson's trichrome stains. Serial sections were also prepared for in situ hybridization and nick-end labelling stained. The extent and severity of virus-induced injury (including coagulation necrosis, contraction band necrosis, and cytopathic effects), inflammation, and tissue fibrosis and calcification was evaluated and scored as previously described (Chow et al., supra).

employed for sham-operated rats, however, the suture was passed through the left ventricular wall and the LAD was not occluded.

Following the surgical procedure, negative pressure in the thoracic was quickly reestablished and the wound closed with a purse-string suture using 3–0 non-absorbable suture material. Butorphanoll (0.1 mg/kg. SQ) was provided post surgery as a prophylactic analgesic. The rats were extubated when they recovered their gag reflex and allowed to recover in a warming chamber.

Seventy-five percent of the rats had large infarcts on their left ventricle free walls and perioperative mortality rate is about 50%, which is comparable to the published data. The heart weight as a percentage of body weight 3–4 weeks post-infarction is increased (see table).

TABLE 2

| Group | No. of Rats | Heart Weight(mg) | Body Weight(g) | HW/BW (mg/g) |
|---|---|---|---|---|
| Sham | 4 | 121.38 +/− 0.09 | 419.23 +/− 62.77 | 2.92 +/− 0.23 |
| Large MI Infarction | 5 | 141.83 +/− 0.74 | 414.06 +/− 49.94 | 3.54 +/− 0.40 |

In situ hybridization for CVB3 viral RNA localization was carried out as previously described (Anderson et al., supra; Hohenadl et al., *Mol. Cell. Probes* 5: 11–20 (1991)). Briefly, tissue sections were incubated overnight in hybridization mixture containing digoxigenin-labelled, CVB3 strand-specific riboprobes. Post-hybridization washing was followed by blocking with 2% normal lamb serum. A sheep anti-digoxigenin polyclonal antibody conjugated to alkaline phosphatase (Boehringer Mannheim PQ, Laval, Canada) was developed in Sigma-Fast nitroblue tetrazolium-BCIP [5-bromo-4-chloro-3-indolylphosphate tuluidinium] (Sigma Chemical Co.). The slides were counterstained in fresh carmalum and examined for reaction product by light microscopy. Poly A+ mRNA was prepared from each of the animals, as described herein, for assessment of differentially expressed genes in the disease states, using microarray analysis in a preferred embodiment. A summary of the findings of the microarray analysis is provided in FIG. 4, and described in detail below.

3. In Vivo Model of Myocardial Infarction a. Left Ventricle Myocardial Infarction In yet another representative example, an in vivo model of cardiac disease, specifically, left ventricle myocardial infarction, was used within the context of the present invention. The rat myocardial infarct (MI) model used is described by Pfeffer et al., *Circ. Res.* 57:84–95 (1985).

Male Sprague-Dawley rats at age 7–10 weeks were anesthetized with ketamine (80 mg/kg. IP) and xylazine (10 mg/kg. IP). The thorax and abdomen was shaved, after which the areas were scrubbed with providone-iodine and 70% isopropyl alcohol a minimum of three times, beginning at the incision line and continuing in a circular motion proceeding toward the periphery. The rats were intubated and placed on a respirator with room air at a rate of 55 breaths/min. A left thoracotomy was performed between the fourth and fifth ribs, after which the heart was exteriorized and the left anterior descending coronary artery (LAD) ligated with silk suture. The same surgical procedure was Tissue was collected 2 week, 4 week, 8 week, 12 week and 16 week post-surgery. Blood was collected the day before surgery and the day before sacrifice for measurement of plasma ANP level. On the day of necropsy, each heart was divided transversely into two halves so that the infarcted area is bisected. One half of the heart was used for histological evaluation, and the other for mRNA microarray analysis. Poly A+ mRNA was prepared from each of the animals, as described herein, for assessment of differentially expressed genes in the disease state, using microarray analysis in a preferred embodiment. A summary of the findings of the microarray analysis is provided in FIG. 4, and described in detail below.

b. Septum Myocardial Infarction

In another representative example, septum tissue was obtained from diseased rat hearts obtained through the left ventricle rat MI model of Pfeffer et al., as described above. Poly A+ mRNA was prepared from each of these septums, as described herein, for assessment of differentially expressed genes in the disease state, using microarray analysis in a preferred embodiment. A summary of the findings of the microarray analysis is provided in FIG. 4, and described in detail below.

4. In Vivo Model of Kidney Disease

In yet another representative example, an in vivo model of kidney disease was used within the context of the present invention. The specific rat model used was an inherited form of autosomal dominant polycystic kidney disease (ADPKD) which develops in Han:SPRD rats (Kaspareit-Rittinghaus et al., *Transplant Proc.* 6: 2582–3 (1990); Cowley et al., *Kidney Int.* 43:522–34 (1993)). Renal cysts and renal failure were evident in six month old male heterozygous rats (Cy/+), whereas control rats (+/+) showed no sign of cysts or renal failure. Five diseased animals (Cy/+) and one normal (+/+) were sacrificed and the kidneys removed. For cDNA microarray analysis, poly At mRNA was prepared, as described previously, for assessment of differentially expressed genes in the disease state, using microarray analysis in a preferred embodiment. A summary of the findings of the microarray analysis is provided in FIG. 4, and described in detail below.

5. Microarray Production from Model DNA

In a preferred embodiment of the present invention, microarray analysis is performed on cDNA obtained from both the normal and disease state models to assess the presence of differentially expressed disease state genes. High quality DNA is important for the microarray printing process. DNA was generated by PCR amplification of the cDNA insert from clones. 10,000 clones per array were generally used. Indeed, it is preferable to use a robust method of template preparation, preferably accomplished in 96-well plates.

Figure 2:
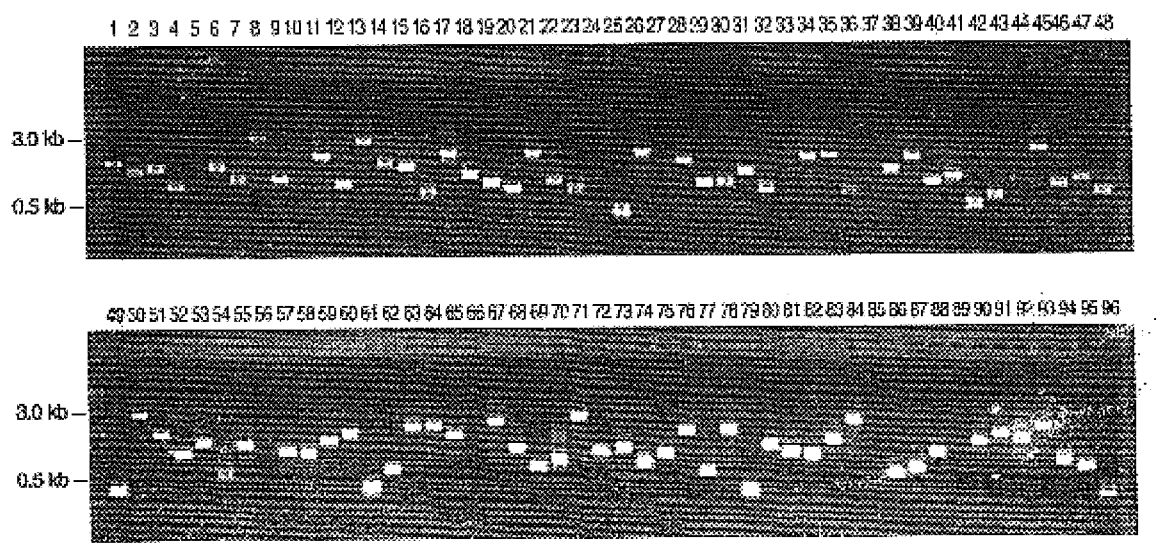

A microtiter plate protocol for PCR amplification of DNA and its subsequent purification was established that provides acceptable quality and quantity of DNA for printing on microarrays for use in a preferred embodiment of the present invention. Specifically, PCR primers were synthesized that amplify insert DNA from the vector pCR2.1, which was used for library construction. After 30 cycles of amplification each PCR product is passed over a gel filtration column to remove unincorporated primers and salts. To maintain robustness, the columns are packed in 96-well filter plates and liquid handling is performed robotically. The yield, per PCR reaction, is generally 2–5 $\mu$g, enough DNA for printing several hundred chips. FIG. 2 shows a gel containing purified PCR products from a single plate of 96 rat cDNA clones. In some samples no amplified DNA was produced (e.g., #37 and #44) and, in some cases, the size of the product indicated that the plasmid lacked an insert (e.g., #49 and #61).

To test the quality of DNA that was prepared by this PCR method, 96 purified samples from a single microtiter plate were produced as a microarray. Using a robotic liquid handler (Biomek 2000, Beckman), 85 $\mu$l of PCR reaction mixture was aliquoted into each well of a thin walled, 0.2 ml 96-well plate. The reaction mixture contained 0.2 mM each dNTP, 1.25 units of Taq polymerase, and 1X Taq buffer (Boehringer Mannheim). Primers, 1 $\mu$m each, are from vector regions, which flank the cloning site of pCR2.1 and include a 5' primary amine with a 6 carbon linker to facilitate attachment of DNA product to the glass surface of the microarray chip. 1.0 $\mu$l of bacterial culture of individual cDNA clones was added to each well. PCR conditions are: 2 min., 95° C. to denature, then 30 cycles of 95°, 30 sec. / 65° C., 40 sec. / 72° C., 1 min. 30 sec., and a final extension of 72° C., 5 min. using a MJResearch PTC 100 thermocycler.

PCR products were purified by gel filtration over Sephacryl 400 (Sigma); Briefly, 400 $\mu$l of pre-swollen Sephacryl 400 was loaded into each well of a 96-well filter plate (PallBiosupport) and spun into a collection plate at 800 g for 1 min. Wells were washed 5 times with 0.2×SSC. PCR reaction mixtures were loaded onto the column and purified DNA (flow-thru) was collected at 800 g for 1 min. Samples are dried down at 50° C. overnight and arrayed.

Fluorescent probe pairs were synthesized by reverse transcription of poly A+ RNA using, separately, Cy3 dCTP and Cy5 dCTP (Amersham). In 16.5 $\mu$l, 1 $\mu$g poly A+ RNA and 2 $\mu$g of oligo dT 21mer, were denatured at 65° C., 5 min. and annealed at 25° C., 10 min. Reverse transcription was performed for 2 hours at 37° C. with Superscript RT (Life Technologies, Gaithersburg, Md.) in 1×buffer, 10 units RNase block, 500 $\mu$M each dATP/dGTP/dTTP, 280 $\mu$M dCTP, 40 $\mu$M Cy5 or Cy3 dCTP, and 200 units RT. RNA is degraded in 0.1 M NaOH, 65° C. for 10 min. Labeled cDNA was purified by successive filtration with Chroma Spin 30 spin columns (Clontech) following manufacturer's instructions. Samples were dried at room temperature in the dark using a covered Speed-Vac. Probes were applied to the test chip for hybridization and the data collected essentially as described in Schena et al., supra. The intensity of hybridization signal at each element reflected the level of expression of the mRNA for each gene in the rat ventricle. Digitized signal data was stored and prepared for analysis. The data from this experiment is presented in FIG. 3.

Referring to FIG. 3, positive signals were detected from most of the elements that contained DNA. A series of control DNA elements were included on each chip to ensure consistency in labeling and hybridization between experiments and to aid in balancing the signal when two fluorescence channels are used. For each element hybridized with dual labeled probes, absolute and relative intensity of signal was determined. The results from these and other experiments indicate that these methods for production of template DNA and labeled cDNA probes are suitable for generating high quality microarrays within a preferred embodiment of the methods of the present invention. The evaluation of tens of thousands of genes for expression generates a large amount of data that can be manipulated by commercially available software packages that facilitate handling this type and quantity of data. The expression data can be stored, analyzed, and sorted from each experiment using this software. In addition, expression of each clone can be tracked from experiment to experiment using known methodologies.

6. Preparation of Normalized cDNA Libraries for Microarray Analysis

In one embodiment of the present invention, to capture as many different genes as possible without the necessity to include all such genes, clones may be randomly picked from a cDNA library, resulting in redundant selection of genes expressed at high and moderate abundance. It is estimated that 50% of all transcripts in a cell derive from ~400 genes (Bishop et al., Nature 250(463):199–204 (1974)). Thus, random picking of 20,000 cDNA clones would represent roughly half that number of different genes, and rare transcripts may be underrepresented.

However, in a separate embodiment of the present invention, a greater number of different clones can be randomly chosen for microarray analysis if cDNA libraries produced from the models of the present invention are first normalized. Methods have been developed to construct libraries that bring the frequency of all clones to near equivalence (Soares et al., Proc. Natl. Acad. Sci. USA 91(20):9228–32 (1994); Bonaldo et al., Genome Res. 6(9) :791–806 (1996)), thus minimizing redundant picking of prevalent clones. In addition, selecting clones from a normalized library also increases the likelihood of choosing clones of rare transcripts.

Following the method of (Bonaldo et al., supra), a normalized version of a cDNA library was generated from normal tissue, cells or blood (e.g., the left ventricle of normal rat). In a particular embodiment, poly A+ RNA was purified from the tissue samples provided by the in vivo disease models described above. A directionally cloned cDNA library was first generated by conventional methods. Briefly, double stranded cDNA was generated by priming first strand synthesis for reverse transcription using oligo dT primers which contain a Not I restriction site. After second strand synthesis, Xba I adapters are added to the 5' end of the cDNA, and the cDNA size was selected for <500 bp and ligated into the corresponding restriction sites of phagemid vector pCR2.1 (Invitrogen, San Diego Calif.).

From the total cDNA library, a normalized library was generated as detailed elsewhere (Bonaldo et al., supra) and described here briefly. Phagemid vector pCR2.1 contains an F1 origin of replication. Thus, the cDNA library can be propagated as single stranded phage with appropriate helper virus. Single stranded, circular DNA was extracted from the phage library and serves as "tester" DNA in the hybridization step of normalization. The other component of the hybridization, "driver" DNA, was generated from the library by PCR amplification using a set of primers specific for the region of the vector, which flanks the cloned inserts. Purified tester DNA (50 ng) and driver DNA (0.5 µg) was combined in 120 mM NaCl, 50% formamide, 10 mM Tris (pH 8.0), 5 mM EDTA, and 1% SDS. A pair of oligonucleotides (10 µg each), corresponding to polylinker sequence (same strand as tester DNA) which is present in the PCR product, was included in the hybridization reaction to block annealing of vector-specific sequences which are in common between tester and driver DNA.

The reaction mixture, under oil, was heated 3 min. at 80° C., and hybridization performed at 30° C. for 24 hr (calculated $C_o t \sim 5$). Single stranded circles were purified from the reaction mixture by hydroxylapatite (HAP) chromatography, converted to double strand DNA, and electroporated into bacteria to yield a normalized cDNA library representative of genes expressed in the left ventricle of rat. To evaluate the effectiveness of the normalization protocol, the frequency of a few clones (ANP, BNP, actin, and myosin) was assessed in both in the starting library and the normalized library. The frequency of abundant cDNAs (actin and myosin) was reduced and roughly equivalent to rarer cDNA clones (ANP and BNP). Clone frequency in the two libraries was determined with standard screening techniques by immobilizing colonies onto nylon membranes and hybridizing with radiolabeled DNA probes.

Certain genes, unexpressed in a normal tissue and turned on in diseased tissue, may be absent from the normalized cDNA library generated from normal tissue. To obtain disease-specific clones to include on the microarray, one can repeat the normalization strategy outlined above using diseased tissue obtained from the appropriate disease model. However, since most genes are expressed commonly between normal and diseased tissue, microarraying normalized libraries from diseased and normal tissue may introduce significant redundancy. In a preferred embodiment, clone redundancy is reduced, yet cDNAs are obtained which are expressed specifically, as well as substantially elevated, in diseased tissue. To obtain disease-specific cDNAs, a subtracted library can be made using protocols similar to those used to generate normalized libraries. Again, the method of Bonaldo et al., supra, described here briefly is used.

To make a subtracted library, a total cDNA library is generated from the tissue obtained from the disease model (e.g., left ventricle taken from a hypertrophic rat (10 week aortic banded)). The cDNA library is directionally cloned in pCR2.1 vector and single stranded tester DNA derived as described above for library normalization. The driver DNA is generated by PCR amplification of cloned inserts from the total cDNA library prepared from the left ventricle of normal rat. Hybridization occurs between sequences, which are in common to normal and diseased hearts. For this subtracted library, the reaction is driven more thoroughly (calculated $C_o t \sim 27$) than normalization by using more driver (1.5 µg vs. 0.5 µg) and longer hybridization time (48 hr vs. 24 hr). Purification of nonhybridized, single stranded circles by HAP chromatography, conversion to double strand DNA, and electroporation into bacteria yields a subtracted cDNA library enriched for genes which are expressed in diseased rat hearts. To test that the library is truly subtracted, colony hybridization is performed with probes for ANP, BNP, actin, and myosin. The subtracted library has a high frequency of ANP and BNP clones since they are elevated significantly in the hypertrophic rat heart. Actin and myosin clones are absent since they are expressed equally in normal and diseased left ventricle.

In use of an exemplary normalized library within the context of the present invention, from two rat left ventricle cDNA libraries, 30,000 clones are picked for microarraying. 25,000 clones are taken from the normalized library generated from normal rats, and 5,000 from the subtracted library made from hypertrophic rats. The subtracted library should be less complex (i.e., fewer unique clones) than the normalized library, therefore, fewer clones need be picked. If, as estimated, only about 1% of all 20,000 genes are unique to the disease state, then the complexity would be only about 200, thus picking 5000 would likely yield a representative of each.

Preferably included on the microarray with the 30,000 unidentified genes are a set of known clones. Rat clones for the list of genes were isolated by PCR amplification from cDNA libraries using specific primer pairs. These known clones were included because they represent genes of particular interest and help evaluate the sensitivity of the microarray methodology. Indeed, any genes of particular interest may be included on such microarrays. By way of example, ANP, BNP, endothelin, β-myosin heavy chain, and α-actin are genes that change expression levels in the LVH model, and thus they serve as useful positive controls in the in vivo model exemplified herein.

7. Alternative Screening Methods

In the examples disclosed herein, the differentially expressed genes preferably are detected by microarray methods, however, differential expression detected by any other means, including but not limited to RNA diagnosticing methods, Northern blotting, immunodetection, protein-protein interactions, biological activity and other methods known in the art fall within the scope of the present invention.

In an alternate embodiment of the present invention, the differentially expressed cardiac genes may be identified through the use of differential screening methods. Differential screening involves the duplicate screening of a cDNA library in which one copy of the library is screened with a total cell cDNA probe corresponding to the mRNA population of one cell type, while a duplicate copy of the cDNA library is screened with a total cDNA probe corresponding to the mRNA population of a second cell type. For example, one cDNA probe can correspond to a total cell cDNA probe of a cell type or tissue derived from a control subject, while the second cDNA probe can correspond to a total cell cDNA probe of the same cell type derived from an experimental subject. Clones hybridizing to one probe, but not to the other, potentially represent clones derived from genes differentially expressed in the cell type of interest in control versus experimental subjects.

Subtractive hybridization techniques generally involve the isolation of mRNA taken from two different sources, e.g., control and experimental tissue, the hybridization of the mRNA or single-stranded cDNA reverse-transcribed from the isolated mRNA, and the removal of all hybridized, and therefore double-stranded, sequences. The remaining non-hybridized, single-stranded cDNAs, potentially represent clones derived from genes that are differentially expressed in the two mRNA sources. Such single-stranded cDNAs are then used as the starting material for the construction of a library comprising clones derived from differentially expressed genes.

The differential display technique describes a procedure, utilizing PCR (U.S. Pat. No. 4,683,202, incorporated herein by reference), which allows for the identification of sequences derived from genes which are differentially expressed. First, isolated RNAs are reverse-transcribed into single-stranded cDNA, using standard techniques known to those of skill in the art. Primers for the reverse transcriptase reaction can include, but are not limited to, oligo dT-containing primers, preferably of the 3' primer type of bligonucleotide described below. Next, this technique uses pairs of PCR primers, as described below, which allow for the amplification of clones representing a random subset of the RNA transcripts present within any given cell. Using different pairs of primers allows each of the mRNA transcripts present in a cell to be amplified. Among such amplified transcripts can be identified those which have been produced from differentially expressed genes.

The pattern of clones resulting from the reverse transcription and amplification of the mRNA of two different cell types is displayed via sequencing gel electrophoresis and compared. Differences in the two banding patterns indicate potentially differentially expressed genes.

Once potentially differentially expressed gene sequences have been identified using techniques such as those described above, the differential expression of such putatively, differentially expressed genes may be corroborated. Corroboration can be accomplished via, for example, such well-known techniques as Northern analysis, quantitative RT-coupled PCR, microarrays, or RNase protection. The differentially expressed genes can be further characterized, and can be identified as target or diagnostic genes, as discussed below.

8. Detection of Differentially Expressed Genes Using Microarray Analysis

Using cDNA obtained from the representative in vivo cardiac hypertrophy model, the in vivo viral myocarditis model, the in vivo left ventricle myocardial infarction model, the in vivo septum myocardial infarction model, and the in vivo kidney disease model, microarrays were constructed and probed as described above.

FIG. 4 provides a detailed summary of the characteristics of twelve representative differentially expressed disease genes of the present invention. The expression data provided relates to the counterpart gene expressed in the in vivo models described supra, and shows the differential expression data of representative genes obtained through the disease models of the present invention and determined via microarray analysis.

Specifically, FIG. 4 provides the clone identification number for the differentially expressed model gene. As discussed in detail below, and as shown in FIG. 4, those representative disease model differentially expressed genes were found to correspond to human genes encoding 1–8U, prostacyclin-stimulating factor, osf-2, tissue specific mRNA, insulin-like growth factor binding protein 6, OSF-1, gas-1, YMP, BTG2, pre-B cell stimulating factor homolog (SDF1a), peripheral benzodiazepine receptor, and cellular ligand of annexin II (p11). As disclosed in detail above, probes were applied to the microarrays for hybridization and the data collected essentially as described in Schena et al., supra. The intensity of hybridization signal at each element reflected the level of expression of the mRNA for each gene. For each element hybridized with dual labeled probes, absolute and relative intensity of signal is determined, which translates into the relative expression levels of the subject genes. The numeric data provided in FIG. 4 reflects the relative expression level of the gene in the disease state as compared to the expression level of the gene in the normal, or non-disease state, in the five representative disease state models delineated above and as determined by microarray analysis. Specifically, the data shown in FIG. 4 provides a positive or negative multiple of the expression level of the gene in the disease state, as compared to the normal state in the representative models.

Data are reported as differential expression values with positive numbers indicative of genes expressed at higher levels in the diseased tissue relative to normal tissue, and negative values indicative of lower expression in disease. Data are the average values from multiple experiments performed with separate DNA arrays (n=4 for MI left ventricle and septum, n=2 for viral myocarditis, n=2 for LVH, and n=1 for PKD). Array probes were generated from RNA pooled from multiple animals (n=4 for MI, n=10–15 for myocarditis, n=3 for LVH, and n=1 for PKD).

The data also reflects expression levels of genes in certain disease models over various time points. For example, gene expression in the myocardial infarction model was compared at 2, 4, 8, 12, and 16 weeks for the representative genes in the disease state versus the normal state. Indeed, such experimentation provides valuable data regarding the temporal relationship of gene expression levels in disease states and provides important insights regarding the treatment, diagnosis, and modulation of differentially expressed disease state genes, as discussed in detail infra.

One to two percent of the clones assayed on microarrays were found to be differentially expressed. Secondary chips may be used for more extensive hybridizations, including examination of individual animals, and more thorough evaluation of time points. In a preferred embodiment, clones that reproducibly scored in microarray analysis to be at least about two-fold elevated or decreased were microarrayed on separate secondary chips and their expression levels determined. It is understood, however, that differentially expressed genes exhibiting less than about a two-fold change in expression, e.g., less than one, one-half, or one-quarter, or greater than about a two-fold change in expression, e.g., greater than three, five, ten, twenty, one hundred-fold, or one thousand-fold, are within the scope of the present invention.

9. Identification of Differentially Expressed Human Genes

In a preferred embodiment of the present invention, and as discussed in detail above, models of disease states were used to find differentially expressed genes through microarray analysis. Amplified sequences of differentially expressed cDNA obtained through microarray analysis can be used to isolate the full-length clones of the corresponding gene. The full-length coding portion of the gene can readily be isolated, without undue experimentation, by molecular biological techniques well known in the art. For example, the isolated differentially expressed amplified fragment can be labeled and used to screen a cDNA library. Alternatively, the labeled fragment can be used to screen a genomic library.

PCR technology can also be utilized to isolate full-length cDNA sequences. As described above, the isolated amplified gene fragments (of about at least 10 nucleotides, preferably longer, of about 15 nucleotides) obtained through differential display have their 5' terminal end at some random point within the gene and have 3' terminal ends at a position corresponding to the 3' end of the transcribed portion of the gene. Once nucleotide sequence information from an amplified fragment is obtained, the remainder of the gene (i.e., the 5' end of the gene, when using differential display) can be obtained using, for example, RT PCR.

In one embodiment of such a procedure for the identification and cloning of full-length gene sequences, RNA can be isolated following standard procedures from an appropriate tissue or cellular source. A reverse transcription reaction can then be performed on the RNA using an oligonucleotide primer complementary to the mRNA that corresponds to the amplified cloned fragment, for the priming of first strand synthesis. Because the primer is anti-parallel to the mRNA, extension will proceed toward the 5' end of the mRNA. The resulting RNA/DNA hybrid can then be tailed with guanines using a standard terminal transferase reaction, the hybrid can be digested with RNase H, and second strand synthesis can then be primed with a poly-C primer. Using the two primers, the 5' portion of the gene is then amplified using PCR. Sequences obtained can then be isolated and recombined with previously isolated sequences to generate a full-length cDNA of the differentially expressed genes of the invention. For a review of cloning strategies and recombinant DNA techniques that can be used, see, e.g., Sambrook et al., *Molecular Cloning, A Laboratory Manual*, Cold Springs Harbor Press (Cold Springs Harbor, N.Y. 1989) and Ausubel et al., supra.

Amplification of nucleic acids from samples is sometimes desirable and can be accomplished by, e.g., PCR. See generally Erlich, ed., PCR *Technology Principles and Applications for DNA Amplification*, Freeman Press (New York, N.Y. 1992); Innis et al., eds., PCR Protocols *A Guide to Methods and Applications*, Academic Press Inc. (San Diego, Calif. 1990); Mattila et al., *Nucleic Acids Res.* 19:4967 (1991); Eckert et al., PCR *Methods and Applications* 1:17 (1991), McPherson et al., eds., PCR, IRL Press (Oxford); and U.S. Pat. No. 4,683,202.

Other suitable amplification methods include the ligase chain reaction (LCR) (see Wu et al., *Genomics* 4:560 (1989), Landegren et al., *Science* 241:1077 (1988)), transcription amplification (Kwoh et al., *Proc. Natl. Acad. Sci. USA* 86:1173 (1989)), and self-sustained sequence replication (Guatelli et al., *Proc. Nat. Acad. Sci. USA*, 87:1874 (1990)) and nucleic acid based sequence amplification (NASBA).

Representative differentially expressed clones obtained from the microarray. analysis of DNA obtained from the disease models were sequenced and compared, in a preferred embodiment, to known human gene sequence databases for matches to known human genes (see FIGS. 5, 6, 7, and 8). Clones, which show no matches to known genes, may require more thorough sequence analysis to search for structural motifs that indicate function.

In a representative sample, twelve differentially expressed disease genes identified by the methods of the present invention were sequenced and compared with human gene nucleotide sequences in the GenBank database. The nucleotide sequences of those twelve representative differentially expressed genes and their human gene counterparts obtained through the GenBank database are provided in FIG. 5. In instances where the differentially expressed genes of the present invention were identical to a known rat gene nucleotide sequence, the known sequence is used for comparison. Specifically, FIG. 5 shows alignment data comparing the cDNA encoding the representative differentially expressed genes discovered through the microarray analysis of the present invention with human cDNA sequences in the GenBank database, which correspond to the human proteins 1–8U (SEQ ID NO:1; SEQ ID NO:2), prostacyclin-stimulating factor (SEQ ID NO:3; SEQ ID NO:4), osf-2 (SEQ ID NO:5; SEQ ID NO:6), tissue specific mRNA (SEQ ID NO:7; SEQ ID NO:8), insulin-like growth factor binding protein 6 (SEQ ID NO:9; SEQ ID NO:10), OSF-1 (SEQ ID NO:11; SEQ ID NO:12), gas-1 (SEQ ID NO:13; SEQ ID NO:14), YMP (SEQ ID NO:15; SEQ ID NO:16), BTG2 (SEQ ID NO:17; SEQ ID NO:18), pre-B cell stimulating factor homolog (SDF1a) (SEQ ID NO:19; SEQ ID NO:20), peripheral benzodiazepine receptor (SEQ ID NO:21; SEQ ID NO:22), and cellular ligand of annexin II (p11) (SEQ ID NO:23; SEQ ID NO:24), respectively.

The complementary nucleic acid sequences of these human genes and their expression products may be used in all embodiments of the present invention. Indeed, all or a portion of the DNA sequences of differentially expressed genes discovered through the methods of the present invention may be found to correspond to known genes or, for example, ESTs or SNPs. In instances where a complete human gene is not found to directly correspond to the differentially expressed genes of the present invention, yet a portion of a known gene, EST, or SNP does correspond, one skilled in the art may preferably elucidate the complete corresponding human gene and/or the differentially expressed gene, or portions thereof, using known methods. This, in turn, may allow for elucidation of the complete differentially expressed human or model gene, which may be used in the methods described infra.

FIG. 6 shows alignment data comparing human cDNA sequences in the GenBank database with multiple cDNA clones encoding the differentially expressed genes discovered through the microarray analysis of the present invention, which correspond to the human proteins 1–8U, tissue specific mRNA, YMP, pre-B cell stimulating factor homolog (SDF1a), peripheral benzodiazepine receptor, and cellular ligand of annexin II (p11). Start and stop codons are underlined.

FIG. 7 shows the nucleotide sequences encoding the polypeptides corresponding to the human genes 1–8U (SEQ ID NO:25), prostacyclin-stimulating factor (SEQ ID NO:26), osf-2 (SEQ ID NO:27),tissue specific mRNA (SEQ ID NO:28), insulin-like growth factor binding protein 6 (SEQ ID NO:29), OSF-1 (SEQ ID NO:30), gas-1 (SEQ ID NO:31), YMP (SEQ ID NO:32); BTG2 (SEQ ID NO:33), pre-B cell stimulating factor homolog (SDF1a) (SEQ ID NO:34), peripheral benzodiazepine receptor (SEQ ID NO:35), and cellular ligand of annexin II (p11) (SEQ ID NO:36).

FIG. 8 shows the amino acid sequences of the polypeptides corresponding to 1–8U (SEQ ID NO:37), prostacyclin-stimulating factor (SEQ ID NO:38), osf-2 (SEQ ID NO:39), tissue specific mRNA (SEQ ID NO:40), insulin-like growth factor binding protein 6 (SEQ ID NO:41), OSF-1 (SEQ ID NO:42), gas-1 (SEQ ID NO:43), YMP (SEQ ID NO:44), BTG2 (SEQ ID NO:45), pre-B cell stimulating factor homolog (SDF1a) (SEQ ID NO:46), peripheral benzodiazepine receptor (SEQ ID NO:47), and cellular ligand of annexin II (p11) (SEQ ID NO:48).

FIG. 9 shows the characteristics of the human cDNA corresponding to the human proteins 1–8U, prostacyclin-stimulating factor, osf-2, tissue specific mRNA, insulin-like growth factor binding protein 6, OSF-1, gas-1, YMP, BTG2, pre-B cell stimulating factor homolog (SDF1a), peripheral benzodiazepine receptor, and cellular ligand of annexin II (p11). Specifically, FIG. 9 provides the GenBank identification number for each of the human genes corresponding to the differentially expressed genes discovered through microarray analysis, the size of the cDNA of each gene, the coding sequence (CDS), the number of amino acids in the encoded human protein, whether or not the human protein has a signal sequence, and whether or not the human protein is a transmembrane protein.

VIII. USE OF DIFFERENTIALLY EXPRESSED GENES

The identified differentially expressed genes may in turn be used to design specific oligonucleotide probes and primers. In certain preferred embodiments, the term "primer" as used here includes any nucleic acid capable of priming template-dependent synthesis of a nascent nucleic acid. In certain other embodiments, the nucleic acid may be able to hybridize a template, but not be extended for synthesis of nascent nucleic acid that is complementary to the template.

In certain embodiments of the present invention the term "template" may refer to a nucleic acid that is used in the creation of a complementary nucleic-acid strand to the "template" strand. The template may be either RNA or DNA, and the complementary strand may also be RNA or DNA. In certain embodiments the complementary strand may comprise all or part of the complementary sequence to the template, or may include mutations so that it is not an exact, complementary strand to the template. Strands that are not exactly complementary to the template strand may hybridize specifically to the template strand in detection assays described here, as well as other assays known in the art, and such complementary strands that can be used in detection assays are part of the invention.

When used in combination with nucleic acid amplification procedures, these probes and primers enable the rapid analysis of cell, tissue, or peripheral blood samples.

In certain aspects of the invention, the term "amplification" may refer to any method or technique known in the art or described herein for duplicating or increasing the number of copies or amount of a target nucleic acid or its complement. The term "amplicon" refers to the target sequence for amplification, or that part of a target sequence that is amplified, or the amplification products of the target sequence being amplified. In certain other embodiments, an "amplicon" may include the sequence of probes or primers used in amplification. This analysis assists in detecting and diagnosing a disease, specifically cardiac, kidney or inflammatory disease, and in determining optimal treatment courses for individuals at varying stages of disease progression.

In light of the present disclosure, one skilled in the art may select segments from the identified genes for use in detection, diagnostic, or prognostic methods, vector constructs, antibody production, kits, or any of the embodiments described herein as part of the present invention. For example, in certain embodiments in which one may be practicing for the identification of a differentially expressed gene of the present invention, the sequences selected to design probes and primers may include repetitive stretches of adenine nucleotides (poly-A tails) normally attached at the ends of the RNA for the identified differentially expressed gene. In certain other embodiments, probes and primers may be specifically designed to not include these or other segments from the identified genes, as one of ordinary skill in the art may deem certain segments more suitable for use in the detection methods disclosed.

For example, where a genomic sequence is disclosed, one may use sequences that correspond to exon regions of the gene in most cases. One skilled in the art may select segments from the published exon sequences, or may assemble them into a reconstructed mRNA sequence that does not contain intronic sequences. Indeed-, one skilled in the art may select or assemble segments from any of the identified gene sequences into other useful forms, such as coding segment reconstructions of mRNA sequences from published genomic sequences of the identified differentially expressed genes, as part of the present invention. Such assembled sequences would be useful in designing probes and primers, as well as providing coding segments for protein translation and for detection, diagnosis, and prognosis embodiments of the invention described herein.

Primers can be designed to amplify transcribed portions of the differentially expressed genes of the present invention that would include any length of nucleotide segment of the transcribed sequences, up to and including the full length of each gene. It is preferred that the amplified segments of identified genes be an amplicon of at least about 50 to about 500 base pairs in length. It is more preferred that the amplified segments of identified genes be an amplicon of at least about 100 to about 400 base pairs in length, or no longer in length than the amplified segment used to normalize the quantity of message being amplified in the detection assays described herein. Such assays include RNA diagnosticing methods, however, differential expression may be detected by other means, and all such methods would fall within the scope of the present invention. The predicted size of the gene segment, calculated by the location of the primers relative to the transcribed sequence, would be used to determine if the detected amplification product is indeed the gene being amplified. Sequencing the amplified or detected band that matches the expected size of the amplification product and comparison of the band's sequence to the known or disclosed sequence of the gene would confirm that the correct gene is being amplified and detected.

The identified differentially expressed genes may also be used to identify and isolate full-length gene sequences, including regulatory elements for gene expression, from genomic human DNA libraries. The cDNA sequences or portions thereof, identified in the present disclosure may be used as hybridization probes to screen genomic human DNA libraries by conventional techniques. Once partial genomic clones have been identified, "chromosomal walking" may isolate full-length genes (also called "overlap hybridization"). See Chinault et al., *Gene* 5:111–26 (1979). Once a partial genomic clone has been isolated using a cDNA hybridization probe, nonrepetitive segments at or near the ends of the partial genomic clone may be used as hybridization probes in further genomic library screening, ultimately allowing isolation of entire gene sequences for the disease, specifically cardiac, kidney or inflammatory disease, state genes of interest. It will be recognized that full length genes may be obtained using small ESTs via technology currently available and described in this disclosure (Sambrook et al., supra; Chinault et al., supra). Sequences identified and isolated by such means may be useful in the detection of disease genes using the detection and diagnostic methods described herein, and are part of the invention.

The identified genes may be used to identify and isolate cDNA sequences. The sequences, or portions thereof, identified in the present disclosure may be used as hybridization probes to screen human cDNA libraries by conventional techniques. Comparison of cloned cDNA sequences with known human or animal cDNA or genomic sequences may be performed using computer programs and databases known in the art. FIG. 5 provides a detailed comparison of the sequence similarity between the twelve representative genes of the present invention and their human counterparts. The nucleotide sequences of clones derived from the models of disease disclosed herein were matched to known human genes among the GenBank database.

IX. METHODS FOR THE IDENTIFICATION OF INTERACTIVE GENES

Any method suitable for detecting protein-protein interactions can be employed for identifying interactive gene products by identifying interactions between gene products and the differentially expressed genes of the present invention. An interactive gene can be differentially expressed and, therefore, can have the characteristics of a target or diagnostic gene. Differentially expressed gene products can be cellular or extracellular proteins. Those gene products that interact with such known gene products represent interactive gene products and the genes that encode them represent interactive genes.

Among the traditional methods employed are co-immunoprecipitation, cross-linking and co-purification through gradients or chromatographic columns. Using procedures such as these allows for the identification of interactive gene products. Once identified, an interactive gene product can be used, in conjunction with standard techniques, to identify its corresponding interactive gene. For example, at least a portion of the amino acid sequence of the interactive gene product can be ascertained using techniques well known to those of skill in the art, such as the Edman degradation technique (see, e.g., Creighton, Proteins: Structures and Molecular Principles, W. H. Freeman & Co. (New York, N.Y. 1983), pp.34–49). The amino acid sequence obtained can be used as a guide for the generation of oligonucleotide mixtures that can be used to screen for interactive gene sequences. Screening can be accomplished, for example, by standard hybridization or PCR techniques. Techniques for the generation of oligonucleotide mixtures and the screening are well known. See, e.g., Ausubel et al., supra, and Innis et al., supra.

Additionally, methods can be employed which result in the simultaneous identification of interactive genes that encode the protein interacting with a protein involved in a disease, specifically cardiac, kidney or inflammatory disease. These methods include, for example, probing expression libraries with a labeled protein known or suggested to be involved in a disease, using this protein in a manner similar to the well known technique of antibody probing of λgt11 libraries.

One method that detects protein interactions in vivo, the yeast two-hybrid system, is described in detail for illustration only and not by way of limitation. One version of this system has been described (Chien et.al., *Proc. Natl. Acad. Sci. USA* 88: 9578–82 (1991)) and is commercially available from Clontech (Palo Alto, Calif.).

Briefly, to utilize the system, plasmids are constructed that encode two hybrid proteins: the first hybrid protein consists of the DNA-binding domain of a transcription factor (e.g., activation protein) fused to a known protein, in this case, a protein known to be involved in a disease, specifically cardiac, kidney or inflammatory disease; the second hybrid protein consists of the transcription factor's activation domain fused to an unknown protein that is encoded by a cDNA which has been recombined into this plasmid as part of a cDNA library. The plasmids are transformed into a strain of the yeast *Saccharomyces cerevisiae* that contains a reporter gene (e.g., lacZ) whose expression is regulated by the transcription factor's binding site. Either hybrid protein alone cannot activate transcription of the reporter gene. The DNA binding hybrid protein cannot activate transcription because it does not provide the activation domain function and the activation domain hybrid protein cannot activate transcription because it lacks the domain required for binding to its target site (e.g., it cannot localize to the transcription activator protein's binding site). Interaction between the DNA binding hybrid protein and the library encoded protein reconstitutes the functional transcription factor and results in expression of the reporter gene, which is detected by an assay for the reporter gene product.

The two-hybrid system or related methodology can be used to screen activation domain libraries for proteins that interact with a known "bait" gene product. By way of example, gene products known to be involved in a disease, specifically cardiac, kidney or inflammatory disease, can be used as the bait gene products. Total genomic or cDNA sequences are fused to the DNA encoding an activation domain. This library and a plasmid encoding a hybrid of the bait gene product fused to the DNA-binding domain are co-transformed into a yeast reporter strain, and the resulting transformants are screened for those that express the reporter gene. For example, the bait gene can be cloned into a vector to translationally fuse to the DNA encoding the DNA-binding domain of the protein. The colonies are purified and the (library) plasmids responsible for reporter gene expression are isolated. The inserts in the plasmids are sequenced to identify the proteins encoded by the cDNA or fragments into a vector such that they are translationally fused to the activation domain of GAL4 generates the library. This library can be co-transformed along with the bait gene-GAL4 fusion plasmid into a yeast strain which contains a lacZ gene whose expression is controlled by a promoter which contains a GALA activation sequence. A cDNA encoded protein fused to GAL4 activation domain that interacts with the bait gene product will reconstitute an active GAL4 transcription factor and thereby drive expression of the lacZ gene. Colonies expressing lacZ can be detected by their blue color in the presence of X-gal. cDNA containing plasmids from such a blue colony can then be purified and used to produce and isolate the bait gene product interacting protein using techniques routinely practiced in the art. Once an interactive gene has been identified and isolated, it can be further characterized, for example, as discussed below.

X. CHARACTERIZATION OF DIFFERENTIALLY EXPRESSED GENES

Differentially expressed genes and interactive genes' as well as genes identified by alternative means, can be further characterized by utilizing methods such as those discussed herein. Analyses such as those described herein yield information regarding the biological function of the identified genes. An assessment of the biological function of the differentially expressed genes, in addition, can lead to their designation as target or diagnostic genes.

Specifically, any of the differentially expressed genes whose further characterization indicates that a modulation of the gene's expression or a inodulation of the gene product's activity can inhibit or treat a disease, specifically cardiac, kidney or inflammatory disease, can be designated "target genes" as defined above. Such target genes and target gene products, along with those discussed below will constitute the focus of the compound discovery strategies discussed below. Further, such target genes, target gene products or modulating compounds can be used as part of disease treatment methods described below.

Any of the differentially expressed genes whose further characterization indicates that such modulations do not positively affect a disease, specifically cardiac, kidney or inflammatory disease, but whose expression pattern contributes to a gene expression "diagnostic" pattern correlative of a disease can be designated a "diagnostic gene." "Diagnostic patterns" are discussed below. Each of the target genes may also function as diagnostic genes, as can all or a portion of the interactive genes.

The interactive genes may also be characterized according to techniques such as those described herein. Those interactive genes which yield information indicating that they are differentially expressed and that modulation of the gene's expression or a modulation of the gene product's activity can inhibit a disease, specifically cardiac, kidney or inflammatory disease, or ameliorate a disease associated symptom can also be designated target genes. Such target genes and target gene products, along with those discussed above, may constitute the focus of the compound discovery strategies and treatment methods described below.

The characterization of one or more of the interactive genes can reveal a lack of differential expression, yet evidence that modulation of the gene's activity or expression can nonetheless ameliorate symptoms of a disease, specifically cardiac, kidney or inflammatory disease. In such cases, these genes and gene products may also be considered a focus of the compound discovery strategies and treatment methods of the present invention.

Where an interactive gene's characterization indicates that modulation of gene expression or gene product activity cannot retard or treat the disease but is differentially expressed and contributes to a gene expression diagnostic pattern correlative of a disease or its disorders, such interactive genes can additionally be designated as diagnostic genes.

A variety of techniques can be utilized to further characterize the identified genes. First, the nucleotide sequence of the identified genes, which can be obtained by utilizing standard techniques well known to those of skill in the art, can be used to further characterize such genes. For example, the sequence of the identified genes can reveal homologies to one or more known sequence motifs, which can yield information regarding the biological function of the identified gene product.

Second, an analysis of the tissue or cell type distribution of the mRNA produced by the identified genes can be conducted, utilizing standard techniques well known to those of skill in the art. Such techniques can include, for example, Northern analyses, microarrrays, RT-coupled PCR, and RNase protection techniques. In a preferred embodiment, microarrays are utilized. Such analyses provide information as to whether the identified genes are expressed in tissues expected to contribute to a disease, specifically cardiac, kidney or inflammatory disease. These techniques can also provide quantitative information regarding steady state mRNA regulation, yielding data concerning which of the identified genes exhibits a high level of regulation preferably in tissues which can be expected to contribute to a disease state.

Additionally, standard in situ hybridization techniques can be utilized to provide information regarding which cells within a given tissue express the identified gene. Specifically, these techniques can provide information regarding the biological function of an identified gene relative to a disease, specifically cardiac, kidney or inflammatory disease, where only a subset of the cells within the tissue is thought to be relevant to the disorder.

Third, the sequences of the identified genes can be used, utilizing standard techniques, to place the genes onto genetic maps, e.g., mouse (Copeland et al., Trends in *Genetics* 7:113–18 (1991)) and human genetic maps (Cohen et al., *Nature* 266:698–701 (1993)). This mapping information can yield information regarding the genes' importance to human disease by identifying genes that map within genetic regions to which known genetic disease disorders map.

Fourth, using relevant in vivo and in vitro systems can more directly assess the biological function of the identified genes. In vivo systems can include animal systems that naturally exhibit symptoms of a disease, specifically cardiac, kidney or inflammatory disease, or ones engineered to exhibit such symptoms as detailed infra.

The role of identified gene products (e.g., OSF-1 gene products) can be determined by transfecting cDNAs encoding these gene products into appropriate cells or cell lines, such as, biopsy specimens from patients having undergone surgical treatment, as described above. Further, these systems can include transgenic animals. In vitro systems can include cell-based systems comprising cell types known or suspected of contributing to a disease, specifically cardiac, kidney or inflammatory disease. Cell types may comprise normal cells or non-normal cells containing modifications known to contribute or suspected of contributing to a disease. Such systems are discussed in detail below. Additional procedures to identify and isolate the human homolog of the differentially expressed genes of the present invention when non-human model systems are utilized are also described below.

In further characterizing the biological function of the identified genes, the expression of these genes (or their expression products) can be modulated within the in vivo or in vitro systems, i.e., either over- or under-expressed, and the subsequent effect on the system then assayed. Alternatively, the activity of the product of the identified gene can be modulated by either increasing or decreasing the level of activity in the in vivo or in vitro system of interest, and its subsequent effect then assayed.

The information obtained through such characterizations can suggest relevant methods for the treatment of a disease, specifically cardiac, kidney or inflammatory disease, involving the gene of interest. For example, treatment can include a modulation of gene expression or gene product activity. Characterization procedures such as those described herein can indicate where such modulation should involve an increase or a decrease in the expression or activity of the gene or gene product of interest.

XII. DIFFERENTIALLY EXPRESSED AND INTERACTIVE GENES

The genes of the present invention can be obtained using cloning methods well known to those skilled in the art, including the use of appropriate probes to detect the genes within an appropriate cDNA or gDNA (genomic DNA) library. (See, e.g., Sambrook et al., supra.) Alternatively, oligonucleotide probes for the novel genes can be synthesized using techniques well known to those of skill in the art based on the human or animal DNA sequences disclosed in the Figures. The probes can be used to screen cDNA libraries prepared from an appropriate cell or cell line in which the gene is transcribed. Genomic DNA libraries can be prepared from any source.

As used herein, "differentially expressed gene" (i.e., target and diagnostic genes) or "interactive gene" also includes (a) a gene comprising at least one of the DNA sequences disclosed herein; (b) any DNA sequence that encodes the amino acid sequence encoded by the DNA sequences disclosed herein or contained within the coding region of the gene to which the DNA sequences disclosed here belong; (c) any DNA sequence that hybridizes to the complement of the coding sequences disclosed herein or contained within the coding region of the gene to which the DNA sequences disclosed herein belong under highly stringent conditions, e.g., hybridization to filter-bound DNA in 0.5M $NaHPO_4$, 7% sodium dodecyl sulfate (SDS), 1 mM EDTA at 65° C., and washing in 0.1×SSC/0.1% SDS at 68° C. (Ausubel et al., supra) and encodes a gene product functionally equivalent to a gene product encoded by a gene of (a) above, including all native sequences and variants thereof; (d) any DNA sequence that hybridizes to the complement of: the coding sequences disclosed herein, or contained within the coding region of the gene to which DNA sequences disclosed herein, belong under less stringent conditions, such as moderately stringent conditions, e.g., washing in 0.2×SSC/0.1% SDS at 42° C. (Ausubel et al., supra), yet which still encodes a gene product functionally equivalent to a gene product encoded by a gene of (a) above, including all native sequences and variants thereof; or (e) the human or animal counterpart of such a gene determined by comparison of the sequence of such a gene, or portions thereof, to known sequence information, e.g., the human GenBank database.

The invention also includes nucleic acid molecules, preferably DNA molecules, which hybridize to, and are therefore the complements of, the DNA sequences (a) through (e), in the preceding paragraph. Such hybridization conditions can be highly stringent or less highly stringent, as described above. In instances wherein the nucleic acid molecules are deoxyoligonucleotides ("oligos"), highly-stringent conditions can refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules can act as target gene antisense molecules, useful, for example, in target gene regulation or as antisense primers in amplification reactions of target, diagnostic, or interactive gene nucleic acid sequences. Further, such sequences can be used as part of ribozyme or triple helix sequences, also useful for target gene regulation. Still further, such molecules can be used as components of diagnostic methods whereby disease, specifically cardiac, kidney or inflammatory disease, disorders can be detected.

The invention also encompasses (a) DNA vectors that contain any of the foregoing coding sequences or their complements (i.e., antisense); (b) DNA expression vectors that contain any of the foregoing coding sequences operatively associated with a regulatory element that directs the expression of the coding sequences; and (c) genetically engineered host cells that contain any of the foregoing coding sequences operatively associated with a regulatory element that directs the expression of the coding sequences in the host cell. As used herein, regulatory elements include inducible and non-inducible promoters, enhancers, operators and other elements known to those skilled in the art that drive and regulate expression. The invention includes fragments of any of the DNA sequences disclosed herein.

XIII. ISOLATION AND AMPLIFICATION OF HOMOLOGOUS DIFFERENTIALLY EXPRESSED GENES

In addition to the gene sequences described above, homologs of these gene sequences can, for example, be present in other species. In instances where the above described differentially expressed gene sequences are not human gene sequences, homologs can be identified and can readily be isolated, without undue experimentation, by molecular biological techniques well known in the art. Further, there can exist genes at other genetic loci within the genome that encode proteins, which have extensive homology to one or more domains of such gene products. These genes can also be identified using similar techniques.

For example, the isolated differentially expressed gene sequence can be labeled and used to screen a cDNA library constructed from mRNA obtained from an organism of interest. Hybridization conditions will be of a lower stringency when the cDNA library was derived from an organism different from the type of organism from which the labeled sequence was derived. Alternatively, the labeled fragment can be used to screen a genomic library derived from the organism of interest, again, using appropriately stringent conditions. Such low stringency conditions will be well known to those of skill in the art, and will vary predictably depending on the specific organisms from which the library and the labeled sequences are derived. For guidance regarding such conditions see, Sambrook et al., supra, and Ausubel et al., supra.

Further, a previously unknown differentially expressed or interactive gene-type sequence can be isolated by performing PCR using two degenerate oligonucleotide primer pools designed on the basis of amino acid sequences within the gene of interest. The template for the reaction can be cDNA obtained by reverse transcription of mRNA prepared from human or non-human cell lines or tissue known or suspected to express a differentially expressed or interactive gene allele. The PCR product can be subcloned and sequenced to ensure that the amplified sequences represent the sequences of a differentially expressed or interactive gene-like nucleic acid sequence.

The PCR fragment can then be used to isolate a full-length cDNA clone by a variety of methods. For example, the amplified fragment can be labeled and used to screen a bacteriophage cDNA library. Alternatively, the labeled fragment can be used to screen a genomic library.

PCR technology can also be utilized to isolate full-length cDNA sequences. For example, RNA can be isolated, following standard procedures, from an appropriate cellular or tissue source. A reverse transcription reaction can be performed on the RNA using an oligonucleotide primer specific for the most 5' end of the amplified fragment for the priming of first strand synthesis. The resulting RNA/DNA hybrid can then be "tailed" with guanines using a standard terminal transferase reaction, the hybrid can be digested with RNase H, and second strand synthesis can then be primed with a poly-C primer. Thus, cDNA sequences upstream of the amplified fragment can easily be isolated. For a review of cloning strategies that can be used, see, e.g., Sambrook et al., supra, and Ausubel et al., supra.

A number of template dependent processes are available to amplify the gene sequences present in a given template sample. One of the best known amplification methods is the polymerase chain reaction (referred to as PCR) which is described in detail in U.S. Pat. Nos. 4,683,195, 4,683,202 and 4,800,159, each of which is incorporated herein by reference in its entirety, and in Innis et al., supra.

Alternatively, RNA species can be quantitated by means that do not necessarily require amplification by PCR. These means may include other amplification techniques, for example, isothermic amplification techniques such as the one developed by Gen-Probe (San Diego, Calif.) or the ligase chain reaction (LCR).

XIV. ISOLATION OF MUTANT DIFFERENTIALLY EXPRESSED GENES

Where the differentially expressed or interactive gene identified is the normal, or wild type gene, this gene can be used to isolate mutant alleles of the gene. Such isolation is preferable in processes and disorders that are known or suspected to have a genetic basis. Mutant alleles can be isolated from individuals either known or suspected to have a genotype contributing to disease, specifically cardiac, kidney or inflammatory disease, symptoms. Mutant alleles and mutant allele products can then be utilized in the therapeutic and diagnostic assay systems described below.

A cDNA of a mutant gene can be isolated, for example, by using PCR. In this case, the first cDNA strand can be synthesized by hybridizing a oligo-dT oligonucleotide to mRNA isolated from tissue known or suspected of being expressed in an individual putatively carrying the mutant allele, and by extending the new strand with reverse transcriptase. The second strand of the cDNA can then be synthesized using an oligonucleotide that hybridizes specifically to the 5'-end of the normal gene. Using these two primers, the product is then amplified via PCR, cloned into a suitable vector, and subjected to DNA sequence analysis through methods known to one skilled in the art. By comparing the DNA sequence of the mutant gene to that of the normal gene, the mutation(s) responsible for the loss or alteration of function of the mutant gene product can be ascertained.

Alternatively, a genomic or cDNA library can be constructed and screened using DNA or RNA, respectively, from a tissue known to express or suspected of expressing the gene of interest in an individual suspected of carrying or known to carry the mutant allele. The normal gene or any suitable fragment thereof can then be labeled and used as a probe to identify the corresponding mutant allele in the library. Clones containing this gene can then be purified through methods routinely practiced in the art, and subjected to sequence analysis as described above.

Additionally, an expression library can be constructed utilizing DNA isolated from or cDNA synthesized from a tissue known to express or suspected of expressing the gene of interest in an individual suspected of carrying or known to carry the mutant allele. In this manner, gene products made by the putatively mutant tissue can be expressed and screened using standard antibody screening techniques in conjunction with antibodies raised against the normal gene product as described below. (For screening techniques see, Harlow et al., eds., *Antibodies: A Laboratory Manual*, Cold Spring Harbor Press (Cold Spring Harbor, N.Y., 1988).) In cases where the mutation results in an expressed gene product with altered function (e.g., as a result of a missense mutation), a polyclonal set of antibodies are likely to cross-react with the mutant gene product. Library crones detected via their reaction with such labeled antibodies can be purified and subjected to sequence analysis as described supra.

XV. NUCLEIC ACID PROBES AND PRIMERS

Molecular cloning and expression techniques for making biological and synthetic oligonucleotides and nucleic acids are well known in the art. Wide varieties of cloning and expression and in vitro amplification methods suitable for the construction of nucleic acids are well known to persons of skill. Examples of techniques and instructions sufficient to direct persons of skill through many cloning exercises for the expression and purification of biological nucleic acids (DNA and RNA) are found in Berger et al., *Guide to Molecular Cloning Techniques, Methods in Enzymology*, volume 152, Academic Press, Inc. (San Diego, Calif.); Sambrook et al., supra; and Ausubel et al., supra. Nucleic acids such as tag nucleic acids can be cloned into cells (thereby creating recombinant tagged cells) using standard cloning protocols such as those described in Berger et al., supra; Sambrook et al., supra; and Ausubel et al., supra.

It is apparent that the nucleic acid sequences within the context of the present invention will find utility in a variety of applications in disease, specifically cardiac, kidney or inflammatory disease, detection, diagnosis, prognosis and treatment. Examples of such applications within the scope of the present disclosure comprise amplification of differentially expressed genes using specific primers, detection of genes by hybridization with oligonucleotide probes, incorporation of isolated nucleic acids into vectors, expression of vector incorporated nucleic acids as RNA and protein, and development of immunologic reagents corresponding to gene encoded products.

In one embodiment, the sequences of isolated nucleic acids disclosed herein find utility as hybridization probes or amplification primers. These nucleic acids may be used, for example, in diagnostic evaluation of biological samples or employed to clone full length cDNAs or genomic clones corresponding thereto. In certain embodiments, these probes and primers comprise oligonucleotide fragments. Such fragments are of sufficient length to provide specific hybridization to an RNA or DNA 'sample extracted from tissue and, in a preferred embodiment, may be used within the context of microarrays. The sequences typically may be 10–20 nucleotides, but may be longer. Longer sequences, e.g., 40, 50, 100, 500 and even up to full length, are preferred for certain embodiments.

In a preferred embodiment, nucleic acid molecules having contiguous stretches of about 10, 15, 17, 20, 30, 40, 50, 60, 75 or 100 or 500 nucleotides of a sequence comprising GenBank Accession numbers X57352, S75725, D13665, X67698, M62402, D90226, L13698, U52101, U72649, L36034, M36035, and M38591, corresponding to the human genes 1–8U (SEQ ID NO:25), prostacyclin-stimulating factor (SEQ ID NO:26), osf-2 (SEQ ID NO:27), tissue specific mRNA (SEQ ID NO:28), insulin-like growth factor binding protein 6 (SEQ ID NO:29), OSF-1 (SEQ ID NO:30), gas-1 (SEQ ID NO:3 ), YMP (SEQ ID NO:32), BTG2 (SEQ ID NO:33), pre-B cell stimulating factor homolog (SDF1a) (SEQ ID NO:34), peripheral benzodiazepine receptor (SEQ ID NO:35), and cellular ligand of annexin II (p11) (SEQ ID NO:36), respectively, are contemplated. Molecules that are complementary to the above mentioned sequences and that bind to these sequences under high stringency conditions are also contemplated. These probes are useful in a variety of hybridization embodiments, such as Southern and Northern blotting and microarray assays and diagnostics. In some cases, it is contemplated that probes may be used that hybridize to multiple target sequences without compromising their ability to effectively diagnose the disease state.

In certain embodiments, it is contemplated that multiple probes may be used for hybridization to a single sample. The use of a hybridization probe of between 17 and 100 nucleotides in length allows the formation of a duplex molecule that is both stable and selective. Molecules having complementary sequences over stretches greater than 20 bases in length are generally preferred in order to increase stability and selectivity of the hybrid, and thereby improve the quality and degree of hybrid molecules. It is generally preferred to design nucleic acid molecules having stretches of 20 to 30 nucleotides, or even longer. Such fragments may be readily prepared by directly synthesizing the fragment by chemical means or by introducing selected sequences into recombinant vectors for recombinant production.

XVI. DIFFERENTIALLY EXPRESSED AND INTERACTIVE GENE PRODUCTS

Differentially expressed or interactive gene products can be produced by synthetic techniques or via recombinant DNA technology using techniques well known in the art. Methods for preparing the differentially expressed or interactive gene polypeptides and peptides of the invention by expressing nucleic acid encoding differentially expressed or interactive gene sequences are described herein. Methods known to those skilled in the art can be used to construct expression vectors containing differentially expressed or interactive gene protein coding sequences and appropriate transcriptional/translational control signals. These methods include in vitro recombinant DNA techniques, synthetic techniques and in vivo recombination/genetic recombination. See, e.g., the techniques described in Maniatis et al., Molecular Cloning, A Laboratory Manual, Cold Spring Harbor Laboratory (New York, N.Y., 1989) and Ausubel et al., supra. Alternatively, RNA capable of encoding differentially expressed or interactive gene protein sequences can be chemically synthesized using, for example, synthesizers. See, for example, the techniques described in Gait, ed., Oligonucleotide Synthesis, IRL Press (Oxford, 1984).

A variety of host-expression vector systems can be utilized to express the differentially expressed or interactive gene coding sequences of the invention. Such host-expression systems represent vehicles by which the coding sequences of interest can be produced and subsequently purified, but also represent cells which can, when transformed or transfected with the appropriate nucleotide coding sequences, exhibit the differentially expressed or interactive gene protein of the invention in situ. These include but are not limited to microorganisms such as bacteria (e.g., *E. coli, B. subtilis*) transformed with recombinant bacteriophage DNA, plasmid DNA or cosmid DNA expression vectors containing differentially expressed or interactive gene protein coding sequences; yeast (e.g., Saccharomyces, Pichia) transformed with recombinant yeast expression vectors containing the differentially expressed or interactive gene protein coding sequences; insect cell systems infected with recombinant virus expression vectors (e.g., baculovirus) containing the differentially expressed or interactive gene protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing differentially expressed or interactive gene protein coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5 K promoter). In a preferred embodiment, Pichia may be utilized.

In bacterial systems, a number of expression vectors can be advantageously selected depending upon the use intended for the differentially expressed or interactive gene protein being expressed. When a large quantity of such a protein is to be produced, for example, for the generation of antibodies or to screen peptide libraries, vectors which direct the expression of high levels of fusion protein products that are readily purified are desirable. Such vectors include the *E. coli* expression vector pUR278 (Rather et al., EMBO J. 2:1791 (1983)), in which the differentially expressed or interactive gene protein coding sequence can be ligated individually into the vector in frame with the lacZ coding region so that a fusion protein is produced and pIN vectors (Inouye et al., *Nucleic Acids Res.* 13:3101–09 (1985); Van Heeke et al., *J. Biol. Chem.* 264:5503–09 (1989)). pGEX vectors can also be used to express foreign polypeptides as fusion proteins with glutathione 5-transferase (GST). In general, such fusion proteins are soluble and can easily be purified from lysed cells by adsorption to glutathione-agarose beads followed by elation in the presence of free glutathione. The pGEX vectors are designed to include thrombin or factor Xa protease cleavage sites so that the cloned target gene protein can be released from the GST moiety.

In mammalian host cells, a number of viral-based expression systems can be utilized. Where adenoviruses are used as expression vectors, the differentially expressed or interactive gene coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a nonessential region of the viral genome (e.g., region E1 or E3) will result in a recombinant virus that is viable and capable of expressing differentially expressed or interactive gene protein in infected hosts (see Logan et al., *Proc. Natl. Acad. Sci. USA* 81:3655–59 (1984)). Specific initiation signals can also be required for efficient translation of inserted differentially expressed or interactive gene coding sequences. These signals include the ATG initiation codon and adjacent sequences. Where an entire identified gene, including its own initiation codon and adjacent sequences, is inserted into the appropriate expression vector, no additional translational control signals can be needed. However, in cases where only a portion of the identified coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced, for example, by inclusion of appropriate transcription enhancer elements or transcription terminators (see Bittner et al., *Methods in Enzymol.* 153:516–44 (1987)).

In addition, a host cell strain can be chosen that modulates the expression of the inserted sequences, or modifies and processes the gene product in the specific fashion desired. Modifications (e.g., glycosylation) and processing (e.g., cleavage) of protein products can be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used. Such mammalian host cells include but are not limited to CHO, VERO, BHK, HeLa, COS, MDCK, 293, 3T3, and W138.

For long-term, high-yield production of recombinant proteins, stable expression is preferred. Cell lines that stably express the differentially expressed or interactive gene protein can be engineered. Rather than using expression vectors which contain viral origins of replication, host cells can be transformed with DNA controlled by appropriate expression control elements (e.g., promoter or enhancer sequences, transcription terminators, and polyadenylation sites) and a selectable marker. Following the introduction of the foreign DNA, engineered cells can be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method advantageously can be used to engineer cell lines that express the identified gene protein. Such engineered cell lines can be particularly useful in screening and evaluation of compounds that affect the endogenous activity of the differentially expressed or interactive gene protein.

An alternative fusion protein system allows for the ready purification of non-denatured fusion proteins expressed in human cell lines (Janknecht et al, Proc. Natl. Acad. Sci. USA 88:8972–76 (1981)). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto ni2$^+$ nitriloacetic acid-agarose columns and histidine-tagged proteins are selectively eluted with imidazole-containing buffers.

When used as a component in assay systems such as that described herein, the differentially expressed or interactive gene protein can be labeled, either directly or indirectly, to facilitate detection of a complex formed between the differentially expressed or interactive gene protein and a test substance. Any of a variety of suitable labeling systems can be used including radioisotopes such as enzyme labeling systems that generate a detectable colorimetric signal or light when exposed to substrate, and fluorescent labels.

Where recombinant DNA technology is used to produce the differentially expressed or interactive gene protein for such assay systems, it can be advantageous to engineer fusion proteins that can facilitate labeling, solubility, immobilization or detection. Indirect labeling involves the use of a third protein, such as a labeled antibody, which specifically binds to either a differentially expressed or interactive gene product. Such antibodies include but are not limited to polyclonal, monoclonal, chimeric, single chain, Fab fragments and fragments produced by a Fab expression library.

The differentially expressed genes of the present invention can be expressed in an expression vector in which the gene is operably linked to a native or other promoter. Usually, the promoter is an eukaryotic promoter for expression in a mammalian cell. The transcription regulation sequences typically include a heterologous promoter and optionally an enhancer, which is recognized by the host. The selection of an appropriate promoter, for example trp, lac, phage promoters, glycolytic enzyme promoters and tRNA promoters, depends on the host selected. Commercially available expression vectors can be used. Vectors can include host-recognized replication systems, amplifiable genes, selectable genes, host sequences useful for insertion into the host genome, and the like.

The means for introducing the expression construct into a host cell may vary depending upon the particular construction and the target host. Suitable means include fusion, conjugation, transfection, transduction, electroporation or injection, as described in Sambrook et al., supra. A wide variety of host cells can be employed for expression of the differentially expressed gene, both prokaryotic and eukaryotic. Suitable host cells include bacteria such as E. coi, yeast (particularly Pichia), filamentous fungi, insect cells, mammalian cells, typically immortalized, e.g., mouse, CHO, human and monkey cell lines and derivatives thereof. Preferred host cells are able to process the differentially expressed gene product to produce an appropriate mature polypeptide. Processing includes glycosylation, ubiquitination, disulfide bond formation, and general post-translational modification.

The differentially expressed protein may be isolated by conventional means of protein biochemistry and purification to obtain a substantially pure product, i.e., 80, 95 or 99% free of cell component contaminants, as described in Jacoby, Methods in Enzymology, Vol. 104, Academic Press (New York, N.Y., 1984); Scopes, Protein Purification, Principles and Practice 2nd Edition, Springer-Verlag, (New York, N.Y. 1987); and Deutscher, ed., Guide to Protein Purification, Methods in Enzymology, Vol. 182 (1990). If the protein is secreted, it can be isolated from the supernatant in which the host cell is grown. If the protein is not secreted, the protein can be isolated from a lysate of the host cells.

In one embodiment, the differentially expressed gene encoding the polypeptide is analyzed to detect putative transmembrane sequences. Such sequences are typically very hydrophobic and are readily detected by the use of sequence analysis software such as Lasergene (DNAstar, Madison, Wis.). The presence of transmembrane sequences is often deleterious when a recombinant protein is synthesized in many expression systems, especially E. coli, as it leads to the production of insoluble aggregates that are difficult to renature into the native conformation of the protein. Deletion of transmembrane sequences typically does not significantly alter the conformation of the remaining protein structure.

Moreover, transmembrane sequences embedded within a membrane are inaccessible. Antibodies to these sequences will not prove useful for in vivo or in situ studies. Deletion of transmembrane-encoding sequences from the genes used for expression may be achieved by conventional techniques. For example, restriction enzyme sites may be used to excise the desired gene fragment, or PCR-type amplification may be used to amplify only the desired part of the gene.

In another embodiment, computer sequence analysis is used to determine the location of predicted major antigenic determinant epitopes of the polypeptide. Software capable of carrying out this analysis is readily available commercially. Such software typically uses conventional algorithms such as the Kyte/Doolittle or Hopp/Woods methods for locating hydrophilic sequences characteristically found on the surface of proteins, which likely act as antigenic determinants.

Once this analysis is made, polypeptides may be prepared which contain at least the essential features of the antigenic determinant and which may be employed in the generation of antisera against the polypeptide. Minigenes or gene fusions encoding these determinants may be constructed and inserted into expression vectors by conventional methods, for example, using PCR cloning methodology.

As an alternative to recombinant polypeptides, synthetic peptides corresponding to the antigenic determinants may be prepared. Such peptides are preferably at least six amino acid residues long, and may contain up to approximately 50 residues, which is the approximate upper length limit of automated peptide synthesis machines, such as those available from PE Applied Biosystems (Foster City, Calif.). Use of such small peptides for vaccination typically requires conjugation of the peptide to an immunogenic carrier protein such as hepatitis B surface antigen, keyhole limpet hemocyanin or bovine serum albumin. Methods for performing this conjugation are well known in the art.

In one embodiment, the expression products of the differentially expressed genes of the present invention may comprise differences of amino acid sequence. These may, for instance, be minor sequence differences of the polypeptide which arise due to natural variation within the population or they may be homologs found in other species and include native sequence polypeptides and their variants. They also may be sequences which do not occur naturally but which are sufficiently similar that they function similarly or elicit an immune response that cross-reacts with natural forms of the polypeptide. Sequence differences may be prepared by conventional methods of site-directed mutagenesis such as those described above for removing the transmembrane sequence.

Amino acid sequence mutants of the polypeptide may be substitutional, insertional or deletion mutants. Deletion mutants differentially expressed lack one or more residues of the native protein which are not essential for function or immunogenic activity, and are exemplified by the mutants lacking a transmembrane sequence described above. Another common type of deletion mutants is one lacking secretory signal sequences or signal sequences directing a protein to bind to a particular part of a cell. An example of the latter sequence is the SH2 domain, which induces protein binding to phosphotyrosine residues.

Substitutional mutants typically exchange one amino acid for another at one or more sites within the protein and may be designed to modulate one or more properties of the polypeptide, such as stability against proteolytic cleavage. Substitutions preferably are conservative, that is, one amino acid is replaced with another of similar shape and charge.

Insertional mutants include fusion proteins such as those used to allow rapid purification of the polypeptide and also may include hybrid proteins containing sequences from other homologous proteins and polypeptides. For example, an insertional mutant may include portions of the amino acid sequence of the polypeptide from one species, together with portions of the homologous polypeptide from another species. Other insertional mutants may include those in which additional amino acids are introduced within the coding sequence of the polypeptide. These typically are smaller insertions than the fusion proteins described above and are introduced, for example, to disrupt a protease cleavage site.

In one embodiment, major antigenic determinants of the polypeptide are identified by an empirical approach in which portions of the gene encoding the polypeptide are expressed in a recombinant host, and the resulting proteins tested for their ability to elicit an immune response. For example, PCR may be used to prepare a range of peptides lacking successively longer fragments of the C-terminus of the protein. The immunoprotective activity of each of these peptides then identifies those fragments or domains of the polypeptide which are essential for this activity. Further studies in which only a small number of amino acids are removed at each iteration then enables the location of the antigenic determinants of the polypeptide.

Another embodiment for the preparation of polypeptides according to the disclosure is the use of peptide mimetics. Mimetics are peptide-containing molecules which mimic elements of protein secondary structure. See, e.g., Johnson et al., *Biotechnology and Pharmacy*, Chapman and Hall (New York, N.Y., 1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule.

Successful applications of the peptide mimetic concept have thus far focused on mimetics of β-turns within proteins, which are known to be highly antigenic. Computer-based algorithms as discussed above may predict likely α-turn structure within a polypeptide. Once the component amino acids of the turn are determined, peptide mimetics may be constructed to achieve a similar spatial orientation of the essential elements of the amino acid side chains.

Differentially expressed and interactive gene products include those proteins, or portions thereof, encoded by the differentially expressed and interactive gene sequences obtained by the methods of the present invention. Specifically, differentially expressed and interactive gene products can include differentially expressed and interactive gene polypeptides encoded by the differentially expressed and interactive gene sequences contained in the coding regions of the genes to which clones and DNA sequences of the differentially expressed genes of the present invention belong.

In addition, differentially expressed and interactive gene products can include proteins that represent functionally equivalent gene products. An equivalent differentially expressed or interactive gene product can contain deletions, additions or substitutions of amino acid residues within the amino acid sequence encoded by the differentially expressed or interactive gene sequences described above, but which result in a silent change thus producing a functionally equivalent differentially expressed on interactive gene product. Amino acid substitutions can be made based on similarity in polarity, charge, solubility, hydrophobicity, hydrophilicity, or the amphipatic nature of the residues involved.

"Functionally equivalent" includes a protein capable exhibiting a substantially similar in vivo activity as the endogenous differentially expressed or interactive gene products encoded by the differentially expressed or interactive gene sequences of the present invention. Alternatively, when utilized as part of assays such as those described below, "functionally equivalent" includes peptides capable of interacting with other cellular or extracellular molecules in a manner substantially similar to the way in which the corresponding portion of the endogenous differentially expressed or interactive gene product would.

XVII. GENETIC LESION DETECTION

The methods of the invention can also be used to detect genetic lesions in a differentially expressed gene of the present invention, thereby determining if a subject with the lesioned gene is at risk for a disorder characterized by differentially expressed gene expression or polypeptide activity. In preferred embodiments, the methods include detecting, in a biological sample from a subject, the presence or absence of a genetic lesion characterized by, for example, an alteration affecting the integrity of a gene encoding an polypeptide or the misexpression of the gene. For example, such genetic lesions can be detected by ascertaining the existence of at least one of: a deletion of one or more nucleotides from a gene; an addition of one or more nucleotides to a gene; a substitution of one or more nucleotides of a gene; a chromosomal rearrangement of a gene; an alteration in the level of a messenger RNA transcript of a gene; aberrant modification of a gene, such as of the methylation pattern of the genomic DNA; the presence of a non-wild type splicing pattern of a messenger RNA transcript of a gene; a non-wild type level of a gene protein; allelic loss of a gene; and inappropriate post-translational modification of a gene protein. As described herein, there are a large number of assay techniques known in the art that can be used for detecting lesions in a gene.

In certain embodiments, detection of a lesion may involve the use of a probe/primer in PCR (see, e.g. U.S. Pat. Nos. 4,683,195 and 4,683,202), such as anchor PCR or RACE PCR, or, alternatively, in LCR (see, e.g., Landegran et al., Science 241: 1077–80 (1988); and Nakazawa et al., Proc. Natl. Acad. Sci. USA 91: 360–64 (1994)), the latter of which can be particularly useful for detecting point mutations in the cardiac gene (see Abravaya et al., Nucleic Acids Res. 23: 675–82 (1995)). This method can include the steps of collecting a biological sample from a subject, isolating nucleic acid (e.g., genomic, mRNA or both) from the cells of the sample, contacting the nucleic acid sample with one or more primers which specifically hybridize to an differentially expressed gene under conditions such that hybridization and amplification of the cardiac gene (if present) occurs, and detecting the presence or absence of an amplification product, or detecting the size of the amplification product and comparing the length to a control sample.

In an alternative embodiment, mutations in a differentially expressed gene from a sample can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see U.S. Pat. No. 5,498,531) can be used to score for the presence of specific mutations by development or loss of a ribozyme cleavage site.

XVIII. MUTATION DETECTION

In yet another embodiment, any of a variety of sequencing reactions known in the art can be used to directly sequence the differentially expressed gene and detect mutations by comparing the sequence of the sample differentially expressed gene with the corresponding wild-type (normal) sequence. Examples of sequencing reactions include those based on techniques developed by Maxim and Gilbert, (Maxim et al., Proc. Natl. Acad. Sci. USA 74:560 (1977)) or Sanger (Sanger, Proc. Natl. Acad. Sci. 74:5463 (1977)). A variety of automated sequencing procedures can be utilized when performing the diagnostic assays, including sequencing by mass spectrometry (see, e.g., PCT Published Application No. WO 94/16101; Cohen et al., Adv. Chromatogr. 36:127–62 (1966); and Griffin et al., Appl. Biochem. Biotechnol. 38:147–59 (1993)).

Other methods for detecting mutations in the differentially expressed gene include methods in which protection from cleavage agents is used to detect mismatched bases in RNA/RNA or RNA/DNA duplexes (Myers et al., Science 230:1242 (1985)); Cotton et al., Proc. Natl. Acad. Sci. USA 85:4397 (1988); Saleeba et al., Meth. Enzymol. 2(17) :286–95 (1992)), electrophoretic mobility of mutant and wild type nucleic acid is compared (Orita et al., Proc. Natl. Acad. Sci. USA 86:2766 (1989); Cotton, Mutat. Res. 285:125–44 (1993); and Hayashi, Genet. Anal. Tech. Appl. 9:73–79 (1992)), and movement of mutant or wild-type fragments in polyacrylamide gels containing a gradient of denaturant is assayed using denaturing gradient gel electrophoresis (Myers et al., Nature 313:495 (1985)). Examples of other techniques for detecting point mutations include oligonucleotide hybridization, amplification, and selective primer extension.

In addition to substantially full-length native polypeptides (and variants thereof) expressed by the differentially expressed genes, the present invention includes biologically active fragments of the polypeptides, or analogs thereof, including organic molecules, which simulate the interactions of the peptides. Biologically active fragments include any portion of the full-length polypeptide, which confers a biological function on the differentially expressed gene product, including ligand binding, and antibody binding. Ligand binding includes binding by nucleic acids, proteins or polypeptides, small biologically active molecules, or large cellular structures.

Further aspects of the present disclosure concern the purification, and in particular embodiments, the substantial purification, of an encoded protein or peptide. The term "purified protein or peptide" includes compositions, isolatable from other components, wherein the protein or peptide is purified to any degree relative to its naturally-obtainable state, i.e., relative to its purity within a cell extract. A purified protein or peptide therefore also refers to a protein or peptide, free from the environment in which it may naturally occur.

There is no general requirement that a protein or peptide always be provided in its most purified state. Indeed, it is contemplated that less substantially purified products have utility in certain embodiments. Partial purification may be accomplished by using fewer purification steps in combination, or by using different forms of the same general purification scheme. For example, one skilled in the art appreciates that a cation-exchange column chromatography performed utilizing an HPLC apparatus generally results in a greater-fold purification than the same technique utilizing a low pressure chromatography system. Methods exhibiting a lower degree of relative purification may have advantages in total recovery of protein product, or in maintaining the activity of an expressed protein.

XIX. ANTIBODIES SPECIFIC FOR DIFFERENTIALLY EXPRESSED OR INTERACTIVE GENE PRODUCTS

In another preferred embodiment of the present invention antibodies are produced that bind with high specificity to the protein products of the differentially expressed genes of the present invention, e.g., all or a portion of the amino acid sequence of the human genes 1–8U (SEQ ID NO:37), prostacyclin-stimulating factor (SEQ ID NO:38), osf-2 (SEQ ID NO:39),tissue specific mRNA (SEQ ID NO:40), insulin-like growth factor binding protein 6 (SEQ ID NO:41), OSF-1 (SEQ ID NO:42), gas-1 (SEQ ID NO:43), YMP (SEQ ID NO:44), BTG2 (SEQ ID NO:45), pre-B cell stimulating factor homolog (SDF1a) (SEQ ID NO:46), peripheral benzodiazepine receptor (SEQ ID NO:47), and cellular ligand of annexin II (p11) (SEQ ID NO:48), respectively. Means for preparing and characterizing antibodies are well known in the art (see, e.g., Harlow et al., supra).

Described herein are methods for the production of antibodies capable of specifically recognizing one or more differentially expressed or interactive gene epitopes. Such antibodies can include, but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope binding fragments of any of the above. Such antibodies can be used, for example, in the detection of a diagnostic, target, or interactive gene in a biological sample, or, alternatively, as a method for the inhibition of abnormal target gene activity. Thus, such antibodies can be utilized as a disease, specifically cardiac, kidney or inflammatory disease, treatment method, or can be used as part of diagnostic techniques whereby patients can be tested for abnormal levels of diagnostic, target, or interactive gene proteins, or for the presence of abnormal forms of such proteins. See Kohler et al., Nature 256:495–97 (1975), U.S. Pat. No. 4,376,110, Kosbor et al., Immunology Today 4:72 (1983); Cole et al., Proc. Natl. Acad. Sci. USA 80:2026–30 (1983), Cole et al., Monoclonal Antibodies And Cancer Therapy, Alan R. Uss, Inc. (1985), pp. 77–96, Morrison et al., supra; Neuberger et al., Nature, 312:604–08 (1984); Takeda et al., Nature, 314:452–54 (1985); and U.S. Pat. No. 4,816,567 for representative antibody techniques. Alternatively, techniques described for the production of single chain antibodies (U.S. Pat. No. 4,946,778; Bird, Science 242:423–26 (1988); Huston et al., Proc. Natl. Acad. Sci. USA 85:5879–83 (1988); and Ward et al., Nature 334:544–46 (1989)) and for making humanized monoclonal antibodies (U.S. Pat. No. 5,225,539, which is incorporated herein by reference in its entirety) can be utilized to produce anti-differentially expressed or anti-interactive gene product antibodies. Diagnostic kits comprising one or more or such antibodies are contemplated and described in greater detail infra.

Antibody fragments recognizing specific epitopes can be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries can be constructed (Huse et al., Science 246:1275–81 (1989)) to allow rapid and easy identification of monoclonal Fab fragments with the desired specificity.

XX. CELL- AND ANIMAL-BASED MODEL SYSTEMS

Described herein are cell- and animal-based systems which represent reliable models for disease, specifically cardiac, kidney or inflammatory disease, disorders. These systems can be used in a variety of applications. For example, the cell- and animal-based model systems can be used to identify differentially expressed genes via the models described above. Such systems can also be used to further characterize differentially expressed and interactive genes, for example, as a target gene. Additionally, such assays can be utilized as part of screening strategies designed to identify compounds, which are capable of preventing or ameliorating symptoms of a disease, specifically cardiac, kidney or inflammatory disease, disorders. Thus, the animal- and cell-based models can be used to identify drugs, pharmaceuticals, therapies and interventions which can be effective in treating a disease and related disorders. In addition, such animal models can be used to determine the $LD_{50}$ and the $ED_{50}$ in animal subjects, and such data can be used to determine the in vivo efficacy of potential disease treatments.

A. ANIMAL-BASED SYSTEMS

Animal-based in vivo model systems of a disease, specifically cardiac, kidney or inflammatory disease, can include both non-recombinant animals as well as recombinantly engineered transgenic animals. Non-recombinant animal models for a disease, specifically cardiac, kidney or inflammatory disease, include, for example, murine models of myocardial infarction, cardiac hypertrophy, and kidney disease as described supra. Models based on cardioactive drugs may be generated, for example, by introducing such drugs into syngeneic mice. After an appropriate period of time, the diseases that result from these injections of drugs can be detected and the mice used as models.

The role of identified gene products can be determined by transfecting cDNA encoding such gene products into the appropriate cell line and analyzing its effect on the cells' ability to induce a disease, specifically cardiac, kidney or inflammatory disease, in animal models such as these. The role of the identified gene products may be further analyzed by culturing cells derived from the diseases which develop in the animal models, introducing these cultured cells into animals, and subsequently measuring the level of identified gene product present in the resulting disease. In this manner, cell line variants are developed which can be useful in analyzing the role of quantitative or qualitative differences in the expression of the identified genes on the cells' ability to induce a disease.

Additionally, recombinant animal models exhibiting characteristics or symptoms of a disease, specifically cardiac, kidney or inflammatory disease, can be utilized. Further, recombinant animal models for a disease can be engineered by utilizing, for example, target gene sequences, in conjunction with techniques for producing transgenic animals that are well known to those of skill in the art. For example, target gene sequences can be introduced into, and overexpressed in, the genome of the animal of interest, or if endogenous target gene sequences are present, they can either be overexpressed, or alternatively, can be disrupted in order to underexpress or inactivate target gene expression.

In order to overexpress a target gene sequence, the coding portion of the target gene sequence can be ligated to a regulatory sequence capable of driving gene expression in the animal and cell type of interest. Such regulatory regions are known to those of skill in the art.

To obtain underexpression of an endogenous target gene sequence, such a sequence can be introduced into the genome of the animal of interest such that the endogenous target gene alleles will be inactivated. Preferably, an engineered sequence comprising at least part of the target gene sequence is utilized and is introduced, via gene targeting, such that the endogenous target sequence is disrupted upon integration of the engineered target gene sequence into the animal's genome. Gene targeting is discussed below.

Animals of any species, including, but not limited to, mice, rats, rabbits, guinea pigs, pigs, micro-pigs, goats, and non-human primates, e.g., baboons, monkeys, and chimpanzees, can be used to generate animal models of a disease, specifically cardiac, kidney or inflammatory disease. Any technique known in the art can be used to introduce a target gene transgene into animals to produce the founder lines of transgenic animals. Such techniques include, pronuclear microinjection (Hoppe et al., U.S. Pat. No. 4,873,191 (1989)); retrovirus mediated gene transfer into germ lines (Van der Fatten et al., *Proc. Natl. Acad. Sci. USA* 82:6148–52 (1985)); gene targeting in embryonic stem cells (Thompson et al., *Cell* 56:313–21 (1989)); electroporation of embryos (Lo, *Mol. Cell. Biol.* 3:1803–14 (1983)); and sperm-mediated gene transfer (Lavitrano et al., *Cell* 57:717–23 (1989)). For a review of such techniques, see Gordon, *Intl. Rev. Cytol.* 115:171–229 (1989).

The present invention provides for transgenic animals that carry the transgene in all their cells, as well as animals which carry the transgene in some, but not all their cells, i.e., mosaic animals. The transgene can be integrated, either as a single transgene or in concatamers, e.g., head-to-head tandems or head-to-tail tandems. The transgene can also be selectively introduced into and activated in a particular cell type by following, for example, the teaching of Lasko et al., *Proc. Natl. Acad. Sci. USA* 89:6232–36 (1992). The regulatory sequences required for such a cell-type specific activation depends upon the particular cell type of interest, and will be apparent to those of skill in the art.

When it is desired that the target gene transgene be integrated into the chromosomal site of the endogenous target gene, gene targeting is preferred. Briefly, when such a technique is to be utilized, vectors containing some nucleotide sequences homologous to the endogenous target gene of interest are designed for the purpose of integrating, via homologous recombination with chromosomal sequences, into and disrupting the function of the nucleotide sequence of the endogenous target gene. The transgene can also be selectively introduced into a particular cell type, thus inactivating the endogenous gene of interest in only that cell type, by following the teaching of Gu et al. (*Science* 265:103–06 (1994)). The regulatory sequences required for such a cell-type specific inactivation depends upon the particular cell type of interest, and will be apparent to those of skill in the art.

Once transgenic animals have been generated, the expression of the recombinant target gene and protein can be assayed using standard techniques. Initial screening can be accomplished by Southern blot analysis or PCR techniques to analyze animal tissues to assay whether integration of the transgene has taken place. The level of mRNA expression of the transgene in the tissues of the transgenic animals can also be assessed using techniques which include Northern blot analysis of tissue samples obtained from the animal, in situ hybridization analysis, and RT-coupled PCR. Samples of target gene-expressing tissue can also be evaluated immunocytochemically using antibodies specific for the transgenic product of interest.

The target gene transgenic animals that express target gene mRNA or target gene transgene peptide (detected immunocytochemically, using antibodies directed against target gene product epitopes) at easily detectable levels should then be further evaluated to identify those animals which display disease characteristics or symptoms. Additionally, specific cell types within the transgenic animals can be analyzed for cellular phenotypes characteristic of a disease, specifically cardiac, kidney or inflammatory disease. Such cellular phenotypes can include, for example, differential gene expression characteristic of cells within a given disease state of interest. Further, such cellular phenotypes can include an assessment of a particular cell type diagnostic pattern of expression and its comparison to known diagnostic expression profiles of the particular cell type in animals exhibiting a disease, specifically cardiac, kidney or inflammatory disease. Such transgenic animals serve as suitable models.

Once target gene transgenic founder animals are produced (i.e., those animals which express target gene proteins in cells or tissues of interest, and which preferably exhibit disease characteristics), they can be bred, inbred, outbred, or crossbred to produce colonies of the particular animal.

B. CELL-BASED ASSAYS

Cells that contain and express target gene sequences which encode target gene protein, and further, exhibit cellular phenotypes associated with disease, specifically cardiac, kidney or inflammatory disease, disorders, can be utilized to identify compounds that exhibit an ability to prevent, treat or identify a disease, and include the in vitro models described supra. For example, the diagnostic pattern of gene expression of cells of interest can be analyzed and compared to the normal diagnostic pattern. Those compounds which cause cells exhibiting cellular phenotypes of disease, specifically cardiac, kidney or inflammatory disease, disorders to produce a diagnostic pattern more closely resembling a normal diagnostic pattern for the cell of interest can be considered candidates for further testing regarding an ability to ameliorate the symptoms of such diseases. Such cells include cardiac myocytes, cardiac fibroblasts, monocyte/macrophages, and kidney epithelial cells.

Further, cells which can be used for such assays can also include recombinant, transgenic cell lines. For example, the animal models of the present invention can be used to generate cell lines, containing one or more cell types involved in a disease, specifically cardiac, kidney or inflammatory disease, that can be used as cell culture models for these disorders. For examples of techniques which can be used to derive a continuous cell line from transgenic animals, see Small et al., *Mol. Cell Biol.* 5:642–48 (1985).

Alternatively, cells of a cell type known to be involved in disease can be transfected with sequences capable of increasing or decreasing the amount of target gene expression within the cell. For example target gene sequences can be introduced into, and over expressed in, the genome of the cell of interest, or if endogenous target gene sequences are present, they can either be overexpressed or, be disrupted in order to underexpress or inactivate target gene expression.

To overexpress a target gene sequence, the coding portion of the target gene sequence can be ligated to a regulatory sequence capable of driving gene expression in the cell type of interest. Such regulatory regions are well known to those of skill in the art.

For underexpression of an endogenous target gene sequence, such a sequence can be isolated and engineered so that reintroduction into the genome of the cell type of interest disrupts the endogenous target gene alleles. Preferably, the engineered target gene sequence is introduced via gene targeting such that the endogenous target sequence is disrupted upon integration of the engineered target gene sequence into the cell's genome.

Transfection of target gene sequence nucleic acids can be accomplished by using standard techniques. See, e.g., Ausubel et al, supra. Transfected cells should be evaluated for the presence of the recombinant target gene sequences, for expression and accumulation of target gene mRNA, and for the presence of recombinant target gene protein production. Where a decrease in target gene expression is desired, standard techniques can be used to demonstrate whether a decrease in endogenous target gene expression or in target gene product production is achieved.

XXI. SCREENING ASSAYS FOR COMPOUNDS THAT INTERACT WITH THE TARGET GENE PRODUCT

In models designed to identify differentially expressed genes that are involved in a disease, specifically cardiac, kidney or inflammatory disease, compounds known to have an ameliorative effect on the disease can also be used in in vivo and in vitro models to detect differentially expressed genes. Such compounds can include known therapeutics, as well as compounds that are not useful as therapeutics due to their harmful side effects. For example, cells from disease states that are cultured can be exposed to these compounds and analyzed for differential gene expression with respect to untreated cells, according to the methods described below. In a preferred embodiment, microarray analysis is used for analysis of differential gene expression. In principle, these compounds can treat any cell type involved in a disease and disorders thereof at any stage of the disease process.

Cells involved in a disease, specifically cardiac, kidney or inflammatory disease, can also be compared to unrelated cells (e.g., fibroblasts), which have been treated with the compound, such that any generic effects on gene expression that might not be related to the disease or its treatment may be identified. Such generic effects might be manifest, for example, by changes in gene expression that are common to the test cells and the unrelated cells upon treatment with the compound. By these methods, the genes and gene products upon which these compounds act can be identified and used in the assays described below to identify novel therapeutic compounds for inhibition of a disease and related disorders.

Specifically, the present invention provides methods for identifying compounds or agents, which can be used to treat a disease, specifically cardiac, kidney or inflammatory disease, associated with differential gene expression or polypeptide activity. These drug screening assays typically include the step of screening a candidate/test compound or agent for the ability to interact with (e.g., bind to) a polypeptide, to modulate the interaction of a polypeptide and a target molecule, or to modulate nucleic acid expression or polypeptide activity. Candidate/test compounds or agents which have one or more of these abilities can be used as drugs to treat disorders characterized by differential nucleic acid expression or polypeptide activity. Candidate/test compounds include, for example, peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- or L- configuration amino acids; phosphopeptides (e.g., members of random and partially degenerate, directed phosphopeptide libraries, see, e.g., Songyang et al., *Cell* 72:767–78 (1993); antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and small organic and inorganic molecules (e.g., molecules obtained from combinatorial and natural product libraries).

Another aspect of the invention relates to methods, e.g., screening assays, for identifying a compound or agent for treating a disorder characterized by differentially expressed gene expression or polypeptide activity. These methods typically include assaying the ability of the compound or agent to modulate the expression of the differentially expressed gene or the activity of its polypeptide, thereby identifying a compound or agent for treating a disease, specifically cardiac, kidney or inflammatory disease, characterized by differential expression of a gene or its expression product. See, e.g., U.S. Pat. No. 5, 846,720, which is incorporated herein by reference in its entirety. In a preferred embodiment, the method involves contacting a biological sample obtained from a subject having a disease, specifically cardiac, kidney or inflammatory disease, with the compound or agent, determining the amount of differentially expressed gene nucleic acid expressed or measuring the activity of the polypeptide in the biological sample, comparing the amount of differentially expressed gene expressed in the biological sample or the measurable differentially expressed gene biological activity in the cell to that of a normal sample. An alteration in the amount of differentially expressed gene expression or polypeptide activity in the cell exposed to the compound or agent in comparison to the normal sample is indicative of a modulation of differentially expressed gene expression or polypeptide activity. Microarrays, in a preferred embodiment, are utilized to assess differentiated gene expression.

The invention also pertains to methods for modulating a cell associated activity, e.g., proliferation, differentiation, or cytokine production. Such methods include contacting the cell with an differentially expressed gene modulator such that a cell associated activity is altered relative to a cell associated activity (e.g., the same cell associated activity) of the cell in the absence of the agent. The differentially expressed gene modulator can stimulate polypeptide activity or differentially expressed gene expression. Examples of such stimulatory differentially expressed gene modulators include small molecules, active polypeptides, and nucleic acids encoding the differentially expressed gene that have been introduced into the cell. Alternatively, the differentially expressed gene modulator can inhibit polypeptide activity or differentially expressed gene expression. Examples of such inhibitory modulators include small molecules, antisense nucleic acid molecules, and antibodies that specifically react with an epitope of the gene or its expression product. In a preferred embodiment, the cell is present within a subject, and the agent is administered to the subject.

The nucleic acid molecules, polypeptides, polypeptide homologs, modulators, and antibodies described herein preferably can be used in drug screening assays, diagnostic assays, and methods of treatment. The isolated nucleic acid molecules of the invention can be used to express polypeptides (e.g., via a recombinant expression vector in a host cell in gene therapy applications), to detect differentially expressed gene mRNA (e.g., in a biological sample) or a genetic lesion in a gene, and to modulate differentially expressed gene activity. In addition, the differentially expressed gene proteins can be used to screen drugs or compounds which modulate polypeptide activity as well as to treat disorders characterized by insufficient production of polypeptide or production of polypeptide forms which have decreased activity compared to a normal subject. Moreover, anti-differentially expressed gene antibodies of the invention can be used to detect and isolate expressed polypeptide and modulate differentially expressed disease, specifically cardiac, kidney or inflammatory disease, gene polypeptide activity.

In one embodiment, the invention provides assays for screening candidate/test compounds, which interact with differentially expressed disease genes. Typically, the assays may be cell-free assays which include the steps of combining a polypeptide, or a bioactive fragment thereof, and a candidate/test compound, under conditions which allow for interaction of the candidate/test compound to the polypeptide or fragment thereof to form a complex, and detecting the formation of a complex, in which the ability of the candidate compound to interact with the polypeptide or fragment thereof is indicated by the presence of the candidate compound in the complex. Formation of complexes between the polypeptide and the candidate compound can be quantitated, for example, using standard immunoassays.

In another embodiment, the invention provides screening assays to identify candidate/test compounds which modulate the interaction (and most likely differentially expressed gene activity as well) between a polypeptide and a molecule (target molecule) with which the polypeptide normally interacts. Examples of such target molecules includes proteins in the same signaling path as the polypeptide, e.g., proteins which may function upstream (including both stimulators and inhibitors of activity) or downstream of the polypeptide in a interactive involving regulation of myocyte ion channels. Typically, the assays are cell-free assays which include the steps of combining polypeptide or a bioactive fragment thereof, differentially expressed gene target molecule (e.g., an differentially expressed gene ligand) and a candidate/test compound under conditions where but for the presence of the candidate compound, the polypeptide or biologically active portion thereof interacts with the target molecule. A complex which includes the polypeptide and the target molecule is then formed or the interaction/reaction of the polypeptide and the target molecule is detected. Detection of complex formation can include direct quantitation of the complex by measuring inductive effects of the polypeptide.

A statistically significant change, such as a decrease, in the interaction of the differentially expressed gene and target molecule (e.g., in the formation of a complex between the differentially expressed gene and the target molecule) in the presence of a candidate compound (relative to what is detected in the absence of the candidate compound) is indicative of a modulation of the interaction between the polypeptide and the target molecule. Modulation of the formation of complexes between the polypeptide and the target molecule can be quantitated using an immunoassay.

To perform the above drug screening assays, it is desirable to immobilize either the differentially expressed gene or its target molecule to facilitate separation of complexes from uncomplexed forms of one or both of the proteins, as well as to accommodate automation of the assay. Interaction of differentially expressed gene with a target molecule, in the presence and absence of a candidate compound, can be accomplished in any vessel suitable for containing the reactants. Examples of such vessels include microtiter plates, test tubes, and microcentrifuge tubes. In one embodiment, a fusion polypeptide can be provided which adds a domain that allows the polypeptide to be bound to a matrix.

For example, glutathione S-transferase/differentially expressed gene fusion polypeptides can be adsorbed onto glutathione sepharose beads (Sigma Chemical, St. Louis, Mo.) or glutathione derivatized microtiter plates, which are then combined with the cell lysates (e.g. $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and the radiolabel determined directly, or in the supernatant after the complexes are dissociated. Alternatively, the complexes can be dissociated from the matrix, separated by SDS-PAGE, and the level of differentially expressed disease, specifically cardiac, kidney or inflammatory disease, gene-binding polypeptide found in the bead fraction quantitated from the gel using standard electrophoretic techniques.

In yet another embodiment, the invention provides a method for identifying a compound (e.g., a screening assay) capable of use in the treatment of a disorder characterized by (or associated with) differentially expressed disease gene expression or polypeptide activity. This method typically includes the step of assaying the ability of the compound or agent to modulate the expression of the differentially expressed gene or the activity of the polypeptide, thereby identifying a compound for treating a disorder characterized by differentially expressed gene expression or polypeptide activity. Disorders characterized by differentially expressed gene expression or polypeptide activity are described herein. Methods for assaying the ability of the compound or agent to modulate the expression of the differentially expressed gene nucleic acid or activity of the polypeptide are typically cell-based assays. For example, cells sensitive to ligands which transduce signals via an interactive involving differentially expressed gene can be induced to overexpress an polypeptide in the presence and absence of a candidate compound. Candidate compounds that produce a statistically significant change in gene-dependent responses (either stimulation or inhibition) can be identified. In one embodiment, expression of the differentially expressed disease gene nucleic acid or activity of a polypeptide is modulated in cells and the effects of candidate compounds on the readout of interest (such as rate of cell proliferation or differentiation) are measured. For example, the expression of genes, which are up- or down-regulated in response to gene-dependent signal cascade, can be assayed. In preferred embodiments, the regulatory regions of such genes, e.g., the 5' flanking promoter and enhancer regions, are operably linked to a detectable marker (such as luciferase) which encodes a gene product that can be readily detected. Phosphorylation of differentially expressed gene or differentially expressed gene target molecules can also be measured, for example, by immunoblotting.

Alternatively, modulators of differentially expressed disease gene expression (e.g., compounds which can be used to treat a disease, specifically cardiac, kidney or inflammatory disease, or related disorders characterized by differentially expressed gene expression or polypeptide activity) can be identified in a method wherein a cell is contacted with a candidate compound and the expression of differentially expressed gene mRNA or polypeptide in the cell is determined. In a preferred embodiment, microarrays are utilized to assess expression levels. The level of expression of differentially expressed gene mRNA or polypeptide in the presence of the candidate compound is compared to the level of expression of differentially expressed gene mRNA or polypeptide in the absence of the candidate compound. The candidate compound can then be identified as a modulator of differentially expressed gene expression based on this comparison and be used to treat a disorder characterized by aberrant differentially expressed gene expression. For example, when expression of differentially expressed gene mRNA or polypeptide is greater (preferably statistically significantly greater) in the presence of the candidate compound than in its absence, the candidate compound may be identified as a stimulator of differentially expressed gene expression. Alternatively, when differentially expressed gene expression is less (preferably statistically significantly less) in the presence of the candidate compound than in its absence, the candidate compound may be identified as an inhibitor of differentially expressed gene expression. The level of differentially expressed gene expression in the cells can be determined by methods described herein for detecting differentially expressed gene mRNA or protein.

In yet another aspect of the invention, the polypeptides can be used as "bait proteins" in a two-hybrid assay (see, e.g., U.S. Pat. No. 5,283,317; Zervos et al., *Cell* 72:223–32 (1993); Madura et al. *Biol. Chem.* 268:12046–54 (1993); Bartel et al., *Biotechniques* 14:920–24 (1993); Iwabuchi et al., *Oncogene* 8:1693–96 (1993); and PCT Application WO 94/10300), to identify other proteins, which bind to or interact with differentially expressed gene, ("gene-binding proteins" or "gene-bp") and modulate polypeptide activity. Such gene binding proteins are also likely to be involved in the propagation of signals by the polypeptides as, for example, upstream or downstream elements of the differentially expressed gene interaction.

Compounds identified via assays such as those described herein can be useful, for example, in elaborating the biological function of the target gene product, and for ameliorating symptoms of a disease, specifically cardiac, kidney or inflammatory disease. In instances when a disease state or disorder results from a lower overall level of target gene expression, target gene product, or target gene product activity in a cell involved in the disease, compounds that interact with the target gene product can include ones accentuating or amplifying the activity of the bound target gene protein. Such compounds would bring about an effective increase in the level of target gene activity, thus ameliorating symptoms of the disease disorder or state. Where mutations within the target gene cause aberrant target gene proteins to be made, which have a deleterious effect that leads to a disease, compounds that bind target gene protein can be identified that inhibit the activity of the bound target gene protein.

XXII. IN VITRO SCREENING ASSAYS FOR COMPOUNDS THAT BIND TO A TARGET GENE PRODUCT

Another aspect of the invention pertains to methods for identifying compounds or agents for treating a disorder characterized by differential gene expression associated with a disease, specifically cardiac, kidney or inflammatory disease. These methods typically include assaying the ability of the compound or agent to modulate the expression of the differentially expressed gene or the activity of a polypeptide encoded by that gene thereby identifying a compound or agent for treating a disease, specifically cardiac, kidney or inflammatory disease, characterized by differential nucleic acid expression or polypeptide activity. In a preferred embodiment, the method involves contacting a biological sample, e.g., a cell or tissue sample obtained from a subject, with the compound or agent, determining the amount of thee differentially expressed gene expressed or measuring the activity of the polypeptide encoded by that gene in the biological sample, comparing the amount of differentially expressed gene in the biological sample or the measurable biological activity of the encoded polypeptide in the cell to that of a sample from a normal subject. An alteration in the amount of the differentially expressed gene expression or polypeptide activity in the cell exposed to the compound or agent in comparison to the control is indicative of a modulation of the differentially expressed gene expression or polypeptide activity.

In vitro systems can be designed to identify compounds capable of binding the target gene products of the invention. Compounds identified can be useful, for example, in modulating the activity of normal or mutant target gene products, preferably mutant target gene proteins, can be useful in elaborating the biological function of the target gene product, can be utilized in screens for identifying compounds that disrupt normal target gene interactions, or can in themselves disrupt such interactions.

The principle of the assays used to identify compounds that bind to the target gene product involves preparing a reaction mixture of the target gene protein and the test compound under conditions and for a time sufficient to allow the two components to interact and bind, thus forming a complex which can be removed or detected in the reaction mixture. These assays can be conducted in a variety of ways. For example, one method to conduct such an assay would involve anchoring target gene product or the test substance onto a solid phase and detecting target gene product/test compound complexes anchored on the solid phase at the end of the reaction. In one embodiment of such a method, the target gene product can be anchored onto a solid surface, and the test compound, which is not anchored, can be labeled either directly or indirectly.

In practice, microtiter plates can conveniently be utilized as the solid phase. The anchored component can be immobilized by non-covalent or covalent attachments. Non-covalent attachment can be accomplished by simply coating the solid surface with a solution of the protein and drying. Alternatively, an immobilized antibody, preferably a monoclonal antibody, specific for the protein to be immobilized can be used to anchor the protein to the solid surface. The surfaces can be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously immobilized component is pre-labeled, the detection of label immobilized on the surface indicates that complexes were formed. Where the previously nonimmobilized component is not pre-labeled, an indirect label can be used to detect complexes anchored on the surface, e.g., using a labeled antibody specific for the immobilized component (the antibody, in turn, can be directly labeled or indirectly labeled with a labeled anti-Ig antibody).

Alternatively, a reaction can be conducted in a liquid phase, the reaction products separated from unreacted components, and complexes detected, e.g., using an immobilized antibody specific for target gene or the test compound to anchor any complexes formed in solution, and a labeled antibody specific for the other component of the possible complex to detect anchored complexes.

XXIII. ASSAYS FOR CELLULAR PROTEINS THAT INTERACT WITH THE TARGET GENE PRODUCT

Any method suitable for detecting protein-protein interactions can be employed for identifying novel target product-cellular or extracellular protein interactions. The methods outlined, supra, for the identification of interactive genes can be utilized herein with respect to the identification of proteins, which interact with identified target proteins. In such a case, the target gene serves as the known "bait" gene.

XXIV. ASSAYS FOR COMPOUNDS THAT INTERFERE WITH TARGET GENE/CELLULAR PRODUCT INTERACTION

The target gene products of the invention can, in vivo, interact with one or more cellular or extracellular macromolecules, such as proteins. Such macromolecules include nucleic acid molecules and those products identified via methods such as those described above. Such cellular and extracellular macromolecules are referred to herein as "binding partners." Compounds that disrupt such interactions can be useful in regulating the activity of the target gene product, especially mutant target gene products.

In a preferred embodiment, the assay systems used to identify compounds that interfere with the interaction between the target gene product and its cellular or extracellular binding partner or partners involve preparing a reaction mixture containing the target gene product and the binding partner under conditions and for a time sufficient to allow the two products to interact and bind, thus forming a complex. To test a compound for inhibitory activity, the reaction mixture is prepared in the presence and absence of the test compound. The test compound can be initially included in the reaction mixture, or can be added at a time subsequent to the addition of target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases where it is desirable to identify compounds that disrupt interactions of mutant but not normal target gene products.

The assay for compounds that interfere with the interaction of the target gene products and binding partners can be conducted in a heterogeneous or homogeneous format. Heterogeneous assays involve anchoring either the target gene product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. Test compounds interfering with the interaction between the target gene products and the binding partners, e.g., by competition, can be identified by conducting the reaction in the presence of the test substance; i.e., by adding the test substance to the reaction mixture prior to or simultaneously with the target gene product and interactive cellular or extracellular binding partner. Alternatively, test compounds that disrupt pre-formed complexes, e.g., compounds with higher binding constants that displace one of the components from the complex, can be tested by adding the test compound to the reaction mixture after complexes have been formed. The various formats are described briefly below.

In a heterogeneous assay system, either the target gene product or the interactive cellular or extracellular binding partner, is anchored onto a solid surface, while the non-anchored species is labeled, either directly or indirectly. In practice, microtiter plates are conveniently utilized. The anchored species can be immobilized by non-covalent or covalent attachments. Non-covalent attachment can be accomplished simply by coating the solid surface with a solution of the target gene product or binding partner and drying. Alternatively, an immobilized antibody specific for the species to be anchored can be used to anchor the species to the solid surface. The surfaces can be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the target gene product and the interactive cellular or extracellular binding partner product is prepared in which either the target gene products or their binding partners are labeled, but the signal generated by the label is quenched due to complex formation (see, e.g., U.S. Pat. No. 4,109,496, which utilizes this approach for immunoassays). The addition of a test substance that competes with and displaces one of the species from the preformed complex will result in the generation of a signal above background. In this way, test substances disrupting target gene product-cellular or extracellular binding partner interaction can be identified.

In a particular embodiment, the target gene product can be prepared for immobilization using recombinant DNA techniques described supra. For example, the target gene coding region can be fused to a glutathione-S-transferase (GST) gene using a fusion vector such as pGEX-5X-1, in such a manner that its binding activity is maintained in the resulting fusion product. The interactive cellular or extracellular product can be purified and used to raise a monoclonal antibody, using methods routinely practiced in the art and described above. In a heterogeneous assay, the GST-Target gene fusion product can be anchored to glutathione-agarose beads. The interactive cellular or extracellular binding partner product can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the target gene product and the interactive cellular or extracellular binding partner can be detected by measuring the amount of radioactivity that remains associated with the glutathione-agarose beads. A successful inhibition of the interaction by the test compound will result in a decrease in measured radioactivity.

Alternatively, the GST-target gene fusion product and the interactive cellular or extracellular binding partner product can be mixed together in liquid in the absence of the solid glutathione-agarose beads. The test compound can be added either during or after the binding partners are allowed to interact. This mixture can then be added to the glutathione-agarose beads and unbound material is washed away. Again the extent of inhibition of the binding partner interaction can be detected by adding the labeled antibody and measuring the radioactivity associated with the beads.

In another embodiment of the invention, these same techniques can be employed using peptide fragments that correspond to the binding domains of the target gene product and the interactive cellular or extracellular binding partner (in case where the binding partner is a product), in place of one or both of the full length products. Any number of methods routinely practiced in the art can be used to identify and isolate the protein's binding site. These methods include, but are not limited to, mutagenesis of one of the genes encoding one of the products and screening for disruption of binding in a co-immunoprecipitation assay. Compensating mutations in the gene encoding the second species in the complex can be selected. Sequence analysis of the genes encoding the respective products will reveal the mutations that correspond to the region of the product involved in interactive binding. Alternatively, one product can be anchored to a solid surface, and allowed to interact with and bind to its labeled binding partner, which has been treated with a proteolytic enzyme, such as trypsin. After washing, a short labeled peptide comprising the binding domain can remain associated with the solid material, which can be isolated and identified by amino acid sequencing. Also, once the gene coding for the cellular or extracellular binding partner product is obtained, short gene segments can be engineered to express peptide fragments of the product, which can then be tested for binding activity and purified or synthesized.

XXV. ASSAYS FOR AMELIORATION OF DISEASE SYMPTOMS

Any of the binding compounds, including compounds such as those identified in the foregoing assay systems, can be tested for the ability to prevent or ameliorate symptoms of a disease, specifically cardiac, kidney or inflammatory disease. Cell-based and animal model-based assays for the identification of compounds exhibiting an ability to prevent or ameliorate disease symptoms are described herein.

In a preferred embodiment, cell-based in vitro systems such as those described above can be used to identify compounds that can act to ameliorate symptoms of a disease. For example, such cell systems can be exposed to a compound suspected to exhibit an ability to ameliorate a disease or its symptoms, at a sufficient concentration and for a time sufficient to elicit such an amelioration in the exposed cells. After exposure, the cells are examined to determine whether one or more disease disorder phenotypes has been altered to resemble a more normal or more wild-type disease phenotype.

In another preferred embodiment, animal-based in vivo models can be used to identify compounds capable of ameliorating symptoms of a disease, specifically cardiac, kidney or inflammatory disease. Such animal models can be used as test substrates for the identification of drugs, pharmaceuticals, therapies, and interventions which can be effective in treating a disease, specifically cardiac, kidney or inflammatory disease, and related disorders. For example, animal models can be exposed to a compound suspected to exhibit an ability to ameliorate a disease or its symptoms at a sufficient concentration and for a time sufficient to elicit such amelioration in the exposed animals. The response of the animals to the exposure can be monitored by assessing the reversal of disorders associated with a disease. Concerning intervention, any treatments that reverse any aspect of symptoms of a disease, specifically cardiac, kidney or inflammatory disease, should be considered as candidates for human therapeutic intervention in the treatment of a disease. Dosages of test agents can be determined by deriving dose-response curves, as discussed below.

Further, gene expression patterns can be utilized to assess the ability of a compound to ameliorate symptoms of a disease, specifically cardiac, kidney or inflammatory disease. For example, diagnostic gene expression or a diagnostic pattern can then be used in such an assessment. Diagnostic gene expression and diagnostic patterns are described below.

Diagnostic patterns can be characterized for known disease states within the cell- or animal-based model systems. Subsequently, these known diagnostic patterns can be compared to ascertain the effect a test compound has to modify such diagnostic patterns and to cause the pattern to more closely resemble that of a more desirable diagnostic pattern.

For example, administration of a compound can cause the diagnostic pattern of a disease, specifically cardiac, kidney or inflammatory disease, model system to more closely resemble a control, normal system. Administration of a compound can alternatively cause the diagnostic pattern of a control system to begin to mimic a disease state.

XXVI. MONITORING OF EFFECTS DURING CLINICAL TRIALS

Monitoring the influence of compounds in a disease, specifically cardiac, kidney or inflammatory disease, can be applied not only in basic drug screening, but also in clinical trials. In such clinical trials, the expression of a panel of genes that have been discovered by the methods of the present invention can be used as a indicator of the disease, specifically cardiac, kidney or inflammatory disease, state of a particular cell.

For example, in a clinical trial, peripheral blood can be isolated, and RNA prepared and analyzed by microarray as described supra, The levels of expression of the diagnostic genes can be quantified by microarray or RT-PCR, or alternatively by measuring the amount of protein produced. In this way, the diagnostic profiles can serve as putative biomarkers indicative of the disease. Thus, by monitoring the level of expression of a differentially expressed gene of the present invention, a protocol for suitable drugs can be developed based on the gene expression potential of the subject cardiac cells. Indeed, biological samples can be periodically obtained from a treated subject for measurement of gene expression so that the efficacy of a drug can be measured by monitoring the degree of restored expression of the gene.

XXVII. COMPOUNDS AND METHODS FOR TREATMENT OF A DISEASE

The present invention relates to methods and compositions that can be used to ameliorate symptoms of a disease, specifically cardiac, kidney or inflammatory disease, and its related disorders by target gene modulation. Target gene modulation can be of a positive or negative nature, depending on the specific situation involved, but each modulatory event preferably yields a net result in which disease, specifically cardiac, kidney or inflammatory disease, symptoms are ameliorated.

"Negative modulation," as used herein, refers to a reduction in the level or activity of target gene product relative to the level or activity of the target gene product in the absence of the modulatory treatment.

"Positive modulation," as used herein, refers to an increase in the level or activity of target gene product relative to the level or activity of target gene product in the absence of modulatory treatment.

Another aspect of the invention pertains to methods for treating a subject, e.g., a human, having a disease or disorder characterized by (or associated with) differentially expressed gene expression or polypeptide activity. These methods include the step of administering a differentially expressed gene modulator to the subject such that treatment occurs. The terms "treating" or "treatment" include the reduction or alleviation of at least one adverse effect or symptom of a disorder or disease, e.g., a disorder or disease characterized by or associated with differentially expressed gene expression.

As used herein, a differentially expressed gene modulator is a molecule, which can modulate differentially expressed gene expression or polypeptide activity. For example, a differentially expressed gene modulator can modulate, e.g., upregulate (activate) or downregulate (suppress), differentially expressed gene expression. In another example, a differentially expressed gene modulator can modulate (e.g., stimulate or inhibit) expression product or polypeptide activity. If it is desirable to treat a disease, specifically cardiac, kidney or inflammatory disease, associated with differentially expressed gene expression or polypeptide activity by inhibiting differentially expressed agene expression, an differentially expressed gene modulator can be an antisense molecule. Examples of antisense molecules which can be used to inhibit differentially expressed gene expression include antisense molecules which are complementary to a portion of the 5' untranslated region of the coding sequence of the gene (e.g., SEQ ID NO:25) which also includes the start codon and antisense molecules which are complementary to a portion of the 3' untranslated region of the gene.

A differentially expressed gene modulator that inhibits differentially expressed gene expression can also be a small molecule or other drug, e.g., a small molecule or drug identified using the screening assays described herein, which inhibits differentially expressed gene expression. If it is desirable to treat a disease or disorder characterized by (or associated with) differentially expressed gene expression or polypeptide activity by stimulating differentially expressed gene expression, a differentially expressed gene modulator can be, for example, a nucleic acid molecule encoding differentially expressed gene (e.g., a nucleic acid molecule comprising a nucleotide sequence homologous to the nucleotide sequence of SEQ ID NO:25) or a small molecule (e.g., a peptide) or drug identified using the screening assays described herein, which stimulates differentially expressed gene expression. Indeed, the modulator can be the differentially expressed gene or expression product itself.

Alternatively, if one desires to treat a disease, specifically cardiac, kidney or inflammatory disease, or its related disorder associated with differentially expressed gene expression or polypeptide activity by inhibiting polypeptide activity, an differentially expressed gene modulator can be an anti-differentially expressed gene antibody or a small molecule or other drug, e.g., a small molecule or drug identified using the screening assays described herein, which inhibits polypeptide activity. If it is desirable to treat a disease or disorder characterized by (or associated with) differentially expressed gene expression or polypeptide activity by stimulating polypeptide activity, an differentially expressed gene modulator can be an active polypeptide or portion thereof, including the differentially expressed polypeptide itself (e.g., an polypeptide or portion thereof having an amino acid sequence which is homologous to the amino acid sequence of SEQ ID NO:37 (or a portion thereof)) or a small molecule or other drug, e.g., a small molecule or drug identified using the screening assays described herein, which stimulates polypeptide activity. The modulator can be the differentially expressed gene or expression product itself.

Other aspects of the invention pertain to methods for modulating a cell associated activity. These methods include contacting the cell with an agent (or a composition which includes an effective amount of an agent) which modulates polypeptide activity or differentially expressed gene expression such that a cell associated activity is altered relative to a cell associated activity of the cell in the absence of the agent. A "cell associated activity" refers to a normal or abnormal activity or function of a cell. Examples of cell associated activities include proliferation, migration, differentiation, production or secretion of molecules such as proteins, and cell survival. In a preferred embodiment, the cell may be a cardiac cell of the heart, e.g., a cardiac myocyte.

The term "altered" relates to a change, e.g., an increase or decrease, of a cell associated activity. In one embodiment, the agent stimulates polypeptide activity or nucleic acid expression. Examples of such stimulatory agents include an active gene protein, a nucleic acid molecule encoding differentially expressed gene that has been introduced into the cell, and a modulatory agent which stimulates polypeptide activity or differentially expressed gene expression and which is identified using the drug screening assays described herein.

In another embodiment, the agent inhibits polypeptide activity or differentially expressed gene expression. Examples of such inhibitory agents include an antisense differentially expressed gene nucleic acid molecule, an anti-differentially expressed gene antibody, and a modulatory agent which inhibits polypeptide activity or differentially expressed gene expression and which is identified using the drug screening assays described herein. These modulatory methods can be performed in vitro (e.g., by culturing the cell with the agent) or, alternatively, in vivo (e.g., by administering the agent to a subject). In a preferred embodiment, the modulatory methods are performed in vivo, i.e., the cell is present within a subject and the subject has a disorder or disease characterized by or associated with abnormal or aberrant polypeptide activity or differentially expressed gene expression.

It is possible that a disease can be brought about, at least in part, by an abnormal level of differentially expressed gene product, or by the presence of a gene product exhibiting abnormal activity. As such, the reduction in the level or activity of such gene products would bring about the amelioration of disease symptoms. Negative modulatory techniques for the reduction of target gene expression levels or target gene product activity levels are discussed below.

Alternatively, it is possible that a disease, specifically cardiac, kidney or inflammatory disease, can be brought about, at least in part, by the absence or reduction of the level of gene expression, or a reduction in the level of a gene product's activity. As such, an increase in the level of gene expression or the activity of such gene products would bring about the amelioration of a disease, specifically cardiac, kidney or inflammatory disease, symptoms.

By way of example, diagnostic genes discovered by the methods of the present invention are observed to be down-regulated in the disease state (e.g., BTG-2). A positive modulatory technique that increases such gene expression in cells within a disease state should, therefore, act to ameliorate the symptoms of such a state. Further, because the gene product may exhibit suppressor features, it is possible that a positive modulatory technique could ameliorate symptoms of many disease events. Positive modulatory techniques for increasing the target gene expression levels or target gene product activity levels are discussed below.

XXVIII. NEGATIVE MODULATORY TECHNIQUES

As discussed above, treatment of disease, specifically cardiac, kidney or inflammatory disease, symptoms and disorders involving such a disease, can be brought about by techniques that serve to inhibit the expression or activity of target gene products. For example, compounds within the context of the present invention that exhibit negative modulatory activity can be used in accordance with the invention to prevent or ameliorate symptoms of a disease, specifically cardiac, kidney or inflammatory disease. Such molecules can include, but are not limited to peptides, phosphopeptides, small organic or inorganic molecules, or antibodies (including, for example, polyclonal, monoclonal, humanized. anti-idiotypic, chimeric or single chain antibodies, and Fab, F(ab')$_2$ and Fab expression library fragments, and epitope-binding fragments thereof). Negative modulatory techniques involving antibody administration are described below, as well as techniques for the determination and administration of such compounds.

Further, antisense and ribozyme molecules which inhibit expression of the target gene can also be used in accordance with the invention to reduce the level of target gene expression, thus effectively reducing the level of target gene activity. Still further, triple helix molecules can be utilized in reducing the level of target gene activity The invention also pertains to methods for modulating a cell associated activity. Such methods include contacting the cell with a modulator of the differentially expressed gene such that a cell associated activity is altered relative to a cell associated activity (e.g., the same cell associated activity) of the cell in the absence of the agent. The differentially expressed gene modulator can stimulate polypeptide activity or nucleic acid expression related to the differentially expressed gene. Examples of such stimulatory modulators include small molecules, active polypeptides encoded by the differentially expressed gene, and nucleic acids encoding the differentially expressed gene that have been introduced into the cell. Alternatively, the modulator can inhibit the polypeptide activity of the differentially expressed gene or nucleic acid expression. Examples of such inhibitory modulators include small molecules, antisense nucleic acid molecules, and antibodies that specifically react with an epitope of the differentially expressed gene product. In a preferred embodiment, the cell is present within a subject and the agent is administered to the subject.

The nucleic acid molecules, polypeptides, polypeptide homologs, modulators, and antibodies described herein preferably may be used in drug screening assays, diagnostic assays, and methods of treatment. A differentially expressed gene polypeptide of the invention has one or more of the activities described herein and can thus be used, for example, to modulate a function in a cell involved in a disease, specifically cardiac, kidney or inflammatory disease. The isolated nucleic acid molecules of the invention can be used to express polypeptide encoded by a differentially expressed gene of the present invention (e.g., via a recombinant expression vector in a host cell in gene therapy applications), to detect mRNA of the differentially expressed gene (e.g., in a biological sample) or a genetic lesion in a differentially expressed gene, or to modulate activity of the differentially expressed gene or polypeptides encoded thereby, as described further below.

In addition, the polypeptides encoded by the differentially expressed genes of the present invention can be used to screen drugs or compounds which modulate polypeptide activity related to the differentially expressed gene as well as to treat disorders characterized by insufficient production of polypeptide encoded by the differentially expressed gene or production of polypeptide forms which have decreased activity compared to wild type forms of the polypeptides encoded by the differentially expressed genes of the present invention. Moreover, antibodies to the polypeptides encoded by the differentially expressed genes of the present invention can be used to detect and isolate such polypeptides and modulate polypeptide activity.

XXIX. NEGATIVE MODULATORY ANTISENSE, RIBOZYME AND TRIPLE HELIX APPROACHES

Among the compounds exhibiting the ability to prevent or ameliorate symptoms of a disease, specifically cardiac, kidney or inflammatory disease, are antisense, ribozyme, and triple helix molecules. Such molecules can be designed to reduce or inhibit either normal or, if appropriate, mutant target gene activity. Techniques for the production and use of such molecules are well known to those of skill in the art.

Anti-sense RNA and DNA molecules act to directly block the translation of mRNA by hybridizing to targeted mRNA and preventing protein translation. With respect to antisense DNA, oligodeoxyribonucleotides derived from the translation initiation site, e.g., between the −10 and +10 regions of the target gene nucleotide sequence of interest, are preferred.

Ribozymes are enzymatic RNA molecules capable of catalyzing the specific cleavage of RNA (Rossi, *Current Biology* 4:469–71 (1994)). The mechanism of ribozyme action involves sequence specific hybridization of the ribozyme molecule to complementary target RNA, followed by an endonucleolytic cleavage. The composition of ribozyme molecules must include one or more sequences complementary to the target gene mRNA and must include the well-known catalytic sequence responsible for mRNA cleavage. For this sequence, see U.S. Pat. No. 5,093,246, which is incorporated by reference herein in its entirety. Within the scope of the present invention are engineered hammerhead motif ribozyme molecules that specifically and efficiently catalyze endonucleolytic cleavage of RNA sequences encoding target gene proteins.

Specific ribozyme cleavage sites within any potential RNA target are initially identified by scanning the molecule of interest for ribozyme cleavage sites which include the following sequences, GUA, GUU and GUC. Once identified, short RNA sequences of between 15 and 20 ribonucleotides corresponding to the region of the target gene containing the cleavage site can be evaluated for predicted structural features, such as secondary structure, that can render the oligonucle tide sequence unsuitable. The suitability of candidate sequences can also be evaluated by testing their accessibility to hybridization with complementary oligonucleotides, using ribonuclease protection assays.

Nucleic acid molecules preferably used in triplex helix formation for the inhibition of transcription are single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences can be pyrimidine- based, which will result in TAT and CGC+ triplets across the three associated strands of the resulting triple helix. The pyrimidine-rich molecules provide base complementarily to a purine-rich region of a single strand of the duplex in a parallel orientation to that strand. In addition, nucleic acid molecules can be chosen that are purine-rich, for example, contain a stretch of G residues. These molecules form a triple helix with a DNA duplex that is rich in GC pairs, in which the majority of the purine residues are located on a single strand of the targeted duplex, resulting in GGC triplets across the three strands in the triplex.

Alternatively, creating a "switchback" nucleic acid molecule can increase the potential sequences that can be targeted for triple helix formation. Switchback molecules are synthesized in an alternating 5'×3', 3'–5' manner, such that they base pair with first one strand of a duplex and then the other, eliminating the necessity for a sizeable stretch of either purines or pyrimidines to be present on one strand of a duplex.

In instances wherein the antisense, riboiyme, or triple helix molecules described herein are utilized to reduce or inhibit mutant gene expression, it is possible that the technique utilized can also efficiently reduce or inhibit the transcription (triple helix) or translation (antisense, ribozyme) of mRNA produced by normal target gene alleles such that the concentration of normal target gene product present is lower than is necessary for a normal phenotype. In such cases, to ensure that substantially normal levels of target gene activity are maintained, nucleic acid molecules that encode and express target gene polypeptides exhibiting normal target gene activity can be introduced into cells via gene therapy methods, such as those described below, that do not contain sequences susceptible to the antisense, ribozyme, or triple helix treatments utilized. Alternatively, where the target gene encodes an extracellular protein, it can be preferable to co-administer normal target gene protein into the cell or tissue in order to maintain the requisite level of cellular or tissue target gene activity.

Antisense RNA and DNA, ribozyme and triple helix molecules of the invention can be prepared by any method known in the art for the synthesis of DNA and RNA molecules. These include techniques for chemically synthesizing oligodeoxyribonucleotides and oligoribonucleotides well known in the art such as solid phase phosphoramidite chemical synthesis. Alternatively, RNA molecules can be generated by in vitro and in vivo transcription of DNA sequences encoding the antisense RNA molecule. Such DNA sequences can be incorporated into a variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Another class of antisense molecules, the phosphorothioates, has a sulfur in the oligonucleotide backbone instead of an oxygen atom and is a DNA analog capable of use in the present invention. For example, modification at the 2'-position of the sugar by creating methoxyethyl, aminopropyl, and fluorine conjugates has dramatic effects on stability and target-binding efficiency. Nonspecific effects due to their association with proteins and to the base sequence of the oligonucleotide can limit or even alter the expected antisense effects.

Another class of compounds, the PNAs (peptide nucleic acids) can also be utilized. PNAs have a peptide-like backbone instead of the normal sugar and phosphate groups of DNA. PNA may be used to turn on specific genes by binding to a promoter region of a gene to initiate RNA transcription. Chimeric molecules of PNA and DNA may also be considered. The DNA portion will allow enzymes attacking DNA-RNA hybrids to cut the RNA part of the complex into pieces (leading to dissociation of the drug molecule, which can then be reused), whereas the PNA portion will contribute stability and selectivity.

Genetic drugs can also be directed at the gene itself. The first chemical approach to target double-stranded DNA has been to use oligonucleotides to bind in the major groove of DNA and form a specific local triple helix. Tests of blocking transcription of the HIV genes nef and pol in cell cultures was performed by using oligonucleotides linked to intercalators. Some PNA sequences bind to double-stranded DNA by an invasion mechanism: two PNA molecules form a triplex structure with the complementary DNA target sequence, whereas the other strand of the DNA duplex is displaced into a single-stranded loop. Once formed, such PNA-DNA complexes are extremely stable. Minor-groove binding polyamides that contain combinations of three different aromatic amino acids, which pair and uniquely recognize each of the four Watson-Crick base pairs may also be used. Hairpin polyamides bind specifically to predetermined DNA sequences with the affinity and specificity of protein transcription factors. Cells are believed to be permeable to these polyamides, a property that may be related to the fact that they are significantly smaller than oligonucleotide analogs used in antisense approaches. These synthetic DNA binding ligands can enter the nucleus and inhibit expression of specific genes by blocking promoter-specific transcription factors.

The arrays of immobilized DNA fragments may also be used for genetic diagnostics. To illustrate, a microarray containing multiple forms of a mutated gene or genes can be probed with a labeled mixture of a subject DNA, which will preferentially interact with only one of the immobilized versions of the gene.

The detection of this interaction can lead to a medical diagnosis. Arrays of immobilized DNA fragments can also be used in DNA probe diagnostics. For example, the identity of a differentially expressed gene of the present invention can be established unambiguously by hybridizing a sample of a subject's DNA to an array comprising known differentially expressed DNA. Other molecules of genetic interest, such as cDNAs and RNAs can be immobilized on the array or alternately used as the labeled probe mixture that is applied to the array.

XXX. NEGATIVE MODULATORY ANTIBODY TECHNIQUES

Antibodies can be generated which are both specific for target gene product and which reduce target gene product activity. Such antibodies may, therefore, by administered in instances whereby negative modulatory techniques are appropriate for the treatment of a disease, specifically cardiac, kidney or inflammatory disease. Antibodies can be generated using standard techniques against the expressed proteins themselves or against peptides corresponding to portions of the proteins. The antibodies include polyclonal, monoclonal, Fab fragments, single chain antibodies, chimeric antibodies.

In instances where the target gene protein to which the antibody is directed is intracellular and whole antibodies are used, internalizing antibodies can be preferred. However, lipofectin or liposomes can be used to deliver the antibody or a fragment of the Fab region that binds to the target gene epitope into cells. Where fragments of the antibody are used, the smallest inhibitory fragment that binds to the target protein's binding domain is preferred. For example, peptides having an amino acid sequence corresponding to the domain of the variable region of the antibody that binds to the target gene protein can be used. Such peptides can be synthesized chemically or produced via recombinant DNA technology using methods well known in the art (see, e.g., Creighton, supra; and Sambrook et al., supra). Alternatively, single chain neutralizing antibodies that bind to intracellular target gene product epitopes can also be administered. Such single chain antibodies can be administered, for example, by expressing nucleotide sequences encoding single-chain antibodies within the target cell population by utilizing, techniques such as those described in Marasco et al. (Marasco et al., *Proc. Natl. Acad. Sci. USA* 90:7889–93 (1993)). In instances where the target gene protein is extracellular, or is a transmembrane protein, any of the administration techniques described below that are appropriate for peptide, can be utilized to effectively administer inhibitory target gene antibodies to their site of action.

XXXI. POSITIVE MODULATORY TECHNIQUES

As discussed above, successful treatment of disease, specifically cardiac, kidney or inflammatory disease, symptoms and disorders involving such diseases can be brought about by techniques which serve to increase the level of target gene expression or to increase the activity of a target gene product. For example, compounds that exhibit positive modulatory activity can be used in accordance with the invention to ameliorate disease symptoms. Such molecules can include, but are not limited to, peptides, phosphopeptides, small organic or inorganic molecules, or antibodies (including, for example, polyclonal, monoclonal, humanized, anti-idiotypic, chimeric or single chain antibodies, and Fab, F(ab')$_2$ and Fab expression library fragments, and epitope-binding fragments thereof. For example, a target gene protein, at a level sufficient to ameliorate a disease, specifically cardiac, kidney or inflammatory disease, can be administered to a patient. Any of the techniques discussed below can be utilized for such administration. One of skill in the art will readily know how to determine the concentration of effective, non-toxic doses of the normal target gene protein, using known techniques.

In instances wherein administered compound is a peptide, DNA sequences encoding the peptide compound can, alternatively, be directly administered to a patient exhibiting disease symptoms, at a concentration sufficient to generate the production of an amount of target gene product adequate to ameliorate the disease symptoms. Any of the techniques described below, which achieve intracellular administration can be utilized for the administration of such DNA molecules. The DNA molecules can be produced by known recombinant techniques.

In the case of peptide compounds which act extracellularly, the DNA molecules encoding such peptides can be taken up and expressed by any cell type, so long as a sufficient circulating concentration of peptide results for the elicitation of a reduction in disease, specifically cardiac, kidney or inflammatory disease, symptoms.

In the case of compounds which act intracellularly, the DNA molecules encoding such peptides may be taken up and expressed by cells involved in the disease at a sufficient level to bring about the reduction of disease symptoms. Any technique that selectively serves to administer DNA molecules to a cell involved in a disease is preferred for the DNA molecules encoding intracellularly acting peptides.

Further, patients can be treated for symptoms of a disease, specifically cardiac, kidney or inflammatory disease, by gene replacement therapy. One or more copies of a normal target gene or a portion of the gene that directs the production of a normal target gene protein with target gene function can be inserted into cells, using vectors which include, adenovirus, adeno-associated virus, and retrovirus vectors, in addition to other particles that introduce DNA into cells, such as liposomes. Techniques such as those described above can be utilized for the introduction of normal target gene sequences into human cells.

In instances wherein the target gene encodes an extracellular, secreted gene product, such gene replacement techniques may be accomplished either in vivo or in vitro. For such cases, the cell types expressing the target gene is less important than achieving a sufficient circulating concentration of the extracellular molecules for the amelioration of disease symptoms to occur. In vitro, target gene sequences can be introduced into autologous cells. Cells expressing the target gene sequence of interest can then be reintroduced, preferably by intravenous administration, into the patient such that there results an amelioration of disease symptoms.

In instances wherein the gene replacement involves a gene encoding a product which acts intracellularly, it is preferred that gene replacement is accomplished in vivo. Further, because the cell type in which the gene replacement must occur is the cell type involved in a disease, specifically cardiac, kidney or inflammatory disease, such techniques must successfully target such cells.

Taking a down-regulated differentially expressed gene of the present invention as an example (e.g., BTG2), an increase in expression may serve to ameliorate disease, specifically cardiac, kidney, or inflammatory disease, symptoms. Therefore, any positive modulatory agent which increases the gene productor gene product activity to a level that is sufficient to ameliorate cardiac disease symptoms represents a successful therapeutic treatment.

XXXII. PHARMACEUTICAL PREPARATIONS AND METHODS OF ADMINISTRATION

The identified compounds that inhibit target gene expression, synthesis or activity can be administered to a patient at therapeutically effective doses to prevent, treat or ameliorate a disease, specifically cardiac, kidney or inflammatory disease, or its symptoms. A therapeutically effective dose refers to that amount of the compound sufficient to result in treatment or amelioration of symptoms of a disease, specifically cardiac, kidney or inflammatory disease.

A. EFFECTIVE DOSE

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds exhibiting large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

Data obtained from cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound, which achieves a half-maximal inhibition of symptoms) as determined in cell culture. Such information can be used to accurately determine useful doses in humans. Levels in plasma can be measured, for example, by high performance liquid chromatography.

B. FORMULATIONS AND USE

Pharmaceutical compositions for use in accordance with the present invention can be formulated in conventional manner using one or more physiologically acceptable carriers or excipients. Thus, the compounds and their physiologically acceptable salts and solvates can be formulated for administration by inhalation or insufflation (either through the mouth or the nose) or oral, buccal, parenteral or rectal administration.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate talc or silica); disintegrants (e.g., potato starch or sodium starch glycolate); or wetting agents (e.g., sodium lauryl sulfate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound. For buccal administration the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing or dispersing agents. Alternatively, the active ingredient can be in powder form for constitution with a suitable vehicle, e.g., sterile pyrogen-free water, before use. The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example,.as a sparingly soluble salt.

The compositions can, if desired, be presented in a pack or dispenser device that can contain one or more unit dosage forms containing the active ingredient. The pack can for example comprise metal or plastic foil, such as a blister pack. The pack or dispenser device can be accompanied by instructions for administration.

XXXIII. DIAGNOSIS OF A DISEASE

A variety of methods can be employed for the diagnosis of a disease, specifically cardiac, kidney or inflammatory disease, and of disorders involving such diseases. Such methods can, for example, utilize reagents such as diagnostic gene nucleotide sequences and antibodies directed against differentially expressed and interactive gene peptides. Specifically, such reagents can be used, for the detection of the presence of target gene mutations, or the detection of either over or under expression of target gene mRNA.

The methods described herein can be performed by utilizing pre-packaged diagnostic kits comprising at least one specific diagnostic gene nucleic acid or anti-diagnostic gene antibody reagent described herein, which can be conveniently used, e.g., in clinical settings, to diagnose patients exhibiting symptoms of a disease, specifically cardiac, kidney or inflammatory diseases. Microarrays as disclosed preferably may be used. In one application, a microarray comprising one or more cDNA clones representing differentially expressed genes is hybridized with total cDNA from a subject to monitor differentially expressed gene expression for research or diagnostic purposes. Labeling total cDNA from a normal cell with one color fluorophore and total cDNA from a diseased cell with another color fluorophore and simultaneously hybridizing the two cDNA samples to the same array of cDNA clones allows for differential gene expression to be measured as the ratio of the two fluorophore intensities. This two-color experiment can be used to monitor differentially expressed gene expression in different tissue types, disease states, or in response to drugs.

In another embodiment, such microarrays may comprise sequences specific for differentially expressed disease, specifically cardiac, kidney or inflammatory disease, genes, preferably chosen from one or more of the group including nucleic acids (and portions thereof) corresponding to the sequences specified in GenBank Accession numbers X57352, S75725, D13665, X67698, M62402, D90226, L13698, U52101, U72649, L36034, M36035, and M38591, as well as nucleic acids (and portions thereof) encoding the human genes 1–8U (SEQ ID NO:37), prostacyclin-stimulating factor (SEQ ID NO:38), osf-2 (SEQ ID NO:39), tissue specific mRNA (SEQ ID NO:40), insulin-like growth factor binding protein 6 (SEQ ID NO:41), OSF-1 (SEQ ID NO:42), gas-1 (SEQ ID NO:43), YMP (SEQ ID NO:44), BTG2 (SEQ ID NO:45), pre-B cell stimulating factor homolog (SDF1a) (SEQ ID NO:46), peripheral benzodiazepine receptor (SEQ ID NO:47), and cellular ligand of annexin II (p11) (SEQ ID NO:48).

XXXIV. DETECTION OF DIAGNOSTIC GENE NUCLEIC ACIDS

DNA or RNA from the cell type or tissue to be analyzed can easily be isolated using procedures known to those in the art. Diagnostic procedures can also be performed directly upon tissue sections (fixed or frozen) of subject tissue obtained from biopsies or resections, such that no nucleic acid purification is necessary. Nucleic acid reagents such as those described above can be used as probes or primers for such in situ procedures (see, e.g., Nuovo, PCR in situ hybridization: *Protocols and Applications*, Raven Press (New York, 1992)).

Diagnostic gene nucleotide sequences, either RNA or DNA, can, be used in hybridization or amplification assays of biological samples to detect gene structures and expression associated with a disease, specifically cardiac, kidney or inflammatory disease. Such assays can include microarray analyses, Southern or Northern analyses, single stranded conformational polymorphism analyses, in situ hybridization assays, and polymerase chain reaction analyses. Such analyses can reveal both quantitative aspects of the expression pattern of the diagnostic gene, and qualitative aspects of the diagnostic gene expression or gene composition. That is, such techniques can include, for example, point mutations, insertions, deletions, chromosomal rearrangements, or activation or inactivation of gene expression.

Preferred diagnostic methods for the detection of diagnostic gene-specific nucleic acid molecules can involve, for example, microarray analysis via contacting and incubating nucleic acids derived from the cell type or tissue being analyzed, with microarrays under conditions favorable for the specific hybridization of these reagents to their complementary sequences within the nucleic acid molecule or interest.

Alternative diagnostic methods for the detection of diagnostic gene specific nucleic acid molecules can involve their amplification, e.g., by PCR (the experimental embodiment set forth in U.S. Pat. No. 4,683,202), ligase chain reaction (Barany, *Proc. Natl. Acad. Sci. USA* 88:189–93 (1991)), self sustained sequence replication (Guatelli et al., supra), transcriptional amplification system (Kwoh et al., supra), Q-Beta Replicase (Lizardi et al., *Bio/Technology* 6:1197 (1988)), or any other nucleic acid amplification method, followed by the detection of the amplified molecules using techniques well known to those of skill in the art. These detection schemes are especially useful for the detection of nucleic acid molecules if such molecules are present in very low numbers.

In addition to methods which focus primarily on the detection of one nucleic acid sequence, diagnostic profiles can also be assessed in such detection schemes. Diagnostic profiles can be generated, by using microarrays, differential display procedures, Northern analysis or RT-PCR.

XXXV. DETECTION OF TARGET GENE PEPTIDES

Antibodies directed against normal or mutant diagnostic gene peptides can also be used in disease, specifically cardiac, kidney or inflammatory disease, diagnostics and prognostics as described above. Such diagnostic methods can be used to detect abnormalities in the level of diagnostic gene protein expression, or abnormalities in the structure or tissue, cellular, or subcellular location of diagnosticing gene protein. Structural differences can include, for example, differences in the size, electronegativity, or antigenicity of the mutant diagnostic gene protein relative to the normal diagnostic gene protein.

Protein from the tissue or cell type to be analyzed can be isolated using techniques known to those of skill in the art. The protein isolation methods employed herein can, be such as those described in (Harlow et al., supra), which is incorporated herein by reference in its entirety.

Preferred diagnostic methods for the detection of normal or mutant diagnostic gene peptide molecules can involve, immunoassays wherein diagnostic gene peptides are detected by their interaction with an anti-diagnostic gene specific peptide antibody. For example, antibodies, or fragments of antibodies useful in the present invention can be used to quantitatively or qualitatively detect the presence of normal or mutant diagnostic gene peptides. This can be accomplished, for example, by immunofluorescence techniques employing a fluorescently labeled antibody coupled with light microscopic, flow cytometric, or fluorimetric detection. Such techniques are especially preferred if the diagnostic gene peptides are expressed on a cell surface.

The antibodies (or fragments thereof) useful in the present invention can, additionally be employed histologically, as in immunofluorescence or immunoelectron microscopy, for in situ detection of target gene peptides. In situ detection can be accomplished by obtaining a biological sample from a patient, and applying thereto a labeled antibody of the present invention. The antibody (or fragment) is preferably applied by overlaying the labeled antibody (or fragment) onto a biological sample. Using such a procedure, it is possible to determine not only the presence of diagnostic gene peptides, but also their distribution in the examined tissue. Using the present invention, those of ordinary skill will readily perceive that any of a variety of histological methods (such as staining procedures) can be modified in order to achieve such in situ detection.

Immunoassays for normal or mutant diagnostic gene peptides may typically comprise incubating a biological sample, such as a biological fluid, a tissue extract, freshly harvested cells, or cells which have been incubated in tissue culture, in the presence of a detectably labeled antibody capable of identifying diagnostic gene peptides, and detecting the bound antibody by any of a number of techniques well-known in the art.

The biological sample can be brought in contact with and immobilized onto a solid phase support or carrier such as nitrocellulose, or other solid support which is capable of immobilizing cells, cell particles or soluble proteins. The support can then be washed with suitable buffers followed by treatment with the detectably labeled diagnostic gene specific antibody. The solid phase support can then be washed with the buffer a second time to remove unbound antibody. The amount of bound label on solid support can then be detected by conventional means.

One of the ways in which the diagnostic gene peptide-specific antibody can be detectably labeled is by linking it to an enzyme and using it in an enzyme immunoassay (ETA) (Voller, "The Enzyme Linked Immunosorbent Assay (ELISA)", *Diagnostic Horizons* 2:1–7, Microbiological Associates Quarterly Publication (Walkersville, Md., 1978); Voller et al., *J. Clin. Pathol.* 31:507–20 (1978); Butler, *Meth. Enzymol.* 73:482–523 (1981); Maggio, ed., *Enzyme Immunoassay*, CRC Press (Boca Raton, Fla., 1980); Ishikawa et al., eds., *Enzyme Immunoassay*, Kgaku Shoin (Tokyo, 1981)). The enzyme, which is bound to the antibody, will react with an appropriate substrate, preferably a chromogenic substrate, in such a manner as to produce a chemical moiety that can be detected by spectrophotometric fluorimetric or by visual means. Detection can also be accomplished using any of a variety of other immunoassays. For example, by radioactively labeling the antibodies or antibody fragments, it is possible to detect diagnostic gene normal or mutant peptides through the use of a radioimmunoassay (RIA) (see, e.g., Weintraub, *Principles of Radioimmunoassays, Seventh Training Course on Radioligand Assay Techniques*, The Endocrine Society, March, 1986). The radioactive isotope can be detected by such means as the use of a gamma counter or a scintillation counter or by autoradiography.

XXXVI. USE OF DIAGNOSTIC GENES AS SURROGATE MARKERS IN CLINICAL TRIALS

The expression pattern of the diagnostic genes of the invention may be utilized as surrogate markers to monitor clinical human trials of drugs being tested for their efficacy as disease treatments, specifically for cardiac, kidney or inflammatory disease, or may additionally be used to monitor patients undergoing clinical evaluation for the treatment of such disease.

The effect of the compound on the diagnostic gene expression normally displayed in connection with a disorder involving a disease, specifically cardiac, kidney or inflammatory disease, can be used to evaluate the efficacy of the compound as a treatment for such a disorder. Additionally, diagnostic gene expression can be used to monitor patients undergoing clinical evaluation for the treatment of the disorder.

According to the invention, the diagnostic gene expression and diagnostic pattern can be used to monitor clinical trials of drugs in human patients. Indeed, the influence of modulating agents on a disease can be measured by performing microarray analysis of mRNA obtained from biological samples of patients undergoing clinical tests.

XXXVII. TREATMENT OF PATIENTS SUFFERING FROM A DISEASE, SPECIFICALLY CARDIAC, KIDNEY OR INFLAMMATORY DISEASE

Another aspect of the present invention pertains to methods for treating a subject having a disease, specifically cardiac, kidney or inflammatory disease, characterized by (or associated with) differential gene expression or polypeptide activity. These methods include the step of administering a modulator of the differential nucleic acid expression or polypeptide activity to the subject such that treatment occurs. As the differentially expressed genes of the present invention are involved in an interactive related to a disease, specifically cardiac, kidney or inflammatory disease, differential activity or expression interferes with the normal system function. The terms "treating" or "treatment," as used herein, refer to reduction or alleviation of at least one adverse effect or symptom of a disease, specifically cardiac, kidney or inflammatory disease, e.g., a disorder or disease characterized by or associated with differentially expressed gene polypeptide activity or nucleic acid expression.

As used herein, a modulator includes a molecule, which can modulate nucleic acid expression or polypeptide activity. For example, a modulator can modulate, e.g., upregulate (activate) or downregulate (suppress), nucleic acid expression. In another example, a modulator can modulate (e.g:, stimulate or inhibit) polypeptide activity. If it is desirable to treat a disease, specifically cardiac, kidney or inflammatory disease, characterized by (or associated with) differential (non-wild-type) nucleic acid expression or polypeptide activity by inhibiting nucleic acid expression, a modulator can be an antisense molecule, e.g., a ribozyme, as described herein. Examples of antisense molecules which can be used to inhibit nucleic acid expression include antisense molecules which are complementary to a portion of the 5' untranslated region of the cDNA encoding the genes and polypeptides of the present invention, e.g., SEQ ID NO:25, which also includes the start codon and antisense molecules which are complementary to a portion of the 3' untranslated region of the cDNA. A modulator that inhibits nucleic acid expression can also be a small molecule or other drug, e.g., a small molecule or drug identified using the screening assays described herein, which inhibits nucleic acid expression.

If it is desirable to treat a disease, specifically cardiac, kidney or inflammatory disease, characterized by (or associated with) differential nucleic acid expression or polypeptide activity by stimulating nucleic acid expression, a modulator can be, for example, a nucleic acid molecule encoding the differentially expressed polypeptide (e.g., a nucleic acid molecule comprising a nucleotide sequence homologous to the nucleotide sequence encoding the polypeptide) or a small molecule or other drug, e.g., a small molecule (peptide) or drug identified using the screening assays described herein, which stimulates nucleic acid expression.

Alternatively, if it is desirable to treat a disease, specifically cardiac, kidney or inflammatory disease, characterized by (or associated with) differential nucleic acid expression or polypeptide activity by inhibiting polypeptide activity, a modulator can be an anti-polypeptide antibody or a small molecule or other drug, e.g., a small molecule or drug identified using the screening assays described herein, which inhibits polypeptide activity. If it is desirable to treat a disease, specifically cardiac, kidney or inflammatory disease, associated with differential nucleic acid expression or polypeptide activity by stimulating polypeptide activity, a modulator can be an active polypeptide or portion thereof (e.g., a polypeptide or portion thereof having an amino acid sequence which is homologous to the amino acid sequence of the polypeptide or a portion thereof) or a small molecule or other drug, e.g., a small molecule or drug identified using the screening assays described herein, which stimulates polypeptide activity. In addition, a subject having a disease, specifically cardiac, kidney or inflammatory disease, can be treated according to the present invention by administering to the subject a polypeptide or portion thereof modulating the differentially expressed nucleic acid expression and or polypeptide activity such that treatment occurs.

Other aspects of the invention pertain to methods for modulating a cell associated activity. These methods include contacting the cell with an agent (or a composition which includes an effective amount of an agent) which modulates polypeptide activity or nucleic acid expression such that a cell associated activity is altered relative to a cell associated activity of the cell in the absence of the agent. As used herein, "a cell associated activity" refers to a normal or abnormal activity or function of a cell. Examples of cell associated activities include proliferation, migration, differentiation, production or secretion of molecules, such as proteins, and cell survival. In a preferred embodiment, the cardiac cell is a myocyte. The term "altered" as used herein refers to a change, e.g., an increase or decrease, in a cell associated activity.

In one embodiment, the agent stimulates polypeptide activity or nucleic acid expression. Examples of such stimulatory agents include an active protein, a nucleic acid molecule encoding polypeptide that has been introduced into the cell, and a modulatory agent which stimulates polypeptide activity or nucleic acid expression and which may be identified using the drug screening assays described herein. In another embodiment, the agent inhibits polypeptide activity or nucleic acid expression. Examples of such inhibitory agents include an antisense nucleic acid molecule, an anti-polypeptide antibody, and a modulatory agent which inhibits polypeptide activity or nucleic acid expression and which is identified using the drug screening assays described herein. These modulatory methods can be performed in vitro (e.g., by culturing the cell with the agent), or alternatively in vivo (e.g., by administering the agent to a subject). In a preferred embodiment, the modulatory methods are performed in vivo, i.e., the cell is present within a subject and the subject has a disease, specifically cardiac, kidney or inflammatory disease, characterized by or associated with differential polypeptide activity or nucleic acid expression.

A nucleic acid molecule, a polypeptide, a modulator, or a compound used in the methods of treatment can be incorporated into an appropriate pharmaceutical composition described herein and administered to the subject through a route, which allows the molecule, polypeptide, modulator, or compound to perform its intended function. Examples of routes of administration are also described herein.

Test patients can be administered compounds suspected of disease, specifically cardiac, kidney or inflammatory disease, modulating activity. Control patients can be given a placebo. Cardiac cell biopsies or peripheral blood can be drawn from each patient after a determined period of treatment and RNA can be isolated as described supra for analysis.

XXXVIII. ANALYSIS OF SAMPLES

The invention also encompasses kits for detecting the presence of differentially expressed genes of the present invention in a biological sample. For example, the kit can comprise a labeled or labelable compound or agent capable of detecting polypeptide or mRNA in a biological sample, means for determining the amount of differentially expressed gene in the sample, and means for comparing the amount of differentially expressed gene in the sample with a standard. The kit may preferably comprise a microarray comprising one or more oligonucleotides complementary to reference DNA or RNA sequences encoding the differentially expressed genes of the present invention obtained from tissue from a normal subject and tissue from a subject exhibiting a disease, specifically cardiac, kidney or inflammatory disease. In one embodiment, a biological sample is obtained from the subject, particularly tissue or blood, from which cDNA probes are made and hybridized on a microarray to create fluorometric, colorimetric or such identifying emissions. The compound or agent can be packaged in a suitable container. The kit can further comprise instructions for using the kit to detect differentially expressed gene mRNA or protein, along with PCR reagents.

The invention further provides kits comprising at least one oligonucleotide of the present invention. In one embodiment, the kits contain one or more pairs of allele-specific oligonucleotides hybridizing to different forms of a polymorphism. In some kits, the allele-specific oligonucleotides are provided immobilized to a substrate. Optional additional components of the kit can include, restriction enzymes, reverse-transcriptase or polymerase, the substrate nucleoside triphosphates, means used to label (e.g., an avidin-enzyme conjugate and enzyme substrate and chromogen if the label is biotin), and the appropriate buffers for reverse transcription, PCR, or hybridization reactions. The kit may also contain instructions for carrying out the methods.

In another preferred embodiment of the present invention the kit may comprise one or more antibodies that bind with high specificity to the protein products of the differentially expressed genes of the present invention, e.g., all or a portion of the amino acid sequence of the human genes 1–8U (SEQ ID NO:37), prostacyclin-stimulating factor (SEQ ID NO:38), osf-2 (SEQ ID NO:39), tissue specific mRNA (SEQ ID NO:40), insulin-like growth factor binding protein 6 (SEQ ID NO:41), OSF-1 (SEQ ID NO:42), gas-1 (SEQ ID NO:43), YMP (SEQ ID NO:44), BTG2 (SEQ ID NO:45), pre-B cell stimulating factor homolog (SDF1a) (SEQ ID NO:46), peripheral benzodiazepine receptor (SEQ ID NO:47), and cellular ligand of annexin II (p11) (SEQ ID NO:48), respectively. Means for preparing and characterizing antibodies are well known in the art (see, e.g., Harlow et al., supra).

All the essential materials and reagents required for detecting disease state genes in a biological sample may be assembled together in a kit. This generally comprises pre-selected primers for specific genes. Also included may be enzymes suitable for amplifying nucleic acids including various polymerases, deoxynucleotides and buffers to provide the necessary reaction mixture for amplification.

Such kits generally comprise, in suitable means, distinct containers for each individual reagent and enzyme as well as for each gene primer pair. Preferred pairs of primers for amplifying nucleic acids are selected to amplify the sequences specified in GenBank Accession numbers X57352, S75725, D13665, X67698, M62402, D90226, L13698, U52101, U72649, L36034, M36035, and M38591, encoding the human genes 1–8U (SEQ ID NO:37), pro stacyclin-stimulating factor (SEQ ID NO:38), osf-2 (SEQ ID NO:39), tissue specific mRNA (SEQ ID NO:40), insulin-like growth factor binding protein 6 (SEQ ID NO:41), OSF-1 (SEQ ID NO:42), gas-1 (SEQ ID NO:43), YMP (SEQ ID NO:44), BTG2 (SEQ ID NO:45), pre-B cell stimulating factor homolog (SDF1a) (SEQ ID NO:46), peripheral benzodiazepine receptor (SEQ ID NO:47), and cellular ligand of annexin II (p11) (SEQ ID NO:48), respectively Such kits generally comprise, in suitable means, distinct containers for each individual reagent and enzyme, as well as for each gene hybridization probe.

In another embodiment, such microarrays may comprise sequences specific for differentially expressed disease, specifically cardiac, kidney or inflammatory disease, genes, preferably chosen from a group including nucleic acids, or portions thereof, corresponding to the sequences specified in GenBank Accession numbers X57352, S75725, D13665, X6769.8, M62402, D90226, L13698, U52101, U72649, L36034, M36035, and M38591, encoding the human genes 1–8U (SEQ ID NO:37), prostacyclin-stimulating factor (SEQ ID NO:38), osf-2 (SEQ ID NO:39), tissue specific mRNA (SEQ ID NO:40), insulin-like growth factor binding protein 6 (SEQ ID NO:41), OSF-1 (SEQ ID NO:42), gas-1 (SEQ ID NO:43), YMP (SEQ ID NO:44), BTG2 (SEQ ID NO:45), pre-B cell stimulating factor homolog (SDF1a) (SEQ ID NO:46), peripheral benzodiazepine receptor (SEQ ID NO:47), and cellular ligand of annexin II (p11) (SEQ ID NO:48), respectively.

XXXVIII. FUNCTIONAL STUDIES IN TISSUE CULTURES

1. Isolation of Neonatal Rat Ventricular Cardiomyocytes

Neonatal rat ventricular cardiomyocytes were isolated from one or two days old rat pups using the following reagents and isolation procedure:

Reagents

Dissociation buffer: CBFHH (Calcium- and Bicarbonate-Free Hanks with Hepes), pH 7.5

NaCl 137 mM; KCl 5.36 mM; $MgSO_4 \times 7H_2O$ 0.81 mM; Dextrose 5.55 mM; $KH_2PO_4 \times 7H_2O$ 0.34 mM; Hepes 20 mM;

Penicillin 50U/ml and Streptomycin 50 $\mu$g/m 0.1% trypsin/0.001% DNaseII or I in dissociation buffer.

DNaseII-Sigma (V, EC3.1, 1,22.1, bovine spleen, filter (0.2 $\mu$m).

trypsin-1:250 from Difco Lab, Cat#0152-13-1, Lot:89568JK Serum-free medium: DMEM21/COON'S F12+1 mg/ml DBA+IXP/S Culture medium: DMEM21/COON'S F12+10% FBS+1X P/S Isolation Roll pups in a small amount of 75% ethanol, decapitate and cut the hoax open, isolate the heart and cut the ventricle out at AV groove and quickly remove to a 50 ml tube containing 30 ml CBFHH+0.3 ml heparin (1000U/ml).

Transfer hearts to a 100-mm Petri dish, wash with CBFHH twice, trim ventricle and cut ventricle into 6–8 pieces.

Transfer heart tissues with wide tip 10-ml pipet to 50 ml tube. Add 10 ml CBFHH with 0.1% trypsin+0.001% DNaseII.

Rock for 10 minutes (do not over-digest the cells).

Gently pipette the tissue 10X.

Let the tissue settle down, then discard the supernatant (mainly cell debris).

Repeat the dissociating procedure and collect the supernatant in a 50 ml tube containing 7 ml of FBS at room temperature (supernatant contains isolated cells). The whole dissociation requires 12–16X.

Collect all supernatant and spin down the pellet at 1000 rpm for 5–6 minutes at room temperature.

Wash the pellet once with DMEM21/COON'S F12+10% FBS+0.001% DNase, make sure than the pellet is well suspended.

Strain cells with a cell strainer (70 $\mu$M), pellet cells again.

Add 40 ml culture medium to the pellet (isolated from about 20 ventricles).

Preplate cells in 100-mm dish—10 ml/dish, for 30–45 minutes at 37° C.

Collect supernatant from the preplated plate (non-myocytes have already attached to the plate but myocytes still in suspension).

Wash the plated with 10 ml culture medium. Bang the empty plate 10 times to detach myocyte that may stick to the plate. Repeat this procedure 4×.

Count cells and determine viability.

Seed cells into fibronectin coated plates at a density of 0.1 million cells/cm$^2$ in culture medium and return to the incubator overnight.

The next day, change to serum-free medium for 24 hours.

Perform experimental incubations.

Cryopreserved human peripheral blood mononuclear cells were purchased from Clonetics Corp. and maintained in short term culture in lymphocyte growth media. Experimental incubations utilized $2 \times 10^5$ cells/well/100 $\mu$l in a 96 well format.

Cryopreserved human cardiac fibroblasts obtained from a single adult male donor (60 years) were purchased from Clonetics Corp. and maintained in short term culture in fibroblast growth media. Experimental incubations utilized $4 \times 10^3$ cells/well/100 $\mu$l in a 96 well format.

2. Cell Incubations and Preparation of RNA

Cells were treated with known stimuli in quadruplet over a time course. The known stimuli reflect the therapeutic areas of inflammation and fibrosis. Cell Type Stimuli Cardiac myocytes CT-1, Ang II, TNF-$\alpha$, IL-1$\beta$, TGF-$\beta$ or recombinant protein Cardiac fibroblasts LPS, TNF-$\alpha$, IL-1$\beta$, IL-6, TGF-$\beta$ or recombinant protein Monocytes/macrophage LPS, TNF-$\alpha$, IL-1$\beta$, IL-6, TGF-$\beta$ or recombinant protein Following incubation, cell culture supernatants were removed and total RNA isolated according to the Qiagen RNeasy® 96 procedure. Total RNA was then analyzed by Quantitative Real Time Polymerase Chain Reaction using an ABI Prism 7700 Sequence Detection System.

Real-time Quantitative PCR uses a fluorogenic 5' nuclease assay performed with the TaqMan®/PCR Reagents designed and optimized for use with a 7700 Sequence Detector. Using this assay, one can detect and monitor target gene sequences. During PCR, a fluorogenic probe, consisting of an oligonucleotide with both a reporter and a quencher dye attached, anneals specifically between the forward and reverse primers. When the probe is cleaved by the 5' nuclease activity of the DNA polymerase, the reporter dye is separated from the quencher dye, and a sequence-specific signal is generated. With each cycle, additional reporter dye molecules are cleaved from their respective probes, and the fluorescence intensity is monitored during the PCR. The 7700 system monitors PCR at every cycle. This real-time detection generates quantitative data based on the PCR at early cycles when PCR fidelity is the highest.

We have designed multiple primer and probe combinations for use in this assay. The genes covered include those genes identified by high density differential display as described hereinbefore, thus allowing us to examine these gene expressions in tissue culture (and human samples) in cells that have been treated with a number of known pathological stimuli pertaining the inflammation or fibrosis. Additionally, a number of assays have been developed which reflect the dieases phenotype themselves. These assays are used to determine whether treatment of a cell type with a recombinantly expressed protein will induce a phenotype which relates to inflammation and/or fibrosis.

3. Results

Figure 10:
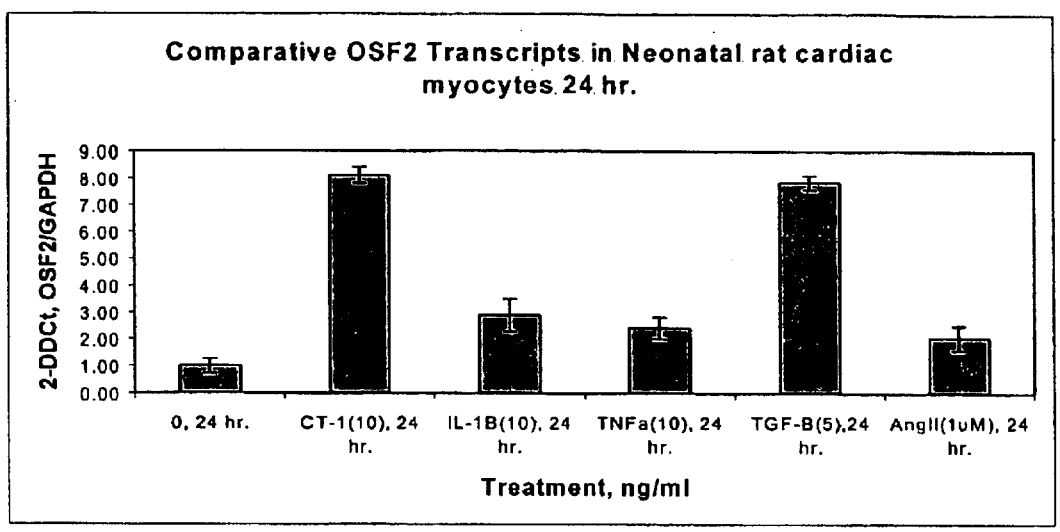
FIG. 10 shows OSF-2 gene expression is neonatal rat cardiac myocytes treated with various stimuli known to induce a hypertrophic response.

RNA isolated from neonatal rat cardiac myocytes treated with stimuli known to induce a hypertrophic response, was analyzed for the expression of OSF-2. The results are illustrated in FIG. 10. Following 24 hours of incubation cardiotrophin (CT-1) and TGF-β were shown to induce OSF-2 by eight-fold compared the untreated cells. Other hypertrophic stimuli (IL-1β, TNF-α and AngII) also induced OSF-2 by three-fold above control. This is the first demonstration of regulation of OSF-2 in a tissue culture setting in response to hypertrophic stimuli.

Figure 11:
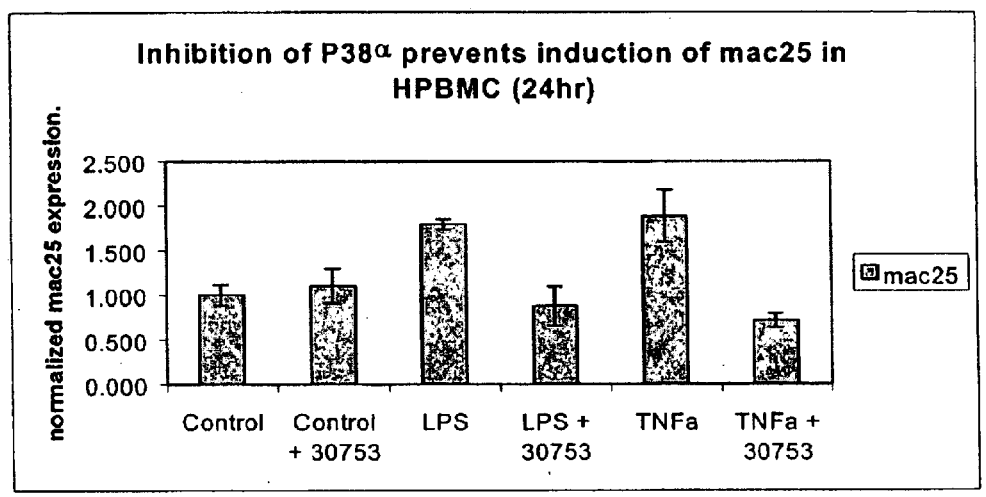
FIG. 11 shows that inhibition of p38α prevents induction of prostacyclin stimulating factor (mac25, IGFBP-7) in human peripheral blood mononuclear cells (HPBMNC).

In another experiment, we have found that treatment of human peripheral blood mononuclear cells with known inflammatory stimuli (LPS and TNF-α) causes an upregulation of prostacyclin stimulating factor (mac25, IGFBP7). As shown in FIG. 11, this gene induction was prevented by inclusion of a p38α inhibitor (NPC-30753) in the incubation media.

Figure 12:
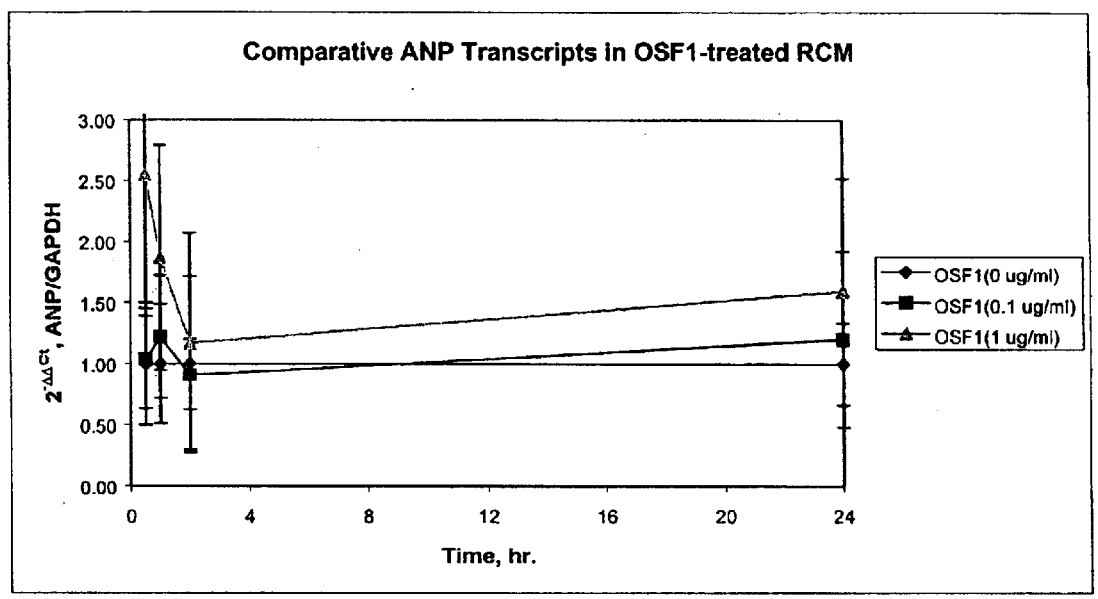
FIG. 12 shows the ANP and GAPDH transcript levels in rat neonatal cardiac myocytes treated with 0, 0.2 or 1 μg/ml doses of OSF-1.

Rat neonatal myocytes were treated with 0, 0.2 or 1 μg/ml OSF-1 for 0.5, 1, 2 and 24 hours. Total RNA was isolated and assayed for ANP and GAPDH transcript levels. The data (FIG. 12) shows a two-fold up-regulation of ANP by OSF-1 at 0.5 hours treated with 1 μg/ml OSF-1, indicating a possible hypertrophy promoting activity of OSF-1.

Human peripheral blood mononuclear cells were treated with 0, 0.1 or 5 μg/ml insulin-like growth factor binding protein 6 (IGFBP-6) for 1, 12, 24 and 48 hours. Total RNA was isolated and assayed for IL-1β, COX-2 and GAPDH transcript levels. The data shown in FIG. 13 show a 15-fold up-regulation of COX-2 and a six-fold up-regulation of IL-1β at 24–48 hours, indicating a proinflammatory activity of IGFBP-6.

Human peripheral blood mononuclear cells were treated with 0, 0.4, 0.8. 2 and 4 nM concentrations of IGFBP-6 for 24 hours. Cell culture supernatants were analyzed for IL-1β protein content by ELISA. The data set forth in FIG. 14 shows a dose-dependent induction of IL-1β protein by IGFBP-6, the EC50 of which is about 1 nM. This data finding reinforces the data shown in FIG. 14, since up-regulation of the IL-1β gene is translated into increased protein synthesis. Additionally, IGFBP-6 was shown to induce synthesis of TNF-α and IL-6. The upregulation of a proinflammatory cytokine, such as these, is a strong indicator of a pro-inflammatory activity of IGFBP-6.

The present invention is not to be limited in scope by the specific embodiments described which are intended as single illustrations of individual aspects of the invention and functionally equivalent methods and components are within the scope of the invention, in addition to those shown and described herein will become apparent to those skilled in the art from the foregoing description and accompanying drawings. Such modifications are intended to fall within the scope of the appended claims.

We claim:

1. An array comprising oligonucleotides of at least 30 nucleotides positioned at known locations on a substrate, said oligonucleotides being capable of hybridization under stringent hybridization conditions to reference DNA or RNA sequences encoding human proteins 1–8U (SEQ ID NO:37), tissue specific mRNA protein (SEQ ID NO:40), OSF-1 (SEQ ID NO:42), YMP (SEQ ID NO:44), BTG2 (SEQ ID NO:45), SDF1a (SEQ ID NO:46), peripheral benzodiazepine receptor (SEQ ID NO:47), and cellular ligand of annexin II (SEQ ID NO:48), said reference DNA or RNA sequences obtained from both a biological sample from a normal subject and a biological sample from a subject exhibiting cardiac, kidney, or inflammatory disease, wherein the stringent hybridization conditions are about 5° to 10° C. lower than a thermal melting point for the array of oligonucleotides to the reference DNA or RNA sequences.

2. The array of claim 1 wherein said subjects are human.

3. The array of claim 2 wherein said subject exhibiting a disease exhibits symptoms of a cardiac or kidney disease.

4. The array of claim 1, wherein said oligonucleotides are also capable of hybridization under stringent hybridization conditions to reference DNA or RNA sequences encoding human proteins selected from the group consisting of prostacyclin-stimulating factor (SEQ ID NO:38), OSF 2 (SEQ ID NO:39), and IGFBP-6 (SEQ ID NO:41).

5. A diagnostic kit for diagnosing cardiac, kidney, or inflammatory disease associated with a differentially expressed gene comprising an array of oligonucleotides of at least 30 nucleotides positioned at known locations on a substrate, said array of oligonucleotides complementary to reference DNA or RNA sequences encoding human proteins 1–8U (SEQ ID NO:37), tissue specific mRNA protein (SEQ ID NO:40), OSF-1 (SEQ ID NO:42), YMP (SEQ ID NO:44), BTG2 (SEQ ID NO:45), SDF1a (SEQ ID NO:46), peripheral benzodiazepine receptor (SEQ ID NO:47), and cellular ligand of annexin II (SEQ ID NO:48), said reference DNA or RNA sequences obtained from a biological sample from a normal subject and a biological sample from a subject exhibiting cardiac, kidney or inflammatory disease, wherein the stringent hybridization conditions are about 5° to 10° C. lower than a thermal melting point for the array of oligonucleotides to the reference DNA or RNA sequences.

6. The kit of claim 5, wherein said kit further comprises control oligonucleotide probes.

7. The kit of claim 5, wherein said kit further comprises PCR reagents.

8. The kit of claim 5 wherein said subjects are human subjects.

9. The kit of claim 5 wherein said biological sample from said normal subject and said biological sample from said subject exhibiting cardiac, kidney or inflammatory disease comprise blood.

10. The kit of claim 5 wherein said biological sample from said normal subject and said biological sample from said subject exhibiting cardiac, kidney or inflammatory disease comprise tissue.

11. The kit of claim 10 wherein said tissue comprises cardiac tissue.

12. The kit of claim 5, wherein said oligonucleotides are also capable of hybridization under stringent hybridization conditions to reference DNA or RNA sequences encoding human proteins selected from the group consisting of prostacyclin-stimulating factor (SEQ ID NO:38), OSF 2 (SEQ ID NO:39), and IGFBP-6 (SEQ ID NO:41).

* * * * *

SEQUENCE LISTING

```
<160> NUMBER OF SEQ ID NOS: 48

<210> SEQ ID NO 1
<211> LENGTH: 362
<212> TYPE: DNA
<213> ORGANISM: Rattus rattus

<400> SEQUENCE: 1
accatgaacc acacttctca agccttcgtg aacgctgcca ctgggggaca accccaaac      60 tacgaaagaa tcaaggaaga atatgaggtg tctgaactgg gggctcccca cggatcggct    120
tctgtcagaa ctaccgtgat caacatgccc agagaggtct ctgtgcctga ccatgtggtc    180
tggtccctgt tcaatacgct cttcatgaac ttctgctgcc tgggcttcat tgcctatgcc    240
tactctgtga agtctaggga tcggaagatg gtgggtgata tgactggagc ccaggcctac    300
gcatccactg ccaaatgcct gaacatcagc tccctggtcc tcagcatcct catggtcatt    360
at                                                                   362

<210> SEQ ID NO 2
<211> LENGTH: 362
<212> TYPE: DNA
<213> ORGANISM: Homo sapiens

<400> SEQUENCE: 2
accatgagtc acactgtcca aaccttcttc tctcctgtca acagtggcca gcccccaac      60 tatgagatgc tcaaggagga gcacgaggtg gctgtgctgg gggggcccca caaccctgct    120
```

-continued

```
cccccgacgt ccaccgtgat ccacatccgc agcgagacct ccgtgcccga ccatgtcgtc    180
tggtccctgt tcaacaccct tcatgaac ccctgctgcc tgggcttcat agcattcgcc     240
tactccgtga agtctaggga caggaagatg gttggcgacg tgaccggggc ccaggcctat    300
gcctccaccg ccaagtgcct gaacatctgg gccctgattc tgggcatcct catgaccatt    360
ct                                                                  362
```

<210> SEQ ID NO 3
<211> LENGTH: 275
<212> TYPE: DNA
<213> ORGANISM: Rattus rattus
<220> FEATURE:
<221> NAME/KEY: misc_feature
<222> LOCATION: (1)...(275)
<223> OTHER INFORMATION: n = a, t, c, or g

<400> SEQUENCE: 3

```
tacgagtgcc acgcgtccaa ttccaaggac aggcttcagc gtcggccaaa attacagtgg    60
ttgatgccat acacgaaata ccagtgaaaa aaggtgaagg tgctcagcta taaacctgcg   120
aatacattag cctctgtagc tgacgcgctc tcagacagct gacagctgta accccactcc   180
tgcctgacat attcctttga acctaacaca ctaacacttt attacagcca gctgattta   240
cagagaaatc naagataaca cataagacta tctac                              275
```

<210> SEQ ID NO 4
<211> LENGTH: 282
<212> TYPE: DNA
<213> ORGANISM: Homo sapiens

<400> SEQUENCE: 4

```
tatgagtgcc atgcatccaa ttcccaagga caggcttcag catcagcaaa aattacagtg    60
gttgatgcct tacatgaaat accagtgaaa aaggtgaag gtgccgagct ataaacctcc    120
agaatattat tagtctgcat ggttaaaagt agtcatggat aactacatta cctgttcttg   180
cctaataagt ttcttttaat ccaatccact aacactttag ttatattcac tggttttaca   240
cagagaaata caaaataaag atcacacatc aagactatct ac                      282
```

<210> SEQ ID NO 5
<211> LENGTH: 256
<212> TYPE: DNA
<213> ORGANISM: Rattus rattus

<400> SEQUENCE: 5

```
aagcaaaatc tatgtgaaag gagtcaatga agacgctttt ggtgaatgag ttgaagtcca    60
aagaatctga catcatgaca acaaacggcg tcattcacgt tgtggacaaa ctcctctatc   120
cagcagacat tccggttgga aatgatcagc tcttggaatt actgaacaaa ctgataaaat   180
acatccaaat taagttcgtt cgtggcagca ccttcaaaga aaatccccat gactgtctat   240
acaactaaaa ttataa                                                   256
```

<210> SEQ ID NO 6
<211> LENGTH: 254
<212> TYPE: DNA
<213> ORGANISM: Homo sapiens

<400> SEQUENCE: 6

```
aagcaaaatc tttctgaaag aagtaaatga tacacttctg gtgaatgaat tgaaatcaaa    60
agaatctgac atcatgacaa caaatggtgt aattcatgtt gtagataaac tcctctatcc   120
```

```
agcagacaca cctgttggaa atgatcaact gctggaaata cttaataaat taatcaaata    180
catccaaatt aagtttgttc gtggtagcac cttcaaagaa atccccgtga ctgtctataa    240
gccaattatt aaaa                                                      254

<210> SEQ ID NO 7
<211> LENGTH: 281
<212> TYPE: DNA
<213> ORGANISM: Rattus rattus
<220> FEATURE:
<221> NAME/KEY: misc_feature
<222> LOCATION: (1)...(281)
<223> OTHER INFORMATION: n = A,T,C or G

<400> SEQUENCE: 7
gatgagcttc ctgaccccac gatcctgctg ctggcgctgg tcgccgccac ccaggccgag     60
cccctgcact tcaaggactg cggttctaag gtgggagtta taaggaagt gaatgtgagc    120 ccatgcccta cccagccctg tcagctacac aaaggccagt cctacagtgt caacgtcacc    180
tttactagcg gcactcagtc ccagaacagc acggccttgg tccacggcat cttggcaggg    240
gtcccagtct acttccctat tcctgagcct gacngttgta a                        281

<210> SEQ ID NO 8
<211> LENGTH: 282
<212> TYPE: DNA
<213> ORGANISM: Homo sapiens

<400> SEQUENCE: 8
gatgcgtttc ctggcagcta cattcctgct cctggcgctc agcaccgctg cccaggccga     60
accggtgcag ttcaaggact gcggttctgt ggatggagtt ataaaggaag tgaatgtgag    120
cccatgcccc acccaaccct gccagctgag caaaggacag tcttacagcg tcaatgtcac    180
cttcaccagc aatattcagt ctaaaagcag caaggccgtg gtgcatggca tcctgatggg    240
cgtcccagtt ccctttccca ttcctgagcc tgatggttgt aa                       282

<210> SEQ ID NO 9
<211> LENGTH: 873
<212> TYPE: DNA
<213> ORGANISM: Rattus rattus

<400> SEQUENCE: 9
ccatgacctg ggacggactg cccacacagc cgctgttgat gctgttaatg ctgttgttcg     60
ctgcgggctc cgagtccgcc ttagcggggt gcccgggctg cgggccgggg gtgcaggagg    120
aagacgcggg gtcgcctgca gacggctgtg cagagaccgg aggctgtttc aggagagagg    180
ggcaaccgtg cggggtctac atccctaagt gcgccccagg actgcagtgc caaccccgag    240
agaacgaaga gacacctttg cggcgctgc tgatcggcca gggccgctgt caacgcgcca    300
gagggccgtc ggaagagact accaaggaga gcaaacccca tggaggcgcc tcccgcccac    360
gtgacagaga ccggcaaaag aatccacgga cctcggctgc ccctataagg cccagtcctg    420
ttcaagatgg tgaaatgggc ccctgccgca gacacttgga ttcagtactg cagcagctcc    480
agactgaggt cttcagaggc ggagcaaatg ggctctatgt gccaaactgt gacctcagag    540
gtttctaccg caagcagcag tgtcgttcct cgcagggaa tcgccgtggt ccctgctggt    600
gtgtggatcc gatgggccag cctttgccag tgtctccaga tggccaggga agctctcagt    660
gctctgccag gagcagcggg tgaaacctgg tgggagcctc caggaccctg gcaggagcat    720
```

| | |
|---|---:|
| ggggctgtca tttgagctct atgtgaagtg atgataactc tgtgccccga gatgagaccc | 780 |
| accttcaagc cctaccccat tgtccctgtc acccctgggc ctttacacag caagttagaa | 840 |
| agattgttgt tggcttgtgt actaataaag ctg | 873 |

<210> SEQ ID NO 10
<211> LENGTH: 887
<212> TYPE: DNA
<213> ORGANISM: Homo sapiens

<400> SEQUENCE: 10

| | |
|---|---:|
| ccatgacccc ccacaggctg ctgccaccgc tgctgctgct gctagctctg ctgctcgctg | 60 |
| ccagcccagg aggcgccttg gcgcggtgcc caggctgcgg gcaagggtg caggcgggtt | 120 |
| gtccaggggg ctgcgtggag gaggaggatg gggggtcgcc agccgagggc tgcgcggaag | 180 |
| ctgagggctg tctcaggagg gaggggcagg agtgcgggt ctacacccct aactgcgccc | 240 |
| caggactgca gtgccatccg cccaaggacg acgaggcgcc tttgcgggcg ctgctgctcg | 300 |
| gccgaggccg ctgccttccg gcccgcgcgc ctgctgttgc agaggagaat cctaaggaga | 360 |
| gtaaacccca agcaggcact gcccgcccac aggatgtgaa ccgcagagac caacagagga | 420 |
| atccaggcac ctctaccacg ccctcccagc ccaattctgc gggtgtccaa gacactgaga | 480 |
| tgggcccatg ccgtagacat ctggactcag tgctgcagca actccagact gaggtctacc | 540 |
| gaggggctca acactctac gtgcccaatt gtgaccatcg aggcttctac cggaagcggc | 600 |
| agtgccgctc ctcccagggg cagcgccgag gtccctgctg gtgtgtggat cggatgggca | 660 |
| agtccctgcc agggtctcca gatggcaatg gaagctcctc ctgccccact gggagtagcg | 720 |
| gctaaagctg ggggatagag gggctgcagg gccactggaa ggaacatgga gctgtcatca | 780 |
| ctcaacaaaa aaccgaggcc ctcaatccac cttcaggccc cgccccatgg gcccctcacc | 840 |
| gctggttgga aagagtgttg gtgttggctg gggtgtcaat aaagctg | 887 |

<210> SEQ ID NO 11
<211> LENGTH: 824
<212> TYPE: DNA
<213> ORGANISM: Rattus rattus

<400> SEQUENCE: 11

| | |
|---|---:|
| ggggagagcg cagccgccca ggcaggagca gcagccagcg atacctggag tccgttgcag | 60 |
| aaacctcgcc ctgcactttg caacaaaggc agcctgctgt cagcgaggac atctgccaag | 120 |
| ccaaaaaatg tcgtcccagc aataccagca gcaacgtcga aaatttgcag ctgccttcct | 180 |
| ggctttgatt ttcatcctgg cagccgtgga cactgctgag gccgggaaaa agagaaaacc | 240 |
| agaaaaaaag gtgaaaaaat ctgactgtgg agaatggcaa tggagtgtgt gcgtgcccac | 300 |
| cagcggggac tgtggtctag gcacccggga gggcactcgc actggtgccg agtgcaaaca | 360 |
| aaccatgaag actcagagat gtaagatccc ttgcaactgg aagaagcagt ttggagctga | 420 |
| gtgcaaatac cagttccagg cttggggaga atgtgacctc aataccgcct tgaagaccag | 480 |
| aactggcagt ctgaagagag ctctgcacaa tgccgactgt cagaaaactg tcaccatctc | 540 |
| caagccctgt ggcaaactca ccaagcccaa gcctcaagcg aatcaaagaa agaagaaaaa | 600 |
| ggaaggcaag aaacaggaga agatgctgga ttaaaagagg ccacctttg tggacaagga | 660 |
| aaaggacatc agcaagcagg atcagttaac tattacattt atacctactg taggcttttt | 720 |
| attcaacagt tatctgtagc ttaagtacat gataggcaaa aacaaagaga aaagaaatgt | 780 |
| ttttgtagta gcatttttt aatgtatacc atagtaccag tagg | 824 |

<210> SEQ ID NO 12
<211> LENGTH: 816
<212> TYPE: DNA
<213> ORGANISM: Homo sapiens

<400> SEQUENCE: 12

```
ggggagagca gcagcggccc aagcaggagc tgcagcgagc cgggtacctg gactcagcgg      60
tagcaacctc gccccttgca acaaaggcag actgagcgcc agagaggacg tttccaactc     120
aaaaatgcag gctcaacagt accagcagca gcgtcgaaaa tttgcagctg ccttcttggc     180
attcattttc atactggcag ctgtggatac tgctgaagca gggaagaaag agaaaccaga     240
aaaaaaagtg aagaagtctg actgtggaga atggcagtgg agtgtgtgtg tgcccaccag     300
tggagactgt gggctgggca cacgggaggg cactcggact ggagctgagt gcaagcaaac     360
catgaagacc cagagatgta agatcccctg caactgaaag aagcaatttg gcgcggagtg     420
caaataccag ttccaggcct ggggagaatg tgacctgaac acagccctga agaccagaac     480
tggaagtctg aagcgagccc tgcacaatgc cgaatgccag aagactgtca ccatctccaa     540
gccctgtggc aaactgacca agcccaaacc tcaagcagaa tctaagaaga gaaaaagga     600 aggcaagaaa caggagaaga tgctggatta aaagatgtca cctgtggaac ataaaaagga     660
catcagcaaa caggatcagt taactattgc atttatatgt accgtaggct ttgtattcaa     720
aaattatcta tagctaagta cacaataagc aaaaacaaaa agaaaagaaa attttttgtag   780 tagcgttttt taaatgtata ctatagtacc agtagg                               816
```

<210> SEQ ID NO 13
<211> LENGTH: 56
<212> TYPE: DNA
<213> ORGANISM: Rattus rattus
<220> FEATURE:
<221> NAME/KEY: misc_feature
<222> LOCATION: (1)...(56)
<223> OTHER INFORMATION: n = A,T,C or G

<400> SEQUENCE: 13

```
agccgggaac ggangagccn ccggccacac gaccttctgc aggcgccttg caccat          56
```

<210> SEQ ID NO 14
<211> LENGTH: 54
<212> TYPE: DNA
<213> ORGANISM: Homo sapiens

<400> SEQUENCE: 14

```
agccggcacg gggacagccg gccgcacaac ggatctgcag gcgcggagca aaat            54
```

<210> SEQ ID NO 15
<211> LENGTH: 134
<212> TYPE: DNA
<213> ORGANISM: Rattus rattus

<400> SEQUENCE: 15

```
gcagccatgt cactcctcct gttggtggtc tctgcccttc acatcctcat tcttgtcttg      60
cttttcgtgg ccactctgga caagtcctgg tggactctcc cagagaagga gtccctgaac    120
ctgtggtatg actg                                                      134
```

<210> SEQ ID NO 16
<211> LENGTH: 134
<212> TYPE: DNA

<213> ORGANISM: Homo sapiens

<400> SEQUENCE: 16

| | | | | | |
|---|---|---|---|---|---|
| gcagccatgt | cactcctctt | gctggtggtc | tcagcccttc | acatcctcat | tcttatactg | 60 |
| cttttcgtgg | ccactttgga | caagtcctgg | tggactctcc | ctgggaaaga | gtccctgaat | 120 |
| ctctggtacg | actg | | | | | 134 |

<210> SEQ ID NO 17
<211> LENGTH: 2456
<212> TYPE: DNA
<213> ORGANISM: Rattus rattus

<400> SEQUENCE: 17

| | | | | | |
|---|---|---|---|---|---|
| cggtatgagc | cacgggaaga | gaaccgacat | gctcccggag | atcgccgccg | ccgtaggttt | 60 |
| cctcaccagt | ctcctgagga | ctcggggctg | cgtgagcgag | cagagactca | aggttttcag | 120 |
| tagggcgctc | caggacgcac | tgaccgatca | ttacaaacac | cactggtttc | agaaaagcc | 180 |
| atccaagggc | tccggctatc | gctgtatccg | catcaaccac | aagatggacc | ccatcatcag | 240 |
| caaggtggcc | agccagatcg | gactcagcca | gccccagctg | caccagctcc | tgcccagcga | 300 |
| gctgaccctg | tgggtcgatc | cctacgaagt | gtcctaccgc | atcggggaag | atggatccat | 360 |
| ctgcgtgctg | tatgaggagg | cgccggtggc | cacctcctac | gggctcctca | cctgcaagaa | 420 |
| ccagatgatg | ctgggcagga | gcagtccatc | gaagaactac | gtgatgactg | tctccagcta | 480 |
| gagaggagcc | gccccgccct | ggcactctac | tgttctcatg | ctgccctgac | aacaggccac | 540 |
| cgtatacctc | aacctgggga | actgtatttt | taaagtgaag | agctatttat | acatgttatt | 600 |
| ttttttttta | agaaaagagg | aggaaaaaaa | ccaaaagttt | ttttttaaaa | aaacaaaaaa | 660 |
| gaaaaaacaa | ttcgttaacg | ggagctgctt | ggaagtggtc | tccccaggtg | cctttggaga | 720 |
| gaactgttct | tgattgagtc | tatgagccag | tgtttgccta | ggggagtggg | ttggggattg | 780 |
| gcctagccaa | ggtaaagggg | gattcttggc | tgatccccca | ggaggtggtg | gaagggagca | 840 |
| aggttagcaa | ctgtgaacga | gaggggtcag | ggtctgctct | gggttaccgt | tcccgctggg | 900 |
| atgcctgtat | tcctggtccc | tctcttactc | agggcattc | aagcctggtc | tcaaataata | 960 |
| ctacattgcc | taatcttctc | ttttgttttt | ctgctgagat | cctgggcaca | cggaaaggcc | 1020 |
| tctcctgtcc | cttccgtctg | agcagagttt | cttgaaactg | tgtctcgttt | ctgatcctac | 1080 |
| cctcggggtc | ctgaagaggt | ggtttcccgg | cctagaatct | atctaaacgt | ttttggaggg | 1140 |
| tgggctataa | ggcagatata | atggagggga | accgcacaaa | ccctttgctt | tgctctgtgc | 1200 |
| tgctttgtat | ggatggatgg | ttaataactt | agggatgatt | tgcaatggaa | ttttgggacc | 1260 |
| caaagagtat | ccaatggggg | tgggtgtttt | ggacctaagc | cctccttttg | ggaaccacgt | 1320 |
| gacagtctga | atgctgctac | cattattcct | ttgagaggtg | gctcaaagct | ccagggaact | 1380 |
| ccaggtcctt | tcttactgcc | ttctcttcaa | gagcaacctc | ccccatttct | tttccctctt | 1440 |
| tcctgcggtt | gggtcctgga | gggcccatt | tcctaggaca | agagttctca | atcactgtgc | 1500 |
| aatagtccca | ggaagctctg | gaactgggcc | tcccagcccc | tcctgattcc | tggtgggttt | 1560 |
| taggaccccg | ccttccccgt | tcttctgact | ggctggtggg | ccttgaggag | atctccctcg | 1620 |
| gccgcaggga | gggcacctgt | gcactgcagg | actacctggt | actcctgtgg | ggctgccacg | 1680 |
| gagagccaaa | cctaggcat | agctttgtct | cctcggtgct | cagagcacct | gcaggggag | 1740 |
| gttgcccccc | tcagtaaaaa | tccaaatttta | tttgtagatg | tgtgcaatat | ttactgttct | 1800 |
| gggttggaga | aaatcgggaa | acactgggaa | gaagtggcct | tccttcaggt | tcagtgacac | 1860 |

-continued

```
tgatgagggc ttctcagaag gcctcgagtc tctcaaacca aaggacagag ctagagccag    1920
ccagtcaccc ttagtgagga tccccttccc catgtctctc cactgccgtg gcatcccatg    1980
tcctggattt ctcaattcct cagtttctac tcaaaggtgc tacttaccaa acactctgcc    2040
cgtcccgctc tccccagctt cgcacagccg tcccaggtgg cttcgtctct cctgctttaa    2100
agttaacttt gggcccacag acccgagagc tgtgggttga agcaaagctg tgaatcgctc    2160
cagatggtcc ctgtgttctg tccacacaca ggtccccgcc tttttagaag cagcctcctg    2220
gtctcatgct taaatctgtt cctcactgcc cgtgttcact ttagaaatgg cagaaccaca    2280
gagctggact gttgagcagg cctgtctctc tcattaaata gaaataagta agtttgtaag    2340
ctattccgac agaagagaca aaggttactg attgtacaat agcgctttta tatggaagac    2400
tgtacagctt tatggacaaa tgtaaaactt ttttgttttt aataaaaatg tagcag        2456
```

<210> SEQ ID NO 18
<211> LENGTH: 2638
<212> TYPE: DNA
<213> ORGANISM: Homo sapiens

<400> SEQUENCE: 18

```
cgacatgagc cacgggaagg gaaccgacat gctcccggag atcgccgccg ccgtgggctt      60
cctctccagc ctcctgagga cccggggctg cgtgagcgag cagaggctta aggtcttcag    120
cggggcgctc caggaggcac tcacagagca ctacaaacac cactggtttc cgaaaaagcc    180
gtccaagggc tccggctacc gctgcattcg catcaaccac aagatggacc ccatcatcag    240
cagggtggcc agccagatcg gactcagcca gccccagctg caccagctgc tgcccagcga    300
gctgaccctg tgggtggacc cctatgaggt gtcctaccgc attggggagg acggctccat    360
ctgcgtcttg tacgaggagg ccccactggc cgcctcctgt gggctcctca cctgcaagaa    420
ccaagtgctg ctgggccgga gcagcccctc caagaactac gtgatggcag tctccagcta    480
ggcccttccg cccccgccct gggcgccgcc gtgctcatgc tgccgtgaca acaggccacc    540
acatacctca acctggggaa ctgtatttt aaatgaagag ctatttatat atattatttt      600
tttttaagaa aggaggaaaa gaaaccaaaa gttttttta agaaaaaaaa tccttcaagg    660
gagctgcttg gaagtggcct ccccaggtgc ctttggagag aactgttgcg tgcttgagtc    720
tgtgagccag tgtctgccta taggaggggg agctgttagg gggtagacct agccaaggag    780
aagtgggaga cgtttggcta gcaccccagg aagatgtgag agggagcaag caaggttagc    840
aactgtgaac agagaggtcg ggatttgccc tgggggagga agagaggcca agttcagagc    900
tctctgtctc ccccagccag acacctgcat ccctggctcc tctattactc agggggcattc    960 atgcctggac ttaaacaata ctatgttatc ttttctttta ttttctaat gaggtcctgg    1020 gcagagagtg aaaaggcctc tcctgattcc tactgtccta agctgctttt cttgaaatca    1080
tgacttgttt ctaattctac cctcaggggc ctgtagatgt tgctttccag ccaggaatct    1140
aaagctttgg gttttctgag gggggagga gggaactgga ggttattggg gttaggatgg    1200
aagggaactc tgcacaaaac ctttgctttg ctagtgctgc tttgtgtgta tgtgtggcaa    1260
ataatttggg ggtgatttgc aatgaaattt tgggacccaa agagtatcca ctgggatgt    1320 tttttggcca aaactcttcc ttttggaacc acatgaaagt cttgatgctg ctgccatgat    1380
ccctttgaga ggtggctcaa aagctacagg gaactccagg tcctttatta ctgccttctt    1440
ttcaaaagca caactctcct ctaaccctcc cctcccccctt cccttctggt cgggtcatag    1500
```

-continued

```
agctaccgta ttttctagga caagagttct cagtcactgt gcaatatgcc ccctgggtcc      1560
caggagggtc tggaggaaaa ctggctatca gaacctcctg atgccctggt gggcttaggg      1620
aaccatctct cctgctctcc ttgggatgat ggctggctag tcagccttgc atgtattcct      1680
tggctgaatg ggagagtgcc ccatgttctg caagactact tggtattctt gtagggccga      1740
cactaaataa aagccaaacc ttgggcactg tttttctcc ctggtgctca gagcacctgt       1800
gggaaaggtt gctgtctgtc tcagtacaat ccaaatttgt cgtagacttg tgcaatatat      1860
actgttgtgg gttggagaaa agtggaaagc tacactggga agaaactccc ttccttcaat      1920
ttctcagtga cattgatgag gggtcctcaa aagacctcga gtttcccaaa ccgaatcacc      1980
ttaagaagga cagggctagg gcatttggcc aggatggcca ccctcctgct gttgcccctt      2040
agtgaggaat cttcacccca cttcctctac ccccaggttc tcctcccac agccagtccc       2100 ctttcctgga tttctaaact gctcaatttt gactcaaagg tgctatttac caaacactct      2160
ccctacccat tcctgccagc tctgcctcct tttcaactct ccacattttg tattgccttc      2220
ccagacctgc ttccagtctt tattgcttta agttcactt tgggcccaca gacccaagag       2280
ctaattttct ggtttgtggg ttgaaacaaa gctgtgaatc actgcaggct gtgttcttgc      2340
atcttgtctg caaacaggtc cctgcctttt tagaagcagc tcatggtct catgcttaat       2400 cttgtctctc ttctcttctt tatgatgttc actttaaaaa caacaaaacc cctgagctgg      2460
actgttgagc aggcctgtct ctcctattaa gtaaaaataa atagtagtag tatgtttgta      2520
agctattctg acagaaaaga caaaggttac taattgtatg atagtgtttt tatatggaag      2580
aatgtacagc ttatggacaa atgtacacct ttttgttact ttaataaaaa tgtagtag        2638
```

<210> SEQ ID NO 19
<211> LENGTH: 236
<212> TYPE: DNA
<213> ORGANISM: Rattus rattus
<220> FEATURE:
<221> NAME/KEY: misc_feature
<222> LOCATION: (1)...(236)
<223> OTHER INFORMATION: n = A,T,C or G

<400> SEQUENCE: 19

```
cctccggcgc gccctcccgc ccacgccatg gacgccaagg tcgtcgccgt gctggccctg       60
gtgctggccg cgctctgcat cagtgacggt aagccagtca gcctgagcta cagatgcccc      120
tgccgattct tcgagagcca gtcgccagan ccaacgtca aacatctgaa atcctcaac        180 actccaaact gtgcccttca gattgttgca aagctgaaaa gcaacaacag acaagt          236
```

<210> SEQ ID NO 20
<211> LENGTH: 236
<212> TYPE: DNA
<213> ORGANISM: Homo sapiens

<400> SEQUENCE: 20

```
ccgcccgccc gcccgcccgc ccgcgccatg aacgccaagg tcgtggtcgt gctggtcctc       60
gtgctgaccg cgctctgcct cagcgacggg aagcccgtca gcctgagcta cagatgccca      120
tgccgattct tcgaaagcca tgttgccaga gccaacgtca agcatctcaa aattctcaac      180
actccaaact gtgcccttca gattgtagcc cggctgaaga caacaacag acaagt           236
```

<210> SEQ ID NO 21
<211> LENGTH: 777
<212> TYPE: DNA
<213> ORGANISM: Rattus rattus

<400> SEQUENCE: 21

| gatctttcca | gaacagcagt | tgcaatcact | atgtctcaat | cctgggtacc | cgccgtgggc | 60 |
| ctcactctgg | tgcccagcct | gggggcttc | atgggagcct | actttgtgcg | tggtgagggc | 120 |
| ctccgctggt | atgctagctt | gcagaaaccc | tcctggcatc | cgcctcgctg | gacactcgct | 180 |
| cccatctggg | gcacactgta | ttcggccatg | ggtatggcc | cctacataat | ctggaaagag | 240 |
| ctggagggtt | tcacagagga | ggctatggtt | cccttgggtc | tctacactgg | tcagctggct | 300 |
| ctgaactggg | catggccccc | catcttcttt | ggtgcccggc | agatgggctg | ggctttggtg | 360 |
| gacctcatgc | ttgtcagtgg | ggtggcaacc | gccactaccc | tggcttggca | ccgagtgagc | 420 |
| ccaccggctg | cccgcttgct | gtatccttac | ctggcctggc | tggcctttgc | caccatgctc | 480 |
| aactactatg | tatggcgtga | taactctggt | cggcgagggg | gctcccggct | cacagagtga | 540 |
| ggacacctag | ccatcaggaa | tgcagccctg | ccagccaggc | atcatgggtt | gaggtcatcc | 600 |
| tgctttcatg | accattgggc | ctgctggtct | acctggtctt | agtccaggaa | gccaccaggt | 660 |
| aggtcaaggt | ggtcagtgct | aagtcccatg | cggggacagt | tgtacctgct | tttctgcact | 720 |
| gctgcaggcg | tgccctagga | gcatggggcc | tttaaagcta | aataaagtct | ttaactt | 777 |

<210> SEQ ID NO 22
<211> LENGTH: 785
<212> TYPE: DNA
<213> ORGANISM: Homo sapiens
<220> FEATURE:
<221> NAME/KEY: misc_feature
<222> LOCATION: (1)...(785)
<223> OTHER INFORMATION: n = A,T,C or G

<400> SEQUENCE: 22

| gagctcccct | gaacagcagc | tgcagcagcc | atggccccgc | cctgggtgcc | cgccatgggc | 60 |
| ttcacgctgg | cgcccagcct | ggggtgcttc | gtgggctccc | gctttgtcca | cggcgagggt | 120 |
| ctccgctggt | acgccggcct | gcagaagccc | tcgtggcacc | cgccccactg | ggtgctgggc | 180 |
| cctgtctggg | gcacgctcta | tcagccatg | gggtacggct | cctacctggt | ctggaaagag | 240 |
| ctggagggct | tcacagagaa | ggctgtggtt | cccctgggcc | tctacactgg | gcagctggcc | 300 |
| ctgaactggg | catggccccc | catcttcttt | ggtgcccgac | aaatgggctg | ggccttggtg | 360 |
| gatctcctgc | tggtcagtgg | ggcggcggcn | gccactaccg | tggcctggta | ccaggtgagc | 420 |
| ccgctggccg | cccgcctgct | ctaccccctac | ctggcctggc | tggccttcgc | gaccacactc | 480 |
| aactactgcg | tatggcggga | caaccatggc | tggcatgggg | gacggcggct | gccagagtga | 540 |
| gtgcccggcc | caccagggac | tgcagctgca | ccagcaggtg | ccatcacgct | tgtgatgtgg | 600 |
| tggccgtcac | gctttcatga | ccactgggcc | tgctagtctg | tcagggcctt | ggcccagggg | 660 |
| tcagcagagc | ttcagaggtt | gccccacctg | agccccacc | cggagcagt | gtcctgtgct | 720 |
| ttctgcatgc | ttagagcatg | ttcttggaac | atggaatttt | ataagctgaa | taaagttttt | 780 |
| gactt | | | | | | 785 |

<210> SEQ ID NO 23
<211> LENGTH: 570
<212> TYPE: DNA
<213> ORGANISM: Rattus rattus

<400> SEQUENCE: 23

| gactgcagcg | cctcagggcc | caggtttcaa | cagattcttc | aaaatgccat | cccaaatgga | 60 |

| | |
|---|---|
| gcatgccatg gaaaccatga tgcttacatt tcacaggttt gcaggggaaa aaaactactt | 120 |
| gacaaaggag gacctgagag tgctcatgga aagggagttc cctgggtttt tggaaaatca | 180 |
| aaaggaccct ctggctgtgg acaaaataat gaaagacctg gaccagtgcc gagatggaaa | 240 |
| agtgggcttc cagagctttc tatcactagt ggcgggctc atcattgcat gcaatgacta | 300 |
| ttttgtagta cacatgaagc agaagaagta ggccaactgg agccctggta cccacacctt | 360 |
| gatgcgtcct ctcccatggg gtcaactgag gaatctgccc cactgcttcc tgtgagcaga | 420 |
| tcaggaccct taggaaatgt gcaaataaca tccaactcca attcgacaag cagagaaaga | 480 |
| aaagttaatc caatgacaga ggagctttcg agttttatat tgtttgcatc cggttgccct | 540 |
| caataaagaa agtcttttt tttaagttcc | 570 |

<210> SEQ ID NO 24
<211> LENGTH: 579
<212> TYPE: DNA
<213> ORGANISM: Homo sapiens

<400> SEQUENCE: 24

| | |
|---|---|
| gtccgccgcg cctcgccaag gcttcaacgg accacaccaa aatgccatct caaatggaac | 60 |
| acgccatgga aaccatgatg tttacatttc acaaattcgc tggggataaa ggctacttaa | 120 |
| caaaggagga cctgagagta tcatggaaa aggagttccc tggattttg gaaaatcaaa | 180 |
| aagaccctct ggctgtggac aaaataatga aggacctgga ccagtgtaga gatggcaaag | 240 |
| tgggcttcca gagcttcttt tccctaattg cgggcctcac cattgcatgc aatgactatt | 300 |
| ttgtagtaca catgaagcag aagggaaaga gtaggcaga aatgagcagt tcgctcctcc | 360 |
| ctgataagag ttgtccaaag ggtcgcttaa ggaatctgcc ccacagcttc ccccatagaa | 420 |
| ggatttcatg agcagatcag gacacttagc aaatgtaaaa ataaaatcta actctcattt | 480 |
| gacaagcaga gaaagaaaag ttaaatacca gataagcttt tgatttttgt attgtttgca | 540 |
| tccccttgcc ctcaataaat aaagttcttt tttagttcc | 579 |

<210> SEQ ID NO 25
<211> LENGTH: 808
<212> TYPE: DNA
<213> ORGANISM: Homo sapiens
<220> FEATURE:
<221> NAME/KEY: CDS
<222> LOCATION: (238)...(639)

<400> SEQUENCE: 25

| | |
|---|---|
| tgctcccttg ggctctagag aggaggcccc tcttagccct cagcccctcc ttcctctcta | 60 |
| tcttaaagta atttgatcct caggaatttg ttccgccctc atctggcccg gccaaatccc | 120 |
| gatttgacaa atgccaggaa aaggaaactg ttgagaaacc gaaactactg gggaaaggga | 180 |
| gggctcactg agtaaccatc ccagtaaccc gaccgccgct ggtcttcgct ggacaccatg | 240 |
| agtcacactg tccaaacctt cttctctcct gtcaacagtg gccagccccc caactatgag | 300 |
| atgctcaagg aggagcacga ggtggctgtg ctggggggc cccacaaccc tgctcccccg | 360 |
| acgtccaccg tgatccacat ccgcagcgag acctccgtgc cgaccatgt cgtctggtcc | 420 |
| ctgttcaaca ccctcttcat gaaccctgc tgcctgggct tcatagcatt cgcctactcc | 480 |
| gtgaagtcta gggacaggaa gatggttggc gacgtgaccg ggcccaggc ctatgcctcc | 540 |
| accgccaagt gcctgaacat ctgggccctg attctgggca tcctcatgac cattctgctc | 600 |
| atcgtcatcc cagtgctgat cttccaggcc tatggataga tcaggaggca tcactgaggc | 660 |

-continued

```
caggagctct gccatgacc tgtatcccac gtactccaac ttccattcct cgccctgccc      720
ccggagccga gtcctgtatc agccctttat cctcacacgc ttttctacaa tggcattcaa      780
taaagtgcac gtgtttctgg tgctgctg                                         808
```

<210> SEQ ID NO 26
<211> LENGTH: 1124
<212> TYPE: DNA
<213> ORGANISM: Homo sapiens
<220> FEATURE:
<221> NAME/KEY: CDS
<222> LOCATION: (23)...(871)

<400> SEQUENCE: 26

```
gccgctgcca ccgcaccccg ccatggagcg gccgtcgctg cgcgccctgc tcctcggcgc      60
cgctgggctg ctgctcctgc tcctgcccct ctcctcttcc tcctcttcgg acacctgcgg     120
cccctgcgag ccggcctcct gcccgcccct gccccgctg gctgcctgc tgggcgagac       180 ccgcgacgcg tgcggctgct gccctatgtg cgcccgcggc gagggcgagc cgtgcggggg     240
tggcggcgcc ggcaggggt actgcgcgcc gggcatggag tgcgtgaaga ccgcaagag      300 gcggaagggt aaagccgggg cagcagccgg cggtccgggt gtaagcggcg tgtgcgtgtg     360
caagagccgc tacccggtgt gcggcagcga cggcaccacc tacccgagcg gctgccagct     420
gcgcgccgcc agccagaggg ccgagagccg cgggggagaag gccatcaccc aggtcagcaa     480
gggcaccctg cagcaaggtc cttccatagt gacgcccccc aaggacatct ggaatgtcac     540
tggtgcccag gtgtacttga gctgtgaggt catcggaatc ccgacacctg tcctcatctg     600
gaacaaggta aaaaggggtc actatggagt tcaaaggaca gaactcctgc ctggtgaccg     660
ggacaacctg gccattcaga cccggggtgg cccagaaaag catgaagtaa ctggctgggt     720
gctggtatct cctctaagta aggaagatgc tggagaatat gagtgccatg catccaattc     780
ccaaggacag gcttcagcat cagcaaaaat tacagtggtt gatgccttac atgaaatacc     840
agtgaaaaaa ggtgaaggtg ccgagctata aacctccaga atattattag tctgcatggt     900
taaaagtagt catggataac tacattacct gttcttgcct aataagtttc ttttaatcca     960
atccactaac actttagtta tattcactgg ttttacacag agaaatacaa aataaagatc    1020
acacatcaag actatctaca aaatttatt atatatttac agaagaaaag catgcatatc     1080
attaaacaaa taaatactt tttatcacaa aaaaaaaaa aaaa                       1124
```

<210> SEQ ID NO 27
<211> LENGTH: 3077
<212> TYPE: DNA
<213> ORGANISM: Homo sapiens
<220> FEATURE:
<221> NAME/KEY: CDS
<222> LOCATION: (28)...(2367)

<400> SEQUENCE: 27

```
aacagaactg caacggagag actcaagatg attcccttt tacccatgtt ttctctacta      60
ttgctgctta ttgttaaccc tataaacgcc aacaatcatt atgacaagat cttggctcat     120
agtcgtatca ggggtcggga ccaaggccca aatgtctgtg cccttcaaca gattttgggc     180 accaaaaga aatacttcag cacttgtaag aactggtata aaagtccat ctgtggacag      240 aaaacgactg ttttatatga atgttgccct ggttatatga aatggaagg aatgaaaggc     300 tgcccagcag ttttgcccat tgaccatgtt tatggcactc tgggcatcgt gggagccacc     360
acaacgcagc gctattctga cgcctcaaaa ctgagggagg agatcgaggg aaagggatcc     420
```

```
ttcacttact ttgcaccgag taatgaggct tgggacaact tggattctga tatccgtaga      480
ggtttggaga gcaacgtgaa tgttgaatta ctgaatgctt tacatagtca catgattaat      540
aagagaatgt tgaccaagga cttaaaaaat ggcatgatta ttccttcaat gtataacaat      600
ttggggcttt tcattaacca ttatcctaat ggggttgtca ctgttaattg tgctcgaatc      660
atccatggga accagattgc aacaaatggt gttgtccatg tcattgaccg tgtgcttaca      720
caaattggta cctcaattca agacttcatt gaagcagaag atgacctttc atcttttaga      780
gcagctgcca tcacatcgga catattggag gcccttggaa gagacggtca cttcacactc      840
tttgctccca ccaatgaggc ttttgagaaa cttccacgag gtgtcctaga aaggttcatg      900
ggagacaaag tggcttccga agctcttatg aagtaccaca tcttaaatac tctccagtgt      960
tctgagtcta ttatgggagg agcagtcttt gagacgctgg aaggaaatac aattgagata     1020
ggatgtgacg gtgacagtat aacagtaaat ggaatcaaaa tggtgaacaa aaaggatatt     1080
gtgacaaata atggtgtgat ccatttgatt gatcaggtcc taattcctga ttctgccaaa     1140
caagttattg agctggctgg aaaacagcaa accaccttca cggatcttgt ggcccaatta     1200
ggcttggcat ctgctctgag gccagatgga gaatacactt tgctggcacc tgtgaataat     1260
gcattttctg atgatactct cagcatggtt cagcgcctcc ttaaattaat tctgcagaat     1320
cacatattga agtaaaagt tggccttaat gagctttaca cgggcaaat actggaaacc       1380 atcggaggca acagctcag agtcttcgta tatcgtacag ctgtctgcat tgaaaattca      1440
tgcatggaga aagggagtaa gcaagggaga aacggtgcga ttcacatatt ccgcgagatc     1500
atcaagccag cagagaaatc cctccatgaa aagttaaaac aagataagcg ctttagcacc     1560
ttcctcagcc tacttgaagc tgcagacttg aaagagctcc tgacacaacc tggagactgg     1620
acattatttg tgccaaccaa tgatgctttt aagggaatga ctagtgaaga aaaagaaatt     1680
ctgatacggg acaaaaatgc tcttcaaaac atcattcttt atcacctgac accaggagtt     1740
ttcattggaa aaggatttga acctggtgtt actaacattt taaagaccac acaaggaagc     1800
aaaatctttc tgaaagaagt aaatgataca cttctggtga atgaattgaa atcaaaagaa     1860
tctgacatca tgacaacaaa tggtgtaatt catgttgtag ataaactcct ctatccagca     1920
gacacacctg ttggaaatga tcaactgctg gaaatactta ataaattaat caaatacatc     1980
caaattaagt ttgttcgtgg tagcacccttc aaagaaatcc ccgtgactgt ctataagcca    2040
attattaaaa aatacaccaa aatcattgat ggagtgcctg tggaaataac tgaaaaagag     2100
acacgagaag aacgaatcat tacaggtcct gaaataaaat acactaggat ttctactgga    2160
ggtggagaaa cagaagaaac tctgaagaaa ttgttacaag aagaggtcac caaggtcacc    2220
aaattcattg aaggtggtga tggtcattta tttgaagatg aagaaattaa aagactgctt     2280
cagggagaca cacccgtgag gaagttgcaa gccaacaaaa aagttcaagg ttctagaaga     2340
cgattaaggg aaggtcgttc tcagtgaaaa tccaaaaacc agaaaaaaat gtttatacaa     2400
ccctaagtca ataacctgac cttagaaaat tgtgagagcc aagttgactt caggaactga    2460
aacatcagca caaagaagca atcatcaaat aattctgaac acaaatttaa tattttttt     2520 tctgaatgag aaacatgagg gaattgtgg agttagcctc ctgtggagtt agcctcctgt    2580
ggtaaaggaa ttgaagaaaa tataacacct tacacccttt ttcatcttga cattaaaagt     2640
tctggctaac tttggaatcc attagagaaa aatccttgtc accagattca ttacaattca     2700
aatcgaagag ttgtgaactg ttatcccatt gaaaagaccg agccttgtat gtatgttatg    2760
```

-continued

| | |
|---|---|
| gatacataaa atgcacgcaa gccattatct ctccatggga agctaagtta taaaaatagg | 2820 |
| tgcttggtgt acaaaacttt ttatatcaaa aggctttgca catttctata tgagtgggtt | 2880 |
| tactggtaaa ttatgttatt ttttacaact aattttgtac tctcagaatg tttgtcatat | 2940 |
| gcttcttgca atgcatattt tttaatctca aacgtttcaa taaaaccatt tttcagatat | 3000 |
| aaagagaatt acttcaaatt gagtaattca gaaaaactca agatttaagt taaaaagtgg | 3060 |
| tttggacttg ggaacag | 3077 |

<210> SEQ ID NO 28
<211> LENGTH: 808
<212> TYPE: DNA
<213> ORGANISM: Homo sapiens
<220> FEATURE:
<221> NAME/KEY: CDS
<222> LOCATION: (11)...(466)

<400> SEQUENCE: 28

| | |
|---|---|
| cggattccgg atgcgtttcc tggcagctac attcctgctc ctggcgctca gcaccgctgc | 60 |
| ccaggccgaa ccggtgcagt tcaaggactg cggttctgtg gatggagtta taaggaagt | 120 |
| gaatgtgagc ccatgcccca cccaaccctg ccagctgagc aaaggacagt cttacagcgt | 180 |
| caatgtcacc ttcaccagca atattcagtc taaaagcagc aaggccgtgg tgcatggcat | 240 |
| cctgatgggc gtcccagttc cctttcccat tcctgagcct gatggttgta agagtggaat | 300 |
| taactgccct atccaaaaag acaagaccta tagctacctg aataaactac cagtgaaaag | 360 |
| cgaatatccc tctataaaac tggtggtgga gtggcaactt caggatgaca aaaaccaaag | 420 |
| tctcttctgc tgggaaatcc cagtacagat cgtttctcat ctctaagtgc ctcattgagt | 480 |
| tcggtgcatc tggccaatga gtctgctgag actcttgaca gcacctccag ctctgctgct | 540 |
| tcaacaacag tgacttgctc tccaatggta tccagtgatt cgttgaagag gaggtgctct | 600 |
| gtagcagaaa ctgagctccg ggtggctggt tctcagtggt tgtctcatgt ctctttttct | 660 |
| gtcttaggtg gtttcattaa atgcagcact tggttagcag atgtttaatt tttttttta | 720 |
| acaacattaa cttgtggcct ctttctacac ctggaaattt actcttgaat aaataaaaac | 780 |
| tcgtttgtct tgtaaaaaaa aaaaaaaa | 808 |

<210> SEQ ID NO 29
<211> LENGTH: 952
<212> TYPE: DNA
<213> ORGANISM: Homo sapiens
<220> FEATURE:
<221> NAME/KEY: CDS
<222> LOCATION: (54)...(776)

<400> SEQUENCE: 29

| | |
|---|---|
| gcagctgcgc tgcgactgct ctggaaggag aggacggggc acaaaccctg accatgaccc | 60 |
| cccacaggct gctgccaccg ctgctgctgc tgctagctct gctgctcgct gccagcccag | 120 |
| gaggcgccctt ggcgcggtgc ccaggctgcg ggcaaggggt gcaggcgggt tgtccagggg | 180 |
| gctgcgtgga ggaggaggat gggggggtcgc cagccgaggg ctgcgcggaa gctgagggct | 240 |
| gtctcaggag ggaggggcag gagtgcgggg tctacacccc taactgcgcc ccaggactgc | 300 |
| agtgccatcc gcccaaggac gacgaggcgc ctttgcgggc gctgctgctc ggccgaggcc | 360 |
| gctgccttcc ggcccgcgcg cctgctgttg cagaggagaa tcctaaggag agtaaacccc | 420 |
| aagcaggcac tgcccgccca caggatgtga accgcagaga ccaacagagg aatccaggca | 480 |
| cctctaccac gccctcccag cccaattctg cgggtgtcca agacactgag atgggcccat | 540 |

```
gccgtagaca tctggactca gtgctgcagc aactccagac tgaggtctac cgaggggctc      600
aaacactcta cgtgcccaat tgtgaccatc gaggcttcta ccggaagcgg cagtgccgct      660
cctcccaggg gcagcgccga ggtccctgct ggtgtgtgga tcggatgggc aagtccctgc      720
cagggtctcc agatggcaat ggaagctcct cctgccccac tgggagtagc ggctaaagct      780
gggggataga ggggctgcag ggccactgga aggaacatgg agctgtcatc actcaacaaa      840
aaaccgaggc cctcaatcca ccttcaggcc ccgccccatg gcccctcac cgctggttgg       900 aaagagtgtt ggtgttggct ggggtgtcaa taaagctgtg cttggggtca aa              952
```

<210> SEQ ID NO 30
<211> LENGTH: 816
<212> TYPE: DNA
<213> ORGANISM: Homo sapiens
<220> FEATURE:
<221> NAME/KEY: CDS
<222> LOCATION: (125)...(631)

<400> SEQUENCE: 30

```
ggggagagca gcagcggccc aagcaggagc tgcagcgagc cgggtacctg gactcagcgg       60
tagcaacctc gccccttgca acaaaggcag actgagcgcc agagaggacg tttccaactc      120
aaaaatgcag gctcaacagt accagcagca gcgtcgaaaa tttgcagctg ccttcttggc      180
attcattttc atactggcag ctgtggatac tgctgaagca gggaagaaag agaaaccaga      240
aaaaaaagtg aagaagtctg actgtggaga atggcagtgg agtgtgtgtg tgcccaccag      300
tggagactgt gggctgggca cacgggaggg cactcggact ggagctgagt gcaagcaaac      360
catgaagacc cagagatgta agatcccctg caactggaag aagcaatttg gcgcggagtg      420
caaataccag ttccaggcct ggggagaatg tgacctgaac acagccctga agaccagaac      480
tggaagtctg aagcgagccc tgcacaatgc cgaatgccag aagactgtca ccatctccaa      540
gccctgtggc aaactgacca agcccaaacc tcaagcagaa tctaagaaga agaaaaagga      600
aggcaagaaa caggagaaga tgctggatta aaagatgtca cctgtggaac ataaaaagga      660
catcagcaaa caggatcagt taactattgc atttatatgt accgtaggct ttgtattcaa      720
aaattatcta tagctaagta cacaataagc aaaaacaaaa agaaaagaaa attttttgtag    780 tagcgttttt taaatgtata ctatagtacc agtagg                               816
```

<210> SEQ ID NO 31
<211> LENGTH: 2828
<212> TYPE: DNA
<213> ORGANISM: Homo sapiens
<220> FEATURE:
<221> NAME/KEY: CDS
<222> LOCATION: (411)...(1448)

<400> SEQUENCE: 31

```
agcagccggc acgggacag ccggccgcac aacggatctg caggcgcgga gcaaaatgca        60
cccgccgcgc cgcgcggtcc tgcagccccg ccacggcccc gcggcccgca ccccccgggg      120
gcgacagtga gcctctcccg ccaccaccgg gggccgagcg gagggctctc gggtgggaga      180
gcgggaccag atctcgacag ctgttcattt ccaggaagcc accgcagcca gagcgaaagg      240
ggaccttctg ccaccagcgg ggcatcagcc agcggcgcgc atggatttat gaagacactc      300
atgcaagaag tggcaggac ttggacaaac ttttccaccg gctccgcgtc cgccgctccc       360
cgcgcctcgt ctcctttccc ctcctctccc ggcggccgcc gctgccgcg atggtggccg       420
```

-continued

| | | | |
|---|---|---|---|
| cgctgctggg | cggcggcggc | gaggcccgcg | gggggacagt gccggcgcc tggctgtgcc | 480 |
| tgatggcgct | gctgcagctg | ctgggctcgg | cgccgcgggg atcggggctg gcgcacggcc | 540 |
| gccgcctcat | ctgctggcag | gcgctgctgc | agtgccaggg ggagccggag tgcagctacg | 600 |
| cctacaacca | gtacgccgag | gcgtgcgcgc | cggtgctggc gcagcacggc ggggcgacg | 660 |
| cgcccggggc | cgccgccgcc | gctttccgg | cctcggcccc ctctttctcg tcgcgctggc | 720 |
| gctgcccgag | tcactgcatc | tcggccctca | ttcagctcaa ccacacgcgc cgcgggcccg | 780 |
| ccctggagga | ctgtgactgc | gcgcaggacg | agaactgcaa gtccaccaag cgcgccattg | 840 |
| agccgtgcct | gccccggacg | agcggcggcg | gcgcgggcgg ccccggcgcg ggcggggtca | 900 |
| tgggctgcac | cgaggcccgg | cggcgctgcg | accgcgacag ccgctgcaac ctggcgctga | 960 |
| gccgctacct | gacctactgc | ggcaaagtct | tcaacgggct gcgctgcacg gacgaatgcc | 1020 |
| gcaccgtcat | tgaggacatg | ctggctatgc | ccaaggtggc gctgctcaac gactgcgtgt | 1080 |
| gcgacggcct | cgagcggccc | atctgcgagt | cggtcaagga gaacatggcc cgcctgtgct | 1140 |
| tcggcgccga | gctgggcaac | ggccccggca | gcagcggctc ggacggggc ctggacgact | 1200 |
| actacgatga | ggactacgat | gacgagcagc | gcaccggggg cgcgggtggt gagcagccgc | 1260 |
| tggacgacga | cgacggcgtc | ccgcacccac | cgcgcccggg cagcggcgct gctgcatcgg | 1320 |
| gcggccgcgg | ggacctgccc | tatgggcctg | ggcgcaggag cagcggcggc ggcggccgct | 1380 |
| tggcgcccccg | gggcgcctgg | accccactcg | cctccatctt gctgctgctg cttgggccgc | 1440 |
| tcttttagcc | ctcgcgcccc | ccgccgttgg | ctgcgggaga gcccgcgtcc cactcccgtg | 1500 |
| ctcgcctcga | ccccgcgccg | ggcacctgtg | gcttgggaca gatagaaggg atggttgggg | 1560 |
| atacttccca | aaacttttc | caagtcaact | tggtgtagcc ggttccccgg ccacgactct | 1620 |
| gggcacttcc | cctgaagctc | ctctccggag | cttgacttct tggacctcct ccccgcccc | 1680 |
| aattccaagc | tccagaaact | cccaactcgt | ctgccgtcca gaaagctagc tgcagtgttc | 1740 |
| aggacgtccg | ggaggaagca | agcatgtggg | ggacagaaca gtagtcctgg actcgaaagg | 1800 |
| gaaggtgctg | accagtgggg | ccttagcaat | ttgaagggtt gggaaggagg aattatattt | 1860 |
| gcaaagggc | tgtctattag | catatttcct | ttgaggggc aaaaaaagt gccagtatcg | 1920 |
| actttacag | attgtggcca | gtgaggatat | tataatccta tgtaaacaga aaagtcccac | 1980 |
| ttaccgattc | attctttcac | tgtttgtatc | tgcgcccaga attctcagtg acgtgggggt | 2040 |
| gagggtgggt | ggcgattgcc | ttagagggaa | ccctaaatt ggttttggat aagtttgagc | 2100 |
| ccttgacctt | aatttcattg | ctaccactct | gatctcttag cacatttctt aggattaagg | 2160 |
| gtccaaaat | gctgatctaa | ggggttgcca | tggtgttgaa caatgcaact ttttattaa | 2220 |
| aaaagctctg | cactgccatg | tatgaaagtc | tctttatgat gtttgttttt ttgtcatttt | 2280 |
| tgttctttac | atcaagaaat | tttatgttta | aatatgcgga gaatgtatat tgcctctgct | 2340 |
| cctatcaggg | ttgctaaacc | ctggtacatc | gtatataaaa tgtattaaaa ctggggtttg | 2400 |
| ttaccagttg | ctgtactttg | tatatagaat | ttttataaat tgtatgcttc agaaataatt | 2460 |
| tatttttaaa | aagaaattaa | aagttttaaa | ctcacatcca tattacacct ttccccctg | 2520 |
| aaatgtatag | aatccatttg | tcatcaggaa | tcaaaaccca cagtccattg tgaagtgtgc | 2580 |
| tatatttaga | acagtcttaa | aatgtacagt | gtattttata gaattgaagt taacattctt | 2640 |
| attttcaaga | gaatttatgg | acgttgtaga | aatgtacaaa tgcatttcca aactgcctta | 2700 |
| aacgttgtat | ttttatagac | atgttttttt | aaaaatccta agttttaaa taactatgga | 2760 |
| tttgtgtatt | tttttggtt | atttgtttta | ttaaaacatg tacatcagta aagagtttta | 2820 |

```
aacaatga                                                                2828
```

```
<210> SEQ ID NO 32
<211> LENGTH: 600
<212> TYPE: DNA
<213> ORGANISM: Homo sapiens
<220> FEATURE:
<221> NAME/KEY: CDS
<222> LOCATION: (50)...(541)

<400> SEQUENCE: 32
ccgactccag ctctgacttt tttcgcggct ctcggcttcc actgcagcca tgtcactcct      60
cttgctggtg gtctcagccc ttcacatcct cattcttata ctgcttttcg tggccacttt     120
ggacaagtcc tggtggactc tccctgggaa agagtccctg aatctctggt acgactgcac     180
gtggaacaac gacaccaaaa catgggcctg cagtaatgtc agcgagaatg ctggctgaa      240
ggcggtgcag gtcctcatgg tgctctccct cattctctgc tgtctctcct tcatcctgtt     300
catgttccag ctctacacca tgcgacgagg aggtctcttc tatgccaccg gcctctgcca     360
gctttgcacc agcgtggcgg tgtttactgg cgccttgatc tatgccattc acgccgagga     420
gatcctggag aagcacccgc gaggggcag cttcggatac tgcttcgccc tggcctgggt      480
ggccttcccc ctcgccctgg tcagcggcat catctacatc cacctacgga agcgggagtg     540
agcgccgcgc ctcgctcggc tgccccgcc ccttccgggc cccctgccg cgcgtcctcc       600
```

```
<210> SEQ ID NO 33
<211> LENGTH: 2717
<212> TYPE: DNA
<213> ORGANISM: Homo sapiens
<220> FEATURE:
<221> NAME/KEY: CDS
<222> LOCATION: (72)...(548)

<400> SEQUENCE: 33
cagggtaacg ctgtcttgtg gacccgcact tcccacccga gacctctcac tgagcccgag      60
ccgcgcgcga catgagccac gggaagggaa ccgacatgct cccggagatc gccgccgccg     120
tgggcttcct ctccagcctc ctgaggaccc ggggctgcgt gagcgagcag aggcttaagg     180
tcttcagcgg ggcgctccag gaggcactca cagagcacta caacaccac tggtttcccg      240
aaaagccgtc caagggctcc ggctaccgct gcattcgcat caaccacaag atggaccccca    300
tcatcagcag ggtggccagc cagatcggac tcagccagcc ccagctgcac cagctgctgc     360
ccagcgagct gaccctgtgg gtggaccccct atgaggtgtc ctaccgcatt ggggaggacg     420
gctccatctg cgtcttgtac gaggaggccc cactggccgc ctcctgtggg ctcctcacct     480
gcaagaacca agtgctgctg gccggagca gcccctccaa gaactacgtg atggcagtct      540
ccagctaggc ccttccgccc cgccctgggc gccgccgtg ctcatgctgc cgtgacaaca      600
ggccaccaca tacctcaacc tggggaactg tattttaaa tgaagagcta tttatatata      660
ttattttttt ttaagaaagg aggaaaagaa accaaaagtt ttttttaaga aaaaaatcc      720
ttcaagggag ctgcttggaa gtggcctccc caggtgcctt tggagagaac tgttgcgtgc     780
ttgagtctgt gagccagtgt ctgcctatag gaggggagc tgttagggg tagacctagc      840
caaggagaag tgggagacgt ttggctagca ccccaggaag atgtgagagg gagcaagcaa     900
ggttagcaac tgtgaacaga gaggtcggga tttgccctgg gggaggaaga gaggccaagt    960
tcagagctct ctgtctcccc cagccagaca cctgcatccc tggctcctct attactcagg    1020
```

-continued

| | |
|---|---|
| ggcattcatg cctggactta acaatacta tgttatcttt tcttttattt ttctaatgag | 1080 |
| gtcctgggca gagagtgaaa aggcctctcc tgattcctac tgtcctaagc tgcttttctt | 1140 |
| gaaatcatga cttgtttcta attctaccct caggggcctg tagatgttgc tttccagcca | 1200 |
| ggaatctaaa gctttgggtt ttctgagggg gggaggaggg aactggaggt tattggggtt | 1260 |
| aggatggaag ggaactctgc acaaaacctt tgctttgcta gtgctgcttt gtgtgtatgt | 1320 |
| gtggcaaata atttgggggt gatttgcaat gaaattttgg gacccaaaga gtatccactg | 1380 |
| gggatgtttt ttggccaaaa ctcttccttt tggaaccaca tgaaagtctt gatgctgctg | 1440 |
| ccatgatccc tttgagaggt ggctcaaaag ctacagggaa ctccaggtcc tttattactg | 1500 |
| ccttcttttc aaaagcacaa ctctcctcta accctcccct ccccttccc ttctggtcgg | 1560 |
| gtcatagagc taccgtattt tctaggacaa gagttctcag tcactgtgca atatgccccc | 1620 |
| tgggtcccag gagggtctgg aggaaaactg gctatcagaa cctcctgatg ccctggtggg | 1680 |
| cttagggaac catctctcct gctctccttg ggatgatggc tggctagtca gccttgcatg | 1740 |
| tattccttgg ctgaatggga gagtgcccca tgttctgcaa gactacttgg tattcttgta | 1800 |
| gggccgacac taaataaaag ccaaaccttg ggcactgttt tttctccctg gtgctcagag | 1860 |
| cacctgtggg aaaggttgct gtctgtctca gtacaatcca aatttgtcgt agacttgtgc | 1920 |
| aatatatact gttgtgggtt ggagaaaagt ggaaagctac actgggaaga aactcccttc | 1980 |
| cttcaatttc tcagtgacat tgatgagggg tcctcaaaag acctcgagtt tcccaaaccg | 2040 |
| aatcaccta agaaggacag ggctagggca tttggccagg atggccaccc tctgctgtt | 2100 |
| gccccttagt gaggaatctt caccccactt cctctacccc caggttctcc tcccacagc | 2160 |
| cagtcccctt tcctggattt ctaaactgct caattttgac tcaaaggtgc tatttaccaa | 2220 |
| acactctccc tacccattcc tgccagctct gcctcctttt caactctcca cattttgtat | 2280 |
| tgccttccca gacctgcttc cagtctttat tgctttaaag ttcactttgg gcccacagac | 2340 |
| ccaagagcta atttctggt tgtgggttg aaacaaagct gtgaatcact gcaggctgtg | 2400 |
| ttcttgcatc ttgtctgcaa acaggtccct gccttttag aagcagcctc atggtctcat | 2460 |
| gcttaatctt gtctctcttc tcttctttat gatgttcact ttaaaaacaa caaaacccct | 2520 |
| gagctggact gttgagcagg cctgtctctc ctattaagta aaaataaata gtagtagtat | 2580 |
| gtttgtaagc tattctgaca gaaaagacaa aggttactaa ttgtatgata gtgtttttat | 2640 |
| atggaagaat gtacagctta tggacaaatg tacacctttt tgttacttta ataaaaatgt | 2700 |
| agtaggataa aaaaaaa | 2717 |

<210> SEQ ID NO 34
<211> LENGTH: 1847
<212> TYPE: DNA
<213> ORGANISM: Homo sapiens
<220> FEATURE:
<221> NAME/KEY: CDS
<222> LOCATION: (80)...(349)

<400> SEQUENCE: 34

| | |
|---|---|
| tctccgtcag ccgcattgcc cgctcggcgt ccggcccccg accgtgctc gtccgcccgc | 60 |
| ccgcccgccc gccgcgcca tgaacgccaa ggtcgtggtc gtgctggtcc tcgtgctgac | 120 |
| cgcgctctgc ctcagcgacg ggaagcccgt cagcctgagc tacagatgcc catgccgatt | 180 |
| cttcgaaagc catgttgcca gagccaacgt caagcatctc aaaattctca acactccaaa | 240 |
| ctgtgccctt cagattgtag cccggctgaa gaacaacaac agacaagtgt gcattgaccc | 300 |

-continued

```
gaagctaaag tggattcagg agtacctgga gaaagcttta aacaagtaag cacaacagcc        360
aaaaaggact ttccgctaga cccactcgag gaaaactaaa accttgtgag agatgaaagg        420
gcaaagacgt gggggagggg gccttaacca tgaggaccag gtgtgtgtgt ggggtgggca        480
cattgatctg ggatcgggcc tgaggtttgc agcatttaga ccctgcattt atagcatacg        540
gtatgatatt gcagcttata ttcatccatg ccctgtacct gtgcacgttg gaacttttat        600 tactgggggtt tttctaagaa agaaattgta ttatcaacag cattttcaag cagttagttc       660
cttcatgatc atcacaatca tcatcattct cattctcatt ttttaaatca acgagtactt       720
caagatctga atttggcttg tttggagcat ctcctctgct cccctgggga gtctgggcac       780
agtcaggtgg tggcttaaca gggagctgga aaaagtgtcc tttcttcaga cactgaggct       840
cccgcagcag cgcccctccc aagaggaagg cctctgtggc actcagatac cgactggggc       900 tgggggcgccg ccactgcctt cacctcctct ttcaaacctc agtgattggc tctgtgggct      960
ccatgtagaa gccactatta ctgggactgt ctcagagacc cctctcccag ctattcctac       1020
tctctccccg actccgagag catgcttaat cttgcttctg cttctcattt ctgtagcctg       1080
atcagcgccg caccagccgg gaagagggtg attgctgggg ctcgtgccct gcatccctct       1140
cctcccaggg cctgccccac agctcgggcc ctctgtgaga tccgtctttg gcctcctcca       1200
gaatggagct ggccctctcc tggggatgtg taatggtccc cctgcttacc cgcaaaagac       1260
aagtctttac agaatcaaat gcaattttaa atctgagagc tcgcttgagt gactgggttt       1320
gtgattgcct ctgaagccta tgtatgccat ggaggcacta acaaactctg aggtttccga       1380
aatcagaagc gaaaaaatca gtgaataaac catcatcttg ccactacccc ctcctgaagc       1440
cacagcaggg gttcaggttc caatcagaac tgttggcaag gtgacatttc catgcataga       1500
tgcgatccac agaaggtcct ggtggtattt gtaactttt gcaaggcatt tttttatata        1560
tatttttgtg cacatttttt tttacgattc tttagaaaac aaatgtattt caaaatatat       1620
ttatagtcga acaagtcata tatatgaatg agagccatat gaatgtcagt agtttatact       1680
tctctattat ctcaaactac tggcaatttg taaagaaata tatatgatat ataaatgtga       1740
ttgcagcttt tcaatgttag ccacagtgta ttttttcact tgtactaaaa ttgtatcaaa       1800
tgtgacatta tatgcactag caataaaatg ctaattgttt catggta                    1847
```

<210> SEQ ID NO 35
<211> LENGTH: 821
<212> TYPE: DNA
<213> ORGANISM: Homo sapiens
<220> FEATURE:
<221> NAME/KEY: CDS
<222> LOCATION: (62)...(571)
<221> NAME/KEY: misc_feature
<222> LOCATION: (1)...(821)
<223> OTHER INFORMATION: n = A,T,C or G

<400> SEQUENCE: 35

```
agtgcccttc ccggagcgtg ccctcgccgc tgagctcccc tgaacagcag ctgcagcagc        60
catggccccg ccctgggtgc ccgccatggg cttcacgctg gcgcccagcc tggggtgctt       120
cgtgggctcc cgctttgtcc acggcgaggg tctccgctgg tacgccggcc tgcagaagcc       180
ctcgtggcac ccgcccccact gggtgctggg ccctgtctgg ggcacgctct actcagccat      240
ggggtacggc tcctacctgg tctggaaaga gctgggaggc ttcacagaga aggctgtggt      300 tccctgggc ctctacactg gcagctggcc cctgaactgg gcatggcccc ccatcttctt       360
tggtgcccga caaatgggct gggccttggt ggatctcctg ctggtcagtg gggcggcggc      420
```

```
ngccactacc gtggcctggt accaggtgag cccgctggcc gcccgcctgc tctacccta      480 cctggcctgg ctggccttcg cgaccacact caactactgc gtatggcggg acaaccatgg     540
ctggcatggg ggacggcggc tgccagagtg agtgcccggc ccaccaggga ctgcagctgc     600
accagcaggt gccatcacgc ttgtgatgtg gtggccgtca cgctttcatg accactgggc     660
ctgctagtct gtcagggcct tggcccaggg gtcagcagag cttcagaggt tgccccacct     720
gagcccccac ccgggagcag tgtcctgtgc tttctgcatg cttagagcat gttcttggaa     780
catggaattt tataagctga ataaagtttt tgacttcctt t                         821
```

<210> SEQ ID NO 36
<211> LENGTH: 649
<212> TYPE: DNA
<213> ORGANISM: Homo sapiens
<220> FEATURE:
<221> NAME/KEY: CDS
<222> LOCATION: (113)...(405)

<400> SEQUENCE: 36

```
agaatacact cacaagccac tccgctgctc gcctctccgc cccgcgtcca gctcgcccag      60
ctcgcccagc gtccgccgcg cctcgccaag gcttcaacgg accacaccaa aatgccatct     120
caaatggaac acgccatgga aaccatgatg tttacatttc acaaattcgc tggggataaa     180
ggctacttaa caaaggagga cctgagagta ctcatggaaa aggagttccc tggattttttg    240 gaaaatcaaa aagaccctct ggctgtgac aaaataatga aggacctgga ccagtgtaga     300
gatggcaaag tgggcttcca gagcttcttt tccctaattg cgggcctcac cattgcatgc     360
aatgactatt ttgtagtaca catgaagcag aagggaaaga agtaggcaga aatgagcagt     420
tcgctcctcc ctgataagag ttgtccaaag ggtcgcttaa ggaatctgcc ccacagcttc     480
ccccatagaa ggatttcatg agcagatcag gacacttagc aaatgtaaaa ataaaatcta    540
actctcattt gacaagcaga gaaagaaaag ttaaatacca gataagcttt tgattttgt      600 attgtttgca tccccttgcc ctcaataaat aaagttcttt tttagttcc                 649
```

<210> SEQ ID NO 37
<211> LENGTH: 133
<212> TYPE: PRT
<213> ORGANISM: Homo sapiens
<220> FEATURE:
<221> NAME/KEY: MUTAGEN
<222> LOCATION: (238)...(639)

<400> SEQUENCE: 37

```
Met Ser His Thr Val Gln Thr Phe Phe Ser Pro Val Asn Ser Gly Gln
 1               5                  10                  15

Pro Pro Asn Tyr Glu Met Leu Lys Glu Glu His Glu Val Ala Val Leu
                20                  25                  30

Gly Gly Pro His Asn Pro Ala Pro Pro Thr Ser Thr Val Ile His Ile
            35                  40                  45

Arg Ser Glu Thr Ser Val Pro Asp His Val Val Trp Ser Leu Phe Asn
        50                  55                  60

Thr Leu Phe Met Asn Pro Cys Cys Leu Gly Phe Ile Ala Phe Ala Tyr
    65                  70                  75                  80

Ser Val Lys Ser Arg Asp Arg Lys Met Val Gly Asp Val Thr Gly Ala
                85                  90                  95

Gln Ala Tyr Ala Ser Thr Ala Lys Cys Leu Asn Ile Trp Ala Leu Ile
                100                 105                 110
```

-continued

```
Leu Gly Ile Leu Met Thr Ile Leu Ile Val Ile Pro Val Leu Ile
            115                 120                 125

Phe Gln Ala Tyr Gly
        130

<210> SEQ ID NO 38
<211> LENGTH: 282
<212> TYPE: PRT
<213> ORGANISM: Homo sapiens

<400> SEQUENCE: 38

Met Glu Arg Pro Ser Leu Arg Ala Leu Leu Leu Gly Ala Ala Gly Leu
  1               5                  10                  15

Leu Leu Leu Leu Pro Leu Ser Ser Ser Ser Ser Asp Thr Cys
                20                  25                  30

Gly Pro Cys Glu Pro Ala Ser Cys Pro Pro Leu Pro Pro Leu Gly Cys
            35                  40                  45

Leu Leu Gly Glu Thr Arg Asp Ala Cys Gly Cys Cys Pro Met Cys Ala
        50                  55                  60

Arg Gly Glu Gly Glu Pro Cys Gly Gly Gly Ala Gly Arg Gly Tyr
 65                  70                  75                  80

Cys Ala Pro Gly Met Glu Cys Val Lys Ser Arg Lys Arg Arg Lys Gly
                85                  90                  95

Lys Ala Gly Ala Ala Ala Gly Gly Pro Gly Val Ser Gly Val Cys Val
            100                 105                 110

Cys Lys Ser Arg Tyr Pro Val Cys Gly Ser Asp Gly Thr Thr Tyr Pro
        115                 120                 125

Ser Gly Cys Gln Leu Arg Ala Ala Ser Gln Arg Ala Glu Ser Arg Gly
    130                 135                 140

Glu Lys Ala Ile Thr Gln Val Ser Lys Gly Thr Cys Glu Gln Gly Pro
145                 150                 155                 160

Ser Ile Val Thr Pro Pro Lys Asp Ile Trp Asn Val Thr Gly Ala Gln
                165                 170                 175

Val Tyr Leu Ser Cys Glu Val Ile Gly Ile Pro Thr Pro Val Leu Ile
            180                 185                 190

Trp Asn Lys Val Lys Arg Gly His Tyr Gly Val Gln Arg Thr Glu Leu
        195                 200                 205

Leu Pro Gly Asp Arg Asp Asn Leu Ala Ile Gln Thr Arg Gly Gly Pro
    210                 215                 220

Glu Lys His Glu Val Thr Gly Trp Val Leu Val Ser Pro Leu Ser Lys
225                 230                 235                 240

Glu Asp Ala Gly Glu Tyr Glu Cys His Ala Ser Asn Ser Gln Gly Gln
                245                 250                 255

Ala Ser Ala Ser Ala Lys Ile Thr Val Val Asp Ala Leu His Glu Ile
            260                 265                 270

Pro Val Lys Lys Gly Glu Gly Ala Glu Leu
        275                 280

<210> SEQ ID NO 39
<211> LENGTH: 779
<212> TYPE: PRT
<213> ORGANISM: Homo sapiens

<400> SEQUENCE: 39

Met Ile Pro Phe Leu Pro Met Phe Ser Leu Leu Leu Leu Leu Ile Val
  1               5                  10                  15
```

-continued

```
Asn Pro Ile Asn Ala Asn Asn His Tyr Asp Lys Ile Leu Ala His Ser
             20                  25                  30

Arg Ile Arg Gly Arg Asp Gln Gly Pro Asn Val Cys Ala Leu Gln Gln
             35                  40                  45

Ile Leu Gly Thr Lys Lys Lys Tyr Phe Ser Thr Cys Lys Asn Trp Tyr
             50                  55                  60

Lys Lys Ser Ile Cys Gly Gln Lys Thr Thr Val Leu Tyr Glu Cys Cys
65                       70                  75                  80

Pro Gly Tyr Met Arg Met Glu Gly Met Lys Gly Cys Pro Ala Val Leu
                     85                  90                  95

Pro Ile Asp His Val Tyr Gly Thr Leu Gly Ile Val Gly Ala Thr Thr
                 100                 105                 110

Thr Gln Arg Tyr Ser Asp Ala Ser Lys Leu Arg Glu Glu Ile Glu Gly
             115                 120                 125

Lys Gly Ser Phe Thr Tyr Phe Ala Pro Ser Asn Glu Ala Trp Asp Asn
             130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                 165                 170                 175

Lys Asp Leu Lys Asn Gly Met Ile Ile Pro Ser Met Tyr Asn Asn Leu
             180                 185                 190

Gly Leu Phe Ile Asn His Tyr Pro Asn Gly Val Val Thr Val Asn Cys
             195                 200                 205

Ala Arg Ile Ile His Gly Asn Gln Ile Ala Thr Asn Gly Val Val His
             210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ile Thr
                     245                 250                 255

Ser Asp Ile Leu Glu Ala Leu Gly Arg Asp Gly His Phe Thr Leu Phe
                 260                 265                 270

Ala Pro Thr Asn Glu Ala Phe Glu Lys Leu Pro Arg Gly Val Leu Glu
             275                 280                 285

Arg Phe Met Gly Asp Lys Val Ala Ser Glu Ala Leu Met Lys Tyr His
             290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                 325                 330                 335

Ser Ile Thr Val Asn Gly Ile Lys Met Val Asn Lys Asp Ile Val
             340                 345                 350

Thr Asn Asn Gly Val Ile His Leu Ile Asp Gln Val Leu Ile Pro Asp
             355                 360                 365

Ser Ala Lys Gln Val Ile Glu Leu Ala Gly Lys Gln Gln Thr Thr Phe
             370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                 405                 410                 415

Thr Leu Ser Met Val Gln Arg Leu Leu Lys Leu Ile Leu Gln Asn His
                 420                 425                 430
```

```
Ile Leu Lys Val Lys Val Gly Leu Asn Glu Leu Tyr Asn Gly Gln Ile
            435                 440                 445

Leu Glu Thr Ile Gly Gly Lys Gln Leu Arg Val Phe Val Tyr Arg Thr
            450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
            485                 490                 495

Lys Ser Leu His Glu Lys Leu Lys Gln Asp Lys Arg Phe Ser Thr Phe
            500                 505                 510

Leu Ser Leu Leu Glu Ala Ala Asp Leu Lys Glu Leu Leu Thr Gln Pro
            515                 520                 525

Gly Asp Trp Thr Leu Phe Val Pro Thr Asn Asp Ala Phe Lys Gly Met
            530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
            565                 570                 575

Phe Glu Pro Gly Val Thr Asn Ile Leu Lys Thr Thr Gln Gly Ser Lys
            580                 585                 590

Ile Phe Leu Lys Glu Val Asn Asp Thr Leu Leu Val Asn Glu Leu Lys
            595                 600                 605

Ser Lys Glu Ser Asp Ile Met Thr Thr Asn Gly Val Ile His Val Val
610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
            645                 650                 655

Arg Gly Ser Thr Phe Lys Glu Ile Pro Val Thr Val Tyr Lys Pro Ile
            660                 665                 670

Ile Lys Lys Tyr Thr Lys Ile Ile Asp Gly Val Pro Val Glu Ile Thr
            675                 680                 685

Glu Lys Glu Thr Arg Glu Glu Arg Ile Ile Thr Gly Pro Glu Ile Lys
690                 695                 700

Tyr Thr Arg Ile Ser Thr Gly Gly Gly Glu Thr Glu Thr Leu Lys
705                 710                 715                 720

Lys Leu Leu Gln Glu Glu Val Thr Lys Val Thr Lys Phe Ile Glu Gly
            725                 730                 735

Gly Asp Gly His Leu Phe Glu Asp Glu Ile Lys Arg Leu Leu Gln
            740                 745                 750

Gly Asp Thr Pro Val Arg Lys Leu Gln Ala Asn Lys Lys Val Gln Gly
            755                 760                 765

Ser Arg Arg Arg Leu Arg Glu Gly Arg Ser Gln
770                 775
```

<210> SEQ ID NO 40
<211> LENGTH: 151
<212> TYPE: PRT
<213> ORGANISM: Homo sapiens

<400> SEQUENCE: 40

```
Met Arg Phe Leu Ala Ala Thr Phe Leu Leu Ala Leu Ser Thr Ala
1               5                   10                  15

Ala Gln Ala Glu Pro Val Gln Phe Lys Asp Cys Gly Ser Val Asp Gly
            20                  25                  30
```

```
Val Ile Lys Glu Val Asn Val Ser Pro Cys Pro Thr Gln Pro Cys Gln
         35                  40                  45

Leu Ser Lys Gly Gln Ser Tyr Ser Val Asn Val Thr Phe Thr Ser Asn
     50                  55                  60

Ile Gln Ser Lys Ser Ser Lys Ala Val Val His Gly Ile Leu Met Gly
 65              70                  75                  80

Val Pro Val Pro Phe Pro Ile Pro Glu Pro Asp Gly Cys Lys Ser Gly
                 85                  90                  95

Ile Asn Cys Pro Ile Gln Lys Asp Lys Thr Tyr Ser Tyr Leu Asn Lys
                100                 105                 110

Leu Pro Val Lys Ser Glu Tyr Pro Ser Ile Lys Leu Val Val Glu Trp
            115                 120                 125

Gln Leu Gln Asp Asp Lys Asn Gln Ser Leu Phe Cys Trp Glu Ile Pro
        130                 135                 140

Val Gln Ile Val Ser His Leu
145                 150

<210> SEQ ID NO 41
<211> LENGTH: 240
<212> TYPE: PRT
<213> ORGANISM: Homo sapiens

<400> SEQUENCE: 41

Met Thr Pro His Arg Leu Leu Pro Pro Leu Leu Leu Leu Leu Ala Leu
  1               5                  10                  15

Leu Leu Ala Ala Ser Pro Gly Gly Ala Leu Ala Arg Cys Pro Gly Cys
             20                  25                  30

Gly Gln Gly Val Gln Ala Gly Cys Pro Gly Gly Cys Val Glu Glu Glu
         35                  40                  45

Asp Gly Gly Ser Pro Ala Glu Gly Cys Ala Glu Ala Glu Gly Cys Leu
     50                  55                  60

Arg Arg Glu Gly Gln Glu Cys Gly Val Tyr Thr Pro Asn Cys Ala Pro
 65              70                  75                  80

Gly Leu Gln Cys His Pro Pro Lys Asp Asp Glu Ala Pro Leu Arg Ala
                 85                  90                  95

Leu Leu Leu Gly Arg Gly Arg Cys Leu Pro Ala Arg Ala Pro Ala Val
            100                 105                 110

Ala Glu Glu Asn Pro Lys Glu Ser Lys Pro Gln Ala Gly Thr Ala Arg
            115                 120                 125

Pro Gln Asp Val Asn Arg Arg Asp Gln Gln Arg Asn Pro Gly Thr Ser
        130                 135                 140

Thr Thr Pro Ser Gln Pro Asn Ser Ala Gly Val Gln Asp Thr Glu Met
145                 150                 155                 160

Gly Pro Cys Arg Arg His Leu Asp Ser Val Leu Gln Gln Leu Gln Thr
                165                 170                 175

Glu Val Tyr Arg Gly Ala Gln Thr Leu Tyr Val Pro Asn Cys Asp His
            180                 185                 190

Arg Gly Phe Tyr Arg Lys Arg Gln Cys Arg Ser Ser Gln Gly Gln Arg
        195                 200                 205

Arg Gly Pro Cys Trp Cys Val Asp Arg Met Gly Lys Ser Leu Pro Gly
    210                 215                 220

Ser Pro Asp Gly Asn Gly Ser Ser Ser Cys Pro Thr Gly Ser Ser Gly
225                 230                 235                 240
```

```
<210> SEQ ID NO 42
<211> LENGTH: 168
<212> TYPE: PRT
<213> ORGANISM: Homo sapiens

<400> SEQUENCE: 42
```

Met Gln Ala Gln Gln Tyr Gln Gln Arg Arg Lys Phe Ala Ala Ala
 1               5                  10                  15

Phe Leu Ala Phe Ile Phe Ile Leu Ala Ala Val Asp Thr Ala Glu Ala
            20                  25                  30

Gly Lys Lys Glu Lys Pro Glu Lys Lys Val Lys Ser Asp Cys Gly
            35                  40                  45

Glu Trp Gln Trp Ser Val Cys Val Pro Thr Ser Gly Asp Cys Gly Leu
 50                  55                  60

Gly Thr Arg Glu Gly Thr Arg Thr Gly Ala Glu Cys Lys Gln Thr Met
65                  70                  75                  80

Lys Thr Gln Arg Cys Lys Ile Pro Cys Asn Trp Lys Lys Gln Phe Gly
                85                  90                  95

Ala Glu Cys Lys Tyr Gln Phe Gln Ala Trp Gly Glu Cys Asp Leu Asn
            100                 105                 110

Thr Ala Leu Lys Thr Arg Thr Gly Ser Leu Lys Arg Ala Leu His Asn
            115                 120                 125

Ala Glu Cys Gln Lys Thr Val Thr Ile Ser Lys Pro Cys Gly Lys Leu
        130                 135                 140

Thr Lys Pro Lys Pro Gln Ala Gly Ser Lys Lys Lys Lys Glu Gly
145                 150                 155                 160

Lys Lys Gln Glu Lys Met Leu Asp
                165

```
<210> SEQ ID NO 43
<211> LENGTH: 345
<212> TYPE: PRT
<213> ORGANISM: Homo sapiens

<400> SEQUENCE: 43
```

Met Val Ala Ala Leu Gly Gly Gly Glu Ala Arg Gly Gly Thr
 1               5                  10                  15

Val Pro Gly Ala Trp Leu Cys Leu Met Ala Leu Leu Gln Leu Leu Gly
            20                  25                  30

Ser Ala Pro Arg Gly Ser Gly Leu Ala His Gly Arg Arg Leu Ile Cys
            35                  40                  45

Trp Gln Ala Leu Leu Gln Cys Gln Gly Glu Pro Glu Cys Ser Tyr Ala
     50                  55                  60

Tyr Asn Gln Tyr Ala Glu Ala Cys Ala Pro Val Leu Ala Gln His Gly
65                  70                  75                  80

Gly Gly Asp Ala Pro Gly Ala Ala Ala Phe Pro Ala Ser Ala
            85                  90                  95

Ala Ser Phe Ser Ser Arg Trp Arg Cys Pro Ser His Cys Ile Ser Ala
            100                 105                 110

Leu Ile Gln Leu Asn His Thr Arg Arg Gly Pro Ala Leu Glu Asp Cys
            115                 120                 125

Asp Cys Ala Gln Asp Glu Asn Cys Lys Ser Thr Lys Arg Ala Ile Glu
        130                 135                 140

Pro Cys Leu Pro Arg Thr Ser Gly Gly Ala Gly Pro Gly Ala
145                 150                 155                 160

Gly Gly Val Met Gly Cys Thr Glu Ala Arg Arg Arg Cys Asp Arg Asp

```
                        165                 170                 175
Ser Arg Cys Asn Leu Ala Leu Ser Arg Tyr Leu Thr Tyr Cys Gly Lys
                180                 185                 190

Val Phe Asn Gly Leu Arg Cys Thr Asp Glu Cys Arg Thr Val Ile Glu
            195                 200                 205

Asp Met Leu Ala Met Pro Lys Val Ala Leu Leu Asn Asp Cys Val Cys
        210                 215                 220

Asp Gly Leu Glu Arg Pro Ile Cys Glu Ser Val Lys Glu Asn Met Ala
225                 230                 235                 240

Arg Leu Cys Phe Gly Ala Glu Leu Gly Asn Gly Pro Gly Ser Ser Gly
                245                 250                 255

Ser Asp Gly Gly Leu Asp Asp Tyr Tyr Asp Glu Asp Tyr Asp Asp Glu
            260                 265                 270

Gln Arg Thr Gly Gly Ala Gly Gly Glu Gln Pro Leu Asp Asp Asp Asp
        275                 280                 285

Gly Val Pro His Pro Pro Arg Pro Gly Ser Gly Ala Ala Ala Ser Gly
    290                 295                 300

Gly Arg Gly Asp Leu Pro Tyr Gly Pro Gly Arg Arg Ser Ser Gly Gly
305                 310                 315                 320

Gly Gly Arg Leu Ala Pro Arg Gly Ala Trp Thr Pro Leu Ala Ser Ile
                325                 330                 335

Leu Leu Leu Leu Leu Gly Pro Leu Phe
                340                 345

<210> SEQ ID NO 44
<211> LENGTH: 163
<212> TYPE: PRT
<213> ORGANISM: Homo sapiens

<400> SEQUENCE: 44

Met Ser Leu Leu Leu Leu Val Val Ser Ala Leu His Ile Leu Ile Leu
  1               5                  10                  15

Ile Leu Leu Phe Val Ala Thr Leu Asp Lys Ser Trp Trp Thr Leu Pro
                20                  25                  30

Gly Lys Glu Ser Leu Asn Leu Trp Tyr Asp Cys Thr Trp Asn Asn Asp
            35                  40                  45

Thr Lys Thr Trp Ala Cys Ser Asn Val Ser Glu Asn Gly Trp Leu Lys
        50                  55                  60

Ala Val Gln Val Leu Met Val Leu Ser Leu Ile Leu Cys Cys Leu Ser
65                  70                  75                  80

Phe Ile Leu Phe Met Phe Gln Leu Tyr Thr Met Arg Arg Gly Gly Leu
                85                  90                  95

Phe Tyr Ala Thr Gly Leu Cys Gln Leu Cys Thr Ser Val Ala Val Phe
            100                 105                 110

Thr Gly Ala Leu Ile Tyr Ala Ile His Ala Glu Glu Ile Leu Glu Lys
        115                 120                 125

His Pro Arg Gly Gly Ser Phe Gly Tyr Cys Phe Ala Leu Ala Trp Val
    130                 135                 140

Ala Phe Pro Leu Ala Leu Val Ser Gly Ile Ile Tyr Ile His Leu Arg
145                 150                 155                 160

Lys Arg Glu

<210> SEQ ID NO 45
<211> LENGTH: 158
<212> TYPE: PRT
```

<213> ORGANISM: Homo sapiens

<400> SEQUENCE: 45

```
Met Ser His Gly Lys Gly Thr Asp Met Leu Pro Glu Ile Ala Ala Ala
  1               5                  10                  15

Val Gly Phe Leu Ser Ser Leu Leu Arg Thr Arg Gly Cys Val Ser Glu
             20                  25                  30

Gln Arg Leu Lys Val Phe Ser Gly Ala Leu Gln Glu Ala Leu Thr Glu
         35                  40                  45

His Tyr Lys His His Trp Phe Pro Glu Lys Pro Ser Lys Gly Ser Gly
     50                  55                  60

Tyr Arg Cys Ile Arg Ile Asn His Lys Met Asp Pro Ile Ile Ser Arg
 65                  70                  75                  80

Val Ala Ser Gln Ile Gly Leu Ser Gln Pro Gln Leu His Gln Leu Leu
                 85                  90                  95

Pro Ser Glu Leu Thr Leu Trp Val Asp Pro Tyr Glu Val Ser Tyr Arg
            100                 105                 110

Ile Gly Glu Asp Gly Ser Ile Cys Val Leu Tyr Glu Glu Ala Pro Leu
        115                 120                 125

Ala Ala Ser Cys Gly Leu Leu Thr Cys Lys Asn Gln Val Leu Leu Gly
    130                 135                 140

Arg Ser Ser Pro Ser Lys Asn Tyr Val Met Ala Val Ser Ser
145                 150                 155
```

<210> SEQ ID NO 46
<211> LENGTH: 89
<212> TYPE: PRT
<213> ORGANISM: Homo sapiens

<400> SEQUENCE: 46

```
Met Asn Ala Lys Val Val Val Leu Val Leu Val Leu Thr Ala Leu
  1               5                  10                  15

Cys Leu Ser Asp Gly Lys Pro Val Ser Leu Ser Tyr Arg Cys Pro Cys
             20                  25                  30

Arg Phe Phe Glu Ser His Val Ala Arg Ala Asn Val Lys His Leu Lys
         35                  40                  45

Ile Leu Asn Thr Pro Asn Cys Ala Leu Gln Ile Val Ala Arg Leu Lys
     50                  55                  60

Asn Asn Asn Arg Gln Val Cys Ile Asp Pro Lys Leu Lys Trp Ile Gln
 65                  70                  75                  80

Glu Tyr Leu Glu Lys Ala Leu Asn Lys
                 85
```

<210> SEQ ID NO 47
<211> LENGTH: 169
<212> TYPE: PRT
<213> ORGANISM: Homo sapiens

<400> SEQUENCE: 47

```
Met Ala Pro Pro Trp Val Pro Ala Met Gly Phe Thr Leu Ala Pro Ser
  1               5                  10                  15

Leu Gly Cys Phe Val Gly Ser Arg Phe Val His Gly Glu Gly Leu Arg
             20                  25                  30

Trp Tyr Ala Gly Leu Gln Lys Pro Ser Trp His Pro His Trp Val
         35                  40                  45

Leu Gly Pro Val Trp Gly Thr Leu Tyr Ser Ala Met Gly Tyr Gly Ser
     50                  55                  60
```

```
Tyr Leu Val Trp Lys Glu Leu Gly Gly Phe Thr Glu Lys Ala Val Val
 65              70                  75                  80

Pro Leu Gly Leu Tyr Thr Gly Gln Leu Ala Leu Asn Trp Ala Trp Pro
             85                  90                  95

Pro Ile Phe Phe Gly Ala Arg Gln Met Gly Trp Ala Leu Val Asp Leu
             100                 105                 110

Leu Leu Val Ser Gly Ala Ala Ala Thr Thr Val Ala Trp Tyr Gln
             115             120                 125

Val Ser Pro Leu Ala Ala Arg Leu Leu Tyr Pro Tyr Leu Ala Trp Leu
         130             135                 140

Ala Phe Ala Thr Thr Leu Asn Tyr Cys Val Trp Arg Asp Asn His Gly
145                 150                 155                 160

Trp His Gly Gly Arg Arg Leu Pro Glu
                 165

<210> SEQ ID NO 48
<211> LENGTH: 97
<212> TYPE: PRT
<213> ORGANISM: Homo sapiens

<400> SEQUENCE: 48

Met Pro Ser Gln Met Glu His Ala Met Glu Thr Met Met Phe Thr Phe
  1               5                  10                  15

His Lys Phe Ala Gly Asp Lys Gly Tyr Leu Thr Lys Glu Asp Leu Arg
             20                  25                  30

Val Leu Met Glu Lys Glu Phe Pro Gly Phe Leu Glu Asn Gln Lys Asp
             35                  40                  45

Pro Leu Ala Val Asp Lys Ile Met Lys Asp Leu Asp Gln Cys Arg Asp
         50                  55                  60

Gly Lys Val Gly Phe Gln Ser Phe Phe Ser Leu Ile Ala Gly Leu Thr
 65              70                  75                  80

Ile Ala Cys Asn Asp Tyr Phe Val Val His Met Lys Gln Lys Gly Lys
             85                  90                  95

Lys
```